(12) United States Patent
Bearne et al.

(10) Patent No.: US 10,589,046 B2
(45) Date of Patent: Mar. 17, 2020

(54) INTERFACE COMPRISING A NASAL SEALING PORTION AND A ROLLING HINGE

(71) Applicant: FISHER & PAYKEL HEALTHCARE LIMITED, Auckland (NZ)

(72) Inventors: Peter David Alexander Bearne, Auckland (NZ); Roheet Patel, Auckland (NZ); Kirstin Elizabeth Middelkoop, Auckland (NZ); Michael John Henri Cox, Auckland (NZ); Fadi Karim Moh'd Mashal, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 1246 days.

(21) Appl. No.: 14/436,464

(22) PCT Filed: Oct. 17, 2013

(86) PCT No.: PCT/NZ2013/000189
§ 371 (c)(1),
(2) Date: Apr. 16, 2015

(87) PCT Pub. No.: WO2014/062070
PCT Pub. Date: Apr. 24, 2014

(65) Prior Publication Data
US 2015/0246198 A1 Sep. 3, 2015

Related U.S. Application Data

(60) Provisional application No. 61/715,234, filed on Oct. 17, 2012.

(51) Int. Cl.
*A61M 16/06* (2006.01)
*A61M 16/08* (2006.01)

(52) U.S. Cl.
CPC ........ *A61M 16/0605* (2014.02); *A61M 16/06* (2013.01); *A61M 16/0611* (2014.02);
(Continued)

(58) Field of Classification Search
CPC .. A61M 16/00; A61M 16/06; A61M 16/0605; A61M 16/0611;
(Continued)

(56) References Cited

U.S. PATENT DOCUMENTS 6,892,730 B2 * 5/2005 Griffiths ................. A62B 18/02
128/205.25
8,028,699 B2 * 10/2011 Ho ........................ A61M 16/06
128/205.25

(Continued)

FOREIGN PATENT DOCUMENTS

EP 2130563 12/2009
GB 2385533 8/2003
(Continued)

OTHER PUBLICATIONS

International Search Report; App. No. PCT/NZ2013/000189; dated Oct. 17, 2013.
(Continued)

*Primary Examiner* — Colin W Stuart
(74) *Attorney, Agent, or Firm* — Knobbe, Martens, Olson & Bear, LLP

(57) ABSTRACT

An interface for positive pressure therapy includes a mask assembly. The mask assembly can include a mask seal that is adapted to underlie the nose. The mask seal extends up the lateral sides of the nose. The mask seal has a primary seal below the nose and a secondary seal alongside the nose. The mask seal can include a rolling hinge that permits one portion of the mask seal to deform relative to another portion of the mask seal. In one configuration, the portion of the
(Continued)

mask seal that underlies the nose is configured to deform relative to a lower portion of the mask seal.

33 Claims, 116 Drawing Sheets

(52) U.S. Cl.
CPC ..... *A61M 16/0616* (2014.02); *A61M 16/0683* (2013.01); *A61M 16/0816* (2013.01); *A61M 2016/0661* (2013.01); *A61M 2210/0606* (2013.01); *A61M 2210/0618* (2013.01)

(58) Field of Classification Search
CPC ...... A61M 2016/0661; A61M 2210/06; A61M 2210/0606; A61M 2210/0612; A61M 2210/0618; A61M 2210/0625; A61M 16/0616; A62B 7/14; A62B 18/00; A62B 18/006; A62B 18/02; A62B 18/025; A62B 18/04
See application file for complete search history.

(56) References Cited

U.S. PATENT DOCUMENTS

| | | | | |
|---|---|---|---|---|
| 8,978,653 | B2* | 3/2015 | Frater | A61M 16/06 128/205.25 |
| 10,220,171 | B2* | 3/2019 | Olsen | A61M 16/06 |
| 2003/0172936 | A1 | 9/2003 | Wilkie et al. | |
| 2007/0125385 | A1 | 6/2007 | Ho et al. | |
| 2009/0107515 | A1* | 4/2009 | Gavriely | A62B 9/02 128/863 |
| 2009/0139526 | A1* | 6/2009 | Melidis | A61M 16/06 128/206.26 |
| 2010/0006101 | A1* | 1/2010 | McAuley | A61M 16/06 128/206.24 |
| 2013/0199537 | A1* | 8/2013 | Formica | A61M 16/06 128/205.25 |
| 2014/0174446 | A1* | 6/2014 | Prentice | A61M 16/06 128/205.25 |

FOREIGN PATENT DOCUMENTS

| | | |
|---|---|---|
| GB | 2393126 | 3/2004 |
| JP | 2008-525123 | 7/2008 |
| WO | WO 2004/071565 | 8/2004 |
| WO | WO 2012/040791 | 4/2012 |
| WO | WO 2013/066195 | 5/2013 |

OTHER PUBLICATIONS

European Patent Office, Examination Report, Application No. 13847504.1, dated Apr. 13, 2017, in 4 pages.
Australian Government IP Australia, Examination Report No. 1, dated Mar. 28, 2017, in 3 pages.

\* cited by examiner

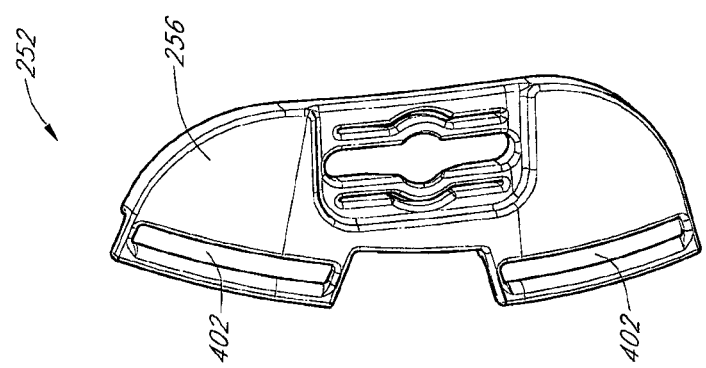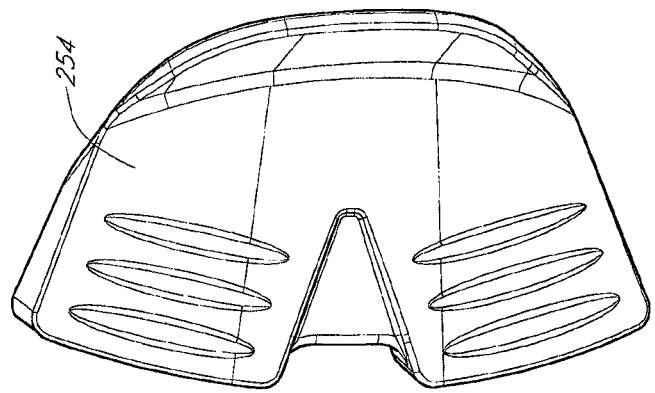
FIG. 34

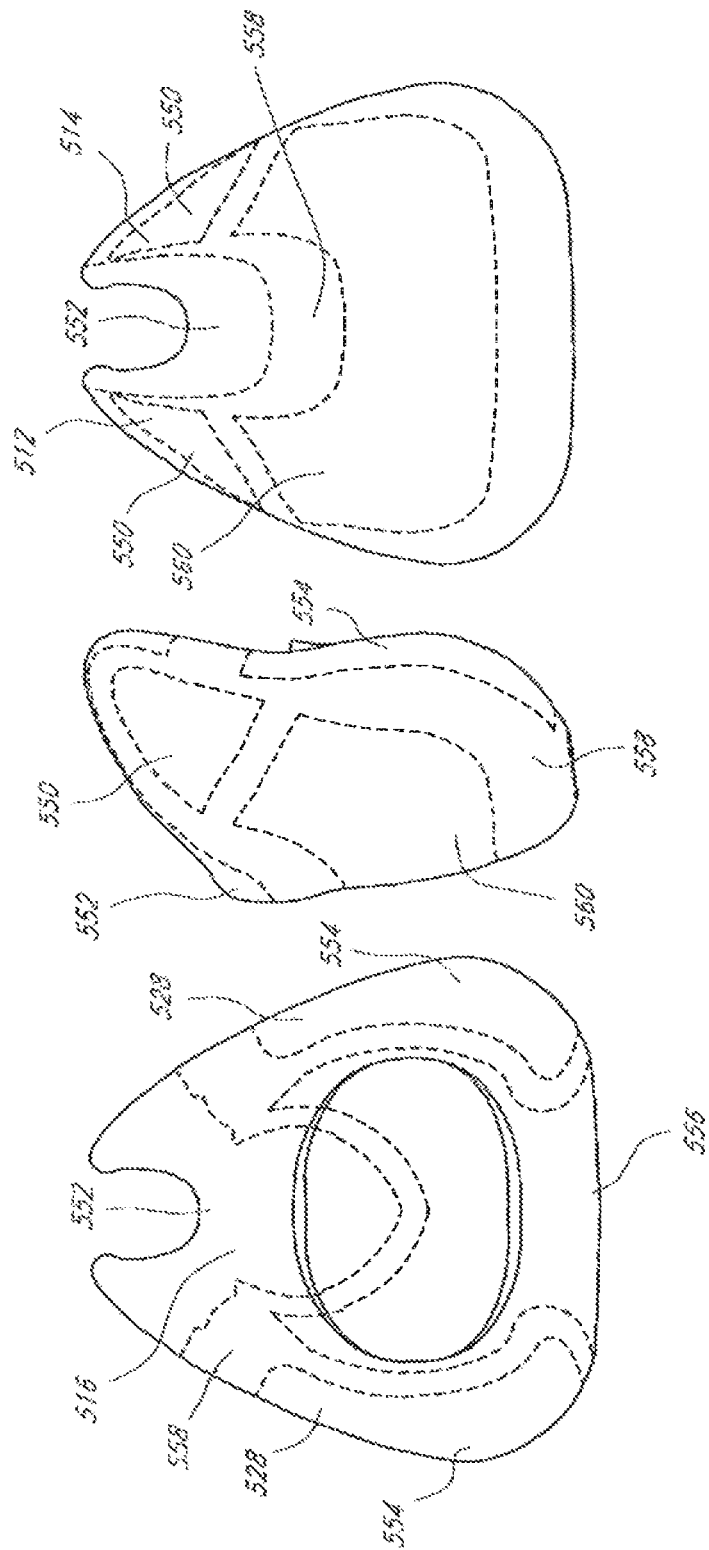

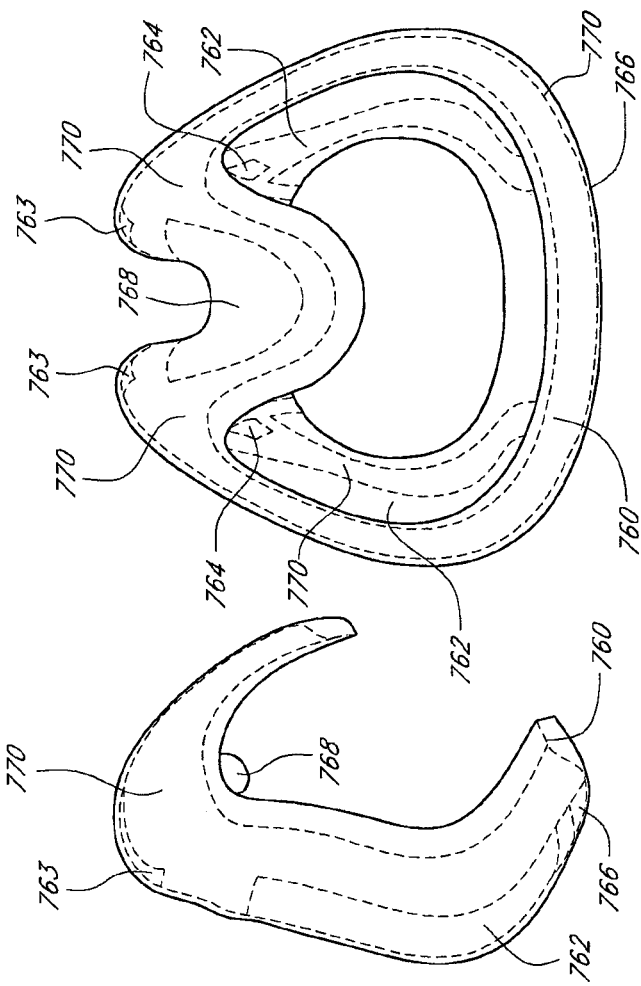
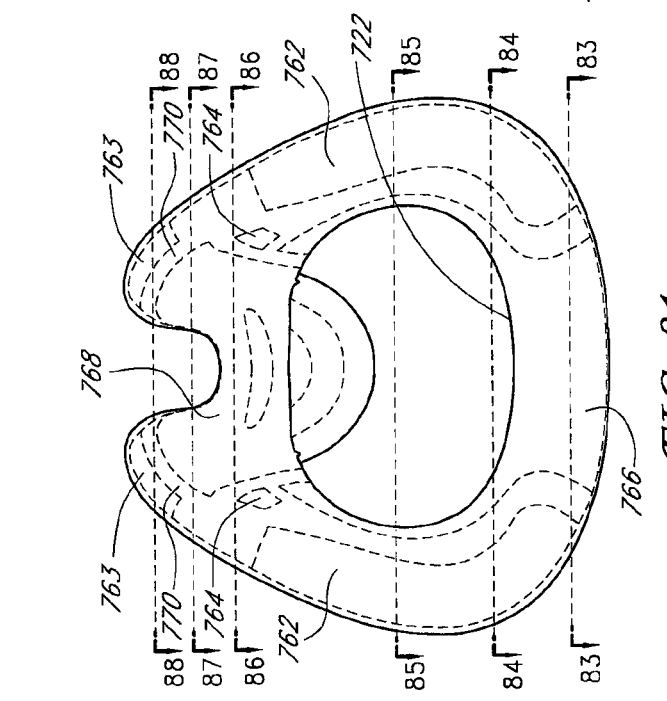

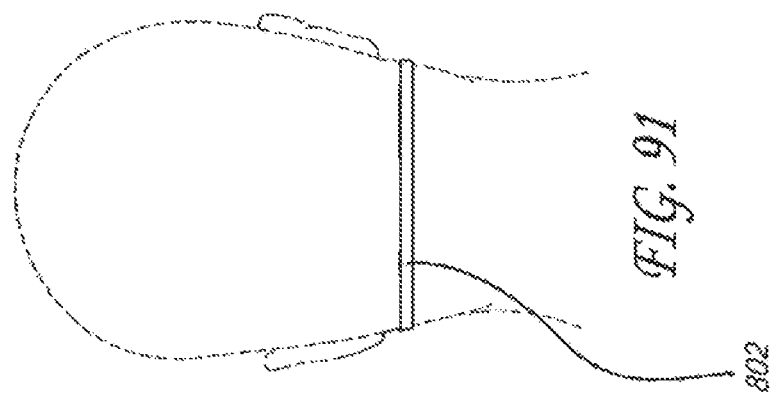
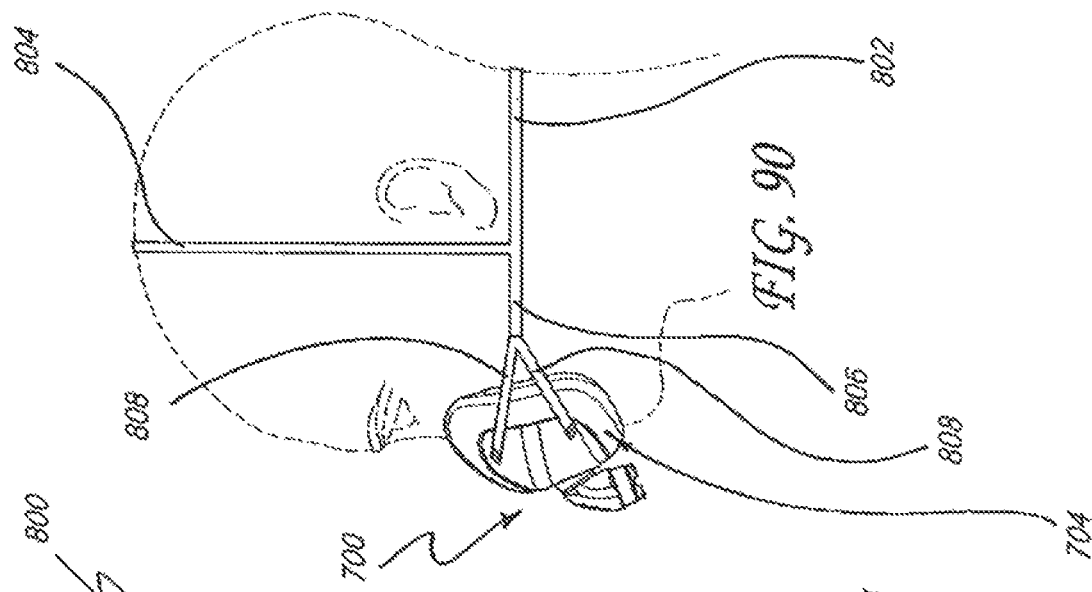
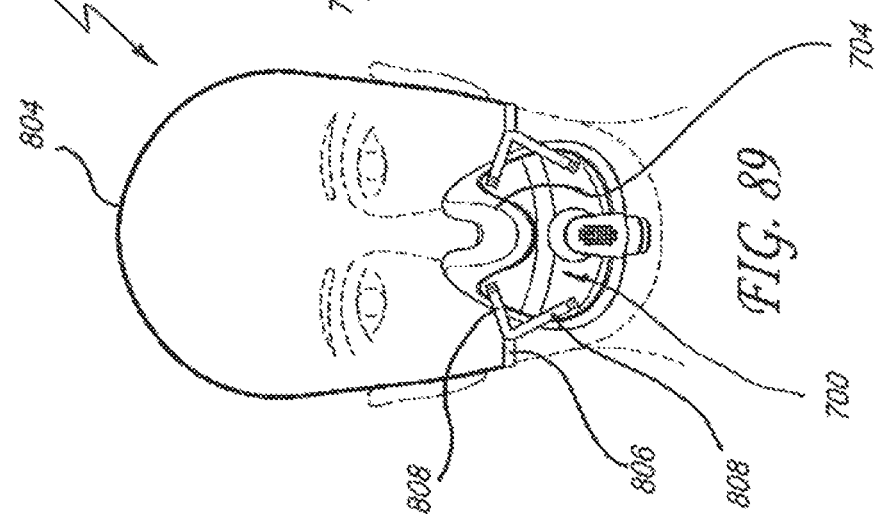

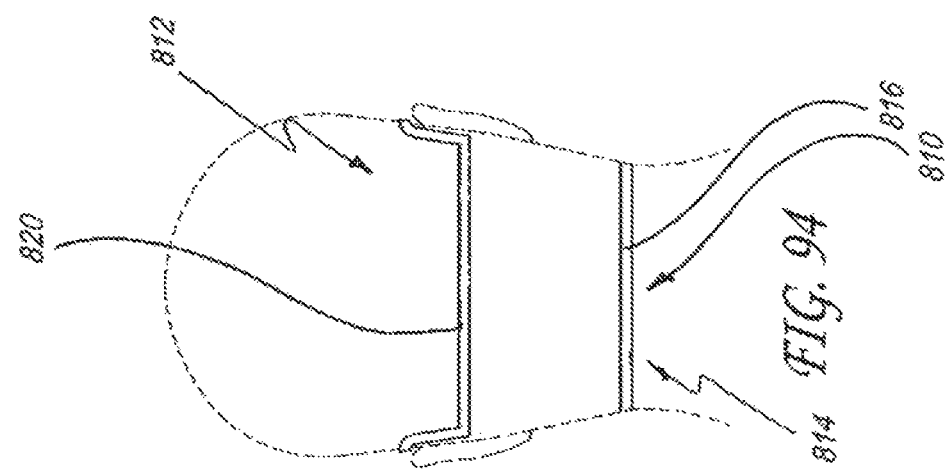
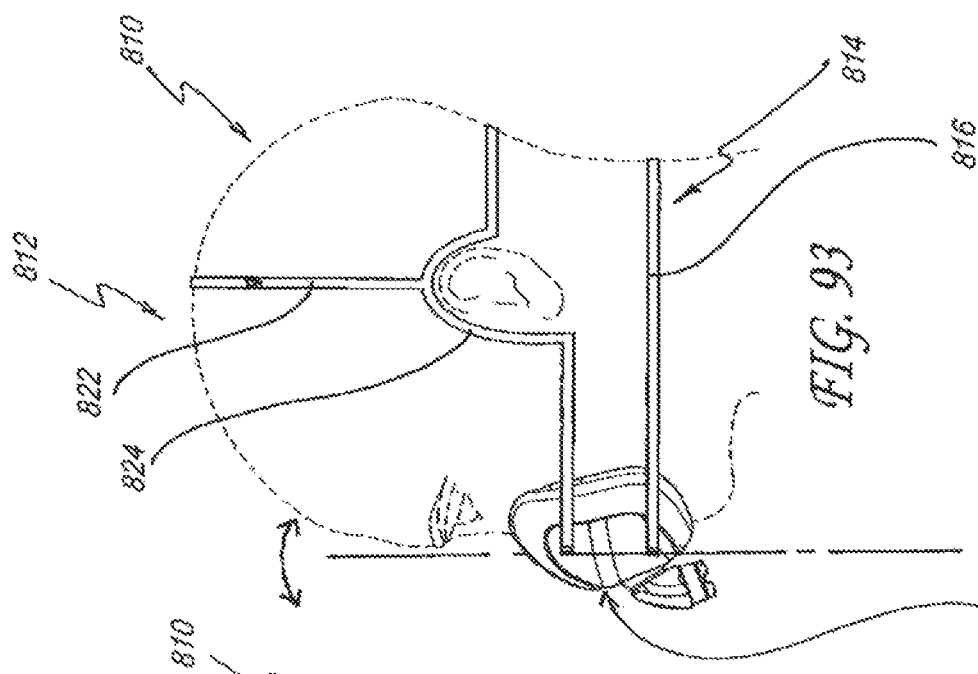
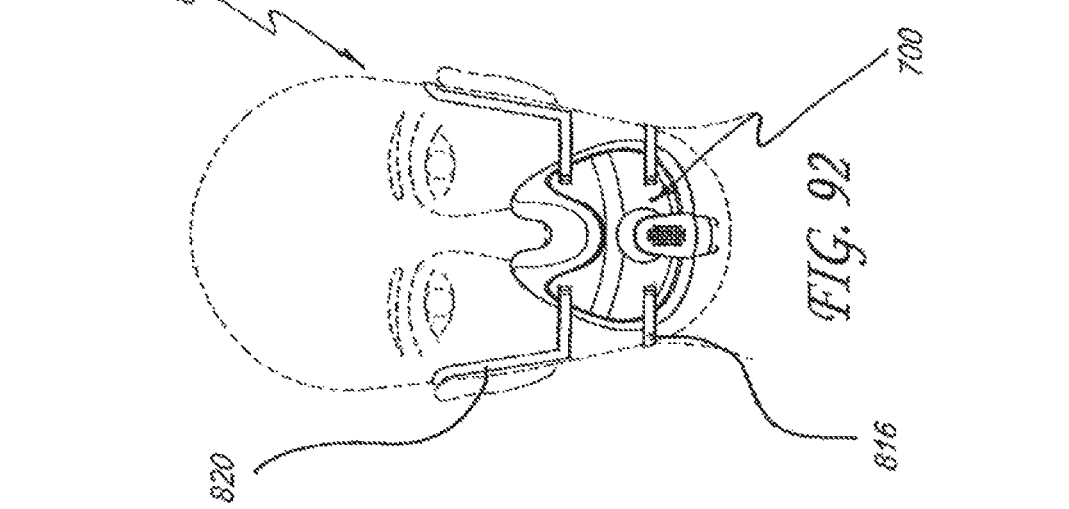

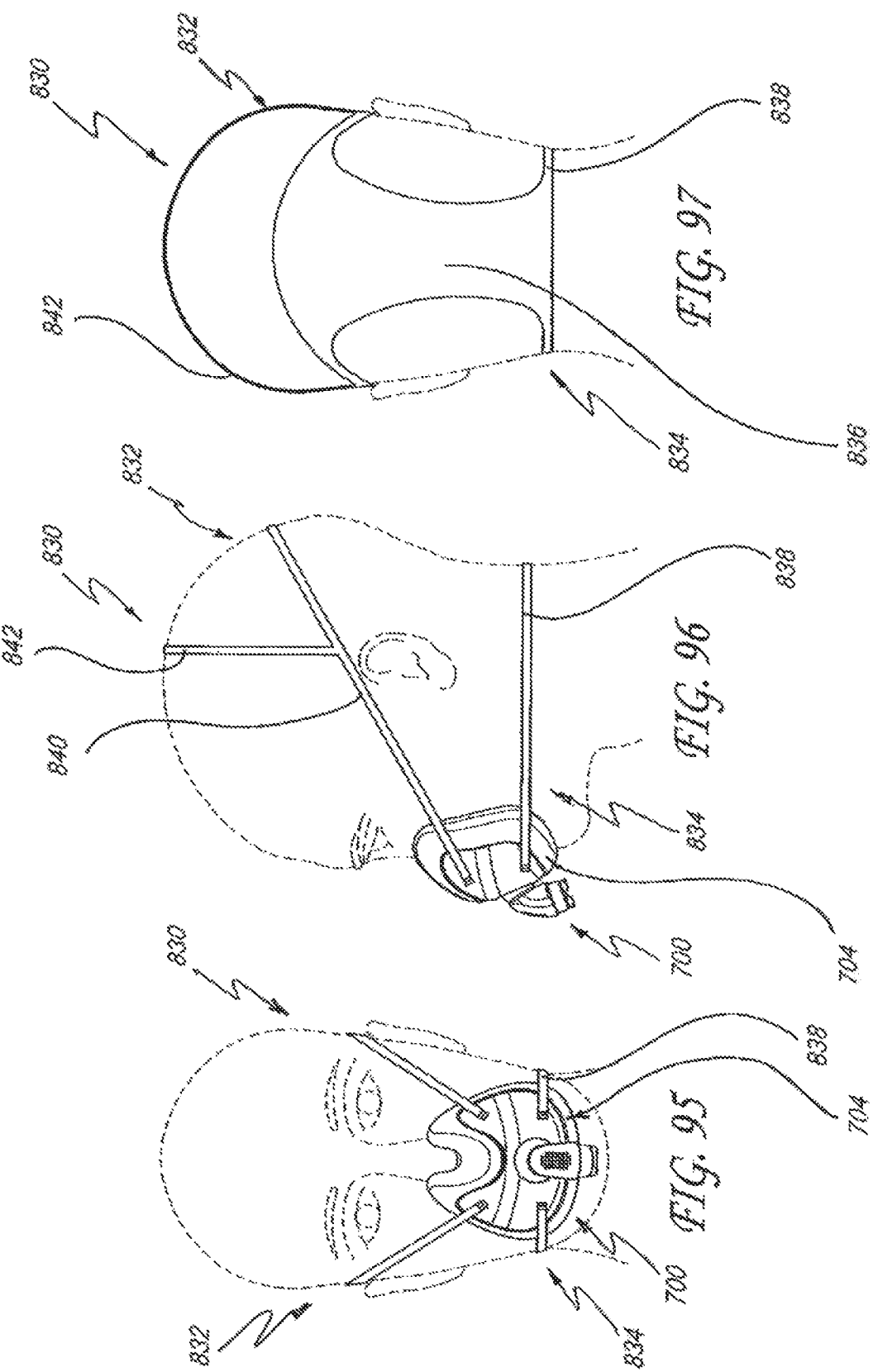

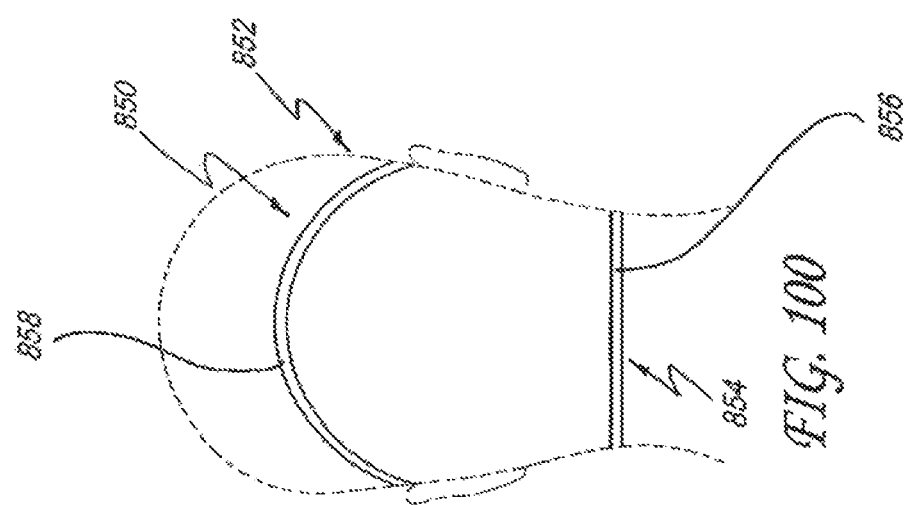
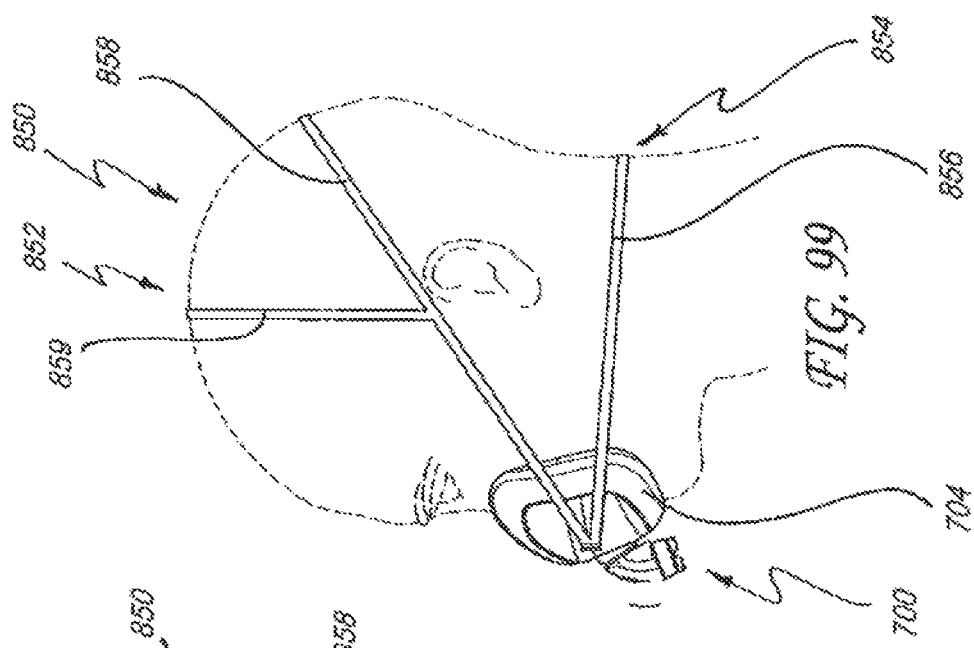
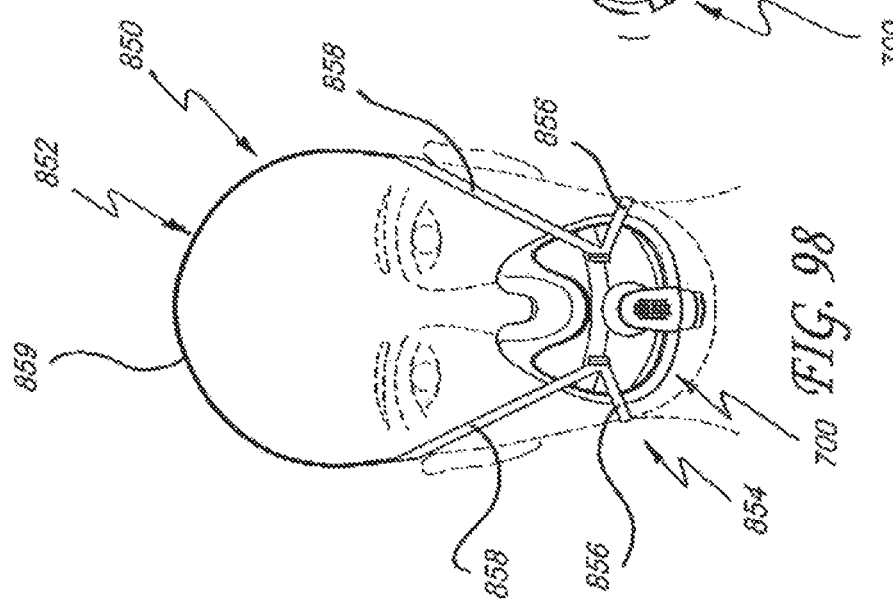

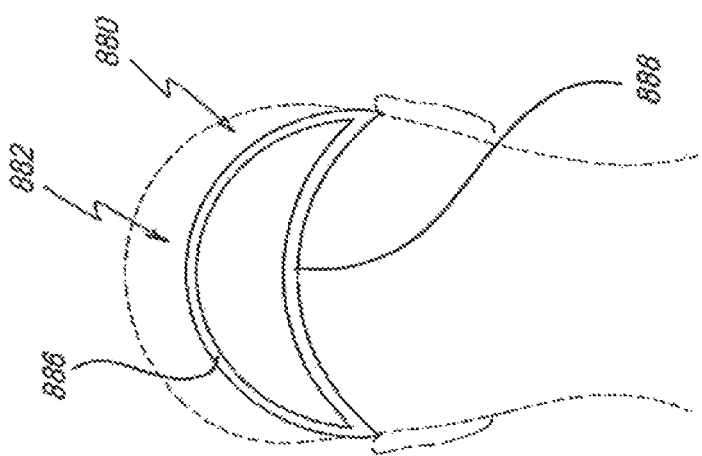
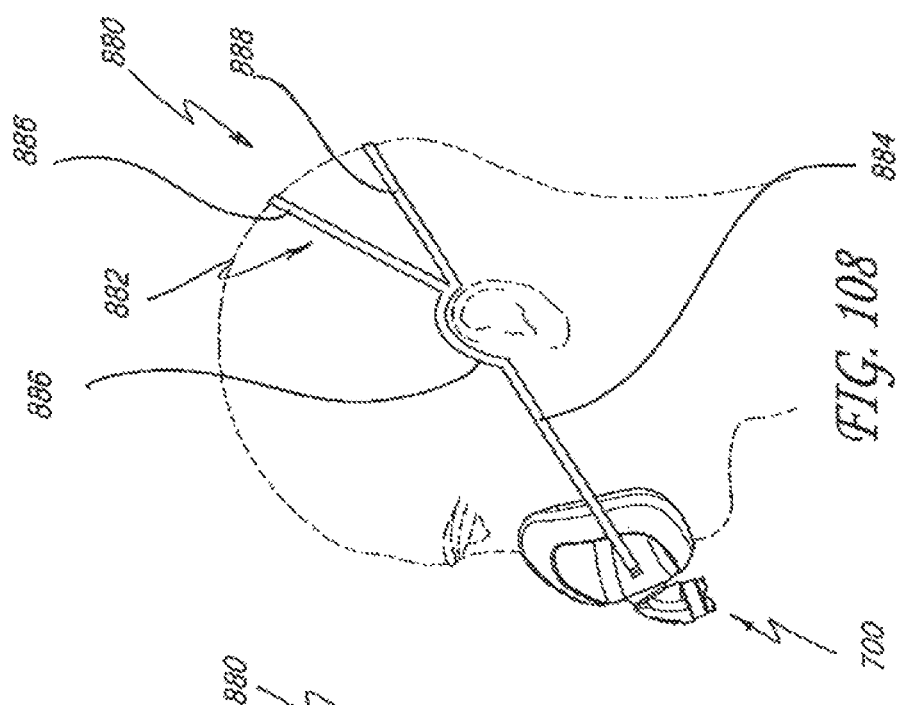
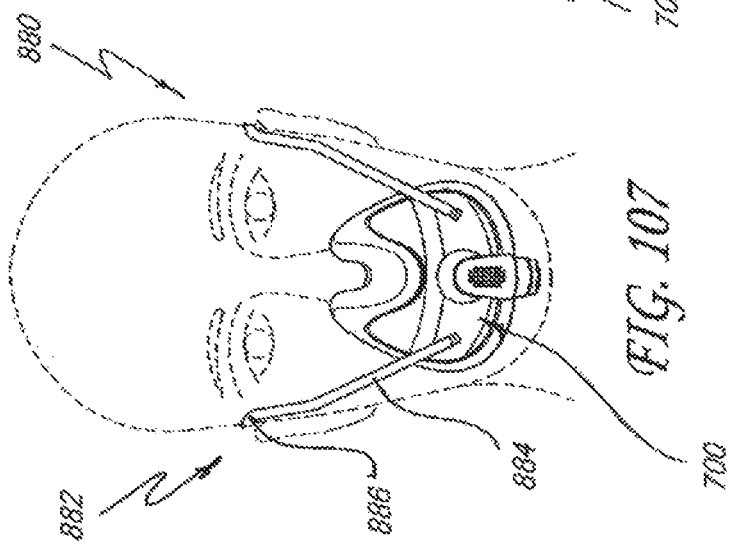

INTERFACE COMPRISING A NASAL SEALING PORTION AND A ROLLING HINGE

INCORPORATION BY REFERENCE OF RELATED APPLICATIONS

The present application incorporates by reference the entireties of the following related applications: U.S. Provisional Patent Application No. 61/553,872, filed on Oct. 31, 2011, PCT/IB2012/000858, filed on Apr. 13, 2012, U.S. Provisional Patent Application No. 61/476,188, filed on Apr. 15, 2011, U.S. Provisional Patent Application No. 61/504,295 filed on Jul. 4, 2011, and U.S. Provisional Patent Application No. 61/553,067, filed on Oct. 28, 2011.

BACKGROUND OF THE INVENTION

Field of the Invention

The present invention generally relates to face masks that cover at least one of a nose and a mouth of a user to supply respiratory gas under positive pressure. More particularly, certain aspects of the present invention relate to such masks that have an improved nasal seal portion and a deformable region or rolling hinge.

Description of the Related Art

Face masks can be used to provide respiratory gases to a user under positive pressure. In configurations in which both a mouth and a nose of a user are covered, the full face mask typically will overlie a bridge of the nose. Generally, a single seal will circumscribe the nose and the mouth of the user. Such a seal passes over a bridge of the user's nose.

Such full face masks commonly are secured to a head of the user with headgear. In order to sufficiently reduce leakage, the headgear typically is tightened, which results in an elevated pressure being exerted on a bridge of a user's nose. In other words, as the headgear is tightened, the silicone seal typically applies a progressively increasing load on the bridge of the nose. The pressure can be a source of discomfort and, in some circumstances, can lead to pressure sores over time.

SUMMARY OF THE INVENTION

It is an object of the present disclosure to provide one or more constructions and/or methods that will at least go some way towards improving on the above or that will at least provide the public or the medical profession with a useful choice.

Accordingly, an interface is provided for use in providing positive pressure respiratory therapy. The interface comprises a mask assembly. The mask assembly comprises a mask seal and a mask base that is removably connected to the mask seal. The mask seal comprises a mask seal clip that is more rigid than at least a portion of the mask seal. The mask seal clip is generally cup-shaped in configuration with an open proximal end and a generally closed distal end. A generally pentagonal lip extends around the proximal end. The mask seal clip comprises an arcuate upper portion with an outer surface. A mask seal clip arc length is defined along the outer surface adjacent an upper extremity of the upper portion between a pair of hinge points. A hinge axis extends laterally across the mask assembly between the hinge points and at least a portion of the upper portion of the mask seal clip is positioned vertically higher than the hinge axis. The mask seal clip upper portion comprises a support surface. A generally central passage extends through the mask clip into a chamber defined by the mask seal. The mask seal comprises a flexible upper portion that is configured to be positioned over a nasal region of a user. The mask seal upper portion is positioned vertically higher than the hinge axis. The mask seal upper portion comprises a region of reduced stiffness located between two regions of increased stiffness. The region of reduced stiffness is capable of rolling to allow pivoting of the mask seal upper portion relative to the mask seal clip. One of the two regions of increased stiffness is positioned adjacent to a small radius bend and the other of the two regions of increased stiffness is position adjacent to a reinforcing component. The small radius bend and the reinforcing component define boundaries between which the upper portion of the mask exhibits rolling during pivoting of the upper portion about the pivot axis. The mask seal upper portion has a first curve length adjacent to the small radius bend and a second curve length adjacent to the reinforcing band. The first curve length being smaller than the second curve length. The curve length increases as a measured location moves away from the mask seal clip. The mask base overlies at least a portion of the mask seal clip. The mask base comprises a first pocket and a second pocket. The first and second pockets are positioned symmetrically relative to a center plane that substantially bisects the mask base. Each of the first pocket and the second pocket comprises a vertical dimension that is larger than a transverse dimension. The mask base also comprises a wall that defines a central opening. The wall extends into the generally central passage of the mask seal clip. A connection port assembly comprises an elbow terminating in a ball shaped member. The ball shaped member is sized and configured to be held by the wall that defines the central opening. The connection port assembly also comprises a removable swivel member. The removable swivel member is secured by a lever. The lever overlies a port. The port is selectively coverable with a flap. The flap also is capable of closing a central passage within the elbow. The port opening is in a general direction of the mask when the elbow is connected to the mask. A headgear assembly comprises a pair of upper straps and a pair of lower straps. One of the pair of upper straps and one of the pair of lower straps is connected to a first clip. Another of the pair of upper straps and another of the pair of lower straps is connected to a second clip. The first clip and the second clip are securable within the pockets of the mask base such that the clips are brought into engagement within the pockets by moving in a direction substantially normal to a strap tensile force direction.

In some configurations, the mask seal is a full face mask.

In some configurations, the mask seal clip is integrated into the mask seal such that the mask seal clip is non-separable from the mask seal.

In some configurations, the mask base is removably connected to the mask seal.

In some configurations, an outer surface of the upper portion rolls onto the support surface of the mask seal clip and the support surface defines an outer surface of the upper portion of the mask seal clip.

In some configurations, the region of reduced stiffness comprises a region of reduced thickness compared to the regions of increased stiffness.

In some configurations, the upper portion of the mask seal comprises an apex defined by a first wall and a second wall and the reinforcing component extends along at least a portion of the first wall and along at least a portion of the second wall. Preferably, the reinforcing component extends over the apex of the upper portion of the mask seal.

In some configurations, the reinforcing component ends at both ends in a location generally vertically higher than the hinge points.

A mask assembly can comprise a mask seal. The mask seal comprises an upper portion and a lower portion. The upper portion is pivotable relative to the lower portion. The upper portion comprises a region of reduced stiffness that is positioned between a first boundary and a second boundary. The first boundary is defined by a stiffness greater than that in the region of reduced stiffness. The second boundary is defined by a stiffness greater than that in the region of reduced stiffness. When the first boundary is moved toward the second boundary, the region of reduced stiffness buckles in a single direction to define a roll of material that changes in size as the first boundary continues to move toward the second boundary.

In some configurations, the region of reduced stiffness facilitates movement of the upper portion of the seal member relative to the lower portion of the seal member. Preferably, the upper portion comprises a nasal bridge portion of the mask and movement of the first boundary toward the second boundary facilitates movement of the nasal bridge portion of the mask relative to the lower portion of the mask.

In some configurations, the second boundary is positioned between the upper portion and the lower portion. Preferably, the mask further comprises a mask seal clip that has an increased rigidity relative to the mask seal and the second boundary is positioned along an end of the mask seal clip. More preferably, the roll of material overlies at least a portion of the mask seal clip.

In some configurations, the first boundary is defined along a reinforcing component. Preferably, the reinforcing component comprises a plastic band.

In some configurations, the region of reduced stiffness is defined with a reduced thickness relative to the first boundary.

In some configurations, the second boundary is defined by a corner having a small radius.

In some configurations, the roll extends over at least a portion of the mask seal.

In some configurations, the roll overlies at least a portion of the mask seal clip when the first boundary is moved fully toward the second boundary.

A mask assembly can comprise a mask seal. The mask seal comprises a nasal region and an oral region. The nasal region and the oral region are integrally formed. The nasal region is movable relative to the oral region such that forces exerted by the nasal region in multiple positions remain substantially constant while forces exerted by the oral region increase.

A mask assembly comprises a mask seal connected to a headgear assembly. The mask seal is configured to encircle a nasal bridge region and an oral region of a user. The mask seal comprises nonpleated means for applying a substantially constant force to the nasal bridge region while applying increasing forces to an oral region when the headgear assembly is tightened.

A mask assembly comprises a seal. The seal comprises a flange that engages a face of a user. The seal is removably connected to a mask base. The mask base comprises a first opening and a second opening. The first opening and the second opening receive a first clip and a second clip from an associated headgear assembly. The mask base further comprises a passageway positioned generally between the first opening and the second opening. The passageway is adapted to receive a breathing tube connector.

In some configurations, the mask assembly further comprises a mask seal clip that is connected to the mask seal and that is removably connected to the mask base. Preferably, the mask base overlies a substantial portion of the mask seal clip. More preferably, the mask base comprises a peripheral edge and at least one recess is defined along the peripheral edge of the mask base at a location that overlies the mask seal clip.

A mask assembly comprises a mask seal. The mask seal comprises a proximal flange adapted to contact a face of a user. The mask seal comprises a distal facing surface. A mask base comprises a peripheral edge and a cover surface extends from the peripheral edge. The mask base cover surface overlies at least a portion of the distal facing surface of the mask seal such that the mask base cover surface is spaced apart in a distal direction from the mask seal distal facing surface whereby the mask base cover surface and the mask seal distal facing surface provide an insulating effect to the mask assembly that reduces humidity rainout.

An interface for providing positive pressure air flow to a user can comprise a mask base and a mask seal removably connected to the mask base. The mask seal comprises a first sealing surface that is adapted to underlie a nose of a user and a second sealing surface that is adapted to extend over at least a fibro-fatty tissue of one or more alar of the nose of the user without wrapping over a tip of the nose of the user.

In some configurations, the first sealing surface is defined by an upper surface. A chamber can be defined within the seal member and an opening through the upper surface can be generally flush with the upper surface.

In some configurations, the second sealing surface comprises a first paddle and a second paddle. The first paddle and the second paddle extend vertically higher than the upper surface and a valley is defined by the first paddle, the upper surface and the second paddle. The valley is adapted such that a tip of the nose of the user is not covered by the mask seal.

In some configurations, the first paddle and the second paddle each comprises an inner pocket that is in fluid communication with the chamber defined within the seal member. Lateral portions of the inner pockets extend vertically higher than the upper surface of the mask seal.

In some configurations, the mask seal further comprises a lip that depends downward from the upper surface and that is adapted to define at least a portion of an oral opening. The oral opening is separated from the opening in the upper surface.

In some configurations, the mask seal further comprises a lip that generally encircles an oral portion of an integrated oral-nasal opening defined in the mask seal.

In some configurations, the interface further includes a clip that connects a first side of the integrated oral-nasal opening to a second side of the integrated oral-nasal opening.

In some configurations, the mask seal comprises a forward facing surface and a rearward facing surface that are connected by a sidewall.

In some configurations, a portion of the rearward facing surface in the first and second paddles has a thickness that is less than a portion of the forward facing surface in the first and second paddles.

In some configurations, a portion of the rearward facing surface in a central chin region of the mask has a thickness that is less than a thickness of a portion of the rearward facing surface laterally outward of the central chin region.

An interface for providing positive pressure air flow to a user comprises a mask base and a mask seal removably connected to the mask base. The mask seal comprises a first paddle and a second paddle that are connected to a first sealing surface. The first paddle and the second paddle define a secondary sealing structure. The first paddle and the second paddle can be movable from a first position in which a first gap is defined between upper portions of the first and second paddles to a second position in which a second gap is defined between the upper portions of the first and second paddles. The first gap is larger than the second gap.

In some configurations, downward movement of the upper surface from a first position to a second position causes movement of the first and second paddles from the first position to the second position.

In some configurations, the mask seal comprises a forward facing surface and a rearward facing surface that are connected by a sidewall.

In some configurations, a portion of the rearward facing surface in the first and second paddles has a thickness that is less than a portion of the forward facing surface in the first and second paddles.

In some configurations, a portion of the rearward facing surface in a central chin region of the mask has a thickness that is less than a thickness of a portion of the rearward facing surface laterally outward of the central chin region.

In some configurations, an interface is provided for use in providing positive pressure respiratory therapy. The interface comprises a mask assembly comprising a mask seal and a mask base. The mask assembly is configured to be fully positioned lower than a bridge of a nose of a face of a user and the mask assembly is configured to provide an exposed tip of the nose of the user. The mask base comprises a central portion and a pair of wings sweeping rearwardly of the central portion. The wings have a greater vertical expanse than the central portion. An opening for a connector is formed on the mask base in the central portion. The mask seal is connected to the mask base. The mask seal comprises a thickened region adjacent to the mask base. The mask seal comprises at least one oral opening on a lower portion and at least one nasal opening on an upper portion. The at least one oral opening is positioned opposite of the opening for the connector and the at least one nasal opening is positioned between the opening for the connector and the oral opening in a front to back direction. The mask seal comprises a first paddle and a second paddle. An upper surface is positioned between the first paddle and the second paddle such that an upwardly-open valley is defined by the first paddle, the upper support surface and the second paddle. At least a portion of the at least one nasal opening is positioned on the upper surface within the valley. The first paddle comprises a first pocket and the second paddle comprises a second pocket. The first and second pockets are in fluid communication with a chamber defined within the mask assembly.

In some configurations, the mask seal is adapted to seal under the nose of the user, along a portion of a face of the user adjacent to the nose and around a mouth of the user.

In some configurations, the mask assembly is configured to not cover any forward facing portion of the nose of the user.

In some configurations, the upper surface is hammocked between inner portions of the first and second paddles.

In some configurations, downward pressure on the upper surface causes the first and second paddles to deflect toward each other.

In some configurations, the seal member comprises a rear surface that is adapted to contact the face of the user and the rear surface comprises a first protrusion and a second protrusion.

In some configurations, at least a portion of the first protrusion and at least a portion of the second protrusion are positioned vertically between the upper surface and an uppermost portion of the at least one oral opening.

In some configurations, the portion of the first protrusion comprises a first peak and wherein the portion of the second protrusion comprises a second peak.

In some configurations, the first peak and the second peak are positioned vertically between a portion of the at least one nasal opening and the at least one oral opening.

In some configurations, the first peak and the second peak are positioned vertically closer to the at least one nasal opening than to the at least one oral opening.

In some configurations, the mask seal is adapted to anchor on two locations of the face.

In some configurations, the mask seal is configured to anchor below the lower lip and below the nose.

In some configurations, the mask seal is configured to anchor below the lower lip but above the chin and below the nose.

In some configurations, the two locations are lower than the bottom of the nose but the mask seal extends upward beyond the bottom of the nose.

In some configurations, the mask seal is adapted to seal against the face in locations vertically above the uppermost anchoring location.

In some configurations, the upper surface slopes downward and rearward in the region surrounding the at least one nasal opening.

In some configurations, the at least one nasal opening comprises a nasal pad insert.

In some configurations, the nasal pad insert is formed of a material different from the mask seal.

In some configurations, the nasal pad insert is secured to the mask seal at a recessed pad support region.

In some configurations, the nasal pad insert and the mask seal comprise correlated keying features.

In some configurations, the nasal pad insert and the mask seal have a sealed interface generally surrounding the at least one nasal opening.

In some configurations, the nasal pad insert comprises a recessed central portion.

In some configurations, the recessed central portion is positioned generally forward of the at least one nasal opening.

In some configurations, outer peripheral portions have an increased rigidity relative to inwardly facing portions of the first paddle and the second paddle.

In some configurations, the outer peripheral portions have an increased thickness relative to the inwardly facing portions of the first paddle and the second paddle.

In some configurations, the first paddle comprises a first ridge positioned between an outwardly facing surface and an inwardly facing surface and the second paddle comprises a second ridge positioned between an outwardly facing surface and an inwardly facing surface, the first and second ridge having an increased rigidity relative to the inwardly facing surface.

In some configurations, the first paddle comprises a first ridge positioned between an outwardly facing surface and an inwardly facing surface and the second paddle comprises a second ridge positioned between an outwardly facing surface and an inwardly facing surface, the first and second ridge having an increased thickness relative to the inwardly facing surface.

In some configurations, the interface comprises a headgear assembly adapted to provide a slightly upward force application between the mask assembly and the face of the user.

In some configurations, the headgear assembly is configured to adjust an angle of the mask assembly.

In some configurations, the headgear does not include a T-piece.

In some configurations, the mask assembly and the headgear assembly are configured such that no portion of the mask assembly or the headgear assembly will contact the face of the user at any location vertically above the eyes at a location horizontally between the outsides of the eyes.

In some configurations, the mask assembly comprises at least one nasal prong.

In some configurations, the at least one nasal prong is inclined toward a medial vertical plane of the mask assembly.

In some configurations, an interface is provided for use in providing positive pressure respiratory therapy. The interface comprises a mask assembly comprising a mask seal and a mask base. The mask assembly is configured to be fully positioned lower than a bridge of a nose of a face of a user and the mask assembly is configured to provide an exposed tip of the nose of the user. The mask base comprises a central portion and a pair of wings sweeping rearwardly of the central portion. An opening for a connector is formed on the mask base in the central portion. The mask seal is connected to the mask base. The mask seal comprises at least one oral opening on a lower portion and at least one nasal opening on an upper portion. The at least one oral opening is positioned opposite of the opening for the connector and the at least one nasal opening is positioned between the opening for the connector and the oral opening in a front to back direction. The mask seal comprises a first paddle and a second paddle. An upper support surface is positioned between the first paddle and the second paddle such that an upwardly-open valley is defined by the first paddle, the upper support surface and the second paddle. At least a portion of the at least one nasal opening is positioned on the upper support surface within the valley. The mask seal comprises a rolling hinge positioned between an upper surface of the mask base and the upper support surface. The rolling hinge permits an upper portion of the mask seal to deform downwardly relative to a lower portion of the mask seal.

In some configurations, the rolling hinge comprises a thin-walled portion positioned between a pair of thick-walled portions.

In some configurations, an upper one of the pair of thick-walled portions is defined at least in part by a thickened band.

In some configurations, the thickened band has a central portion having a first cross-sectional dimension and outer end portions having a second cross-sectional dimension that is greater than the first cross-sectional dimension.

In some configurations, the thickened band is positioned on an interior surface of the mask seal.

In some configurations, a transition portion is provided between the thin-walled portion and one of the pair of thick-walled portions. The transition portion can define a variable wall thickness.

In some configurations, the transition portion defines a first wall thickness that is substantially equal to the thin-walled portion and wherein the transition portion defines a second wall thickness that is substantially equal to the thick-walled portion.

In some configurations, the rolling hinge extends laterally across the mask seal.

In some configurations, the rolling hinge defines a length that is substantially equal to a width of an upper surface of the mask base.

In some configurations, the rolling hinge rolls over a forward facing surface of the mask seal.

In some configurations, the mask seal is adapted to seal under the nose of the user, along a portion of a face of the user adjacent to the nose and around a mouth of the user.

In some configurations, the mask assembly is configured to not cover any forward facing portion of the nose of the user.

In some configurations, the upper support surface is hammocked between inner portions of the first and second paddles.

In some configurations, downward pressure on the upper support surface causes the first and second paddles to deflect toward each other.

In some configurations, the seal member comprises a rear surface that is adapted to contact the face of the user and the rear surface comprises a first protrusion and a second protrusion.

In some configurations, at least a portion of the first protrusion and at least a portion of the second protrusion are positioned vertically between the upper surface and an uppermost portion of the at least one oral opening.

In some configurations, the portion of the first protrusion comprises a first peak and wherein the portion of the second protrusion comprises a second peak.

In some configurations, the first peak and the second peak are positioned vertically between a portion of the at least one nasal opening and the at least one oral opening.

In some configurations, the first peak and the second peak are positioned vertically closer to the at least one nasal opening than to the at least one oral opening.

In some configurations, the mask seal is adapted to anchor on two locations of the face.

In some configurations, the mask seal is configured to anchor below the lower lip and below the nose.

In some configurations, the mask seal is configured to anchor below the lower lip but above the chin and below the nose.

In some configurations, the two locations are lower than the bottom of the nose but the mask seal extends upward beyond the bottom of the nose.

In some configurations, the mask seal is adapted to seal against the face in locations vertically above the uppermost anchoring location.

In some configurations, the upper support surface slopes downward and rearward in the region surrounding the at least one nasal opening.

In some configurations, the at least one nasal opening comprises a nasal pad insert.

In some configurations, the nasal pad insert is formed of a material different from the mask seal.

In some configurations, the nasal pad insert is secured to the mask seal at a recessed pad support region.

In some configurations, the nasal pad insert and the mask seal comprise correlated keying features.

In some configurations, the nasal pad insert and the mask seal have a sealed interface generally surrounding the at least one nasal opening.

In some configurations, the nasal pad insert comprises a recessed central portion.

In some configurations, the recessed central portion is positioned generally forward of the at least one nasal opening.

In some configurations, outer peripheral portions have an increased rigidity relative to inwardly facing portions of the first paddle and the second paddle.

In some configurations, the outer peripheral portions have an increased thickness relative to the inwardly facing portions of the first paddle and the second paddle.

In some configurations, the first paddle comprises a first ridge positioned between an outwardly facing surface and an inwardly facing surface and the second paddle comprises a second ridge positioned between an outwardly facing surface and an inwardly facing surface, the first and second ridge having an increased rigidity relative to the inwardly facing surface.

In some configurations, the first paddle comprises a first ridge positioned between an outwardly facing surface and an inwardly facing surface and the second paddle comprises a second ridge positioned between an outwardly facing surface and an inwardly facing surface, the first and second ridge having an increased thickness relative to the inwardly facing surface.

In some configurations, the interface comprises a headgear assembly adapted to provide a slightly upward force application between the mask assembly and the face of the user.

In some configurations, the headgear assembly is configured to adjust an angle of the mask assembly.

In some configurations, the headgear does not include a T-piece.

In some configurations, the mask assembly and the headgear assembly are configured such that no portion of the mask assembly or the headgear assembly will contact the face of the user at any location vertically above the eyes at a location horizontally between the outsides of the eyes.

In some configurations, the mask assembly comprises at least one nasal prong.

In some configurations, the at least one nasal prong is inclined toward a medial vertical plane of the mask assembly.

BRIEF DESCRIPTION OF THE DRAWINGS

These and other features, aspects and advantages of embodiments of the present invention will be described with reference to the following drawings.

FIG. 34 is an exploded view of the clip of FIG. 33.

FIG. 63 is a rear view of a mask seal of the mask configuration of FIG. 54.

FIG. 64 is a side view of the mask seal of the mask configuration of FIG. 54.

FIG. 65 is a front view of the mask seal of the mask configuration of FIG. 54.

FIG. 80 is a front view of the mask seal of the mask configuration of FIG. 71 showing different regions of thickness.

FIG. 81 is a rear view of the mask seal of the mask configuration of FIG. 71 showing different regions of thickness.

FIG. 82 is a side view of the mask configuration of FIG. 71 showing different regions of thickness.

FIGS. 89-109 are illustrations of different headgear assemblies that can be used with the mask assembly of FIG. 71.

DETAILED DESCRIPTION OF THE PREFERRED EMBODIMENTS

Figure 1:
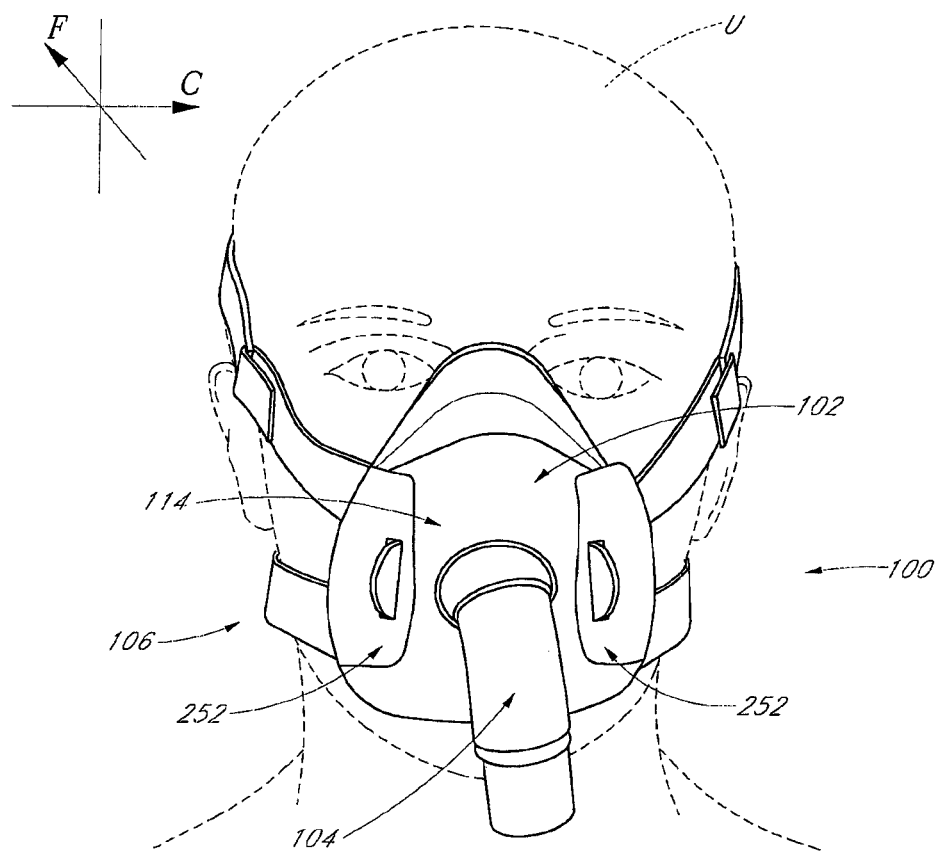
FIG. 1 is front view of a user wearing an interface that is arranged and configured in accordance with certain features, aspects and advantages of the present invention.
Figure 2:
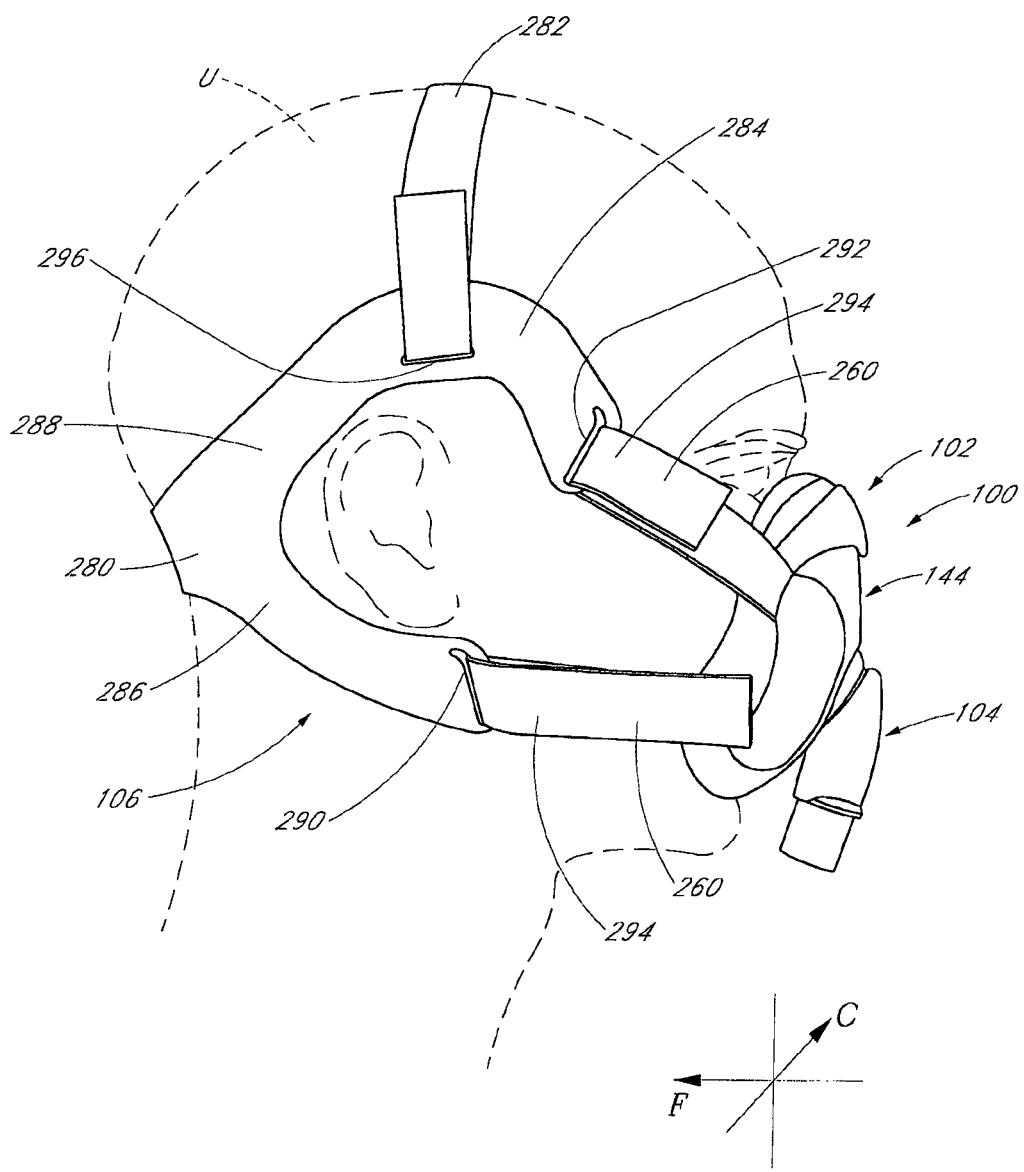
FIG. 2 is a side view of a user wearing the interface of FIG. 1.

With reference initially to FIGS. 1 and 2, an interface 100 is shown in position on a user U. The interface 100 comprises an interface that can be used in the field of respiratory therapy. The interface 100 has particular utility with forms of positive pressure respiratory therapy. For example, the interface 100 can be used for administering continuous positive airway pressure ("CPAP") treatments. In addition, the interface 100 can be used with variable positive airway pressure ("VPAP") treatments and bi-level positive airway pressure ("BiPAP") treatments. The interface can be used with any suitable CPAP system.

The interface 100 can comprise any suitable mask configuration. For example, certain features, aspects and advantages of the present invention can find utility with nasal masks, full face masks, oronasal masks or any other positive pressure mask. The mask illustrated in FIG. 1 is a full face mask. The illustrated interface 100 generally comprises a mask assembly 102, a connection port assembly 104 and a headgear assembly 106.

Figure 13:
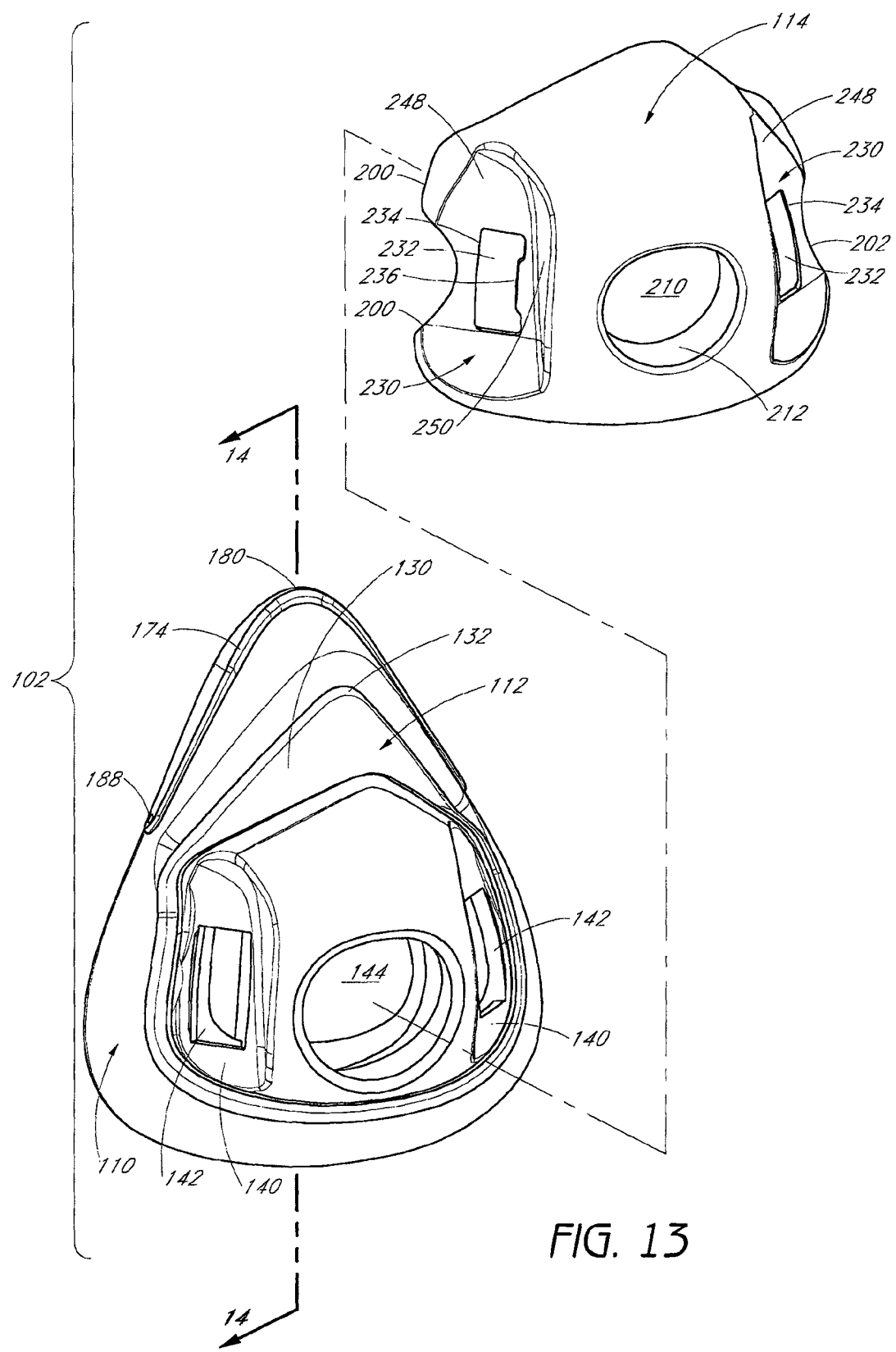
FIG. 13 is an exploded front perspective view of the mask seal, mask seal clip and mask base of the interface of FIG. 1.

With reference to FIG. 13, the mask assembly 102 generally comprises a mask seal 110, which can include a mask seal clip 112, and a mask base 114. As will be described, the mask seal clip 112 preferably connects the mask seal 110 to the mask base 114. While the illustrated mask seal 110 and mask seal clip 112 are formed separately and secured together, in some configurations, the mask seal 110 and the mask seal clip 112 can be integrated into a single component. In some configurations, the mask seal 110 is overmolded onto the mask seal clip 112.

Figure 3:
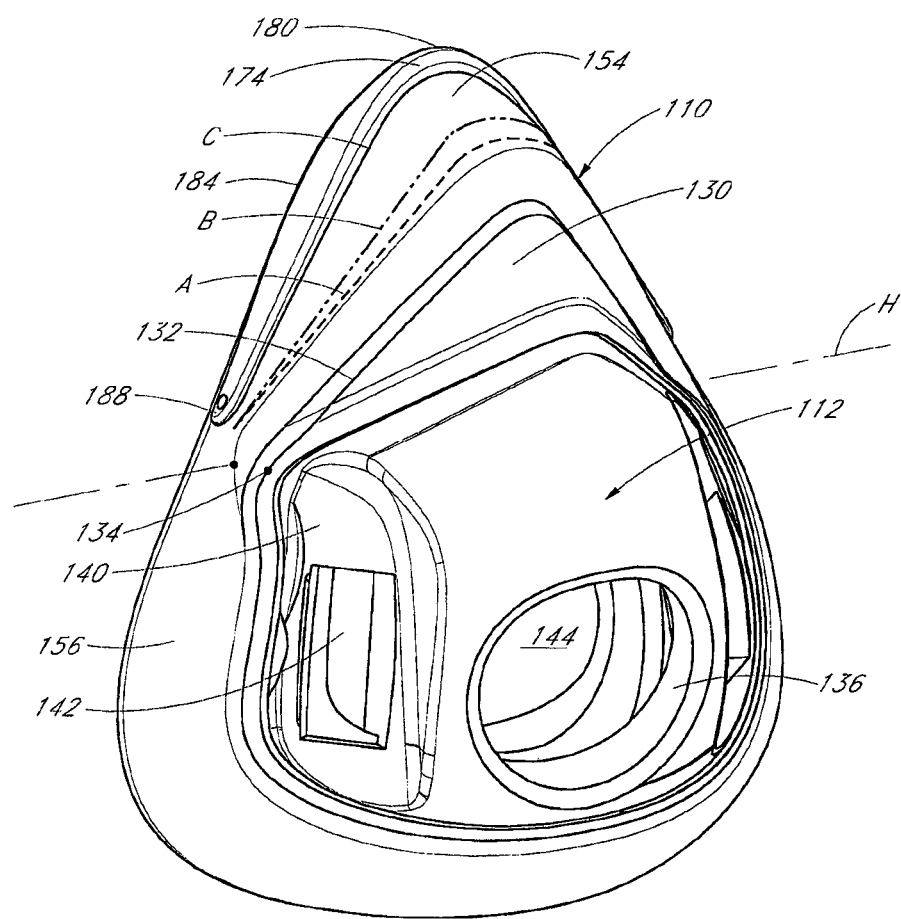
FIG. 3 is a perspective view of a mask seal and mask seal clip of the interface of FIG. 1.

With reference to FIG. 3, the mask seal clip 112 is relatively more rigid, stiffer or more inflexible than the mask seal 110. In some configurations, the mask seal clip 112 is formed of a polycarbonate material. In some configurations, at least a portion of the mask seal clip 112 is formed of a polycarbonate or other rigid or semi-rigid material. In some configurations, the mask seal clip 112 is formed at least partially of silicone or another suitable material. In such configurations, at least the silicone portion of the mask seal clip 112 may be formed to be relatively thicker compared to the more flexible portions of the mask seal 110. The mask seal clip 112 provides structural support to the mask seal 110 in the illustrated configuration.

Figure 14:
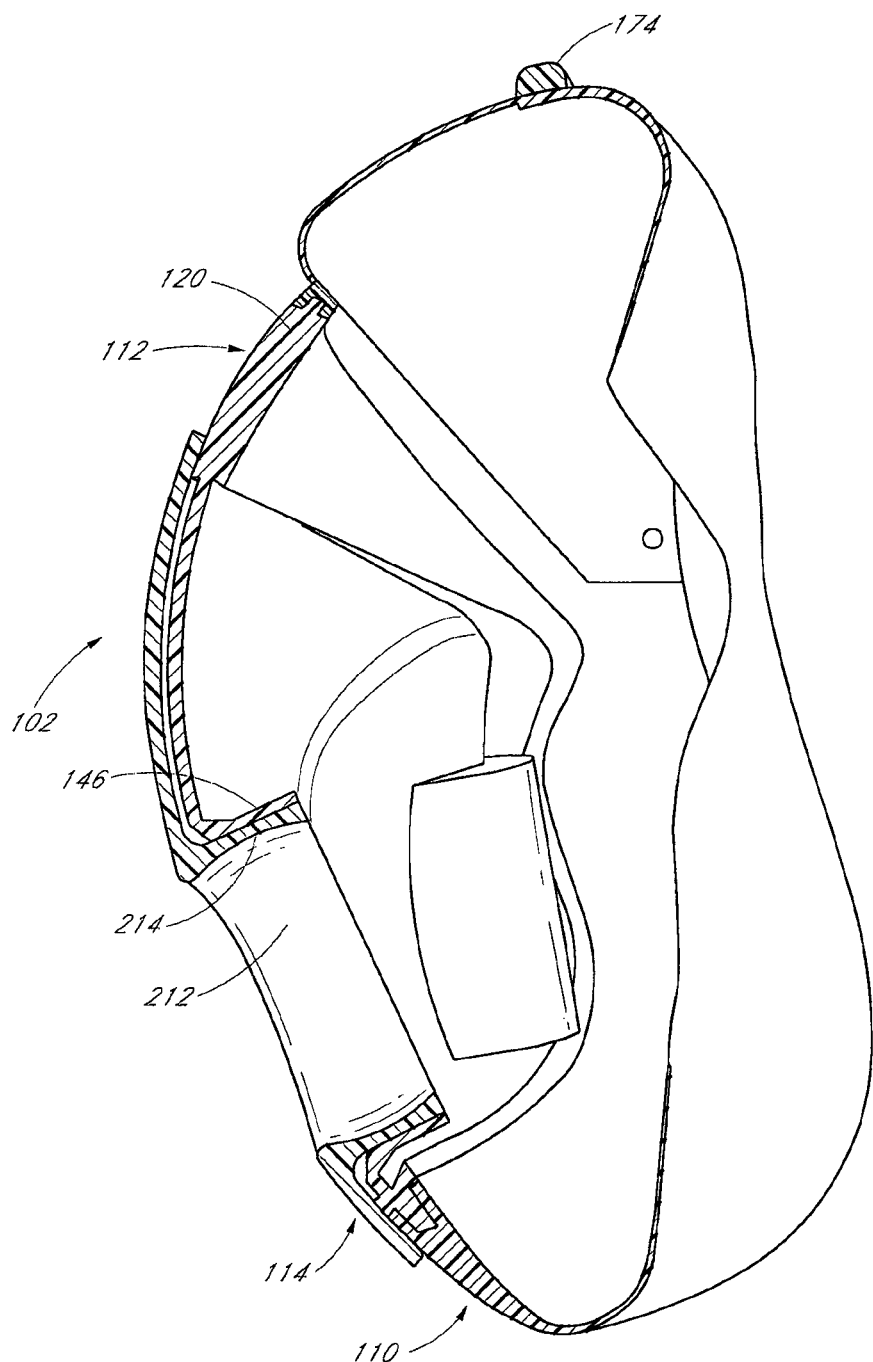
FIG. 14 is a section view of the mask seal, mask seal clip and mask base of FIG. 13.
Figure 25:
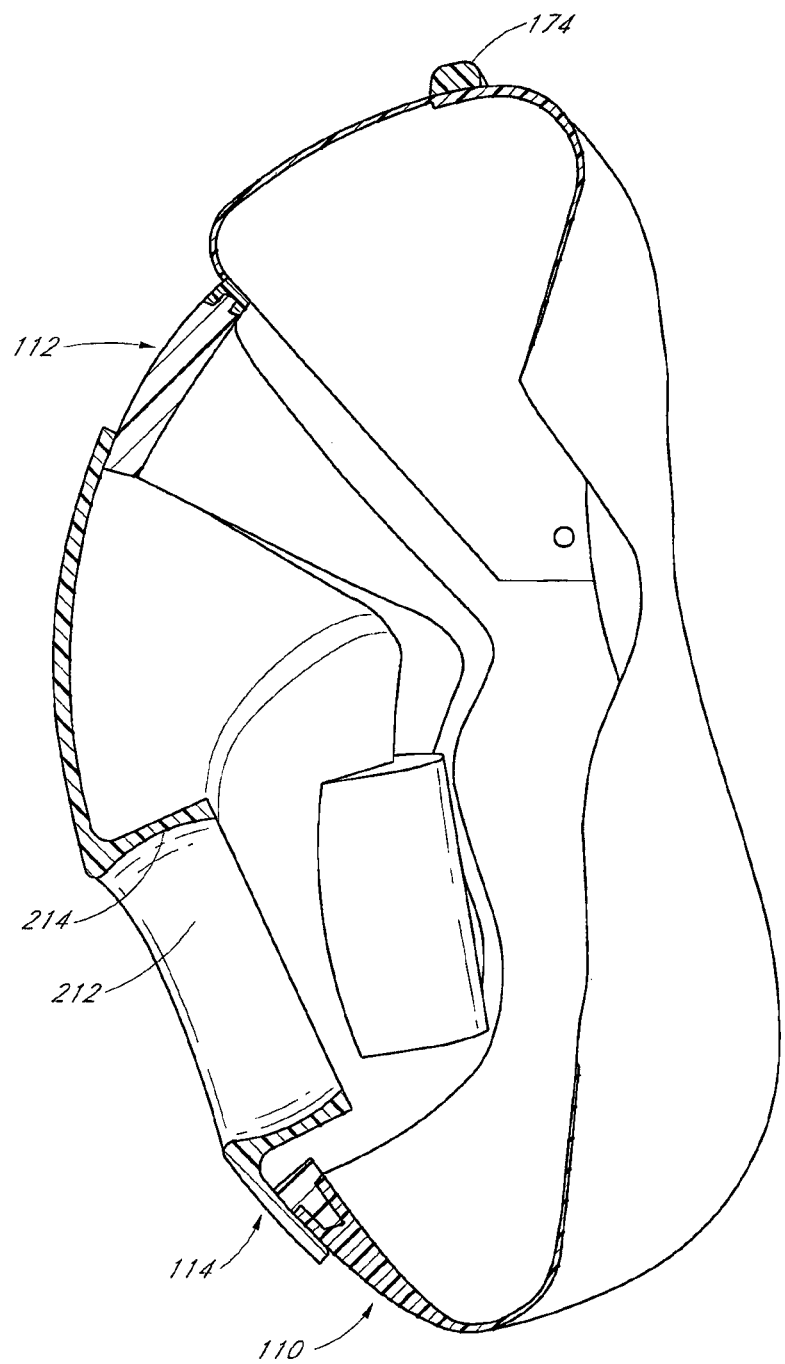
FIG. 25 is a sectioned view similar to the sectioned view of FIG. 14, wherein the mask seal clip has a reduced dimension.
Figure 26:
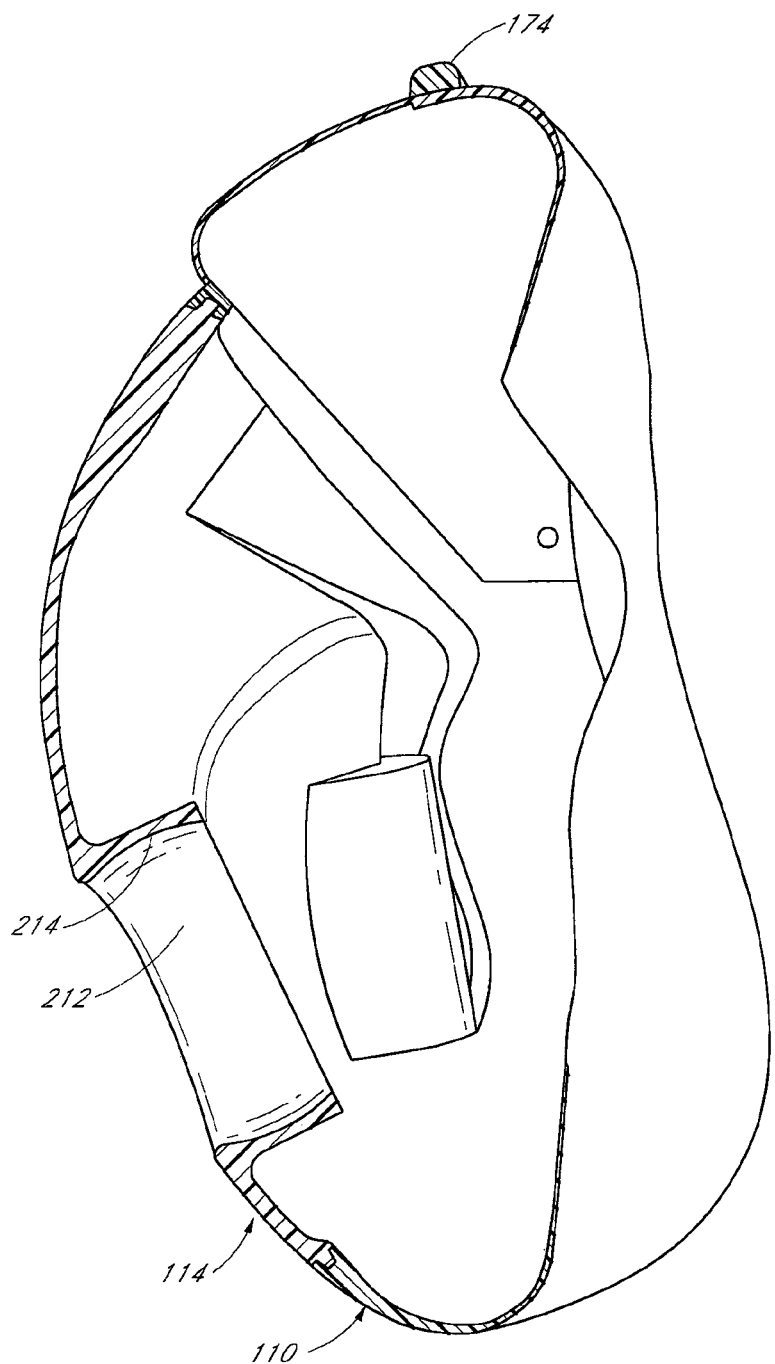
FIG. 26 is a sectioned view similar to the sectioned view of FIG. 14, wherein the mask seal clip is omitted.
Figure 27:
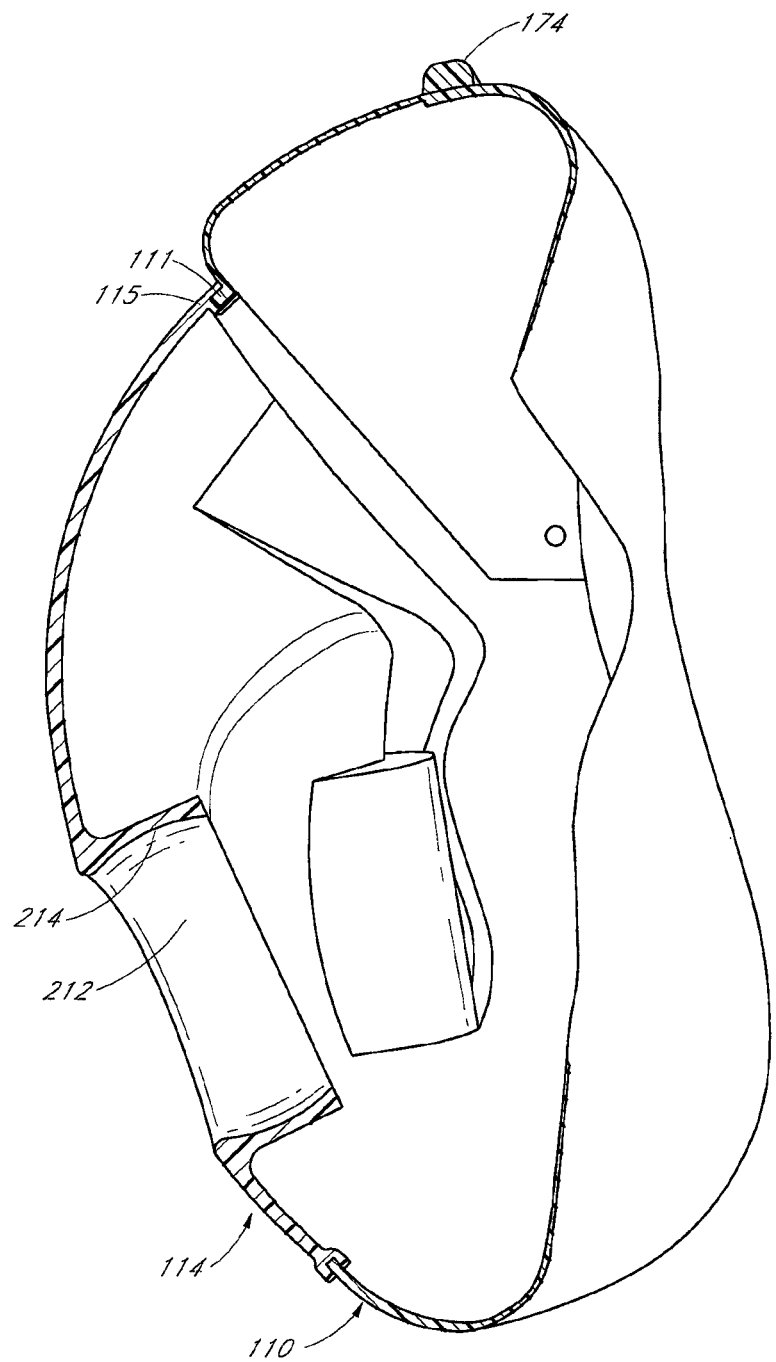
FIG. 27 is a further sectioned view similar to the sectioned view of FIG. 14, wherein the mask seal clip is omitted.

As shown in FIG. 14, the mask seal clip 112 can define a large portion of the mask assembly 102. As shown, the illustrated mask base 114 overlies a significant portion of the mask seal clip 112. With reference to FIGS. 25-27, the mask assembly 102 can be configured with differing constructions, as desired. For example, with reference to FIG. 25, the mask seal clip 112 extends a limited amount from the interface with the mask seal 110. In the configuration illustrated in FIG. 25, the mask base 114 overlies at least a portion of the mask seal clip 112 while the mask seal clip 112 defines a very limited rim-shaped configuration about a portion of the mask seal 110.

With reference to FIG. 26, the mask seal clip is omitted in its entirety and the mask seal 110 is overmolded directly onto the mask base 114. In some configurations, however, the mask seal 110 and the mask base 114 can be configured such that the two components can be separated. For example, as shown in FIG. 27, the mask seal 110 can comprise a peripheral flange 111 while the mask base 114 can comprise a peripheral channel 115 that receives the peripheral flange 111 such that the mask seal 110 can be removably secured to the mask base 114. In some configurations, other suitable manners can be used to secure the mask seal 110 to the mask base 114. Moreover, the illustrated configuration of FIG. 27 shows an embodiment without a mask seal clip 112; the mask seal clip 112 and the mask base 114 have been combined into the mask base 114.

Figure 5:
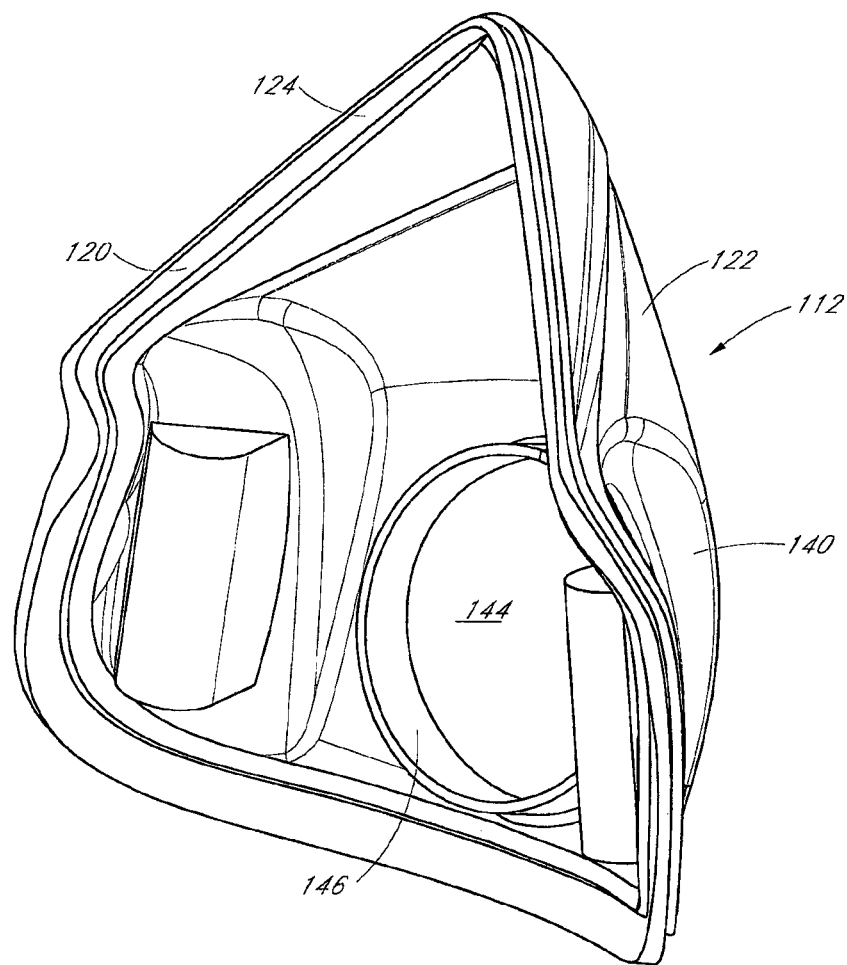
FIG. 5 is a rear perspective view of the mask seal clip of FIG. 3.
Figure 7:
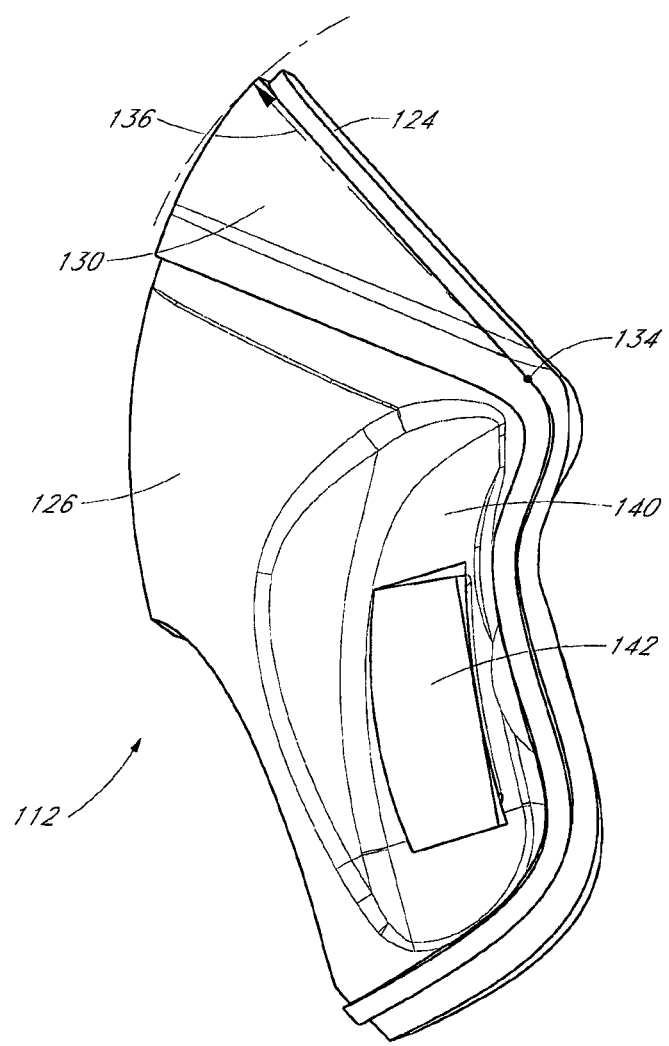
FIG. 7 is a side elevation view of the mask seal clip of FIG. 3.
Figure 8:
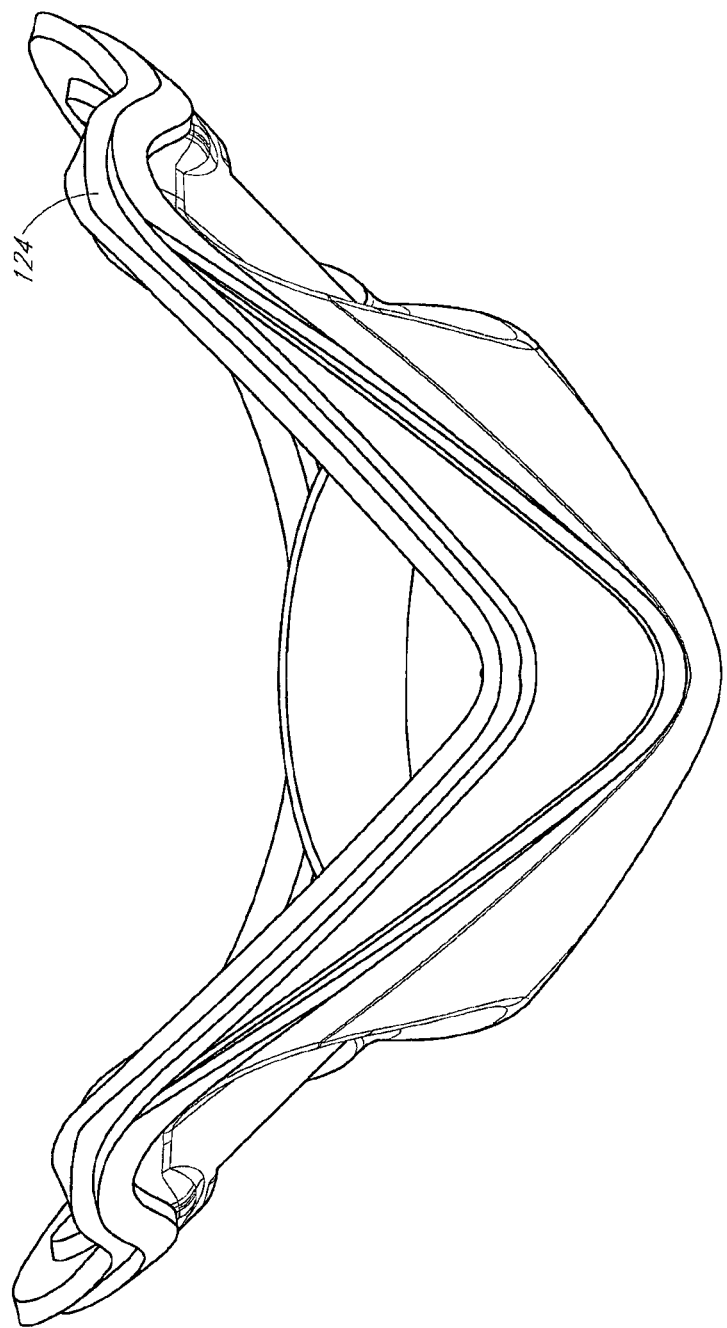
FIG. 8 is a top plan view of the mask seal clip of FIG. 3.

With reference to FIG. 5, the illustrated mask seal clip 112 comprises a substantially cup-shaped configuration. A proximal end 120 defines an open end of the illustrated mask seal clip 112 while a distal end 122 defines a generally closed end of the illustrated mask seal clip 112. In the illustrated configuration, the proximal end 120 is generally circumscribed by a lip 124. The lip 124 is generally pentagonal when viewed from the back (see FIG. 5). As shown in FIG. 7, a wall 126 generally sweeps forward in an arcuate manner. The arcuate shape to the wall 126 provides a three dimensional configuration to the illustrated mask seal clip 112.

With continued reference to FIG. 7, an upper portion 130 of the illustrated mask seal clip 112 is generally arcuate in configuration. In addition, the generally arcuate configuration of the illustrated mask seal clip 112 is configured to accommodate larger noses while not extending upward over the nose to as great an extent as the mask seal 110, as shown in FIGS. 1 and 2.

With initial reference to FIG. 3, the upper portion 130 of the illustrated mask seal clip 112 preferably comprises two arcuate dimensions. First, an arc length 132 can be defined along an upper extremity of the upper portion 130 of the illustrated mask seal clip 112. The arc length 132 can be defined between inflection points 134 found along a perimeter of the illustrated mask seal clip 112.

As shown in FIG. 7, the upper portion 130 of the illustrated mask seal clip 112 also comprises a side profile radius 136. As shown, the upper portion 130 can have a slightly increasing side profile radius 136 such that the radius increases slightly as a distance from the upper end increases. In some configurations, the upper portion 130 can comprise a substantially constant side profile radius 136 or a decreasing side profile radius. Advantageously, the slightly increasing side profile radius 136 provides an increased volume in the mask 100 proximate the user's nose.

Figure 6:
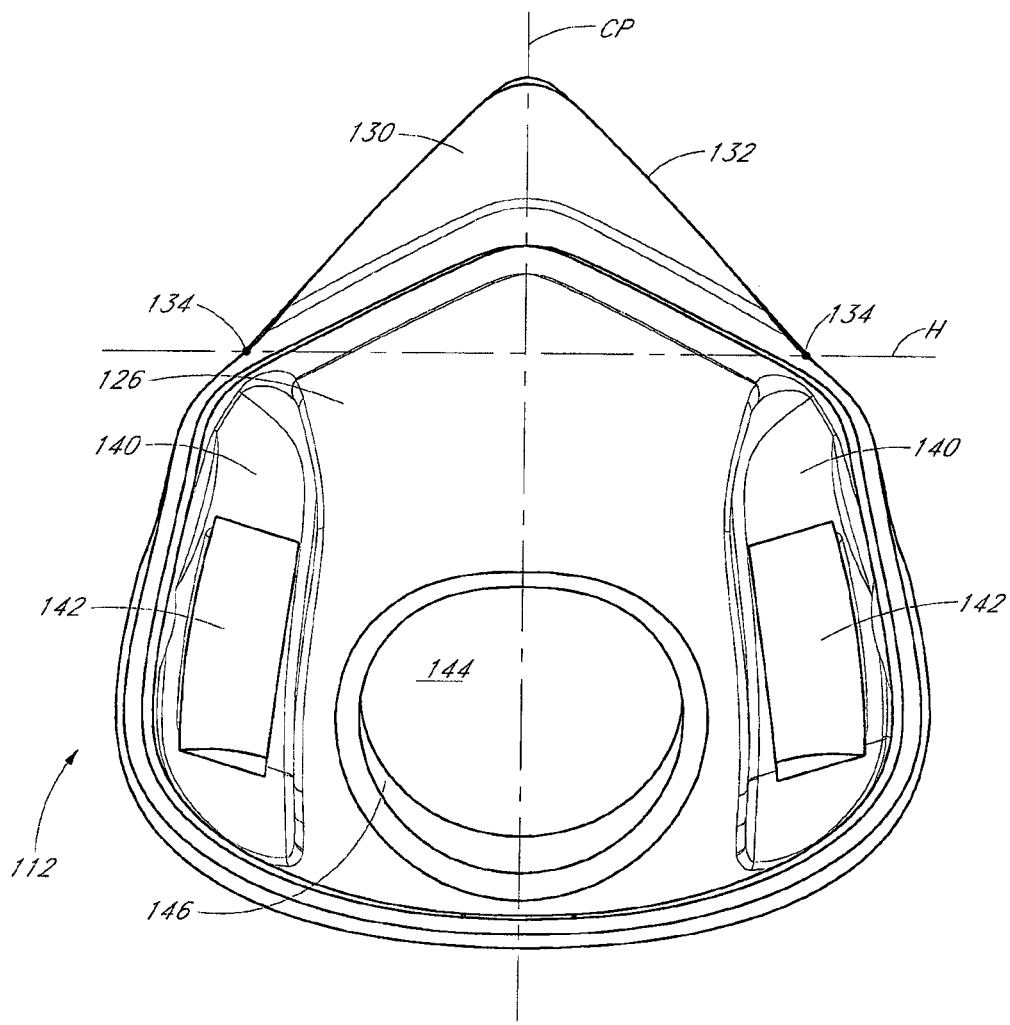
FIG. 6 is a rear elevation view of the mask seal clip of FIG. 3.

With reference to FIG. 3 and FIG. 6, the mask seal clip 112 preferably comprises at least two recesses 140. In the illustrated configuration, the mask seal clip 112 comprises two recesses 140 that are disposed on two lateral sides of a generally vertical center plane CP (see FIG. 6). The generally vertical center plane CP preferably corresponds to a mid-sagittal plane of the user and splits the illustrated mask seal clip 112 into substantially mirror-image halves. The two recesses 140 define two generally enclosed pockets in the illustrated mask seal clip 112. The illustrated recesses 140 comprise further recesses 142 that are used to provide adequate clearance for reasons that will be discussed below while limiting an amount of encroachment into a nasal region of a chamber defined by the mask assembly 102.

The illustrated mask seal also comprises a generally central passage 144 that is defined by a wall 146. In the illustrated configuration, the wall 146 generally encloses the passage 144. Preferably, the wall 146 is generally cylindrical in configuration and extends through the wall 126. Other configurations are possible.

With reference to FIG. 14, the mask seal 110 comprises a flexible portion that extends away from the proximal end 120 of the mask seal clip 112. In the illustrated configuration, the mask seal 110 is overmolded onto the mask seal clip 112 such that the mask seal 110 and the mask seal clip 112 combine to form an integrated and preferably non-separable assembly. In some configurations, attempts to separate the mask seal 110 and the mask seal clip 112 result in the destruction of the interface between the components and/or destruction of one or both of the mask seal 110 and the mask seal clip 112. As described above, other assemblies also can be used to connect the mask seal clip 112 to the mask seal 110. The illustrated configuration, however, advantageously results in a construction that is easy to clean and maintain.

Figure 4:
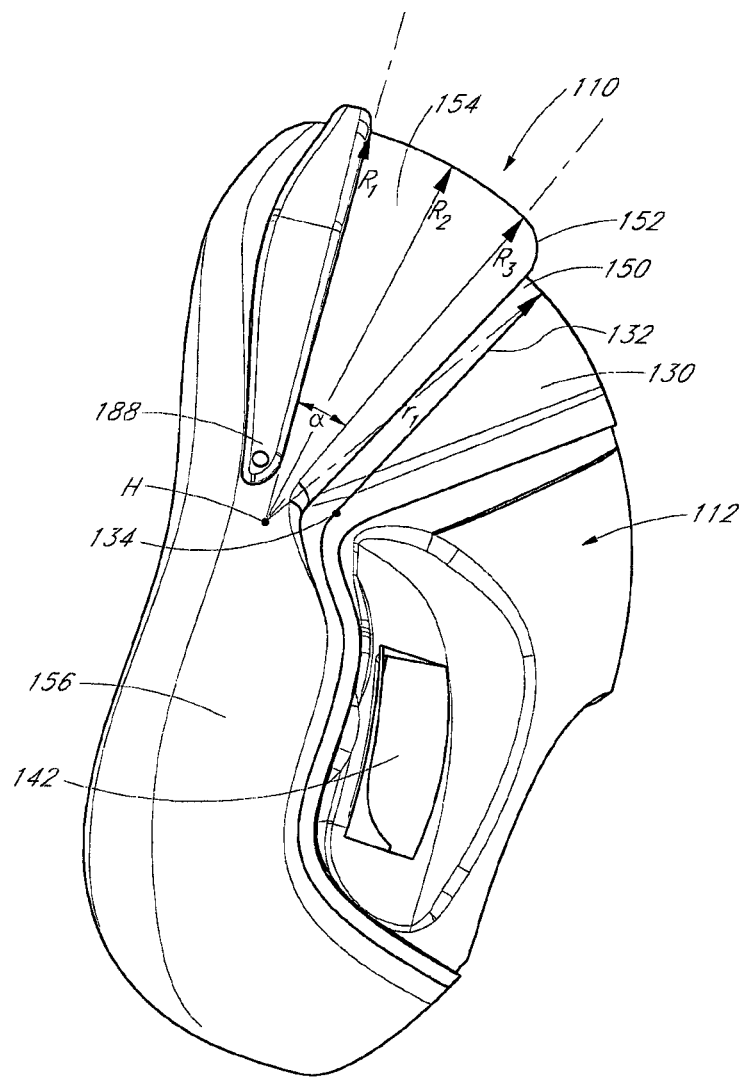
FIG. 4 is a side view of the mask seal and mask seal clip of FIG. 3.

With reference to FIG. 4, the mask seal clip 112 preferably is arranged such that it is generally flush with an inner rim 150 of the mask seal 110. In the illustrated configuration, the mask seal 110 comprises a relatively small radius portion 152 that joins an upper portion 154. The upper portion 154 of the mask seal 110 is configured to extend over a nasal region of the user. In some configurations, the upper portion 154 is configured to extend over a nasal bridge region of the user U.

Figure 9:
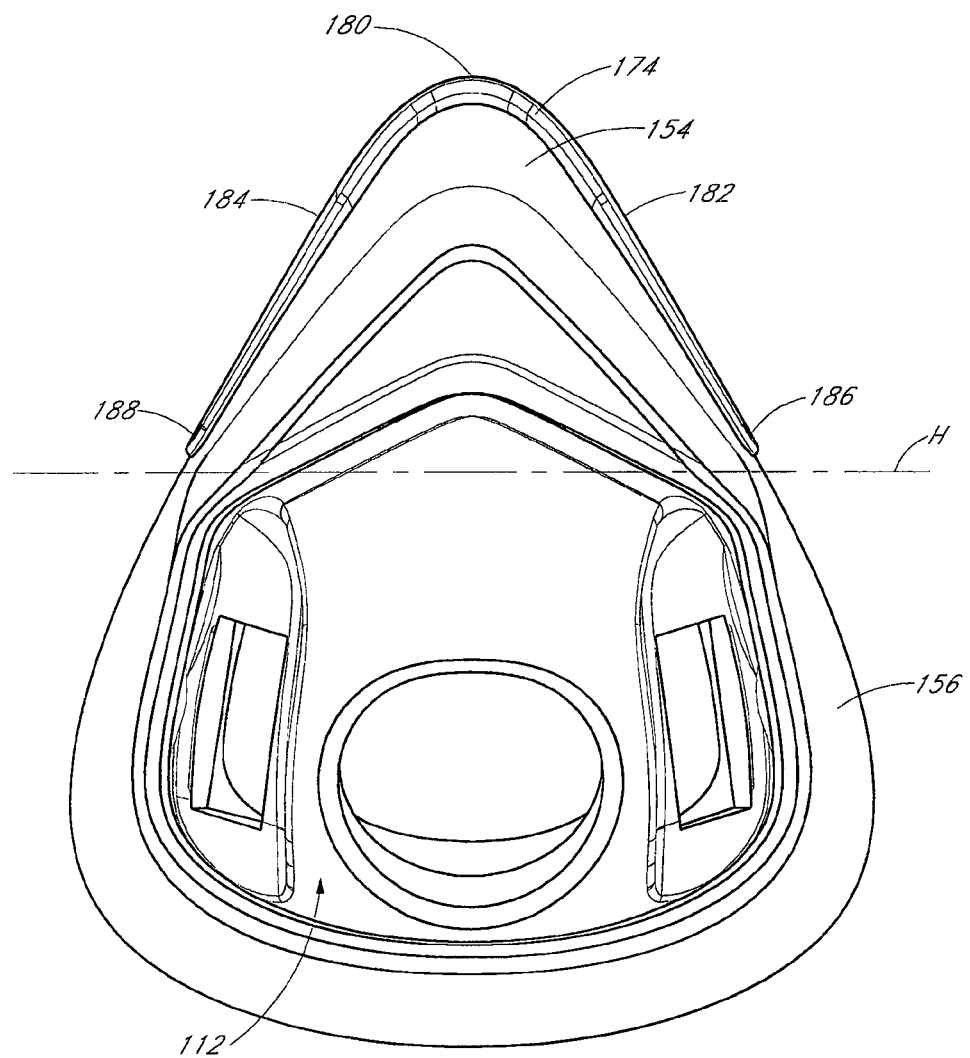
FIG. 9 is a front elevation view of the mask seal and mask seal clip of FIG. 3.
Figure 10:
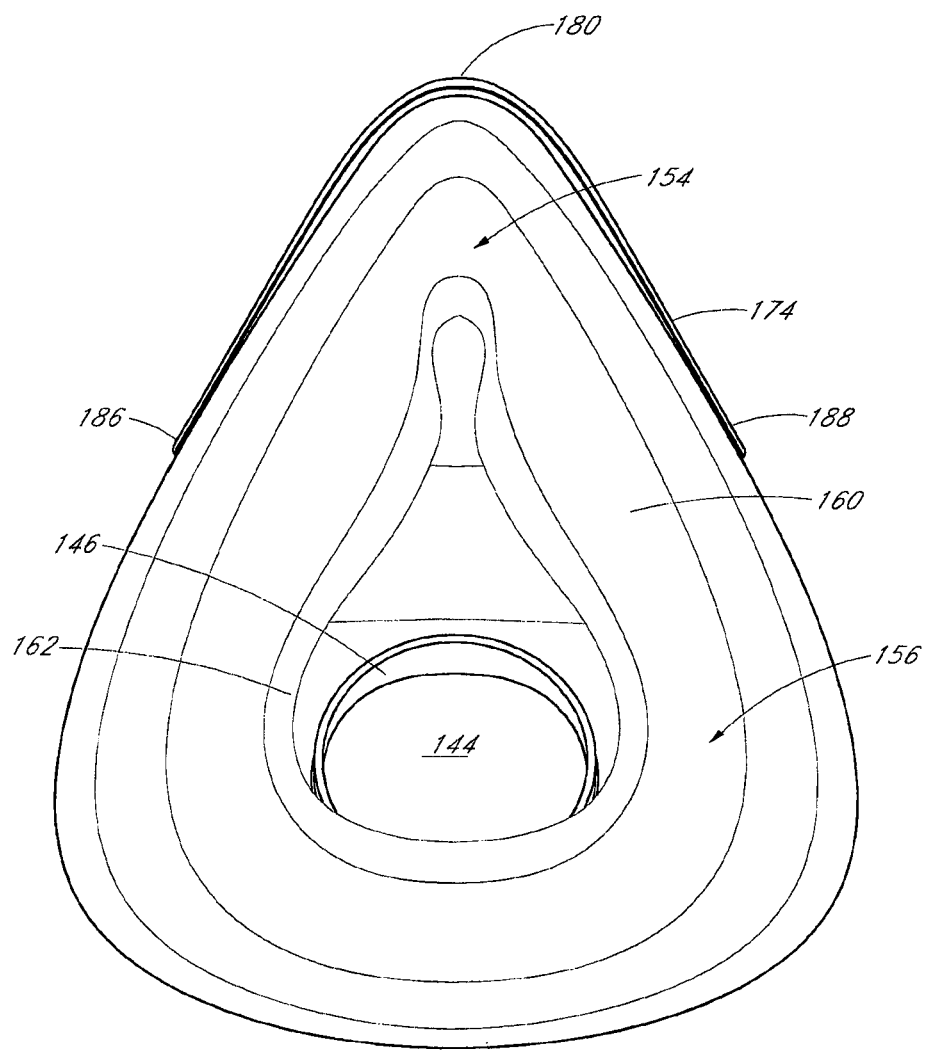
FIG. 10 is a rear elevation view of the mask seal and mask seal clip of FIG. 3.

The upper portion 154 is connected with a lower portion 156 of the mask seal 110. The lower portion 156 extends laterally outward from the mask seal clip 112 as shown in FIG. 9. In addition, the lower portion 156 wraps rearward and inward, as shown in FIGS. 4 and 10 respectively. Together, on a proximal side of the full face mask assembly 102, the upper portion 154 and the lower portion 156 combine to define a face contacting flange 160, which is shown in FIG. 10. The face contacting flange 160 is configured to underlie a lower lip of the user, extend along the outside of the mouth, extend upward along the cheekbones and extend across the bridge of the nose of the user. Thus, the illustrated face contacting flange 160 defines a generally tear-drop shaped opening 162. When the mask assembly 102 is seated on the face of the user, the flange 160 will lie flat over the bridge of the nose, the cheekbones, the outside of the mouth and below the lower lip of the user. With a supply of positive pressure air, the mask seal 110 will balloon and seal against the face of the user to reduce or eliminate the likelihood of leakage between the flange 160 and the face of the user.

Figure 11:
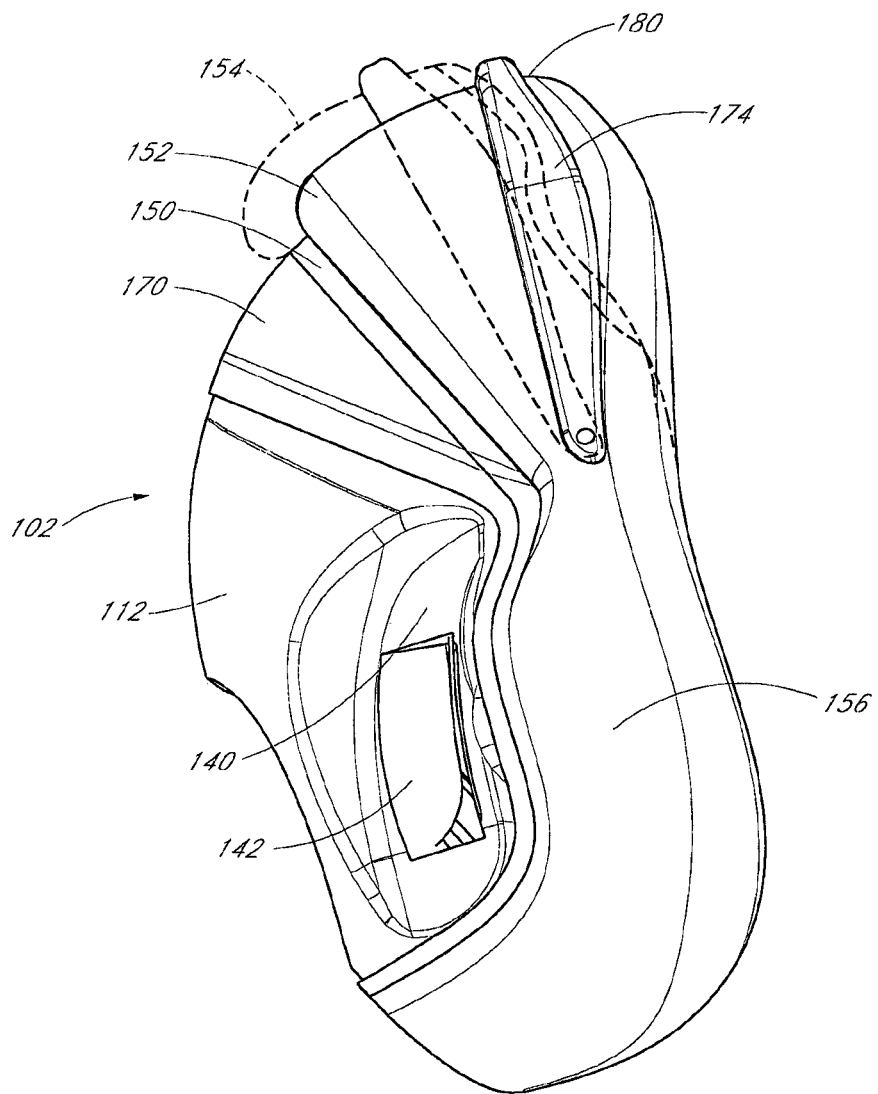
FIG. 11 is a side elevation view of the mask seal and mask seal clip of FIG. 3.
Figure 12A:
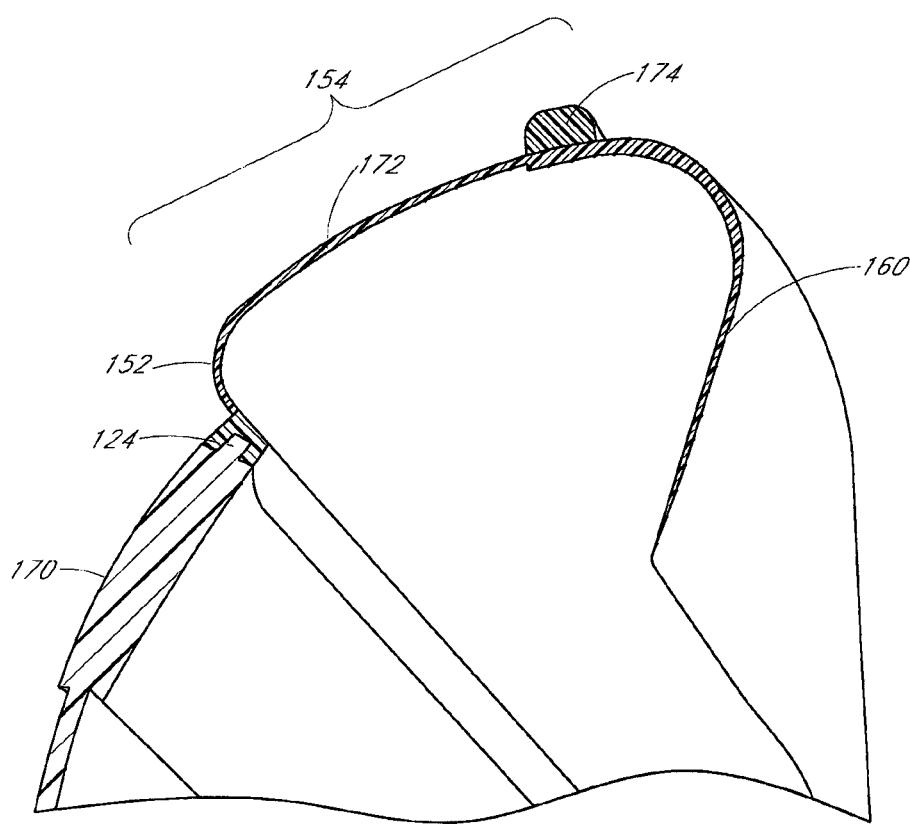
FIGS. 12A-12D are enlarged section views of a portion of the mask seal and mask seal clip of FIG. 3.
Figure 12B:
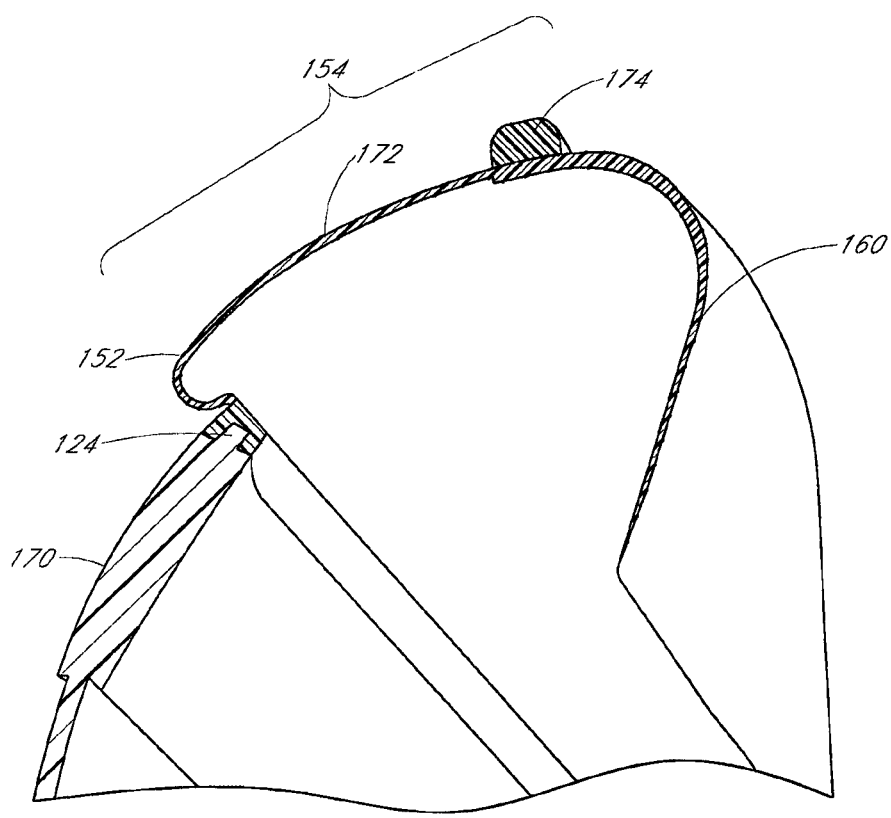
Figure 12C:
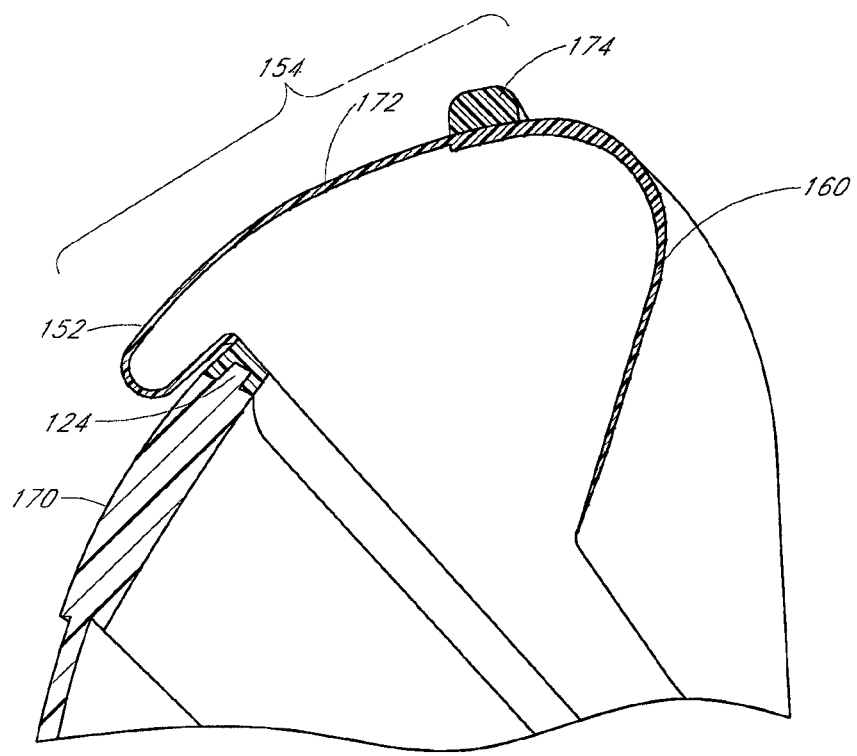
Figure 12D:
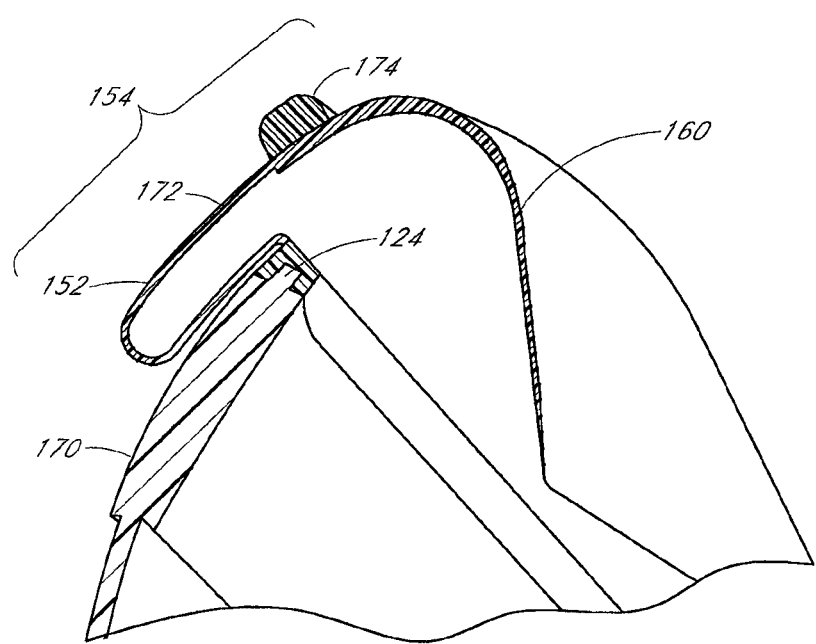

As shown by the dashed lines in FIG. 11, the upper portion 154 of the mask seal 110 is designed to roll over onto an outer surface 170 of the mask assembly 102. In the illustrated configuration, the outer surface of the mask seal 110 smoothly rolls into abutment with the outer surface of the mask seal clip 112 such that the outer surface of the mask seal clip 112 forms a support surface. In some configurations, the outer surface 170 onto which the upper portion 154 rolls comprises at least a portion of the outer surface of the mask seal clip 112. In some configurations, the outer surface 170 onto which the upper portion 154 rolls comprises almost exclusively the outer surface of the mask seal clip 112. In some configurations, the upper portion 154 rolls onto another portion of the mask seal 110. In some configurations, the upper portion 154 rolls onto the mask seal base 114.

With reference to FIG. 12, to assist with the rolling of the upper portion 154, the upper portion 154 can have a varying thickness or a varying stiffness. In the configuration shown in FIG. 12, the upper portion 154 comprises a thick/thin/thick configuration. In other words, to induce the upper portion 154 to roll in a region between the face contacting flange 160 and the small radius 152 proximate the mask seal clip 112, a reduced stiffness region 172 can be incorporated. In the illustrated configuration, the reduced stiffness region 172 is incorporated into the mask seal 110. The reduced stiffness region 172 reduces or eliminates the likelihood of the mask seal 110 buckling or adversely deforming in a region other than the desired region for rolling.

While the illustrated configuration uses a region of reduced thickness, other means for providing the reduced stiffness region 172 also can be used to induce rolling of the seal member 110. For example, the material of the seal member 110 can be configured to have a reduced stiffness through material selection or material properties. In addition, a composite of materials can be used to provide a region of reduced stiffness or rigidity. Moreover, a combination of any suitable techniques can be used. Nevertheless, the illustrated region 172, which is configured with reduced thickness, provides a simple manner of achieving the region of reduced stiffness 172. In addition, by adjusting the stiffness of the reduced stiffness region 172, the force required to induce rolling of the region 172 can be controlled, which controls the force applied against the nose of the user. For example, by varying the stiffness, movement can become increasingly or decreasingly resisted over the range of movement.

When the upper portion 154 comprises the region of reduced stiffness 172, the upper portion 154 of the mask seal 110 tends to balloon outward under internal pressures, such as those encountered during positive pressure therapy regimens, which ballooning is believed to be caused by the region of reduced stiffness 172 that defines a large area of silicone without significant structure. With reference to FIG. 4 and FIG. 12, to reduce the prevalence of ballooning in the upper portion 154 and to provide enhanced structure in the upper portion 154, a reinforcing component or components, such as a band 174, can be positioned along at least a portion of the upper portion 154. The band 174 can be a component formed of a material that is more rigid than, or that features increased stiffness relative to, the silicone or other material forming the mask seal 110. For example, a region of significantly increased thickness relative to the region of reduced stiffness 172, where the region is formed of the same material forming the mask seal 110, can be used to increase the stiffness of the reinforcing component or components.

In some configurations, the band 174 can be a separately formed component that is at least partially encased by the material of the mask seal 110. In the illustrated configuration, the band 174 can be a comolded plastic component or the mask seal 110 can be overmolded onto the band 174. In some configurations, the band 174 can be defined by a portion of the upper portion 154 that has enhanced stiffness relative to surrounding regions. For example, but without limitation, the band 174 can be defined by a portion of increased thickness, a portion of differing materials or material properties that result in increased stiffness or the like.

With reference to FIG. 9, the band 174 extends along at least a portion of the upper portion 154 of the mask seal 110. The upper portion 154 of the mask comprises an apex 180 when viewed from the front. The apex 180 can be defined as a tip, a top and an angular summit of the mask seal 110, which apex 180 is positioned in proximity to the nose of the user when in use. A first wall 182 and a second wall 184 converge at the apex 180 in the illustrated configuration.

In some configurations, at least a portion of the first wall 182 and at least a portion of the second wall 184 are reinforced by one or more components or structures, such as the band 174. In the illustrated configuration, the reinforcing component or components, such as the band 174 for example, reinforces at least a portion of the first wall 182 and at least a portion of the second wall 184. In some configurations, the reinforcing component or components, such as the band 174 for example, reinforces at least a portion of the first wall 182, at least a portion of the second wall 184 and the apex 180.

With continued reference to FIG. 9, the illustrated band 174 has a first end 186 and a second end 188 that is opposite to the first end 186. In some configurations, the band 174 can be formed separate of the mask seal clip 112 and attached to the mask seal clip 112 by one or more flexible components. In some configurations, the band 174 can be connected by a mechanical hinge structure to the mask seal clip 112. In the illustrated configuration, the first end 186 and the second end 188 are positioned on the same side of the hinge axis H as the apex 180. Preferably, the first end 186 and the second end 188 are spaced away from the hinge axis H toward the apex 180.

As shown in FIG. 12, the bend 152 and the stiffer region (e.g., region of thicker cross section) adjacent to the region of reduced stiffness 172 help to initiate rolling of the region of reduced stiffness 172. In other words, a controlled buckling of the region of reduced stiffness 172 occurs with the assistance of the adjacent stiffer portions. In addition, positioning an edge of the relatively more rigid mask seal clip 112 adjacent to the bend 152 further helps to induce rolling in the reduced stiffness region 172. In some configurations, the region of reduced stiffness 172 is bounded by a first boundary and a second boundary, wherein the first boundary and the second boundary have an increased stiffness relative to the region of reduced stiffness. In the illustrated configuration, for example, the first boundary is defined by or alongside the band 174 while the second boundary is defined by or alongside the bend 152. In some configurations, the second boundary can be defined by or alongside an edge of the more rigid mask seal clip 112. In some configurations, the second boundary can be defined along a portion of the mask seal 110 positioned between the mask seal clip 112 and the region of reduced stiffness 172.

As the upper portion 154 of the mask seal 110 is displaced about the hinge axis H, the roll increases in size. In other words, as the first boundary initially moves toward the second boundary, a roll is formed in the mask seal 110. As the first boundary continues to move toward the second boundary, the roll continues to increase in size. Thus, in the illustrated configuration of FIG. 11, the roll defined in the upper portion 154 starts at nothing and progressively increases during displacement of the upper portion 154 as shown in dashed lines. Preferably, the rolling between the first boundary and the second boundary creates a single bend or inflection between the first boundary and the second boundary. The single bend results in legs approaching the bend location that increase in size as the first boundary moves toward the second boundary. In other words, the rolling created by movement of the first boundary toward the second boundary preferably does not result in a fan-folding appearance, such as a pleated configuration.

With reference again to FIG. 3, the mask seal 110 can have a geometry that helps facilitate continued rolling of the region of reduced stiffness 172 following the initiation of the rolling. Arc lengths can be defined in general from a first intersection of the hinge axis H with the mask seal 110, up and over the upper portion 154 of the mask seal 110, and back down to a second intersection of the hinge axis H with the mask seal 110.

As shown in FIG. 3, the illustrated mask seal 110 comprises at least a first arc length A (shown in dashed line), a second arc length B (shown in dash-dot chain line) and a third arc length C (shown along a base of the band 174). The first arc length A preferably is longer than the arc length of the mask seal clip 112 directly adjacent to the first mask arc length A. The second arc length B is positioned between the first arc length A and the third arc length C and the second arc length B preferably is shorter than the third arc length C and longer than the first arc length A. In some embodiments, the arc lengths steadily increase from the bend 152, or another region close to the outer surface 170, proximal toward the band 174. In other words, as an angle α (see FIG. 4) increases from the first arc length A, the arc length generally increases. In some configurations, the arc lengths can be substantially constant from front to rear (i.e., as the angle α increases); however, by increasing the arc lengths away from the portion that initiates the roll, further movement of the apex 180 in a distal direction results in continued rolling of the mask seal 110 over itself and over the outer surface 170, as shown in FIG. 11.

With reference again to FIG. 4, the upper portion 154 of the illustrated mask seal 110 also comprises a variable radius when viewed from the side profile. As shown, R1>R2>R3. Thus, in the illustrated mask seal 110, the radius decreases from proximal to distal as the angle increases. In some configurations, the radius need not decrease in this manner; however, the decreasing radius is believed to aid in rolling of the mask seal 110.

Moreover, a radius r1 of the mask seal clip 112 from the hinge point H preferably is smaller than the radius R3 of the mask seal 110. Given the pliant nature of the mask seal 110, however, it is possible for the radius r1 and the radius R3 to be substantially the same while still providing for the mask seal 110 to roll over the mask seal clip 112. In the illustrated configuration, however, the difference between the radius r1 and the radius R3 results in an offset. The offset provides an ability to slightly increase the side profile radius 136, as described above, without significantly impacting the ability of the mask seal 110 to roll over the mask seal clip 112. If the offset were not provided, the ability to increase the side profile radius 136 would be very limited.

As discussed above, the flange 160 encircles the generally tear-drop shaped opening 162. As is known, hoop stress can be defined as circumferential stress in a cylindrically shaped part as a result of internal pressure. Thus, hoop stress increases as a ring attempts to expand. It is believed that hoop stress resulting from seating a respiratory mask can be a source of some discomfort to the user, especially in the region of the bridge of the nose. The lower portion 156 of the illustrated mask assembly 102 generally is secured in position while the nasal or upper portion 154 moves relative to the nose of the user. Because of the rolling action described above, the illustrated full face mask assembly 102 acts to roll away from the nose, which decreases the incidence of increasing hoop stress, especially around the bridge of nose. Thus, the rolling mask configuration provides a means for maintaining or reducing hoop stress during seating of the mask.

As discussed above and as shown in FIG. 11, the upper portion 154 of the illustrated mask seal 110 rolls over the outer surface 170 in the illustrated configuration. The rolling over an external mask surface makes use of the positive pressure present within the full face mask assembly because the increased air pressure enhances the ability of the mask seal to roll on itself (i.e., the air pressure decreases a surface tension between the two surfaces of the mask seal that slide relative to each other during rolling) and the slight ballooning effect helps to reduce the likelihood of buckling, creasing or undesired folding of the mask seal 110. Furthermore, in some configurations, the external roll over can provide a visual cue of the degree or angle of displacement of the upper portion 154 of the mask seal 110 relative to the lower portion 156 of the mask seal 110.

In order to provide an enhanced indication to the user of the extent to which the upper portion 154 of the mask has rolled, it is possible to employ a visual indicator. For example, in some configurations, a scale can be imprinted, embossed or otherwise arranged on or near the reduced stiffness region 172. In some configurations, a scale can be positioned along a portion of the mask 100 over which the reduced stiffness region 172 will roll. For increased fidelity, the scale preferably is positioned in a central location such that the extent to which the reduced stiffness region 172 rolls can be maximized. The scale can be a numerical scale or a color gradient scale, for example but without limitation.

In some configurations, a ratchet or lock mechanism can be integrated with the mask such that the reduced stiffness region 172 can be set at a desired roll point. For example, a ratchet mechanism with a series of teeth that engage a closure member (e.g., ziptie locking ratchets) can be used. When the upper portion 154 of the mask is displaced about the hinge point, the lock mechanism enables the upper portion 154 to be retained in position when the mask 100 is removed from the face of the user U. Preferably, the lock mechanism allows that locked position to be released easily as desired such that, if the mask is moved too far, the upper portion can be relaxed into a better fitting position. Thus, the user can set the extent to which the upper portion 154 rolls once and each subsequent use would result in the same level of roll.

Figure 28:
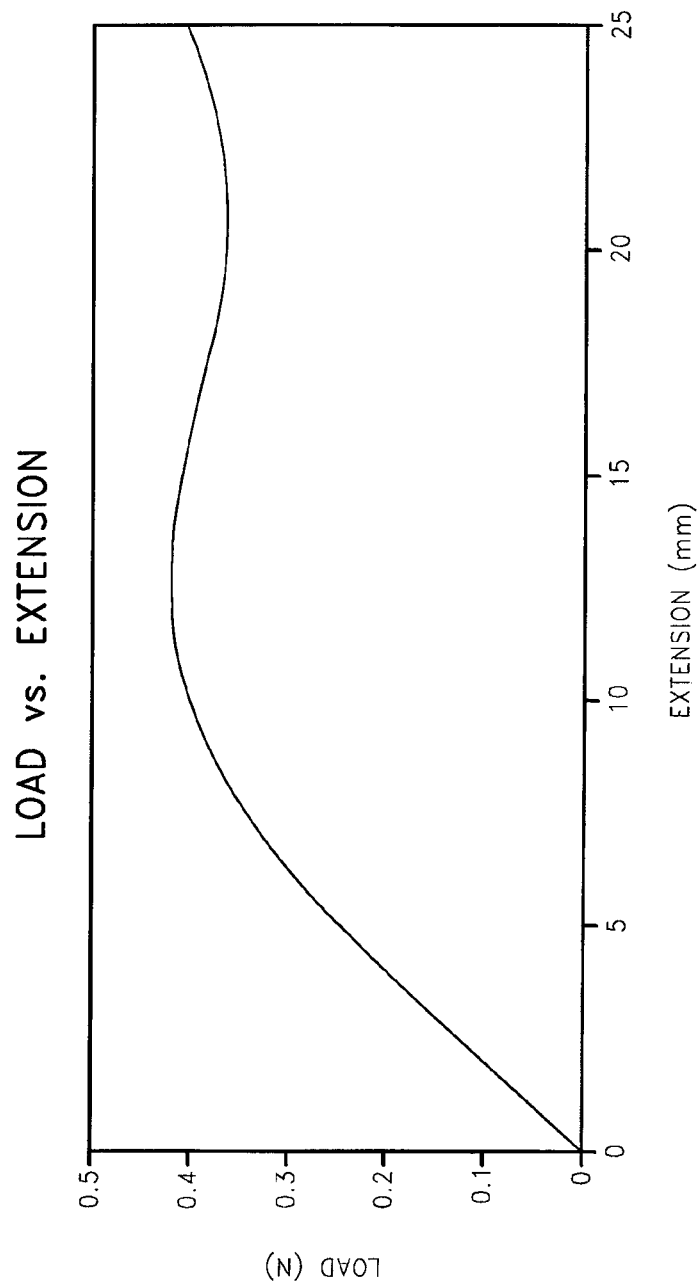
FIG. 28 is a graphical depiction illustrating a relationship between load (or force) on a user's body as a function of mask extension.

By rolling, the upper portion 154 (i.e., the portion of the seal member that contacts the bridge of the nose) moves as increasing pressure is applied by the flange 160 of the mask against the face of the user. As a result of the movement, the force exerted by the upper portion 154 upon the bridge of the nose is substantially constant over a wide range of pressures exerted by the lower portion 156 against the rest of the face of the user. Similarly, the force required to cause the upper portion 154 to move is substantially constant. As shown in FIG. 28, the illustrated configuration results in a full 25 mm change in position of the upper portion with an increase of less than about 0.5 N of force associated with that range of movement. Because the force applied to the nose is generally constant over a range of angles and associated upper portion displacement, the force applied to the bridge of the nose does not vary significantly at various headgear tension levels. Again, such a result is shown in FIG. 28, wherein the total change in force over the range of 5 mm to 25 mm of movement at the apex 180 results in a force change of about 0.2 N. In addition, because the force applied to the nose is generally constant over a range of angles, the mask can be adjusted to improve fitting to a variety of facial geometries while limiting the pressure exerted against the sensitive bridge of the nose region.

When compared to constructions featuring pleated geometries, the use of a rolling configuration provides marked improvement. First, external rolling rather than pleating reduced or eliminates the likelihood of the material of the mask seal encroaching into the chamber designed to contain the nose of the user. Thus, external rolling reduces the likelihood of contact with the nose of the user inside the chamber during movement of the upper portion 154 relative to the lower portion 156. Second, external rolling instead of pleating provides a clean appearance and decreases the number of external cavities, which is believe to improve the user's perception of the full face mask assembly when compared to pleated assemblies.

Figure 24:
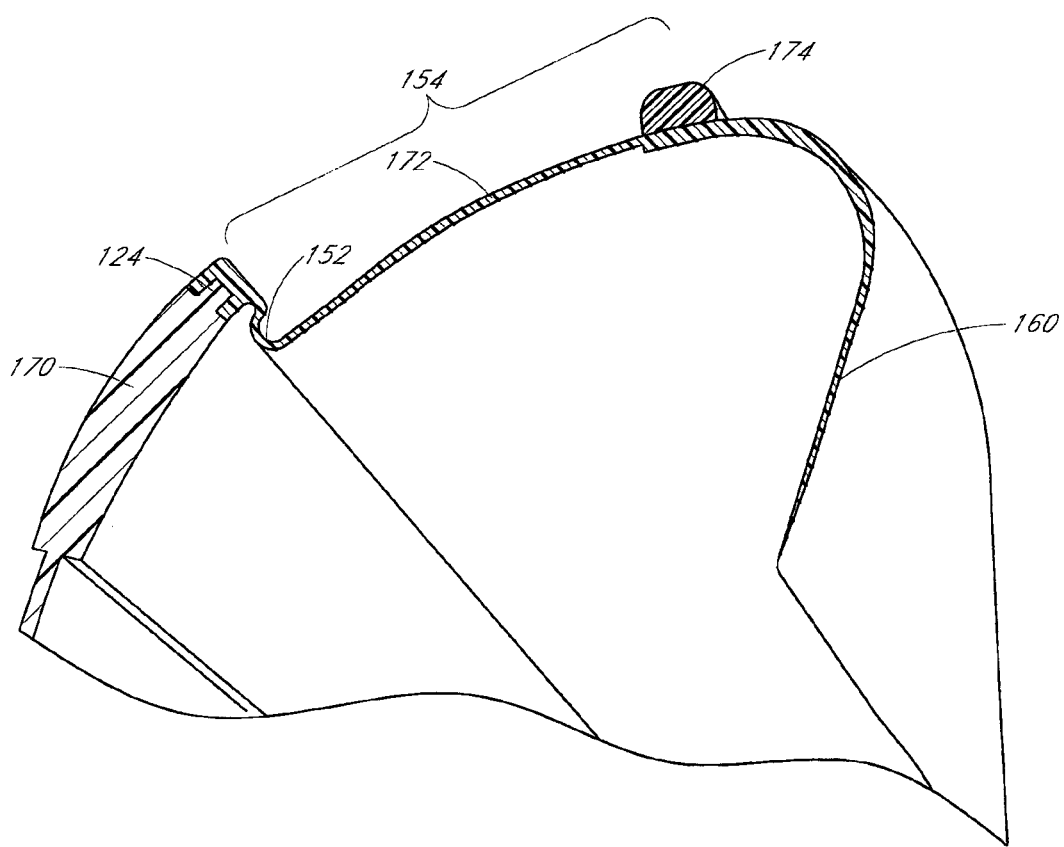
FIG. 24 is a sectioned view similar to the sectioned view of FIG. 12 showing a mask seal configured to roll under a portion of a mask seal clip 112.

With reference to FIG. 24, while the illustrated mask seal 110 rolls over the outer surface 170, the mask seal can be configured to roll inside the mask assembly. In other words, an internal roll over can be used in some configurations. The internal roll over is less desirable relative to the external roll over because the positive pressure tends to hinder rolling and because the rolling action tends to encroach into the chamber that receives the nose. On the other hand, the internal roll over provides a cleaner appearance relative to the external roll over because any ballooning of the seal member is contained within the mask seal clip.

With reference now to FIGS. 1 and 2, the mask assembly 102 includes the mask base 114, which is more rigid than the mask seal 110. The mask base 114 can be formed of any suitable material. In some configurations, the mask base is formed of a polycarbonate material such that it is capable of flexing for connection with the mask seal 110 and/or the mask seal clip 112.

With reference now to FIG. 14, the mask assembly 102 is shown with the mask base 114 secured to the mask seal 110. More particularly, in the illustrated configuration, the mask base 114 is secured to the mask seal clip 112 that is attached to the mask seal 110 in any suitable manner. In some configurations, the mask base 114 and the mask seal 110 or mask seal clip 112 are removably connected. In some configurations, the mask base 114 snaps together with one or both of the mask seal 110 and the mask seal clip 112. Preferably, the mask seal 110 and the mask seal clip 112 can be removed from the mask base 114 and a snap connection secures the mask seal clip 112 to the mask base 114.

Figure 15:
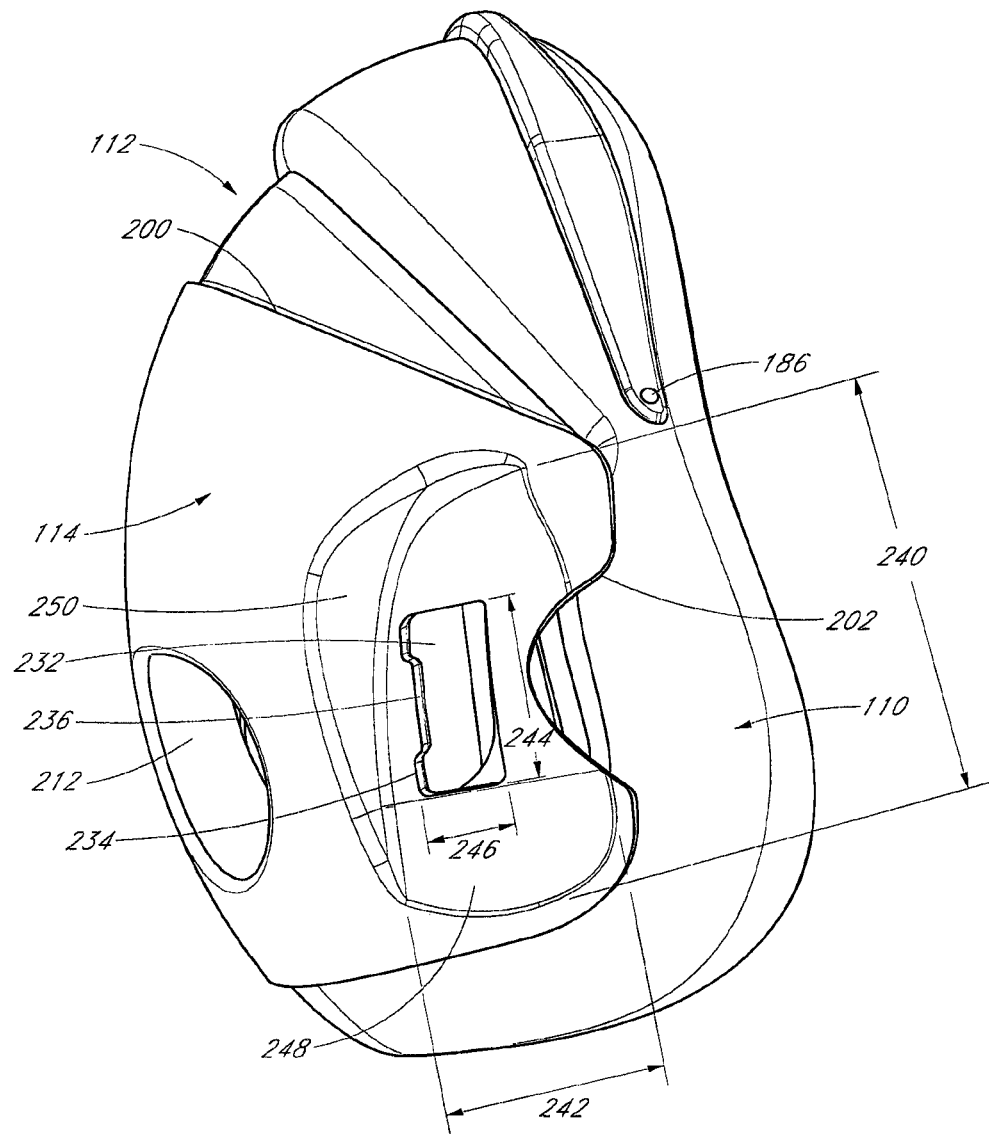
FIG. 15 is a side elevation view of the mask seal, mask seal clip and mask base of FIG. 13.
Figure 16:
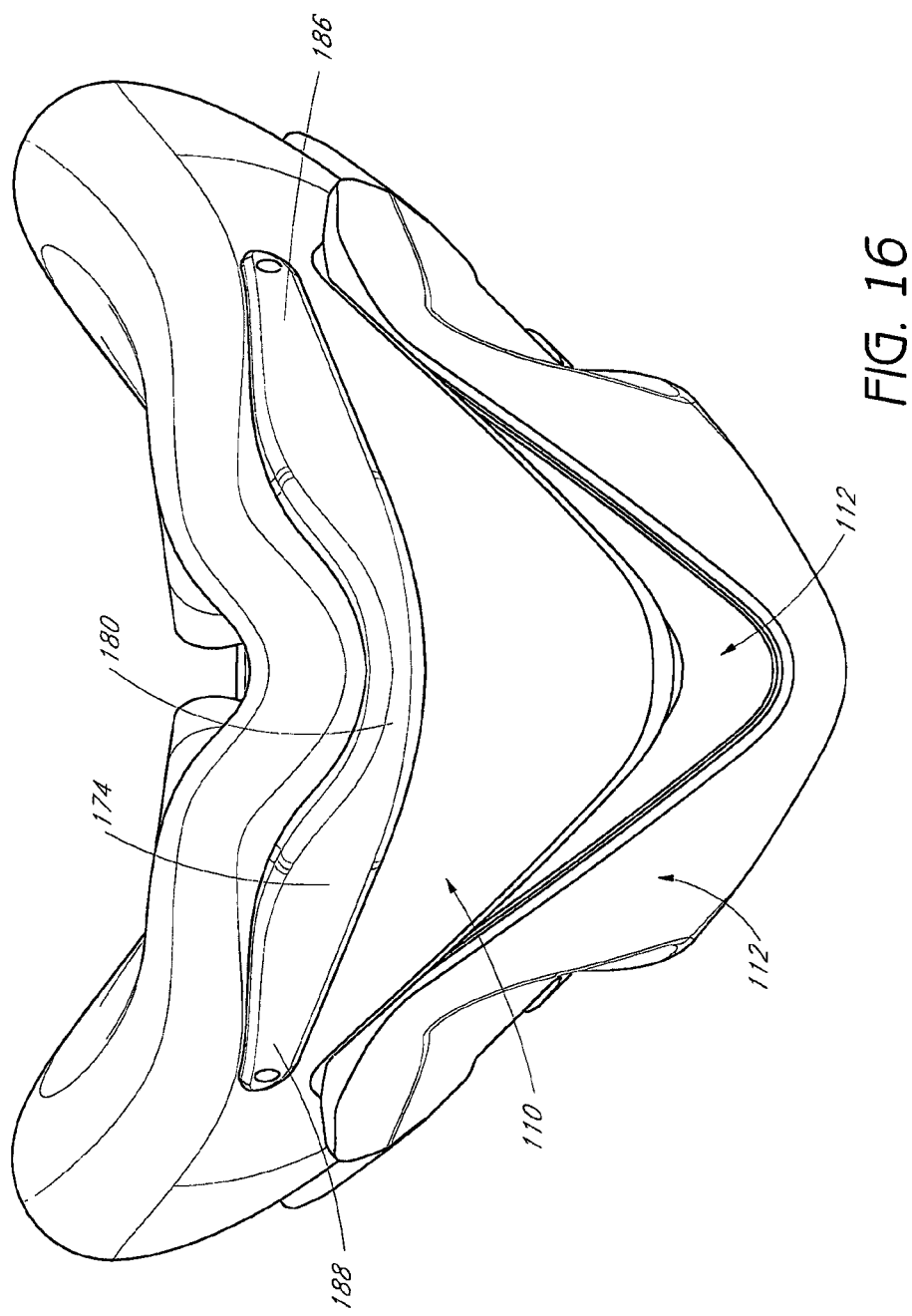
FIG. 16 is a top plan view of the mask seal, mask seal clip and mask base of FIG. 13.

With reference to FIGS. 14 and 15, the illustrated mask base 114 overlies at least a portion of the mask seal clip 112. In some configurations, the mask base 114 almost entirely covers the mask seal clip 112. In some configurations, the mask base 114 extends over more than half of the mask seal clip 112. When the mask base 114 overlies a substantial portion of the mask seal clip 112 or the mask seal 110, a double layer effect is created (e.g., the mask seal clip 112 and the mask base 114). The double layer effect provides increased insulation when a significant portion of the mask base 114 overlaps a significant portion of the mask seal clip 112 or the mask seal 110. The increased insulation provides a warmer inner portion (e.g., mask seal 110 and/or mask seal clip 112), which results in less rain out of humidity during use. Preferably, at least a portion of the mask seal clip 112 is exposed from under the mask base 114 such that the mask base 114 can be more easily separated from the mask seal clip 112. As shown in FIG. 15, to aid in the separation of the mask base 114 from the underlying mask seal 110 and/or mask seal clip 112, the illustrated mask base 114 comprises a peripheral surface 200 on the proximal end. The mask base 114 is concave on the inside to accommodate the underlying components. In other words, the mask base 114 is bowl shaped in a distal direction relative to the proximal peripheral surface 200.

The peripheral surface 200 comprises one or more recessed portions 202. Preferably, the recessed portions 202 comprise at least two recessed portions 202 that are positioned on opposite sides of the mask base 114 from each other. The recessed portions 202 are configured to receive a thumb and a finger such that the mask base 114 can be more easily removed from the front of the underlying mask seal clip 112. While the recessed portions 202 can define means for grasping the assembly underlying the mask base 114 for removal of the mask base, other configurations can be used, such as outwardly extending tabs, protruding portions and the like, for example but without limitation. In addition, while the illustrated recessed portions 202 are disposed on opposing lateral sides of the mask base 114, the recessed portions 202 can be positioned on the top and bottom or on other regions as desired.

As shown in FIG. 13, the mask base 114 preferably comprises an opening 210 that is defined by a wall 212. With reference to FIG. 14 (which is a section through the mask seal 110, the mask seal clip 112, and the mask base 114), the wall 212 that defines the opening 210 through the mask base 114 preferably fits within the wall 146 that defines the passage 144 through the mask seal clip 112. As shown in FIG. 14, the wall 212 can be axially coextensive with the wall 146. In addition, the dimensions and shapes of the walls 146, 212 can be such that the walls interact with each other to reduce relative slippage between the walls 146, 212 and to reduce the likelihood of the mask seal base 114 inadvertently separating from the mask seal clip 112. In some configurations, the walls 146, 212 fit together and reduce the likelihood of leakage through the interface between the walls. Preferably, a taper lock secures the walls 146, 212 together.

Figure 17:
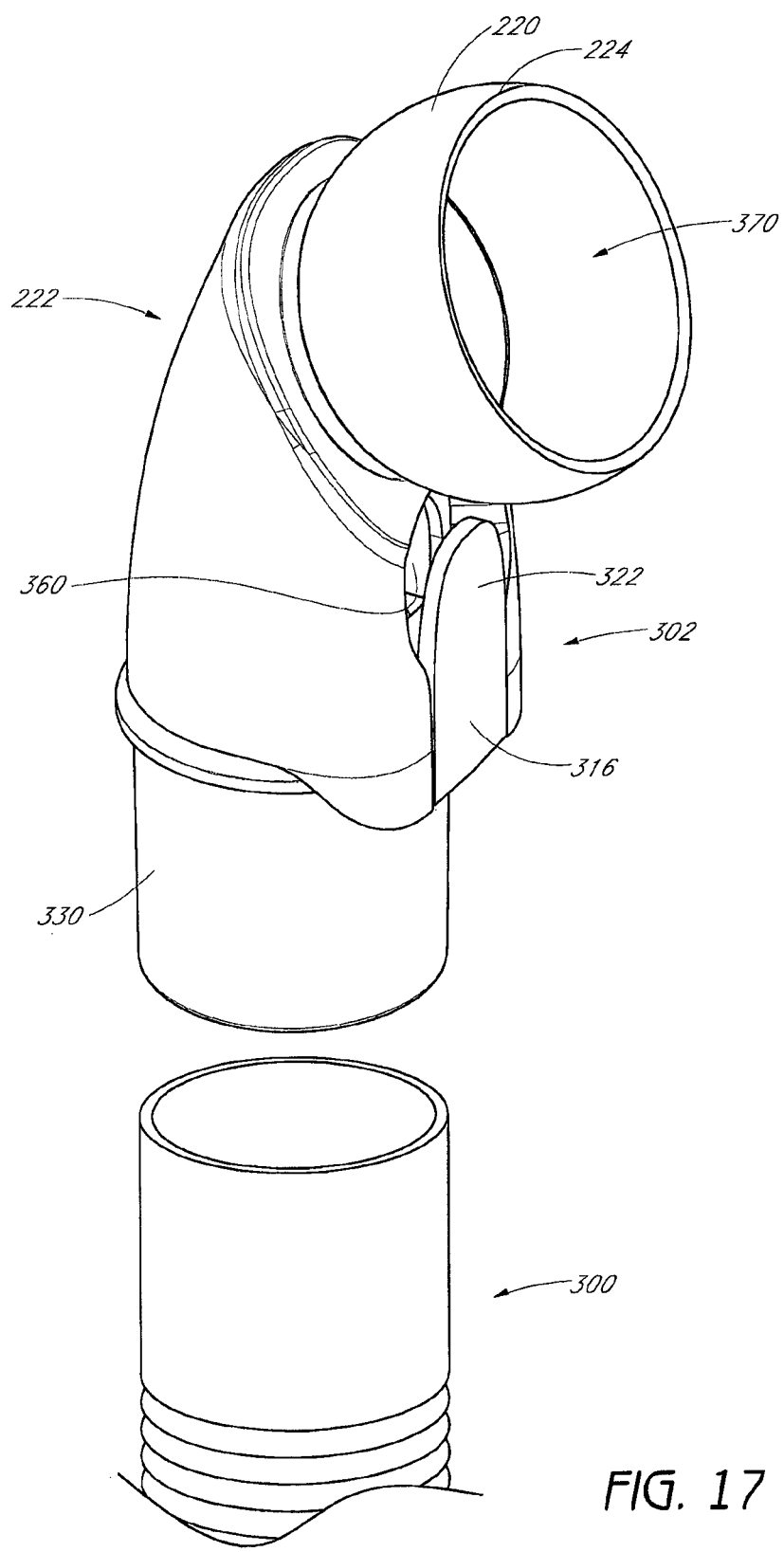
FIG. 17 is a perspective view of the connection port assembly of FIG. 1.
Figure 18:
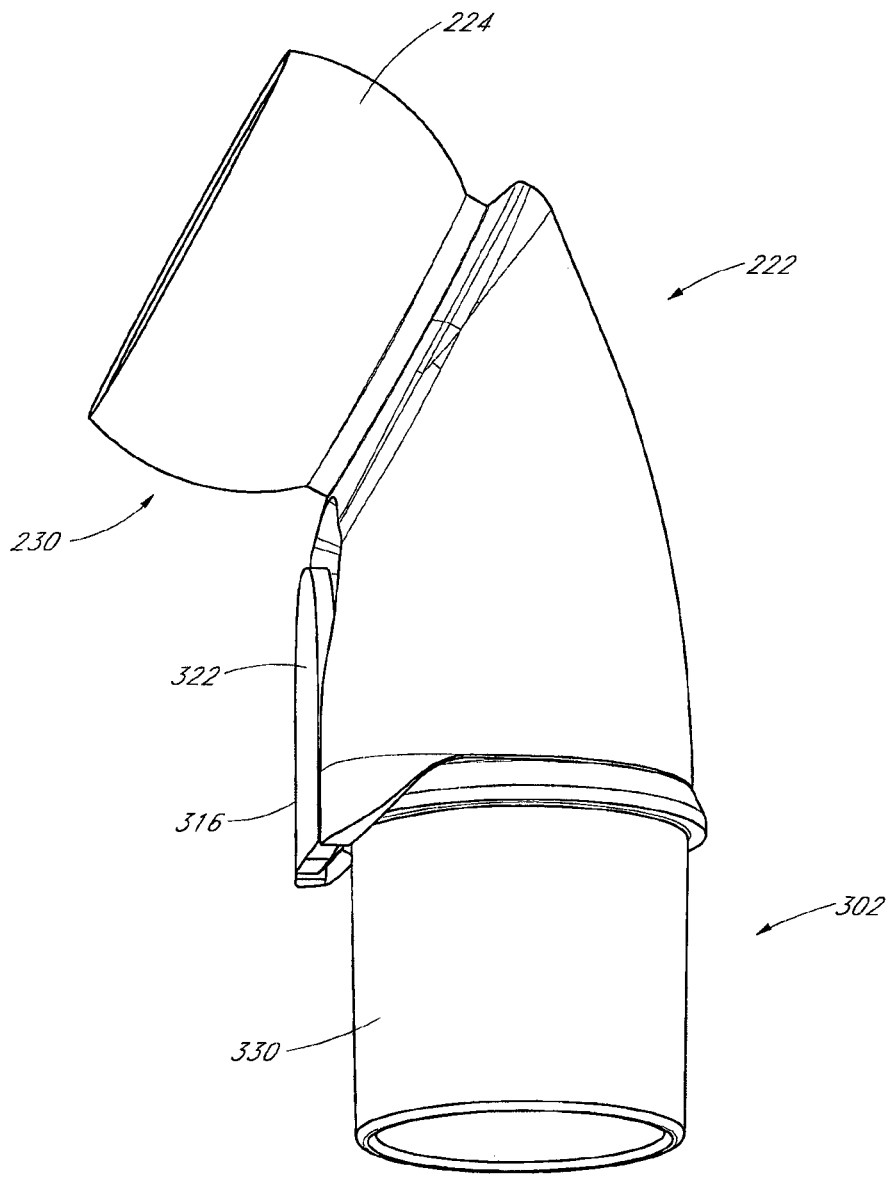
FIG. 18 is a side elevation view of the connection port assembly of FIG. 17.

With reference still to FIG. 14, the wall 212 comprises a contoured inner surface 214. The contoured surface 214 can be radiused to receive a ball end 220 of a swiveling elbow 222, such as that shown in FIG. 17. As better shown in FIG. 18, the ball end 220 has a contoured surface 224 that can be snap fit into the contoured surface 214 formed in the mask base 114. The connection between the two contoured surfaces 214, 224 allows the surfaces to slide relatively freely with each other such that the position of the swiveling elbow 222 can be easily changed. In some configurations, the elbow 222 could be configured for rotation or swiveling without having a ball-joint configuration.

With reference again to FIG. 13, the mask base 114 also comprises at least two pockets 230. The illustrated mask base 114 comprises two pockets 230. The pockets 230 recede into the mask base 114 and protrude rearward from the mask base 114. The pockets 230 are received within the recesses 140 of the mask seal clip 112. Overlying the further recesses 142 formed in the mask seal clip 112 are openings 232 that are defined by a surrounding wall 234.

The illustrated pockets 230 are formed such that one pocket 230 is formed on each lateral side of the mask base 114. The pockets 230 can be positioned to be symmetrical relative to the central plane CP, which plane substantially bisects the mask base 114. In some configurations, as shown in FIG. 15, the pockets 230 have an enlarged vertical dimension 240 relative to a transverse dimension 242. Similarly, as shown in FIG. 15, the openings 232 have an enlarged vertical dimension 244 relative to a transverse dimension 246.

In the illustrated mask base 114, the laterally inward portion of each pocket 230 comprises a support wall 250. The support wall 250 is positioned toward the center plane CP relative to normal to a base surface 248 of the pocket 230. Each of the pockets 230 is configured to receive a clip 252 (see FIG. 22). Once the clip 252 is installed within the pocket 230, the support wall 250 helps to limit rotation of the clip 252 relative to the pocket 230. Moreover, the large vertical dimension helps users to locate the pocket 230 with the clip 252 during installation.

Figure 22:
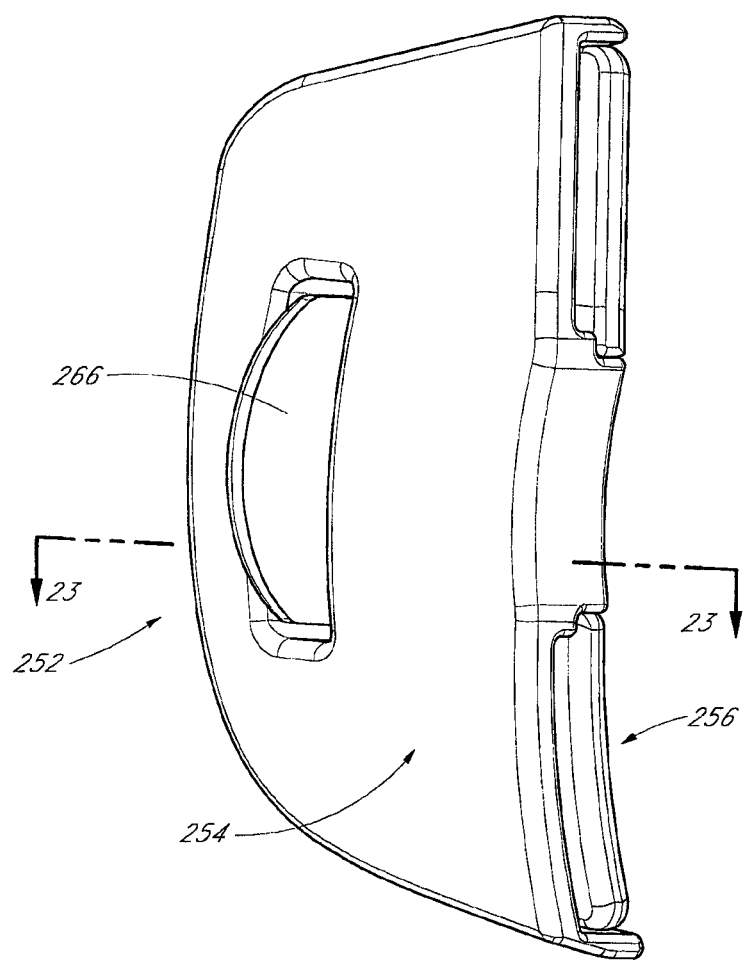
FIG. 22 is a perspective view of the clip assembly of FIG. 1.

With reference to FIG. 22, the clip 252 can have a two part construction: an outer cover 254 and an inner catch 256. Straps 260 can be secured to each clip 252 in any suitable manner. One suitable configuration is illustrated in FIG. 2. In some configurations, the straps 260 can be sandwiched between the outer cover 254 and the inner catch 256. In some configurations, loops or openings or holes could be provided on the clips 252 through which the straps 260 are threaded. Preferably, one clip 252 can be connected to both an upper strap and a lower strap of the headgear assembly 106. Such a configuration facilitates easy connection of the headgear assembly 106 to the full face mask assembly 102 and easy disconnection of the headgear assembly 106 from the full face mask assembly 102.

Figure 23:
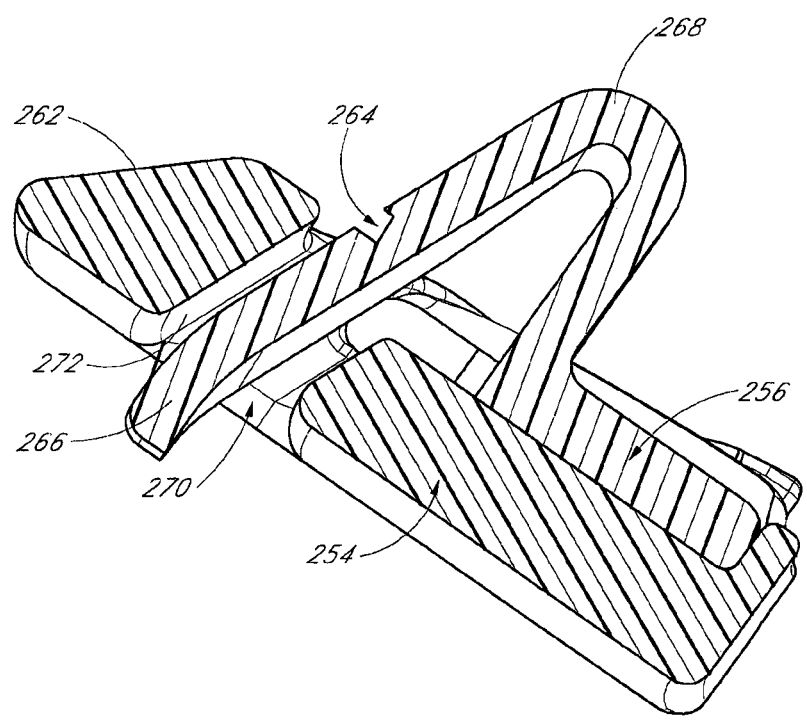
FIG. 23 is a sectioned view of the clip assembly of FIG. 22.

As shown in FIG. 23, the clip 252 comprises a sloping surface 262. The sloping surface 262 can be positioned on the outer cover 254. The sloping surface 262 cooperates with the support wall 250 to help orient the clip 252 relative to the pocket 203 of the mask base 114.

The clip 252 includes an interlock feature 264. The interlock feature 264 is configured for insertion into the opening 232 defined in the pocket 230 of the mask base 114. The interlock feature 264 can engage in a snap-fit manner with a tab 236 defined along the wall 234 that defines the opening 232 in the mask base 114, as shown in FIG. 13. Other manners of interlocking the clip 252 with the pocket 230 also can be used.

Referring to FIG. 23, the interlock feature 264 of the illustrated clip 252 comprises a U-shaped component 268 that terminates in a release lever 266. The U-shaped end 268 protrudes a sufficient distance to allow the connection with the tab 236 but does not protrude so far as to allow the bottom of the further recess 142 in the mask seal clip 112 to stop proper insertion of the interlock feature 264 into the opening 232. The U-shaped end 268 initially makes contact with a wall of the opening 232 during connection of the clip 252 to the mask base 114. In the illustrated configuration, the U-shaped end 268 contacts the wall 234 of the opening 232 during insertion and the wall 234 guides the clip 252 into position within the pocket 230. The opening 232, or one or more surfaces that define the opening 232, generally align the clip 252 relative to the mask base 114 during connection of the clip 252 to the mask base 114.

The end of the release lever 266 protrudes through an opening 270 defined by a wall 272. Preferably, the end of the release lever 266 protrudes through the opening 270 a sufficient distance to allow easy manipulation of the release lever 266. Moving the release lever 266 in manner that closes the U-shape of the interlock feature 264 allows the interlock feature 264 to be removed from engagement with the tab 236 in the wall 234 that defines the opening 232 in the mask base 112.

FIGS. 32-39 illustrate additional configurations of clip assemblies 252 that are configured to secure a mask assembly 102 to a user's head. The clip 252 of FIGS. 32 and 33, for example has a raised edge 400 (sometimes referred to as a finger tab 400) that enables the user to easily detach the headgear 106 from the mask assembly 102. The raised edges 400 are oriented such that the user may merely pull them rearwardly to pop the clips 252 off of the mask base 114. Removing one or more clips 252 from the mask base 114 allows the mask assembly 102 to be easily removed from the user's head. The raised edge 400 provides a grasping point during attachment and removal of the headgear 106 with respect to the mask assembly 102. For example, the user's thumb and index finger may be placed on opposite sides of the raised edge 400 during removal of the clip 252 from the mask assembly 102. In addition, the user may grip the clip 252 and maintain the grip throughout the mask fitting process. This eliminates the need to grasp blindly for the straps 260 during assembly. It also allows the user to attach the clip 252, remove it, and re-attach it while maintaining a grip on the raised edge 400.

Figure 32:
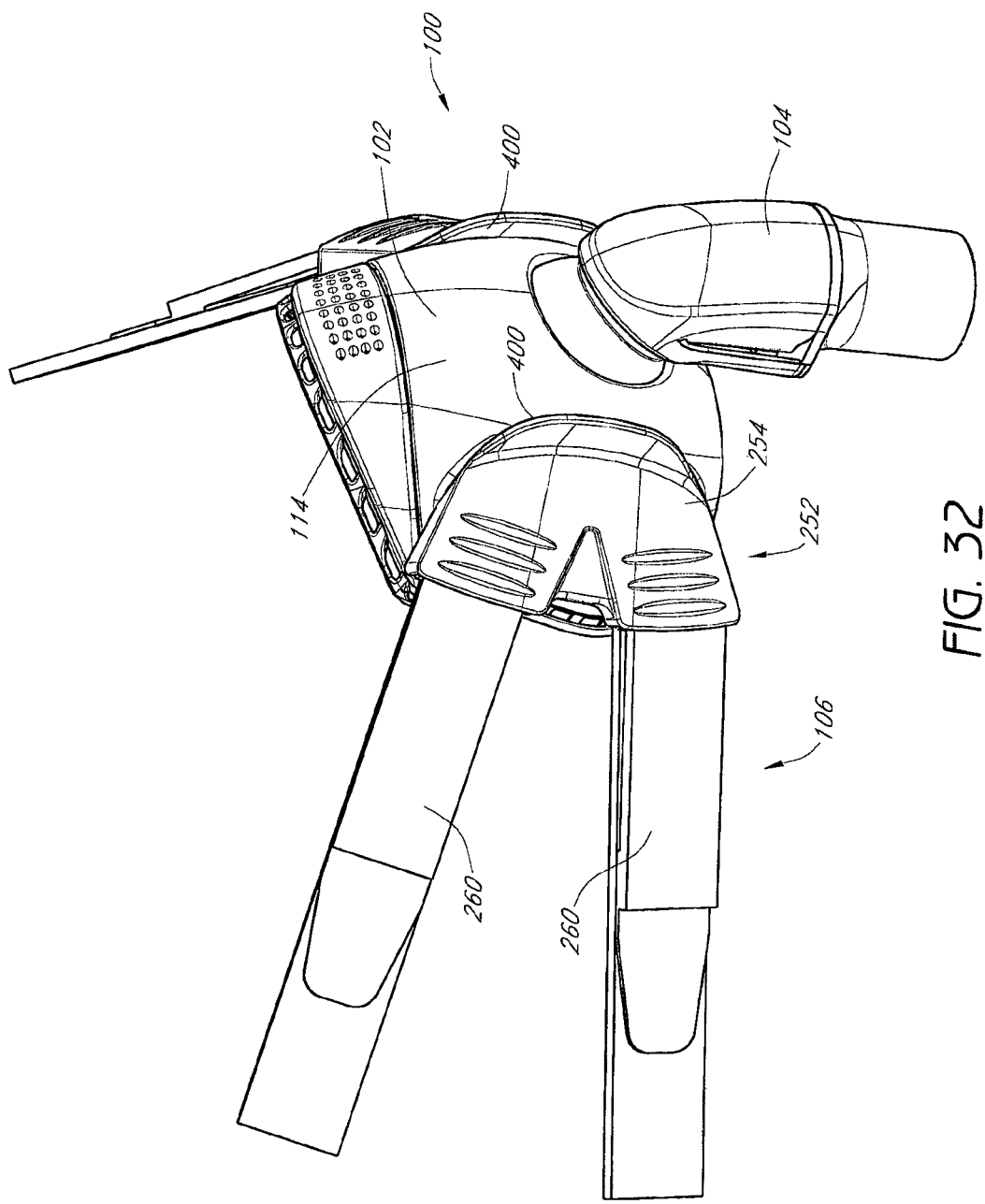
FIG. 32 is a perspective view of a mask assembly comprising a mask, clips, and straps.
Figure 33:
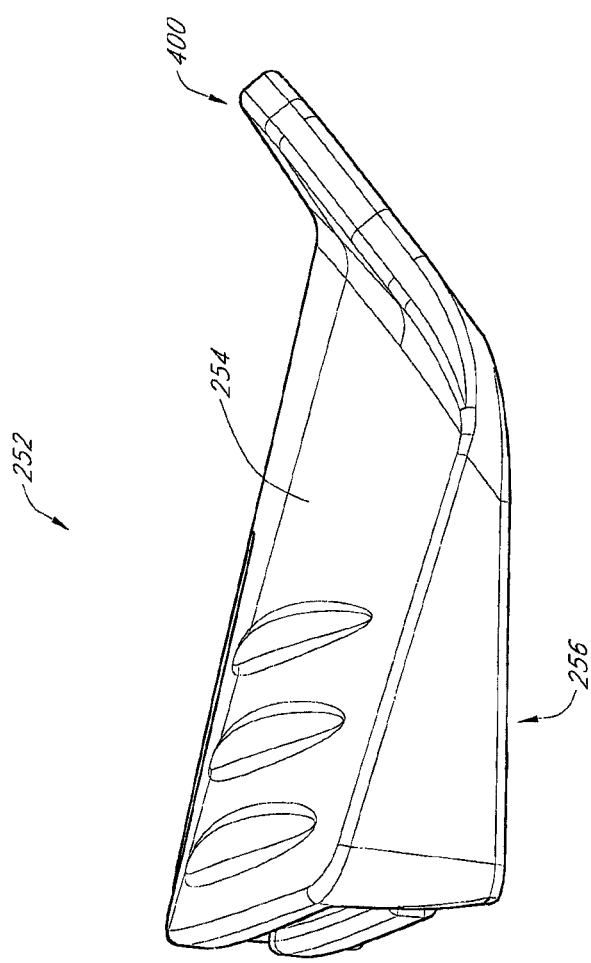
FIG. 33 is a side view of one of the two clips of FIG. 32.
Figure 35:
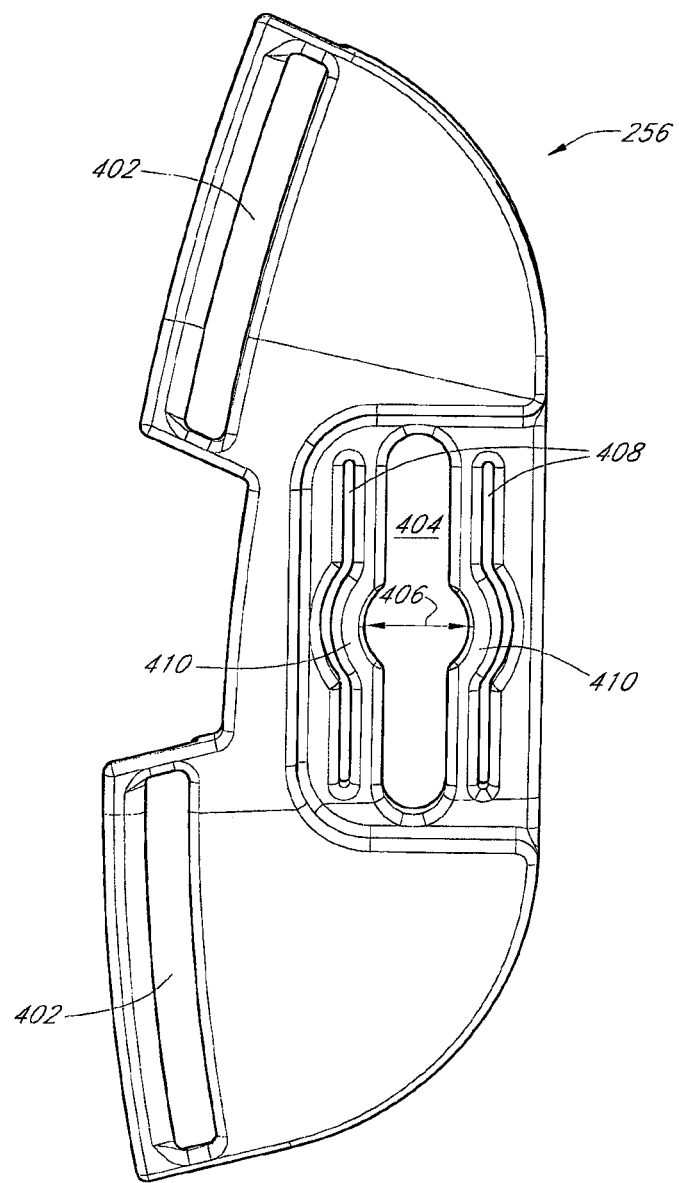
FIG. 35 is a top view of the inner catch of the clip of FIG. 33.

FIG. 34 shows an exploded view of the clip 252 of FIGS. 32 and 33. The clip 252 includes an outer cover 254 and an inner catch 256. The inner catch 256 includes one or more slots 402 to receive the distal end of the headgear straps 260. The inner catch 256 can also include several pressure bumps, such as those shown in connection with the configuration of FIGS. 38 and 39. The pressure bumps provide additional pressure against the outer cover 254 and inner catch 256, so that they are secured to one another. In one configuration, the headgear straps 260 are removable from the assembled clip 252.

Figure 38:
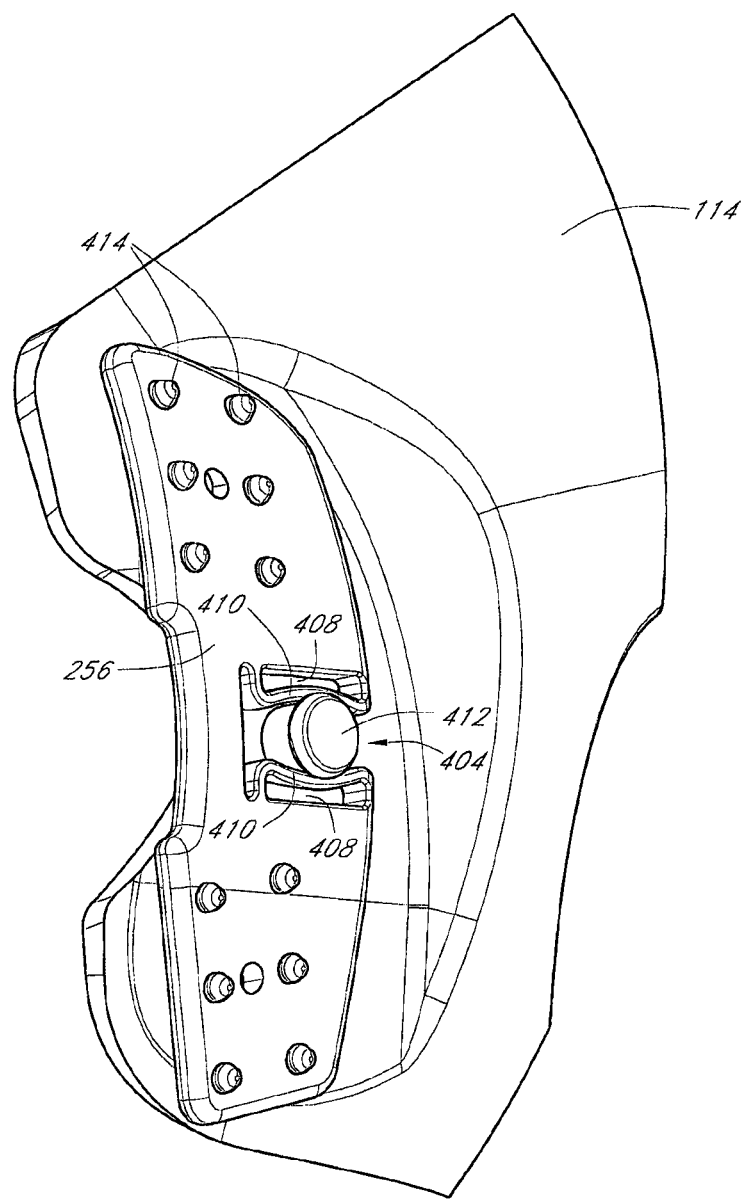
FIGS. 38-47 are additional configurations of clips and associated masks and mounting posts.

The inner catch 256 includes an elongated slot 404, as shown in FIG. 38. The slot 404 includes a circular opening 406 having a diameter larger than the width of the slot 404. The slot 404 and circular opening 406 can include chamfered recesses to help align the clip 252 to the mask assembly 102. The circular opening 406 facilitates attachment and removal of the clip 252 to the mask assembly 102, as will be discussed in greater detail below. Two channels 408 extend parallel to the sides of the slot 404, thereby defining slot walls 410 (sometimes referred to as clip levers) on either side of the slot 404. The channels 408 are sized to permit adequate flexing of the slot walls 410 during attachment and removal of the clip 252 from the mask assembly 102. In addition, the slot walls 410 extend along the longest dimension of the inner catch 256, towards top and bottom, which allows longer slot walls 410 to be employed. Longer slot walls 410 reduces the level of stress on the slot walls when fitting the clip over the mounting post.

Figure 36:
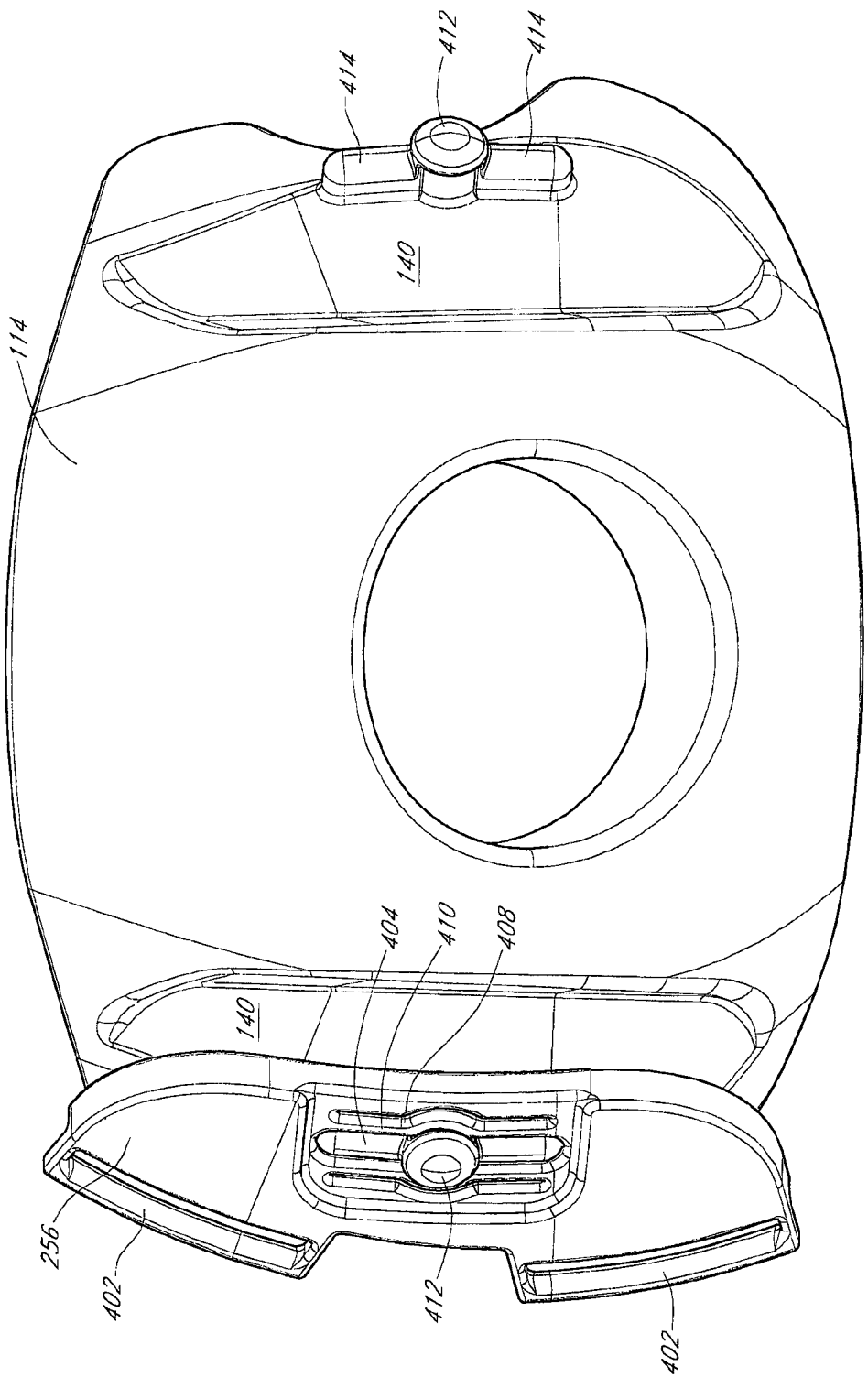
FIG. 36 is a front view of a mask base having two mounting posts, and one inner catch of a clip mounted to the left mounting post.

One configuration of a mask base 114 suitable for use with the clip 252 of FIGS. 32-35 is illustrated in FIG. 36. The mask base 114 includes two recesses 140 symmetrically positioned on opposite sides of the mask base 114. A mounting post 412 extends from the body of the mask base 114 within each recess 140. The mounting post 412 may be integrally formed with the mask base 114, or separately formed and secured to the mask base 114. The mounting post 412 can have a mushroom-shaped configuration to secure the clip 256 to the mask base 114 once the user snaps the clip 256 in place. The rounded top of the bulbous mushrooms-shaped post 412 helps locate and orient the central hole 406. As the clip 252 is pressed onto the post 412, the slot walls 410 deflect outwardly, away from the post 412. Once the head of the post 412 clears the edge of the slot wall 410, the slot walls 410 snap back to their original position, thereby providing tactile, and sometimes audible feedback, that the clip 252 is properly attached to the mask assembly 102.

The mounting post 412 can also comprise an elongated, elliptical, elevated portion 414 (sometimes referred to as a lug or wing) that is sized to mate with the elongated slot 404 of the inner catch 256. The elongated, elevated portion 414 comprises a chamfered edge to help properly align the head gear 106 with respect to the mask assembly 102. The portion 414 also prevents the clip 252 from rotating with respect to the mask assembly 102. This helps assure constant tension on the headgear straps 260 while the user sleeps.

Figure 37:
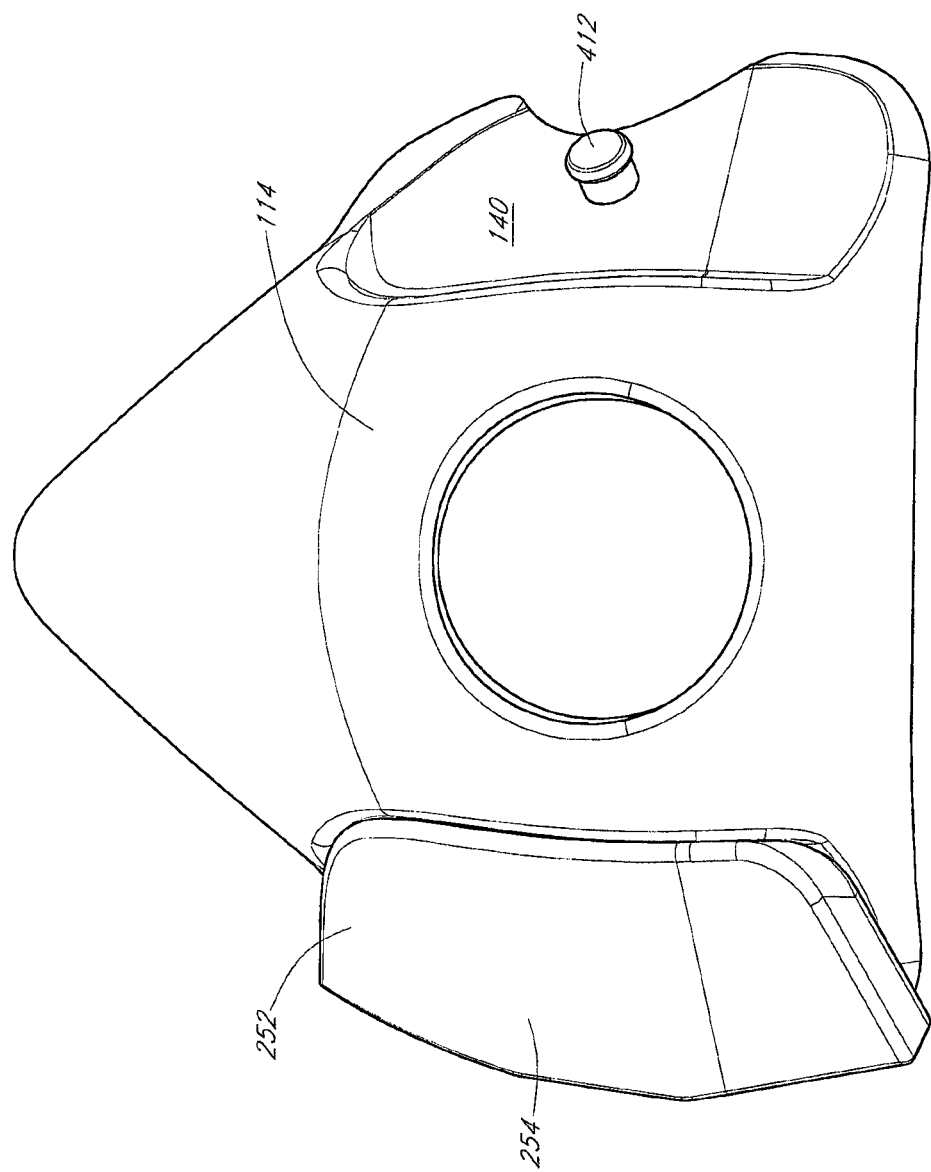
FIG. 37 is a front view of another configuration of a mask base having two mounting posts, and another configuration of a clip mounted to the mask base's left mounting post.
Figure 39:
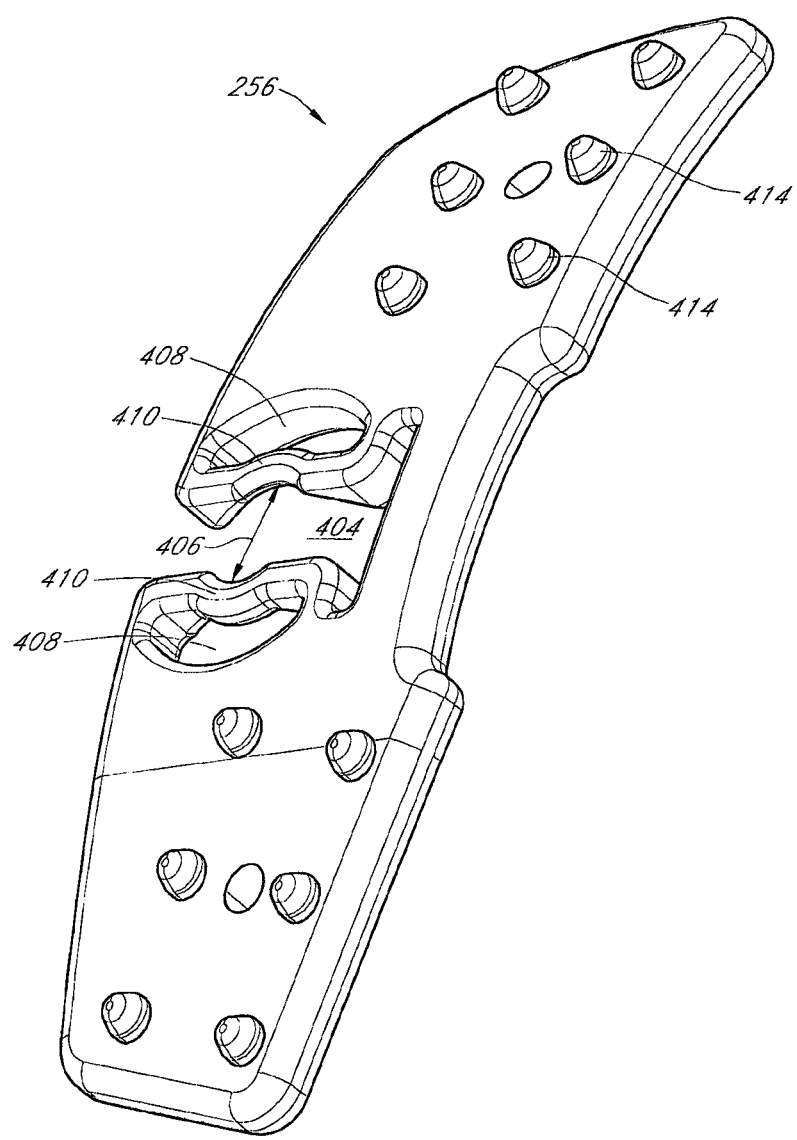
Figure 40:
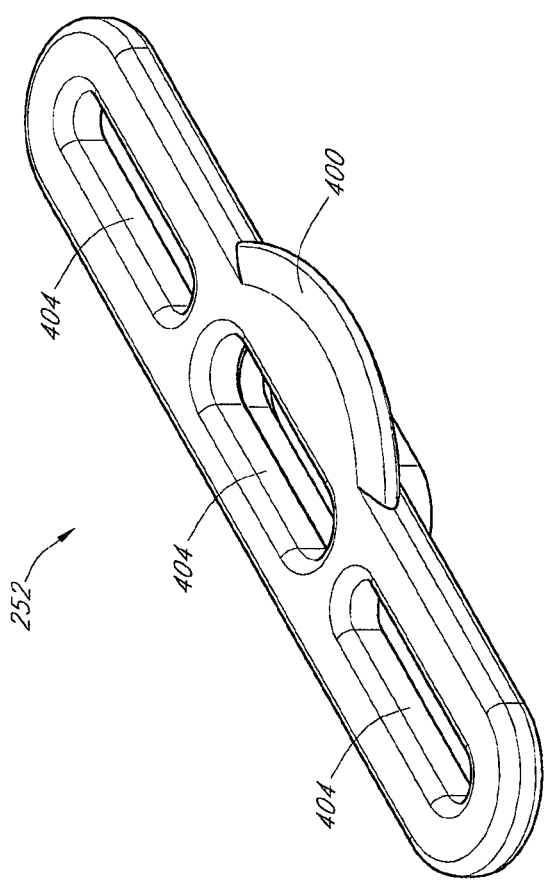
Figure 41:
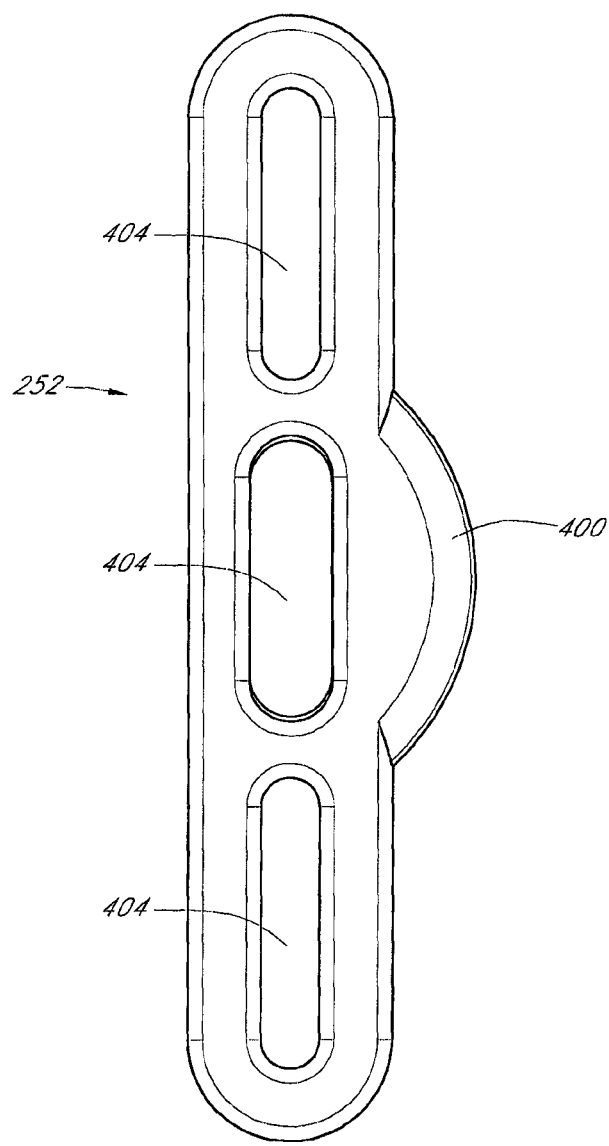
Figure 42:
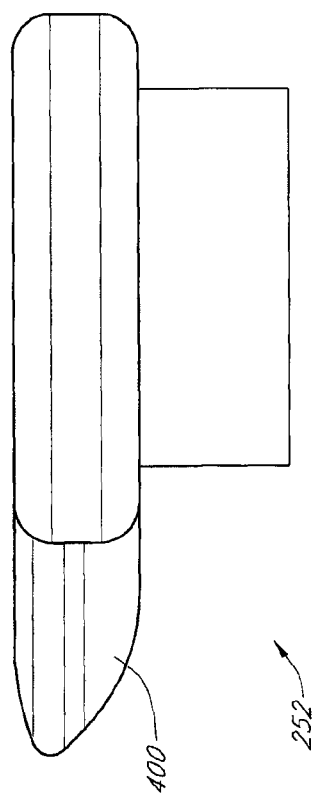

FIG. 37 illustrates a partial assembly of yet another configuration to secure a clip 252 to a mask base 114 of a mask assembly. The clip 252 sits within a recess 140 of the mask base 114. A cylindrical, button-head post 412 extends from the surface of the mask base 114 within the recess 140. The post 412 allows slight rotation of the clip 252 when attached thereto due to its cylindrical configuration. However, as shown in FIGS. 38 and 39, the slot 404, channels 408 and slot walls 410 extend along the shorter planar direction of the inner catch 256, towards its front and back ends.

The inner catch 256 also includes several pressure bumps 414. As discussed above, the pressure bumps provide additional pressure against the outer cover 254 and inner catch 256, so that they are secured to one another.

Figure 43:
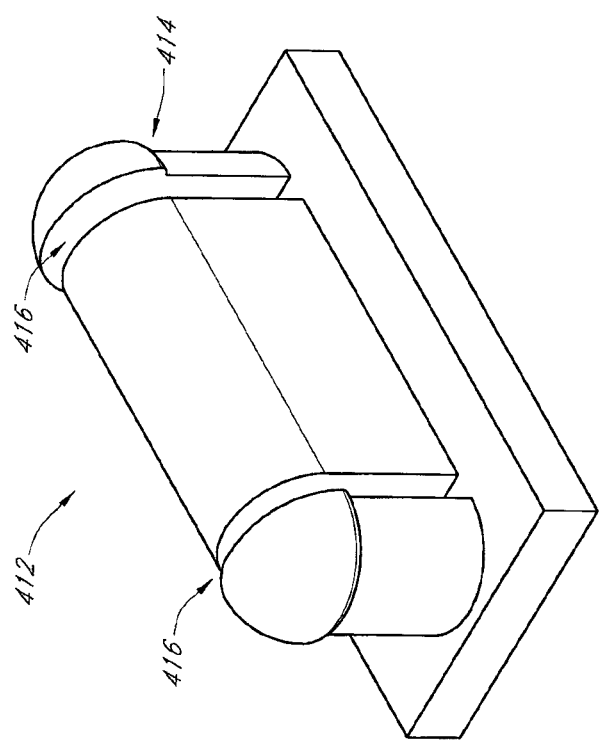
Figure 44:
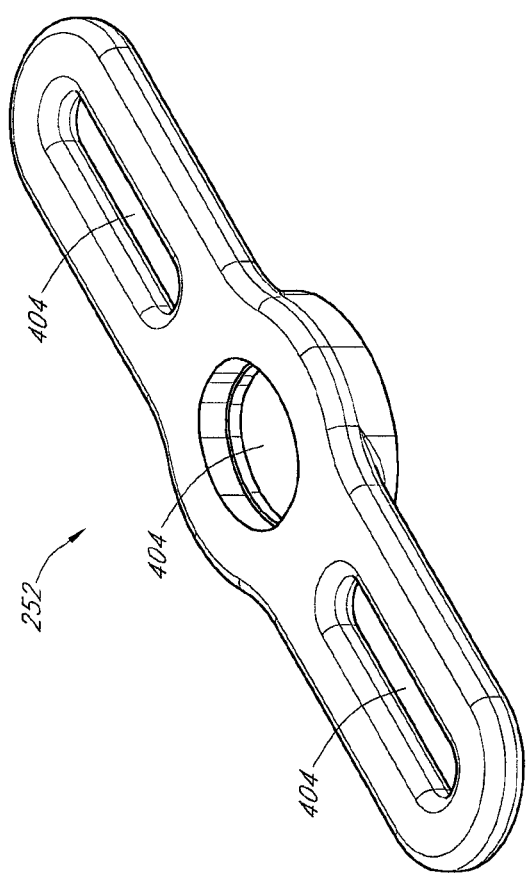
Figure 45:
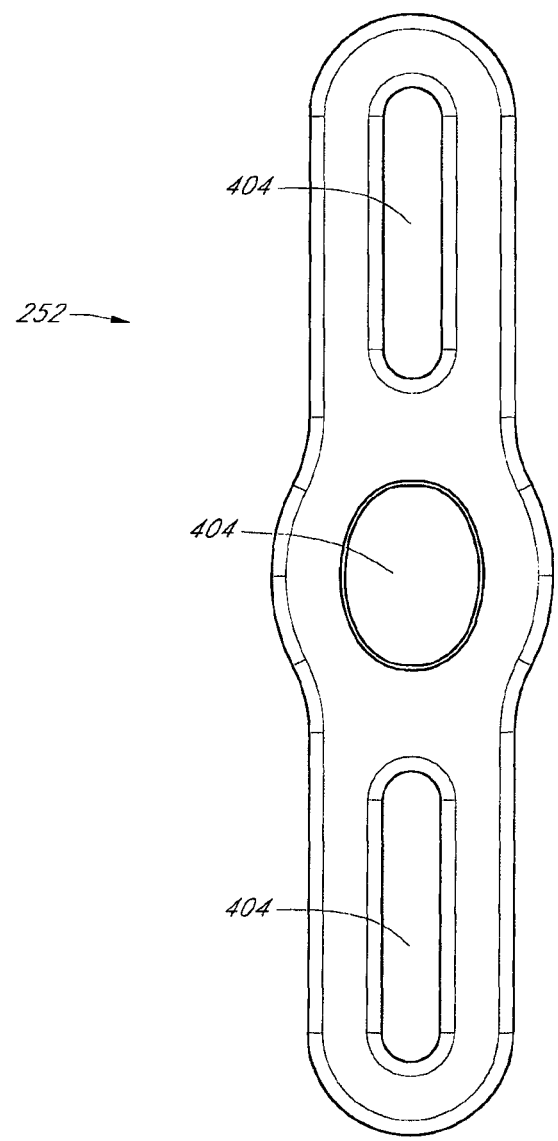
Figure 47:
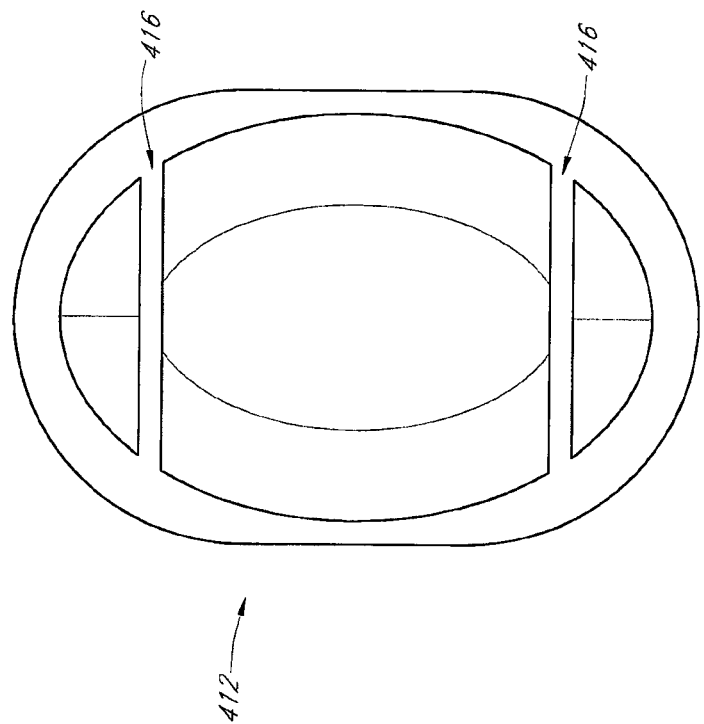
Figure 46:
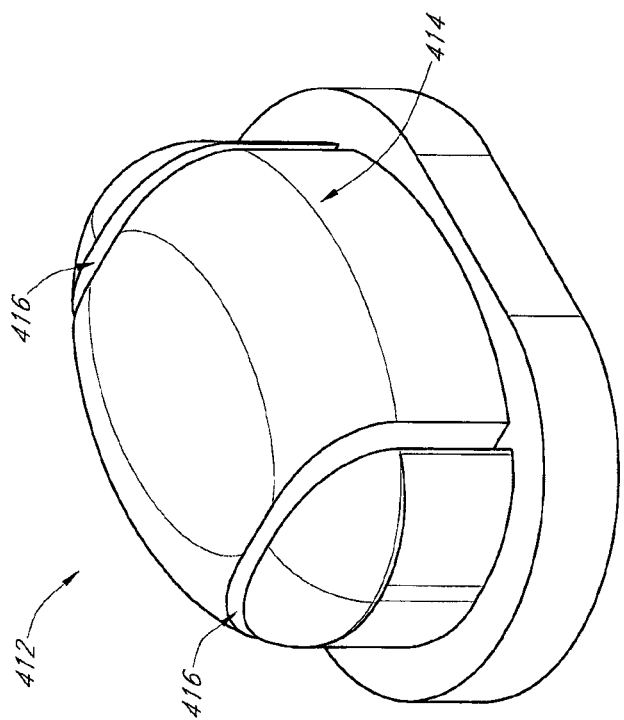
Figure 48:
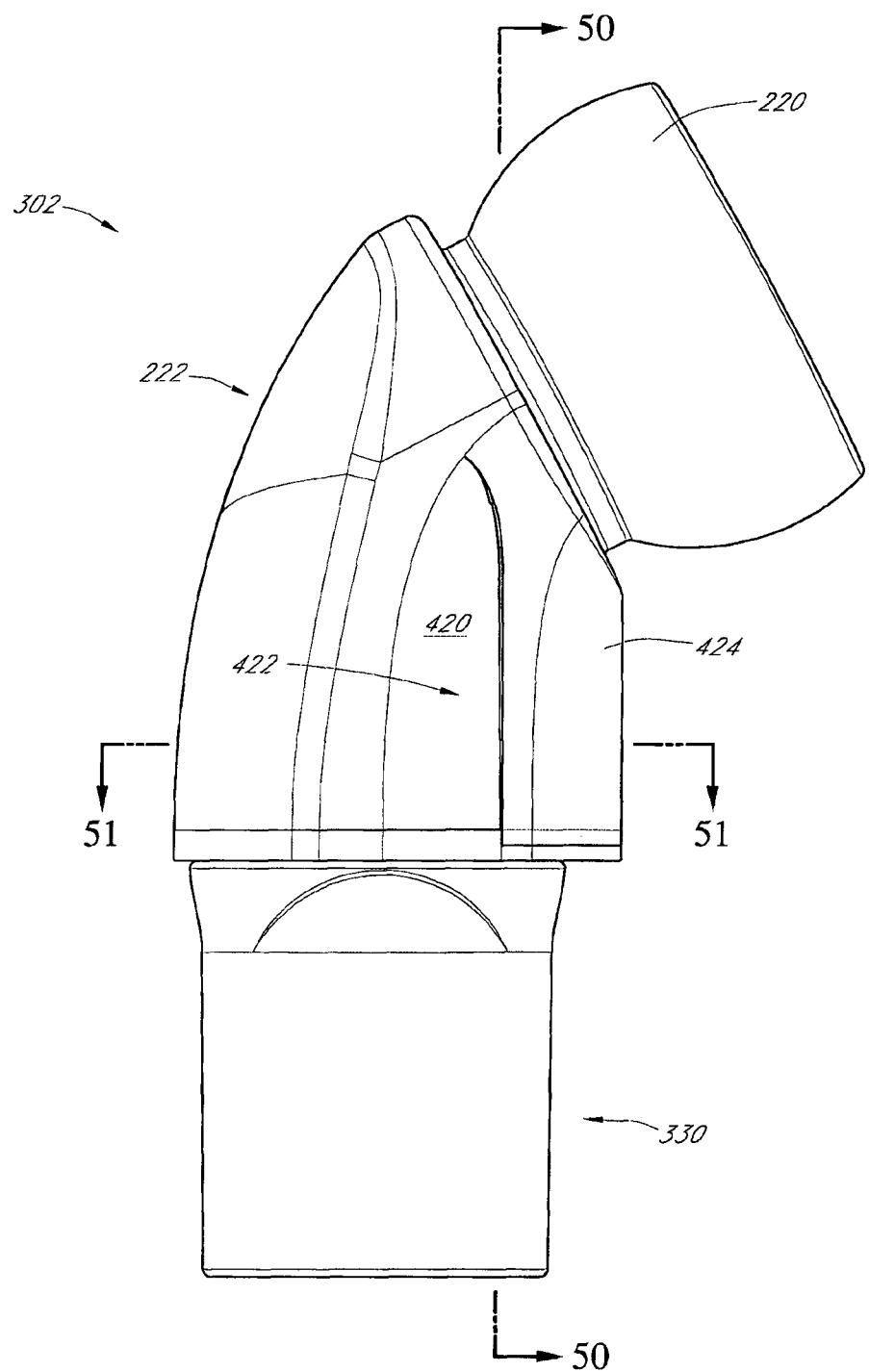
FIG. 48 is a side view of another configuration of a swivel assembly.

Additional configurations of a clip 252 are illustrated in FIGS. 40-47. The clip 252 of FIG. 40 includes three elongated, elliptical slots 404 and a finger tab 400. The finger tab 400 is used to create a lever to release the clip 252 from a mask assembly 102. The central slot 404 is sized to receive a mounting post 412 that extends from the outside surface of the mask body. One such suitable mounting post 412 is illustrated in FIG. 43. The mounting post 412 includes a ridge 414 and two slots 416. As the clip 252 is pressed onto the mounting post 412, the outer portions of the post 412 flex towards each other due to the spacing provided by the slots 416. Once the ridge 414 clears the upper surface of the clip 252, the mounting post 412 snaps back to its original position, and the ridge 414 locks the clip 252 in place, A similar configuration is shown in FIGS. 44-47. The clip 252 of FIG. 45 does not include a finger tab and its central opening 404 has a rounder, more elliptical shape than the elongated slots of FIGS. 40-44.

All of the foregoing configurations simplify the procedure for securing the mask assembly 102 to the user's head. For example, the clips 252 allow the headgear 106 to open up so that it is not a closed loop. By opening up, the headgear 106 may be swung around the head rather than forcing the user to pull his head through it.

With reference to FIG. 2, in addition to the straps 260, the headgear assembly 106 also comprises a back strap 280 and a top strap 282. Other head gear assemblies also can be used. The back strap 280 extends around the back of the head of the user U at a location generally above a nape of the neck but generally below the occipital protuberance. At a location rearward of the ear of the user, the back strap 280 forks into an upper arm 284 and a lower arm 286. The upper arm 284 arcs upward to a location above the ear of the user and then arcs downward to a location generally forward of the ear of the user. The lower arm 286 arcs downward to a location generally below the ear of the user and extends slightly forward of the ear.

The straps 260 can be connected to the back strap 280 in any suitable manner. In the illustrated configuration, the straps 260 connect to the upper arm 284 and the lower arm 286 respectively. Preferably, the upper arm 284 and the lower arm 286 are more rigid than the straps 260 such that the arms 284, 286 generally maintain shape as the headgear assembly 106 is being donned. In some configurations, each of the upper arm 284 and the lower arm 286 supports its own weight. In some configurations, each of the upper arm 284 and the lower arm 286 is structured to be tangle-free during donning. For example, the arms 284, 286 have sufficient torsion stiffness to reduce the likelihood of twisting when being put on.

Preferably, the straps 260 connect to at least one of the upper arm 284 and the lower arm 286 at a location forward of the ear. Such a configuration helps the user to locate the straps 260 without much difficulty. In addition, because the straps 260 in the illustrated configuration are embedded into the clips 252, the ends of the upper arms 284 and the lower arms 286 can comprise slots 290, 292 such that the straps 260 can be threaded through the slots 290, 292. In addition, the straps 260 can comprise an adjustment mechanism 294, such as a Velcro or buckle configuration. The adjustment mechanism 294 allows a force between the mask seal 110 and the face of the user U to be adjusted. Any suitable adjustment mechanism 294 can be used.

As shown in FIG. 2, the top strap 282 preferably is flexible and has an adjustable length. The top strap 282 connects to the upper arms 284 through a slot 296 and reduces the likelihood of the upper arms 284 sliding down the head of the user and contacting the ears of the user. Preferably, the top strap 282 connects to the upper arms 284 at a location generally above the ears of the user.

Advantageously, as shown in FIGS. 1 and 2, the straps 260 exert a force in the direction of the arrow F while they connect to the mask base 114 by movement in the direction C, which direction is generally normal to the direction of the force F. In other words, the straps 360 are tensioned by pulling forward and the clips 252 are connected to the mask base 114 by movement in a direction normal to the forward pull. Such a configuration eases securement of the interface 100 on the face of the user.

Figure 29:
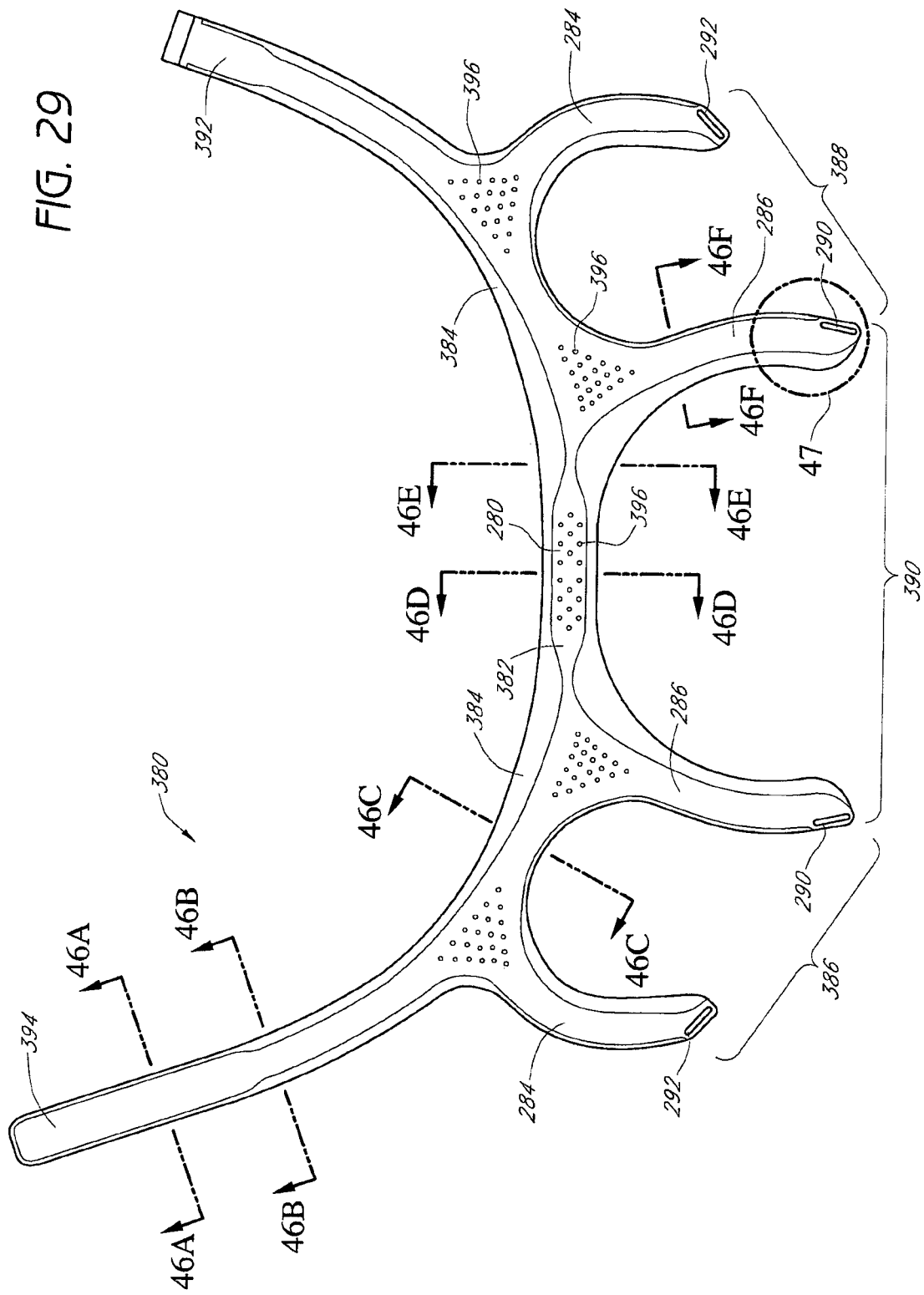
FIG. 29 is a perspective view a backbone compatible with the headgear assembly of FIGS. 1 and 2.

In another configuration, the headgear assembly 106 includes a semi-rigid headgear 380 (as shown in FIG. 29) to secure the mask assembly 102 to the user's head. The semi-rigid headgear 380 is formed as a composite structure comprising a semi-rigid strap 382 that is joined to a soft edging 384. For example, the soft edging 384 can be bonded to the semi-rigid strap 382 by plastic overmolding or by use of an adhesive. As shown in FIG. 29, the soft edging 384 can be butt-joined to the semi-rigid strap 382, without the soft edging 384 overlapping the semi-rigid strap 382, to maintain the continuous profile of the semi-rigid headgear 380. The semi-rigid strap 382 defines and maintains the semi-rigid headgear shape as tension is applied from the straps 260 to pull the mask assembly 102 towards the user's head. In other words, the semi-rigid strap 382 is sufficiently rigid along its planar axis to prevent its upper and lower arms 284, 286 from overly deforming under tension. The semi-rigid strap 382 can be made from a variety of rigid or semi-rigid materials, including plastic or metal. In some configurations, the semi-rigid strap 382 is made from PVC.

Especially in connection with a semi-rigid headgear assembly, it has been found that the shape holding, or self-supporting nature, can result in an overall assembly that is intuitive to fit. In particular, where the connection and/or headgear members are self-supporting such that they maintain a three-dimensional form, the headgear can be fitted in the correct orientation with very little if any instruction. In a self-supporting arrangement, the tendency of the straps to not tangle also reduces the time taken to fit the overall assembly.

As used herein, the term "semi-rigid" is used to denote that the headgear assembly is sufficiently stiff such that the headgear assembly 380 can assume a three-dimensional shape with dimensions approximating the head of the patient for which the headgear is designed to fit while also being sufficiently flexible to generally conform to the anatomy of the patient. For example, some of the other components (e.g., arms or straps) of the headgear assembly 380 may also be partially or wholly "semi-rigid" such that the components are capable of holding a three-dimensional form that is substantially self-supporting. A "semi-rigid" headgear assembly is not intended to mean that each and every component of the headgear assembly is necessarily semi-rigid. For example, the substantially three-dimensional form that the self-supporting headgear assembly 380 may assume may relate primarily to the rear and top portions of the headgear assembly 380. In addition, the semi-rigid headgear assembly 380 may include semi-rigid regions that extend forward of the ears and above the ears when placed on the head of the patient.

The left and right upper and lower arms 284, 286 may be formed of a semi-rigid material, as well. Where used herein, the semi-rigid materials may include molded plastic or sheet materials that include but are not limited to homogeneous plastic materials and bonded non-woven fiber materials.

In some configurations, one or more of arms or straps are formed of a substantially inelastic material. The arms or straps can be formed of a semi-rigid, self-supporting material such that the semi-rigid headgear assembly 380 can assume a substantially three-dimensional shape and generally does not tangle. In some configurations, the material can comprise a laminate structure of both conformable and semi-rigid portions, for example but without limitation. The semi-rigid strap 382 may be of a self-supporting, resilient, substantially inelastic material, such as Santoprene, polyolefin, polypropylene, polyethylene, foamed polyolefin, nylon or non-woven polymer material for example but without limitation. In some configurations, the semi-rigid strap 382 is formed from the polyethylene or polypropylene families. The material can be a low density polyethylene such as Dowlex 2517, which is a linear low density polyethylene that has a yield tensile strength of 9.65 MPa, a break tensile strength of 8.96 MPa, and a flexural modulus—2% secant of 234 MPa. The semi-rigid strap 382 preferably is formed of a material such that the semi-rigid headgear 380 is substantially shape-sustaining under its own weight regardless of its orientation. In some configurations, the semi-rigid strap 382 does not stretch more than approximately 6 mm under a 30 N tensile load. In some configurations, the semi-rigid strap 382 does not stretch more than approximately 3 mm under a 30 N tensile load.

In some configurations, the semi-rigid strap 382 is formed from non woven polyolefin (NWP), which is bonded (e.g., overmolded or laminated) with a polyolefin. In such configurations, the overmolded polyolefin material provides the principle shape sustaining properties. In addition, the softer NWP material is adapted to contact the skin and provide a desired comfort level. Furthermore, the NWP material may assist in providing the desired load bearing properties, such as the desired tensile load bearing properties.

The semi-rigid headgear 380 is generally formed of a semi-rigid material. Where used herein, the semi-rigid materials may include molded plastic or sheet materials that include but are not limited to homogeneous plastic materials and bonded non-woven fiber materials. The upper and lower arms 284, 286 also include such semi-rigid materials, as the arms 284, 286 are formed integrally with and are portions of the semi-rigid headgear 380. Preferably, the right and left lower arms 286 are formed as an integrated component that, in use, will extend around the back of the head and above the neck of the patient.

A soft edging 384 covers or attaches to at least a portion of the periphery of the semi-rigid strap 382. In one configuration, the soft edging 384 does not cover the front or rear faces of the semi-rigid strap 382. For example, the thicknesses of the soft edging 384 and semi-rigid strap 382 can be the same at the location where they are joined together.

The soft edging 384 provides a soft, comfortable interface between the periphery of the semi-rigid strap 382 and the user's skin. The soft edging 384 can be made from a variety of soft materials, including but not limited to a plastic, an elastomer, silicone or thermoplastic polyurethane (TPU) plastic. The soft edging 384 can have a Shore hardness in the range of 10-80 Shore A.

As used herein with respect to headgear and straps, "soft" is used to describe a hand of the material, which means the quality of the material assessed by the reaction obtained from the sense touch. In addition, as used herein with respect to headgear and straps, "conformable" is used to describe the ability of the material to conform to the anatomical features of the patient (e.g., around a facial feature). In particular, a strap including at least an element of "soft" and/or "conformable" material also may be "semi-rigid" and/or axially inelastic.

The soft edging 384 can have a uniform thickness, or in some configurations, an uneven thickness. For example, in some configurations the soft edging 384 is the same thickness as the semi-rigid strap 382. In other configurations, the soft edging 384 is thinner than the semi-rigid strap 382, forms a bulbous end to the semi-rigid strap 382, or is simply thicker than the semi-rigid strap 382. A variety of cross-sectional views of the semi-rigid headgear 380 are shown in FIG. 29. Each cross-sectional view (A-A' through F-F') shows one possible configuration of semi-rigid strap 382 and soft edging 384 thicknesses, which may be combined as desired. For example, any one particular soft edging 384 thickness and shape could apply to a portion or the entire semi-rigid strap 382, or may be combined with any other particular covering thickness and shape shown in FIG. 29.

Many other thickness configurations may be provided, as well. In addition, material thickness may be symmetrically or asymmetrically applied to the semi-rigid strap 382. For example, cross-sectional views C-C' and F-F' are shown as asymmetric; however, in other configurations the thickness of either end the soft edging 384 is symmetrically applied to the semi-rigid strap 382. In some configurations the semi-rigid strap 382 is selectively thickened to provide extra rigidity and support. For example, the second of the two configurations illustrated as cross-sectional view F-F' has such a thickening. Finally, in some configurations, venting through-holes 396 are provided throughout the semi-rigid headgear 380 (such as on the semi-rigid strap 382, as shown in FIG. 29, or on soft edging 384) to provide ventilation and sweat management.

When laid flat, as shown in FIG. 29, the semi-rigid headgear 380 defines three C-shaped, arcuate regions 386, 388, 390. Two ear-surrounding regions 386, 388 are defined by upper and lower arms 284, 286, and a rear region 390 is defined by lower arms 286 and the back strap portion 280. The semi-rigid headgear 380 is flexible enough to bend to adapt to the shape of the user's head, such that the ear-surrounding regions 386, 388 at least partially surround or encircle the user's ears, and the rear region 390 at least partially surrounds or encircles the back of the user's head, above the neck.

The curvature of each arm 280, 284, 286 can be selected to provide a comfortable fit and to facilitate application and removal of the semi-rigid headgear 380 from the user's head. For example, in the illustrated configuration, the upper arms 284 have a concave curvature and the lower arms 286 have a convex curvature with respect to the opening in the upper ear surrounding arcuate regions 386, 388. The back strap portion 280 and the lower arms 286 all have a concave curvature with respect to opening in the neck surrounding arcuate region 390. These curvatures facilitate application and removal of the semi-rigid headgear 380 from the user's head by, for example, providing openings to the arcuate regions sized and oriented to easily fit over a user's neck and ears.

The configuration of FIG. 29 utilizes integrated crown straps comprising first and second crown arms 392, 394 to secure the semi-rigid headgear 380 to the user's head. Once the semi-rigid headgear 380 is positioned to partially surround the user's head, the first and second crown arms 392, 394 are brought into contact with one another to secure the semi-rigid headgear 380 in place. Any of a variety of mechanisms can be provided with the first and second crown arms 392, 394 to enable them to attach to one another. For example, in some configurations, a hook-and-loop fabric (e.g., Velcro), or one or more snaps or clips can be used to attach the first and second crown arms 392, 394 to one another.

The crown straps extend laterally over the top of the skull in line with the ears. When the crown straps extend in this manner and the arcuate regions 386, 388 are positioned to partially encircle the user's ears, the back strap 280 of the semi-rigid headgear 380 should locate on or below the inion. The user's inion is the most prominent projection of the occipital bone at the posterioinferior portion of the skull. In other words, the inion is the highest point of the external occipital protuberance. The semi-rigid headgear 380 can be positioned on the user's head according to any of the configurations described in the applications set forth in the Incorporation by Reference of Related Applications in the first paragraph of this application, which forms an integral part of the present disclosure and are hereby incorporated by reference in their entirety.

For example, the back strap portion 280 is adapted to engage with the rear of head of the user. Preferably, the back strap portion 280 is adapted to engage with the head at a location on or below the external occipital protuberance. The back strap portion 280 spans the distance around the back of the head and extends to each side of the head. In some configurations, the back strap portion 280 comprises a longitudinal center that is adapted to be located about 25 degrees below a horizontal plane that extends through the ear canal of the patient.

On either side of the head, the semi-rigid headgear 380 extends upward and downward into left and right side regions that form arcuate regions 386, 388. The side regions are adapted to extend behind the ears of the patient. Preferably, the side regions also are adapted to extend behind the mastoid processes of the patient. Each of the left and right side regions of the semi-rigid headgear 380 extends into or comprises an arched portion 386, 388. The arched portions 386, 388 bend forward. The arched portions 386, 388 are adapted to extend around the respective ears of the patient. Preferably, each of the arched portions 386, 388 terminates at a respective termination portion. The termination portions preferably are adapted to be located forward of the ears of the patient. In some configurations, the side regions and the arched portions 386, 388 of the semi-rigid headgear 380 do not include a soft inner padding portion but may comprise a self-supporting, resilient material that is in direct contact with the head/hair of the patient.

The top portion of the semi-rigid headgear 380 connects the arched portions 386, 388 together. The top portion can be positioned forward of the ears in some configurations. Preferably, the top portion is positioned generally vertical from the ears. More preferably, a longitudinal center of the top portion is adapted to be spaced more than 13 mm, preferably between 13-100 mm, rearward of a vertical plane that intersects the ear canals. In some configurations, the top portion comprises a first segment 392 and a second segment 394 with the first segment 392 and the second segment 394 combining to form the top portion. The first segment 394 extends upward from an apex of the left arched portion 386 while the second segment 392 extends upward from an apex of the right arched portion 388. Preferably, the top portion is formed of a self-supporting and semi-rigid material. In some configurations, the top portion does not include any backing, including a soft padded backing layer.

Figure 30:
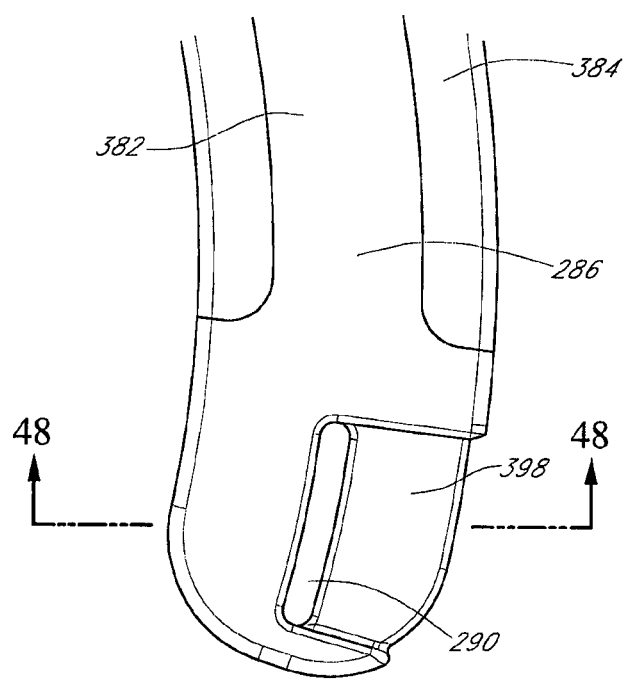
FIG. 30 is an enlarged view of the end region of a lower arm of FIG. 29.
Figure 31:
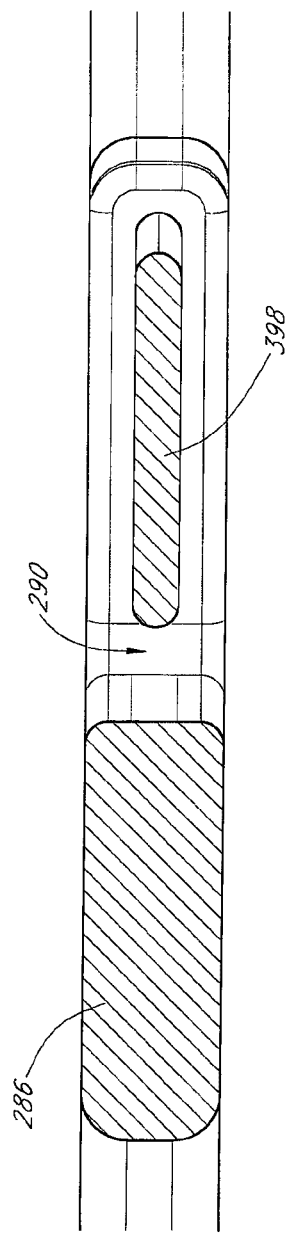
FIG. 31 is an enlarged cross-sectional view of the end region of FIG. 30.

Each of the upper and lower arms 284, 286 comprises a slot 292, 290 near each arm end. Each slot is configured to receive straps 260 from the mask assembly 102, as shown in FIG. 2. In addition, the portion 398 of the semi-rigid headgear 380 covered by straps 260 is thinner than the corresponding arm 284, 286 in order to accommodate the thickness of the strap 260. For example, as shown in FIGS. 30 and 31, the semi-rigid headgear portion 398 is thinner than the arm 286. The portion 398 is dimensioned such that when the strap 260 is inserted into the slot 290 and tensioned, its thickness will not extend beyond the arm 286. By maintaining the strap 260 and portion 398 thickness less than the arm 286 thickness, the strap 260 does not irritate the user when worn.

Figure 52:
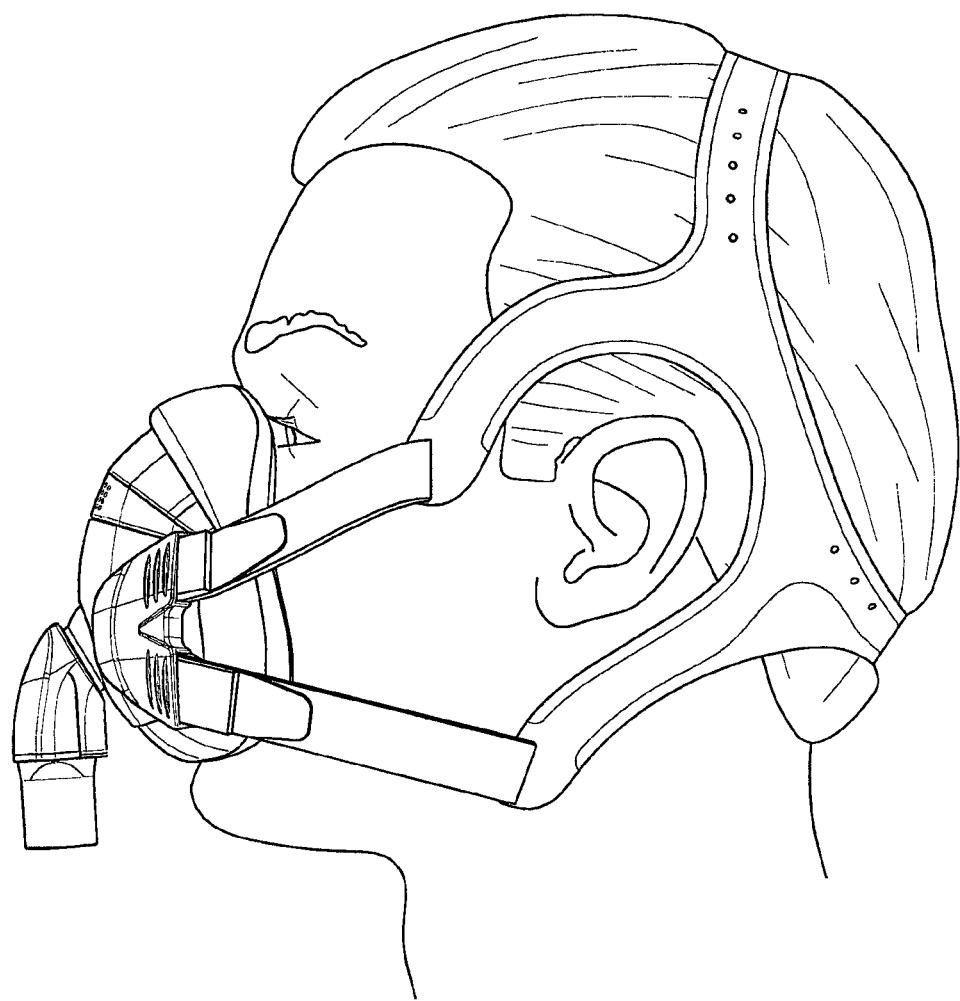
FIG. 52 is a side view of the backbone of FIG. 29 attached to a user's head.
Figure 53:
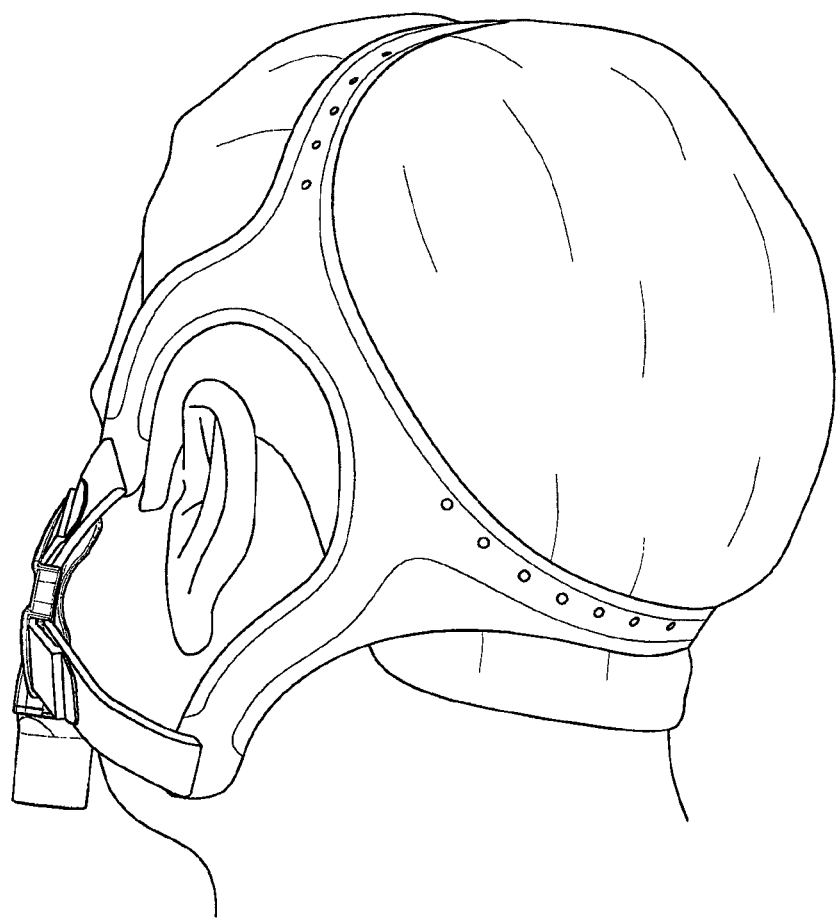
FIG. 53 is a rear perspective view of the backbone of FIG. 29 attached to a user's head.

In addition, the upper arms 284 are configured to extend downward from a location above the user's ear such that the adjustable top straps 260 extend no closer than about 10 mm to the user's eye when worn. The lower arm 286 is configured to be located off of the user's neck when the head is tilted up and down, and the termination point of the lower arm 286 is located generally below the user's ears so that the lower strap as attached to the lower arm 286 angles upwards from the termination point 290 to the mask assembly 120. In such a configuration, as illustrated in FIGS. 52 and 53, the lower straps and the upper straps form a triangle, and the space between the lower straps and the upper straps on the mask is smaller than the space between the lower straps and the upper straps on the headgear, thereby stabilizing the mask assembly 120 against upward and downward movements.

With reference again to FIG. 17, the elbow 222 connects to a conduit 300 through a disconnectable swivel assembly 302. As shown in the section view of FIG. 20, the elbow 222 comprises a stem 304 that comprises an inner wall 306 at the base. The inner wall 306 comprises a recess 308.

Figure 21:
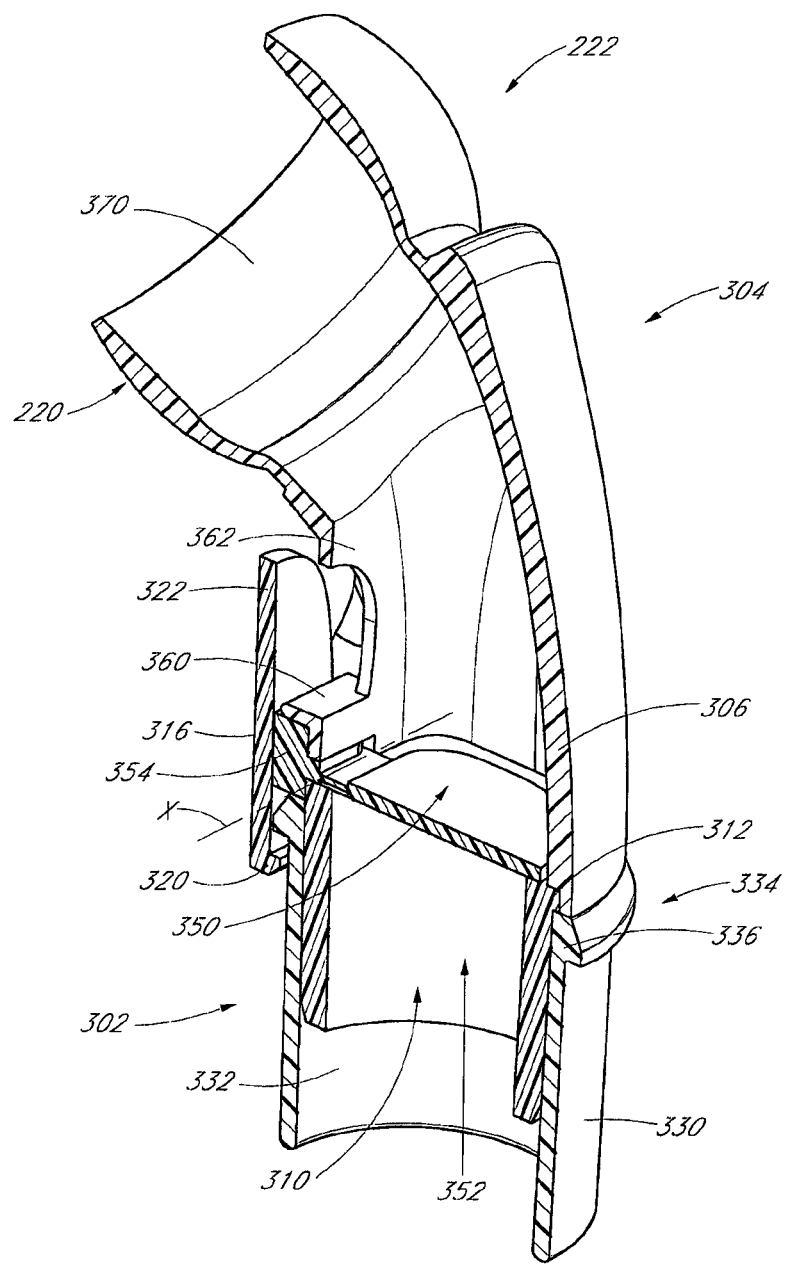
FIG. 21 is a sectioned perspective view of the connection port assembly of FIG. 17.

A sleeve 310 comprises a flange 312 that is received within the recess 308. The sleeve 310 can be secured into position within the elbow 222 using any suitable technique. The sleeve 310 comprises a generally cylindrical outer wall 314. The flange 312 comprises a section that extends outward to connect to a lever 316. Preferably, the flange 312 and the lever 316 are integrally formed. With reference to FIG. 21, the lever 316 includes a lower inwardly extending catch 320 and is capable of pivoting about the section that connects the lever 316 to the flange 312. Thus, pressing inward on an upper portion 322 of the lever 316 results in the catch 320 moving away from the generally cylindrical outer wall 314 of the sleeve 310.

A swivel 330 comprises a generally cylindrical inner wall 332. The inner wall 332 slides over the outer wall 314 of the sleeve 310 such that a sliding fit results between the swivel 330 and the sleeve 310. An upper portion 334 comprises a shoulder 336. The catch 320 of the lever 316 can secure the swivel 330 in axial position on the sleeve 310 by engaging with the shoulder 336. When the upper portion 322 of the lever 316 is depressed, the catch 320 moves away from the shoulder 336, which allows the swivel 330 to be removed from the sleeve 310.

Figure 20:
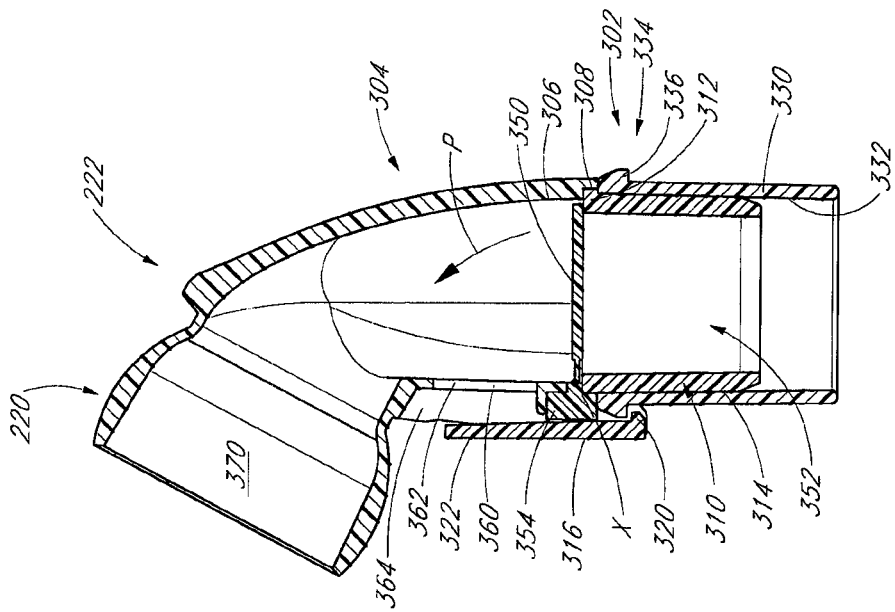
FIG. 20 is a sectioned side elevation view of the connection port assembly of FIG. 17.
Figure 19:
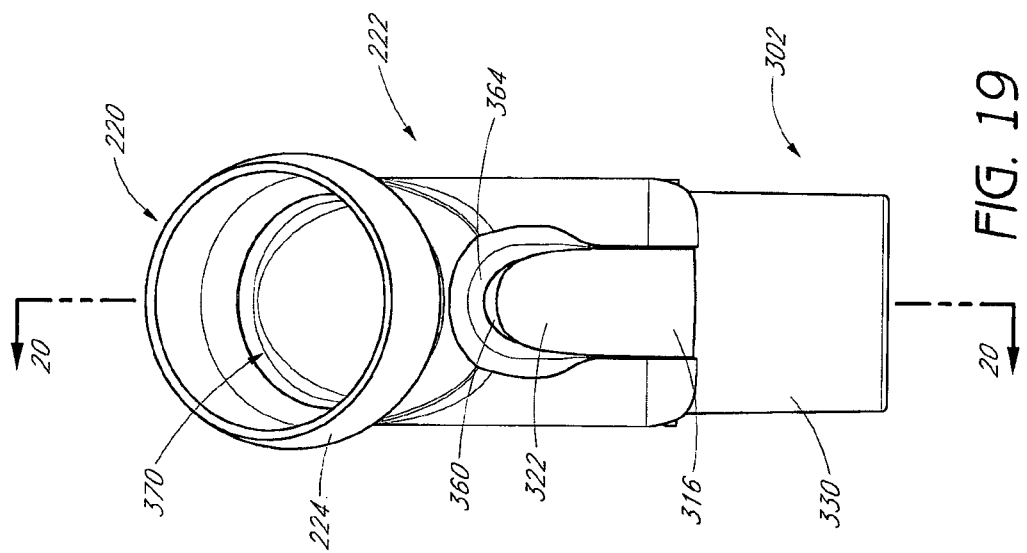
FIG. 19 is a rear elevation view of the connection port assembly of FIG. 17.

A flap 350 can be mounted between the stem 304 and the sleeve 310. In the illustrated configuration, the flap 350 extends into a flow channel 352 from a base 354 that is sandwiched between the stem 304 and the sleeve 310. The flap 350 can pivot upward (as shown in FIG. 20, see arrow P) about an axis X (see FIG. 21) away from the sleeve 310 such that flow from a positive pressure generator can continue generally unobstructed to the user through the interface 100. The flap 350 pivots downward into contact with the sleeve 310 to seal the flow channel 352 in the event that the positive pressure source stops providing a pressurized flow of air. In some configurations, the flap 350 will not fully contact the sleeve 310. In some configurations, the flap 350 will not seal the channel 352 when in the down position.

With reference to FIG. 21, a port 360 is defined through the elbow 222 at a location above the flap 350. The port 360 preferably is positioned along a portion of the elbow 222 that is in the vicinity of the axis X. In some configurations, the port 360 is positioned to be substantially shielded by the flap 350 from an inspiratory flow of air. In other words, as the air pivots the flap 350 away from the sleeve 310, the flap 350 is moved into a position that at least partially or completely covers the port 360.

In some configurations, the port 360 extends through a wall of the elbow 222 that comprises a generally planar inner wall 362. The generally planar inner wall 362 helps the flap 350 to generally seal the port 360 when the flap is moved upward away from the flange 312 of the sleeve 310.

In some configurations, the lever 316 overlies a majority of the port 360 such that the port 360 is generally obscured from view. As shown in FIG. 20, however, a gap 364 preferably surrounds at least a portion of the lever 316 such that a relatively free flow of air can pass through the port 360 when the flap 350 does not overly the port 360. In addition, in some configurations, the port 360 and the lever 316 are positioned on a same side of the elbow 222 as an opening 370 defined within the ball end 220, which opening is positioned within the mask assembly 102 when the connection port assembly 104 is assembled to the mask assembly 102. Advantageously, such a positioning places the port 360 in a position on the elbow 222 that faces the user. Such a location further obscures the port 360 from view during use, which results in a more aesthetically pleasing configuration. Moreover, because flow through the port 360 will be very infrequent, having the port 360 disposed toward the user will not cause any significant discomfort for the user.

While not shown, the elbow 222 also can comprise one or more bias flow vent holes. The bias flow vent holes preferably are positioned in a forwardly directed orientation such that any bias flow does not directly impinge upon the user.

Figure 49:
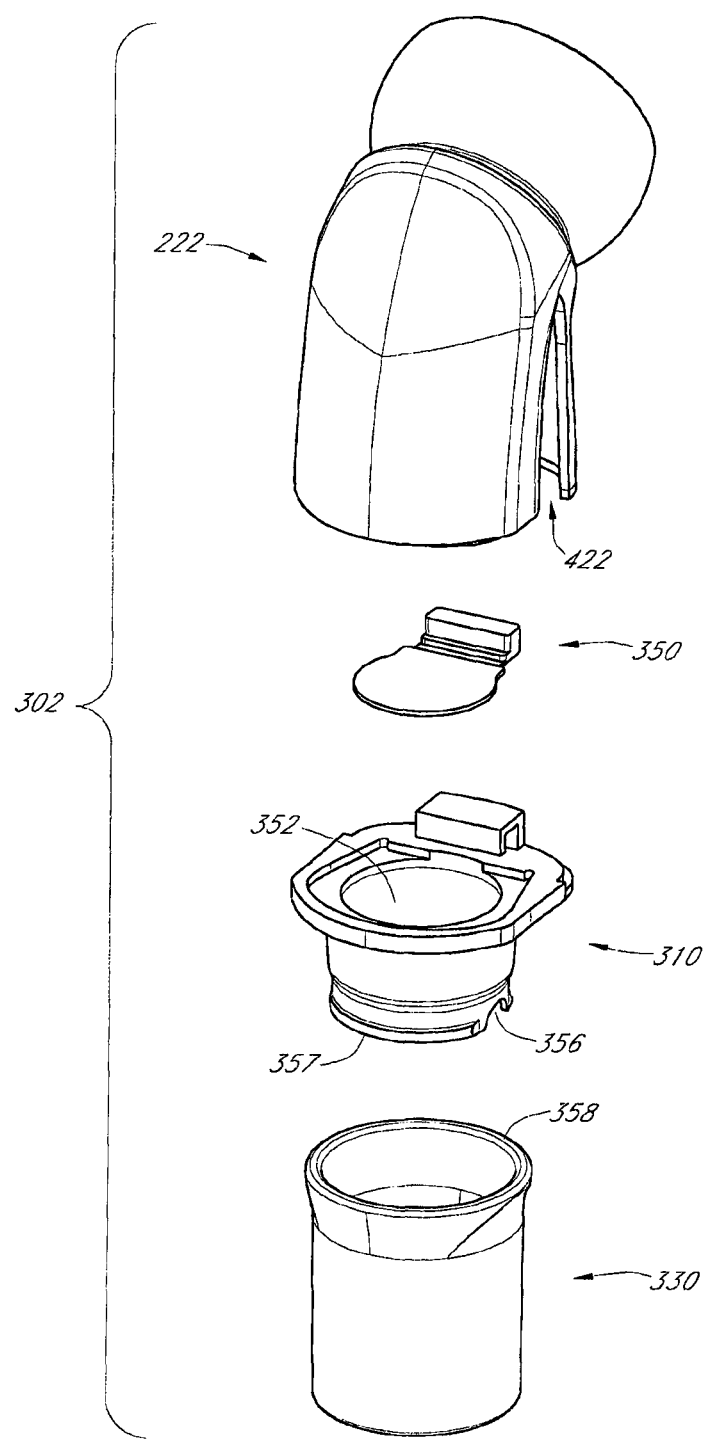
FIG. 49 is an exploded view of the swivel assembly of FIG. 48.
Figure 50:
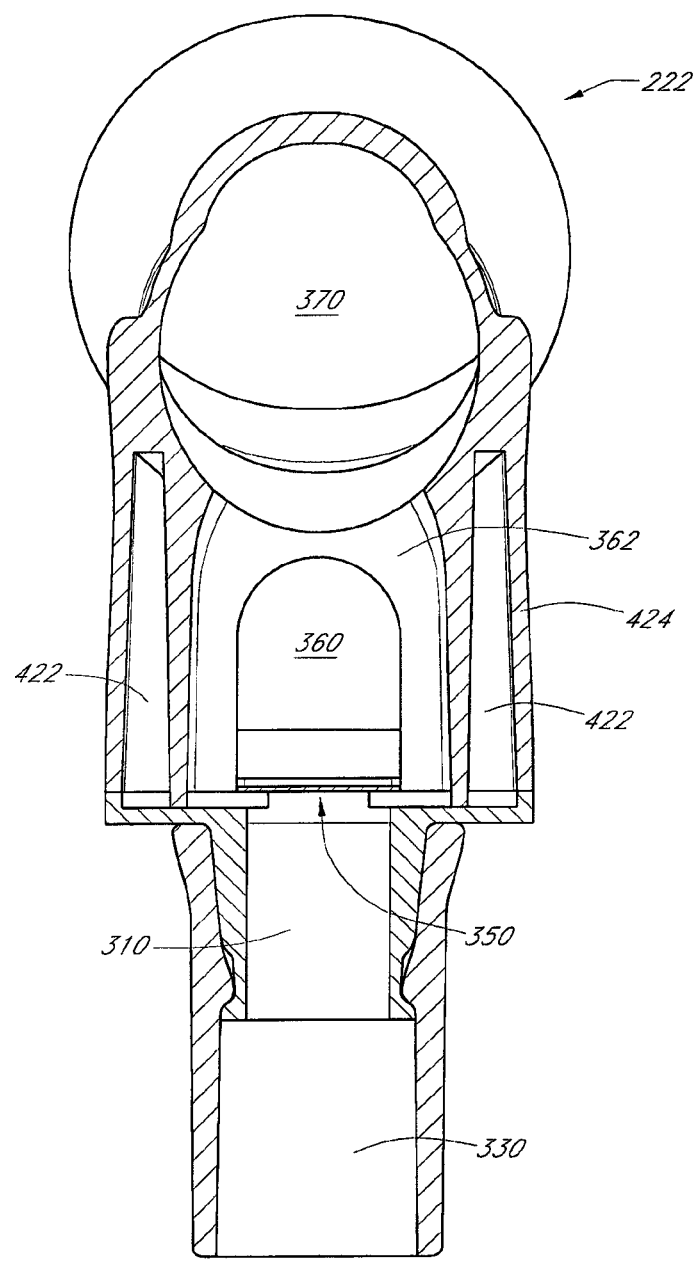
FIG. 50 is a cross-sectional view taken along line 50-50 of FIG. 48.
Figure 51:
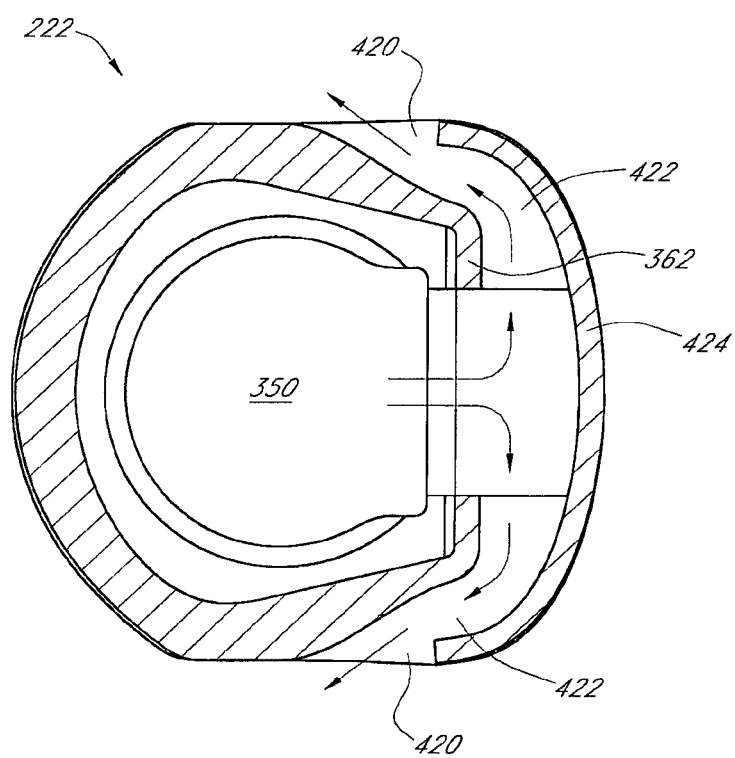
FIG. 51 is a cross-sectional view taken along line 51-51 of FIG. 48.

Another configuration of an elbow assembly 302 is illustrated in FIGS. 48-51. The elbow assembly 302 comprises an elbow 222, a sleeve, 310, and/or a swivel 330, as shown in FIG. 49. In some configurations, the elbow assembly 302 only includes the elbow 222 and sleeve and omits the swivel 330. The swivel may be permanently or removably attached to the sleeve 310 and elbow 222; in some configuration, the swivel 330 is integrally formed with the end of the delivery conduit. A flap 350 is positioned over the sleeve 310 such that it at least partially obstructs the sleeve's flow channel 352. The elbow assembly 302 functions similarly to the elbow assembly 302 of FIGS. 17-21; however, the elbow assembly 302 of FIGS. 48-51 provides the additional benefit of directing gases away from the patient when the flap 350 drops to its closed position (as shown in FIGS. 50 and 51).

With reference to FIG. 49, the sleeve 310 preferably comprises two or more cut out regions or recesses 356. The recesses 356 can have any suitable shape and, in the illustrated configuration, the recesses 356 comprise a semicircular configuration that extends upward into the sleeve 310. The sleeve 310 also comprises at least one bump 357, and preferably two or more bumps 357. Preferably, each of the bumps 357 extends around an arc of about 70 degrees. More preferably, each of the bumps 357 is generally centered between two recesses 356 and each of the bumps 357 extends about 70 degrees around an outer surface of the sleeve 310.

The swivel 330 preferably is generally cylindrical in configuration. As shown in FIG. 49, the swivel 330 has an inwardly extending ridge 358. The ridge 358 preferably encircles the entire inner surface. In some configurations, the ridge 358 can be interrupted. Preferably, however, the ridge 358 does not have any interruptions large enough to accommodate the entire bump 357 such that the ridge 358 and the bump 357 can cooperate to keep the swivel 330 mounted over the sleeve 310. When assembling the swivel 330 to the sleeve 310, the recesses 216 allow the bumps 220 to deflect inward such that the bumps 357 can slide over the ridge 358 and then snap back outward to secure the bumps 357 under the ridge 358.

The elbow 222 comprises openings 420 at its sides that are in fluid communication with an air venting channel 422. The air venting channel 422 is formed by the spacing between the elbow's inner and outer walls 362, 424, as shown in FIGS. 50 and 51.

When the flap 350 drops to its closed position, as shown in FIGS. 50 and 51, air exhaled from the user enters opening 370 of the elbow 222. The exhalation flows through the port 360 in the elbow's inner wall 362, and through the venting channel 422 until it exits the elbow 222 via the opening 420.

The configuration of FIGS. 48-51 provides a reduced overall length and improves product aesthetic by eliminating an unsightly hole positioned at the front of the elbow 222. In addition, the configuration of FIGS. 48-51 and improves patient comfort by preventing air from being directed towards the user. Instead, openings 420 direct air flow out of the sides of the elbow 222 and away from the patient.

Figure 54:
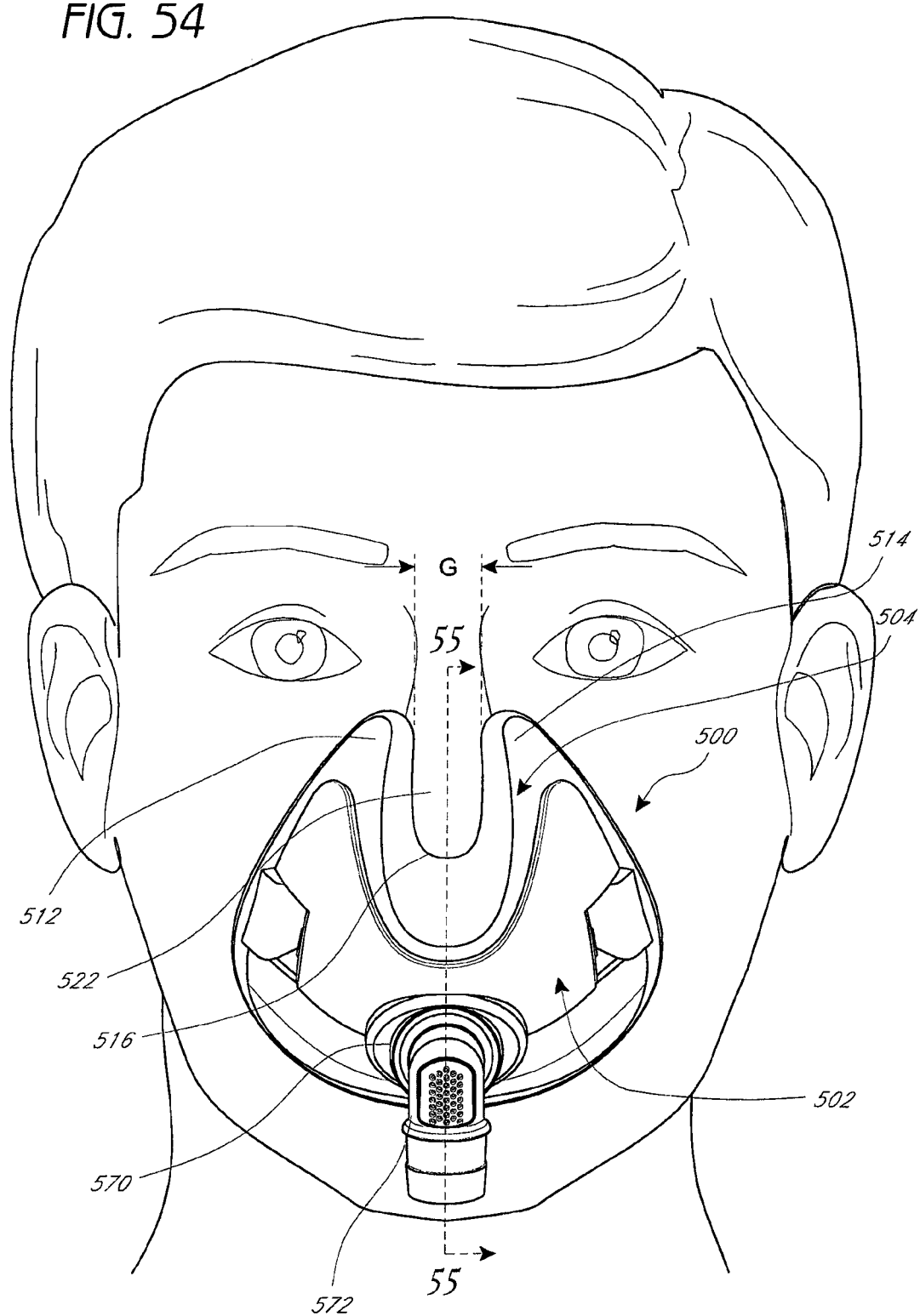
FIG. 54 is a front elevation view of a mask configuration positioned on a face of a user.

FIG. 54 illustrates a further mask configuration 500. The mask configuration 500 illustrated in FIG. 54 has been shown without any accompanying headgear assembly for clarity. Any suitable headgear assembly can be used with the mask configuration 500. For example but without limitation, any headgear assembly disclosed within this specification can be used with the mask configuration 500.

With continued reference to FIG. 54, the illustrated mask configuration 500 generally comprises a mask base 502 and a mask seal 504. The mask base 502 preferably is more rigid that the mask seal 504. For example, in one configuration, the mask base 502 is formed of a polycarbonate material while the mask seal 504 is formed of a silicone material. Other suitable materials also can be used for each of the mask base 502 and the mask seal 504.

The mask seal 504 can be secured to the mask base 502 in any suitable manner, including but not limited to any of those disclosed within this specification. For example but without limitation, with reference to FIG. 55, a flange 506 of the mask seal 504 can be inserted into a groove 510 provided along a periphery of the mask base 502. In some configurations, at least a portion of the mask seal 504 can underlie at least a portion of the mask base 502. In some configurations, a more rigid member, such as a clip for example but without limitation, or a more rigid portion can be integrally formed with the mask seal 504 and the more rigid member or portion can be used to connect the mask seal 504 with the mask base 502.

Figure 62:
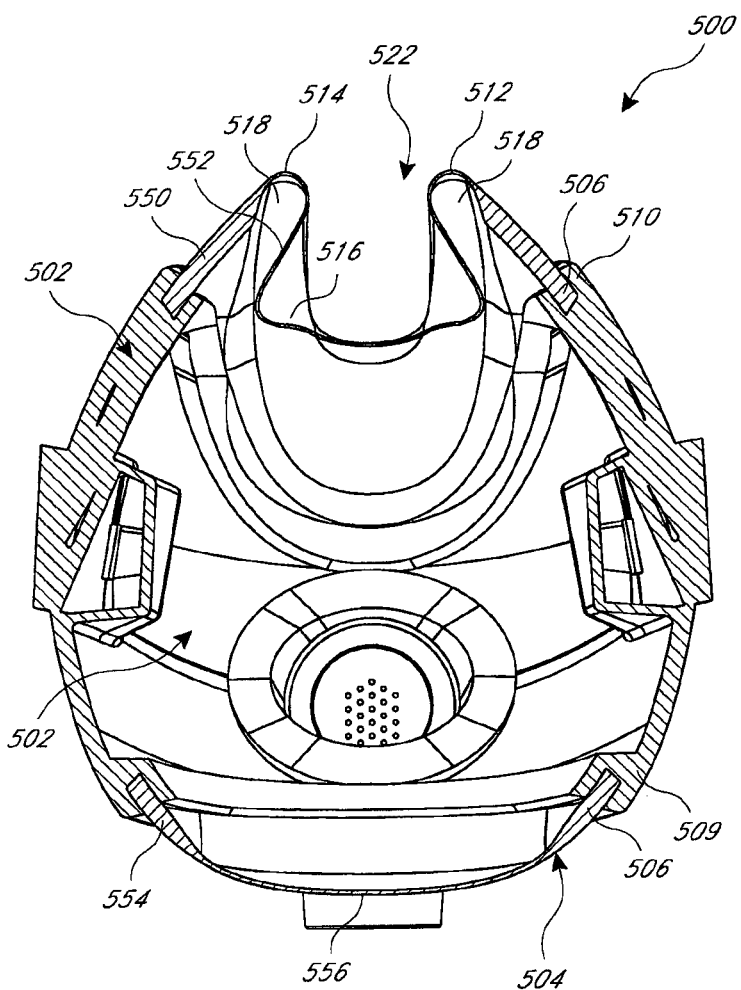
FIG. 62 is a section taken along the line 62-62 in FIG. 61.

As shown in FIG. 54, the mask seal 504 preferably comprises a first paddle or wing 512 and a second paddle or wing 514. Preferably, the first paddle 512 and the second paddle 514 are hollow. As shown in FIG. 62, for example but without limitation, a pocket 518 can be defined within each of the first paddle 512 and the second paddle 514. The pockets 518 are in fluid communication with a chamber 520 defined by the mask seal 504. Accordingly, pressure within the chamber 520 defined by the mask seal 504 can be used to inflate the pockets 518 of the first and second paddles 512, 514.

Figure 55:
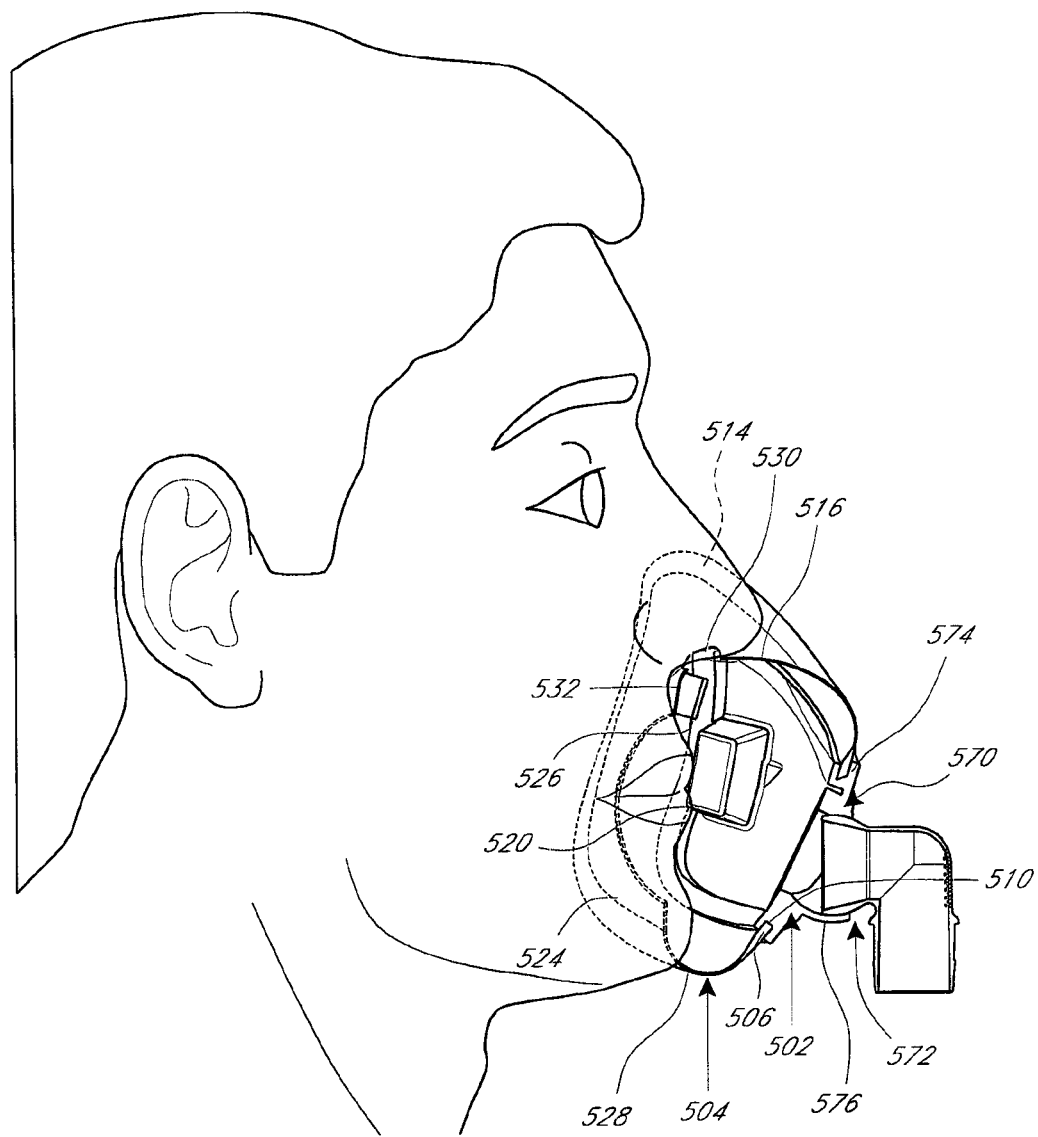
FIG. 55 is a sectioned view of the mask configuration taken along the line 55-55 in FIG. 54.

With reference to FIG. 55, which is a section through the mask assembly 500 taken along the line 55-55 in FIG. 54, the mask seal 504 also preferably comprises an upper surface 516. The paddles 512, 514 extend generally upward from the upper surface 516. Preferably, the pockets 518 defined within the paddles 512, 514 extend above the upper surface 516. More preferably, the pockets 518 are defined on lateral portions such that the pockets 518 extend upward along the lateral sides of the nose. By extending the pockets 518 above the upper surface 516 and along the lateral sides of the nose, a ballooning effect can be used to greatly improve an inwardly-directed ballooning effect to provide an enhanced seal against an outer surface of the nose. Together, the upper surface 516 and the paddles 512, 514 enable an improved seal with a nose to reduce or eliminate the occurrence of pressure-related skin problems. More particularly, because the illustrated configuration does not traverse from left to right the nose in a nasal bridge region, the illustrated mask configuration 500 eliminates the occurrence of pressure-related skin problems along the bridge of the nose.

With reference again to FIG. 54, the first and second paddles 512, 514 together with the upper surface 516 define a valley 522. The valley 522 preferably defines a forwardly disposed opening. In other words, the illustrated valley 522 defines a passage that extends from front to rear of the illustrated mask seal 504. Moreover, the valley 522 preferably accommodates a full size range of users because the nose is received in a region that is generally open from front to rear such that at least a tip of the nose can protrude through the forward opening defined by the valley 522.

As illustrated in FIG. 54 and FIG. 55, the valley 522 preferably accommodates at least a tip of a nose of the user such that the upper surface 516 underlies the nose. Preferably, when viewed from the front, a gap G of between about 5 mm and about 30 mm is defined between the paddles 512, 514. More preferably, the gap G between the paddles 512, 514 is between about 10 mm and about 25 mm. In one configuration, the gap G is about 15 mm. The upper surface 516, by underlying the nose, defines a primary seal between the mask configuration 500 and the face of the user.

Figure 70:
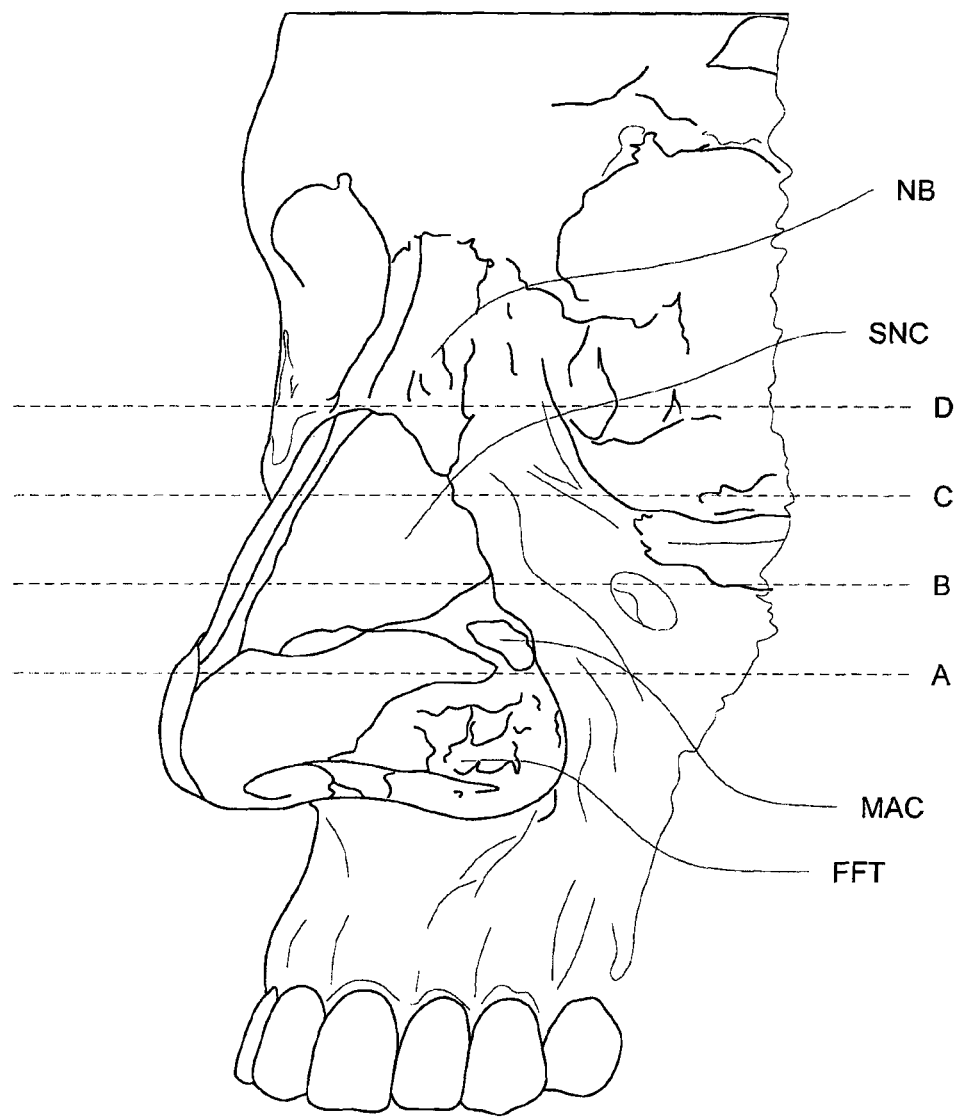
FIG. 70 is a perspective view of a face of a user.

The paddles 512, 514 preferably extend upward to some extent along the lateral sides of the nose. In some configurations, the paddles 512, 514 extend upward to a greater extent than does the sealing upper surface 516. The paddles 512, 514 can be shorter than illustrated or can be longer than illustrated. By extending upward above the upper surface 516 and by extending upward alongside the nose, the paddles 512, 514 create a secondary seal with the face of the user. Preferably, the paddles 512, 514 are adapted to extend upward to at least the fibro-fatty tissue FFT of the alar of the nose, which is represented in FIG. 70 by line A. More preferably, the paddles 512, 514 are adapted to extend upward beyond the fibro-fatty tissue FFT into the region of the minor alar cartilage MAC, which is represented in FIG. 70 by line B. Even more preferably, the paddles 512, 514 are adapted to extend upward beyond the minor alar cartilage MAC into the region of the lateral processes of the septal nasal cartilage SNC, which is represented in FIG. 70 by line C. In some configurations, the paddles 512, 514 extend upward with at least a portion of the paddles 512, 514 extending upward beyond the nasal bone NB (i.e., the bridge) of the nose of the user, which is represented in FIG. 70 by line D. In some configurations, the paddles 512, 514 are adapted to extend along lateral portions of the lateral margins of the nose.

The paddles 512, 514 preferably are configured to extend along a surface of the face generally adjacent to the nose. As shown in FIG. 55, when viewed from the side, the paddles 512, 514, in some configurations, are generally triangular, or fin-shaped. Such a configuration provides a large surface area for sealing the paddles 512, 514 against the side of the nose while also having a reduced side profile to reduce the likelihood of the paddles 512, 514 being forced away from the nose by contact during sleeping, such as when rolling from side to side. While the illustrated configuration comprises two distinct paddles 512, 514, the paddles 512, 514 can be connected together to generally enclose at least a portion of the nose.

Figure 57:
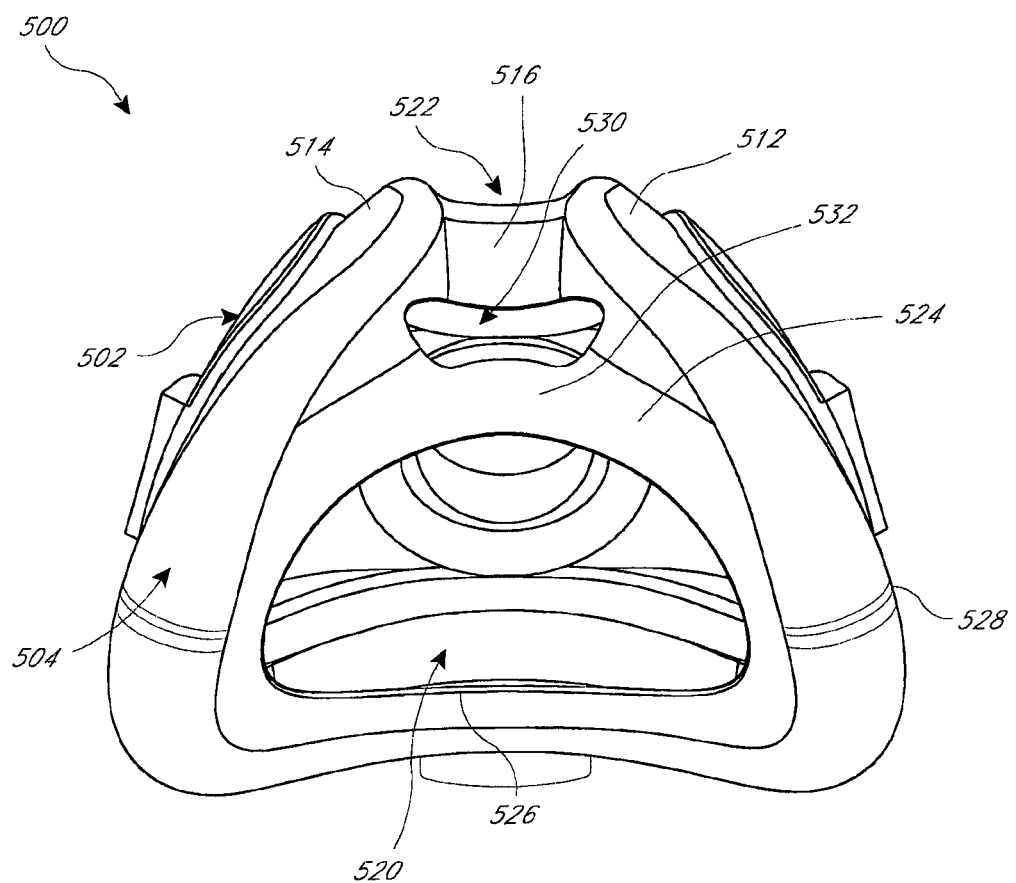
FIG. 57 is a rear perspective view of the mask configuration of FIG. 54.

As shown in FIGS. 55 and 57, the upper surface 516 extends rearward (i.e., toward the face of the user or away from the mask base 502) to a lip 524. The upper surface 516, in the vicinity of the lip 524, underlies the nose and preferably seals against the nose while the lip 524 can seal against the upper lip region of the face just above the vermilion border.

As described above, the upper surface 516 of the mask seal 504 extends rearward to connect with or to define the lip 524. With reference to FIG. 57, the lip 524 preferably encircles an opening 526 into the chamber 520 defined within the mask seal 504 and connects with or defines a portion of a sidewall 528 of the mask seal 504.

Figure 58:
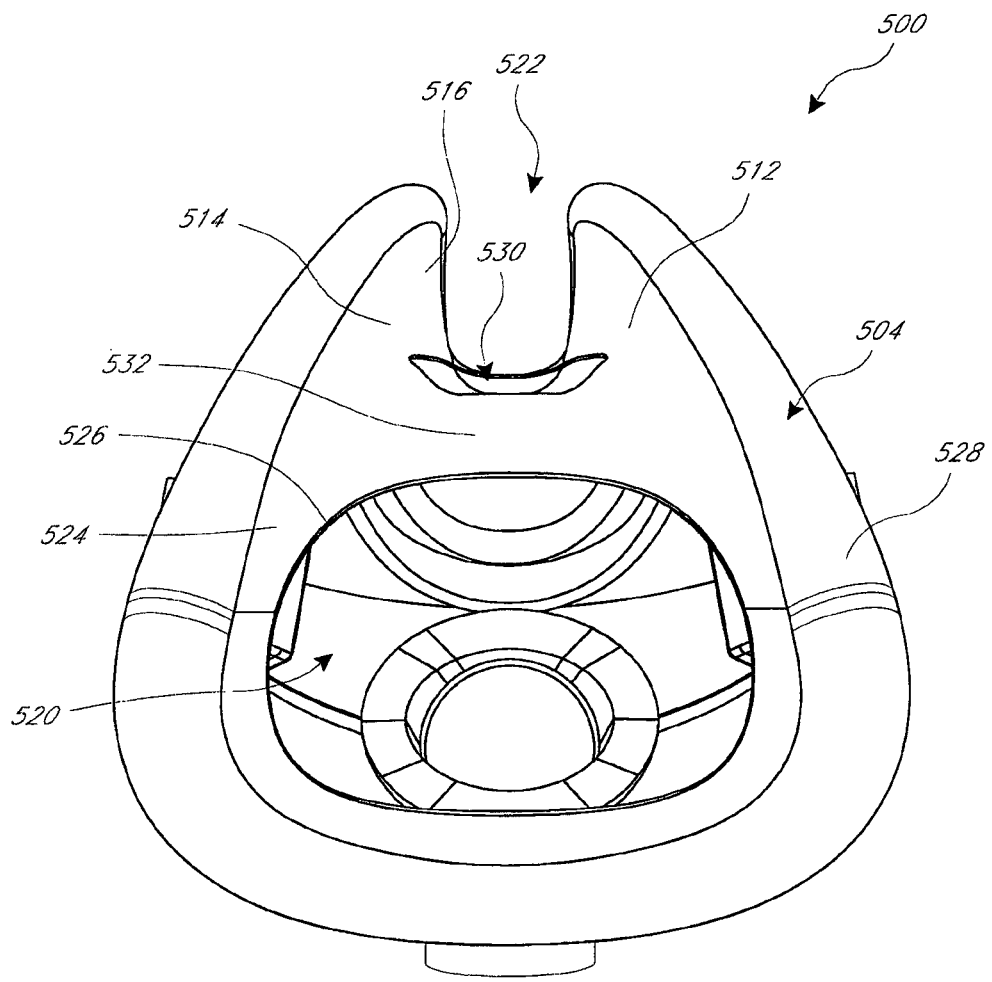
FIG. 58 is a rear view of the mask configuration of FIG. 54.
Figure 59:
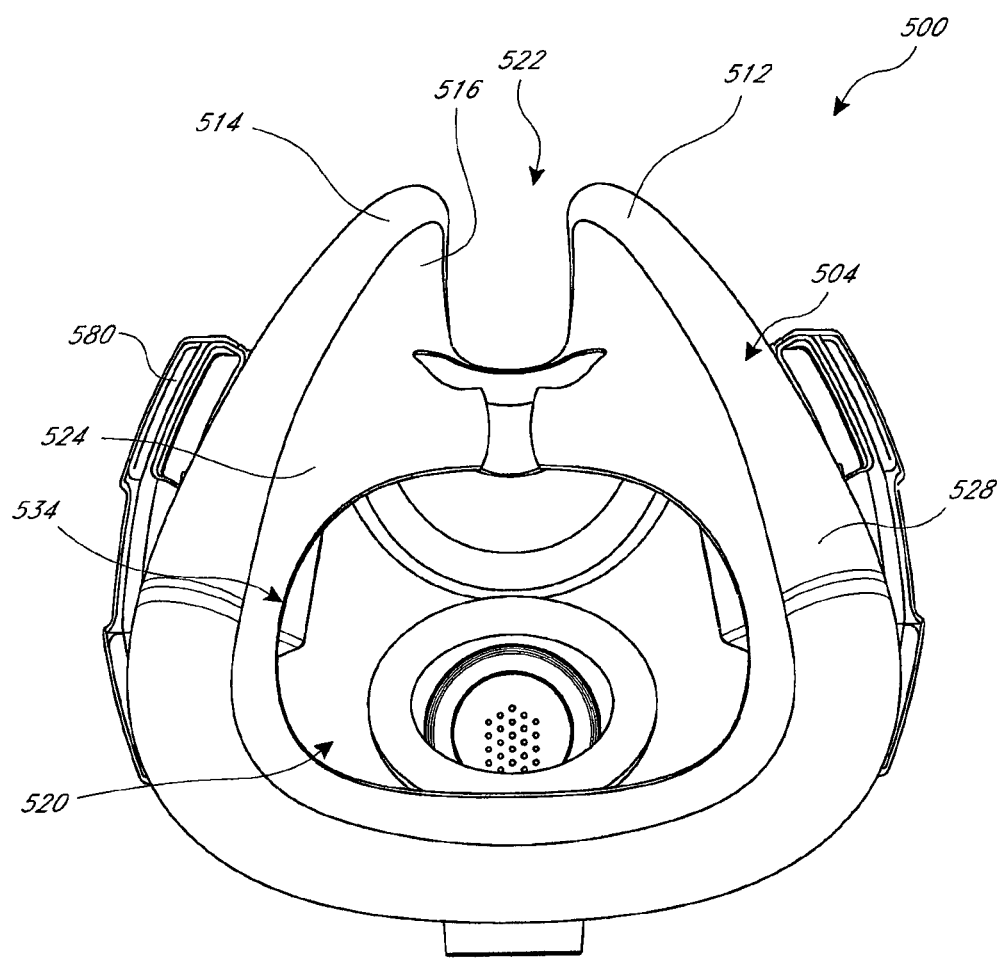
FIG. 59 is a rear view of a mask configuration having a different mask seal relative to the mask configuration of FIG. 54.

As shown in FIG. 57, the upper surface 516 comprises at least a portion of one or more nasal opening 530. The nasal opening 530 can be positioned laterally between the paddles 512, 514 and can be defined through the upper surface 516 to provide communication with the chamber 520 of the mask seal. The nasal opening 530 preferably opens in a substantially upward direction while the oral opening 526 preferably opens in a substantially rearward direction. In the illustrated configuration, the mask seal 504 comprises the oral opening 526 and the separate nasal opening 530. While other configurations having combined nasal and oral openings (e.g., as shown in FIG. 59), the separate openings 526, 530 as shown in FIG. 58 can be helpful and instructive to users in learning how to properly wear the illustrated mask configuration 500.

The upper surface 516 preferably is substantially flat and generally does not protrude upward into the nasal cavities. Preferably, the nasal opening 530 does not extend up into the nasal vestibule, which is the most anterior part of the nasal cavity of the user. More preferably, the nasal opening 530 extends under, but not up into, the nasal vestibule. The nasal opening 530 preferably is generally flush with the upper surface rather than extending upward into some other superstructure. In some configurations, the upper surface 516 could comprise one or more nasal prong, one or more nasal pillow or the like. In the illustrated configuration, the upper surface 516 is supported by the paddles 512, 514 and defines a somewhat arched link to the top ends of the paddles 512, 514. The arched link supports the upper surface 516 by suspending it from a higher pivot point, which allows the nasal sealing surface defined along the upper surface 516, along with the surrounding geometry, to stretch, move and/or contort to noses having differing widths, depths and other geometrical features.

As illustrated in FIG. 57, the lip 524 can define a band 532 that is disposed between the oral opening 526 and the nasal opening 530. As shown by comparing the embodiment shown in FIG. 58 with the embodiment shown in FIG. 59, it is possible to omit the band 532 and a portion of the upper surface 516 that extends between the band 532 and the nasal opening 530 such that the oral opening 524 and the nasal opening 530 merge into a combined oral nasal opening 534.

Figure 60:
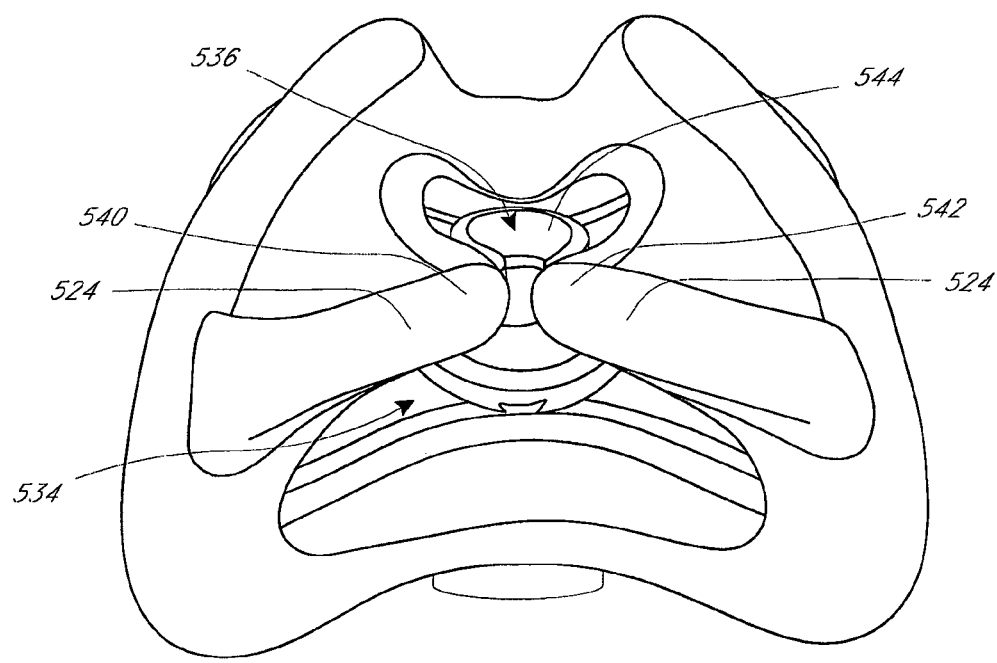
FIG. 60 is a rear perspective view of another mask configuration having a different mask seal relative to the mask configurations of FIGS. 54 and 59.

As shown in FIG. 60, in some configurations featuring the combined oral-nasal opening 534, the two sides of the lip 524 can be interconnected with a clip 536. The illustrated clip 536 generally comprises a shape like an omega (Ω). As illustrated in FIG. 60, the clip 536 can comprise a first foot 540 and a second foot 542 that are interconnected by a body 544 of the clip 536. The body 544 can have any suitable shape and configuration. For example but without limitation, while the illustrated body 544 comprises a U-shape or C-shape, the body 544 could be V-shaped or the like. In some configurations, the clip can be formed of Silicone or any other suitable material.

With reference again to FIG. 57, the sidewall 528 can extend vertically higher than the upper surface 516. Preferably, the sidewall 528 connects to the lip 524, generally encircles the oral opening 526 and extends up to the sides of the nose of the user in the region of the first and second paddles 512, 514. The sidewall 528, because it extends upward beyond the band 532 in the illustrated configuration, provides a taller platform when the mask configuration 500 is viewed from the side (e.g., FIG. 61), which enhances the balancing of the mask seal 504 and which reduces rolling movement of the mask configuration 500 about a generally horizontal axis.

The band 532, as shown in FIG. 57, extends between the oral opening 526 and the nasal opening 530. Thus, the illustrated band 532 connects the sidewall 528 at a location between the two openings 526, 530. In some configurations, the clip 536 connects the sidewall 528 at a location between the two portions that define the combined oral-nasal opening 534. In other configurations, any suitable connecting structure can be used that generally connects the sidewall 528 from opposing sides of the openings 526, 530 or opening 534. The location of the connecting structure can be between an upper extreme and a lower extreme of the openings 524, 530 or the opening 534. In other words, in some configurations, a first lateral side of the sidewall 528 is connected to a second lateral side of the sidewall 528 in a region that bridges the combined opening 534.

By connecting the lateral portions of the sidewall 528, the lateral portions of the sidewall 528 effectively are tethered together. Tethering together the lateral portions of the sidewall 528 improves the stability of the mask seal 504 during sleeping, for example, when the user may roll from one sleeping position to another (e.g., from back to side), which can cause lateral movement of the mask configuration 500 due to the mask being pulled by the CPAP tube or due to contact with the pillow. Moreover, due to the flexibility of the tether (e.g., the band 532 or the clip 536), a wider range of facial profiles can be accommodated. For example, flatter face profiles can be accommodated while still allowing the seal to self-adjust to the more protruded face profiled prevalent in European populations.

The tethering provided by the band 532 or the clip 536, for example, also can help with rolling of the sidewall 528. With reference to FIG. 57, because the band 532 extends laterally and connects to the sidewall 528, forward depression of the band 532 will cause inward rolling of the sidewall 528, which enhances the conformability of the mask seal 504 to a variety of facial geometries. In addition, as the upper surface 516 is depressed downwards, the first and second paddles 512, 514 pivot inwards such that the gap G at the top of the paddles 512, 514 decreases relative to the gap G at the base of the paddles 512, 514.

With reference now to FIGS. 62-65, the illustrated mask seal 504 comprises a variety of rigidities or variety of degrees of flexibility to further enhance the conformability of the mask seal 504, which enhanced conformability helps to reduce leaks when the mask configuration 500 is used in positive pressure applications.

An upper portion of the illustrated mask seal 504 comprise a more rigid support region 550 and ballooning or flexing regions 552. In the illustrated configuration, the support region 550 is more rigid because of thicker cross-sections while the ballooning or flexing regions 552 are less rigid because of thinner cross-sections. Other techniques also can be used to vary the rigidity or flexibility. For example, material choices, material blends or the like can be adjusted to adjust the rigidity or flexibility of different regions of the mask seal 504. By way of further example, some regions can be supported by the mask base 502 or other components to stiffen the region as desired.

The illustrated more rigid support region 550, which is best illustrated in FIG. 64, can be located on a forward-facing surface of the first and second paddles 512, 514. The more rigid support region 550 also is a portion that includes the flange 506 of the mask seal 504 that connects to the groove 510 of the mask base 502. The support regions 550 overlie the ballooning or flexing regions 552 in the illustrated configuration. The illustrated configuration is desired to help control the ballooning and flexing of the ballooning or flexing regions 552 such that the ballooning action can be better directed toward the user.

With continued reference to FIGS. 63-65, in addition to the support regions 550 and the ballooning or flexing regions 552, the illustrated mask seal 504 also comprises lower corner reinforcements 554 and a flexing chin region 556. As with the support regions 550 and the ballooning or flexing regions 552, the corner reinforcements 554 are stiffer than the flexing chin region 556. The stiffer corner reinforcements 554 help control and/or direct ballooning of regions of the mask seal 504 while the more flexible chin region 556 can more easily deform to accommodate users having a wide variety of facial geometries.

As illustrated, the lower corner reinforcements 554 extend downward at or just below the vertical location of the upper surface 516 and the lower corner reinforcements wrap inward toward a generally vertical center plane that generally bisects the mask seal 504. In addition, in the illustrated configuration, the lower corner reinforcements are positioned along the sidewall 528 of the mask seal 504.

The illustrated chin region 556 is positioned between the lower corner reinforcements. Preferably, the chin region 556 also wraps over at least a portion of the sidewall 528. Moreover, the flexible chin region 556 preferably extends upward and around at least a portion of the lip 524 that defines the opening 526 into the chamber 520 of the mask seal 504. In the illustrated configuration, the flexible chin region 556 extends vertically upward to substantially the same extent as the lower corner reinforcements 554. In this manner, the lower corner reinforcements 554 can reinforce the lateral portions of the flexible chin region 556.

Further, in the illustrated configuration, the mask seal 504 comprises a forward-facing stiffener panel 560. The stiffener panel 560 generally encircles a region that will mate with the mask base 502. Because the stiffener panel 560 encircles the mating region, the connection to the mask base 502 can be made more stable.

In some embodiments, the thicknesses are related to each other as follows: the flexing regions 550<the chin region 556<lower corner reinforcements 554<stiffener panel 556<support region 550. In some embodiments, the flexing region 550 has a thickness of between about 0.3 mm and about 1.25 mm, and preferably about 0.8 mm, the chin region 556 has a thickness of about 0.5 mm, the lower corner reinforcements have a thickness of about 1.25 mm, the stiffener panel 560 has a thickness of about 2.0 mm and the support region 550 has a thickness of about 2.5 mm. Preferably, the thicker portions (e.g., the support regions 550) of the mask seal 504 oppose the portions having the thinner thicknesses (e.g., the flexing regions 552). In some configurations, at least a portion of the thickest portion (e.g., the support region 550) overlies at least a portion of the thinnest portion (e.g., the flexing regions 552). Such configurations enable ballooning in a desired direction (i.e., toward the face of the user). Preferably, a transitional framework 558 connects the various regions 550, 552, 554, 556.

The thinner cross sections of the flexing region 552 and the chin region 556 provide soft and flexible surfaces that are adapted to contact the face of the user. Advantageously, the thinner cross section of the flexing region 552 allows that shape defined by the valley 522 to stretch, move and deform such that a larger portion of the population can use the same mask. Preferably, the stretching, moving and deforming accommodates a large range of nose widths. Similarly, the thinner cross section of the flexing region 552 allows the shape of the chin cup region of the mask seal 504 to stretch, move and deform. In other words, the thinner cross sections of one or more of the flexing region 552 and the chin region 556 enable the mask seal 504 to conform to a very wide variety of facial geometries.

As described above and with reference again to FIG. 55, the mask base 502 features a groove 510 that preferably is secured to the flange 506 of the mask seal 504. In some configurations, the mask base 502 can overlie at least a portion of the thicker stiffener panel 560 and/or at least a portion of the support regions 550. By overlying those portions of the mask seal 504, the mask base 502 can reinforce those regions.

With reference still to FIG. 55, the mask base 502 comprises a central opening 570 that receives a connector 572. The connector 572 and the central opening 570 can have any suitable configuration, including but not limited to any configuration described within this specification. Only a portion of the connector 572 is shown in FIG. 54. Other styles of connectors 572 also can be used.

The central opening 570 can be defined by a wall 574 that comprises a contoured inner surface. The contoured surface of the wall 574 can be radiused to receive a ball end 576 of the connector 572, which can comprise a swiveling elbow. The ball end 576 has a contoured surface that can be snap fit into the contoured surface defined by the wall 574. The connection between the two contoured surfaces allows the surfaces to slide relatively freely with each other such that the position of the swiveling connector 572 can be easily changed relative to the mask base 502. In some configurations, the swiveling connector 572 could be configured for rotation or swiveling without having a ball joint configuration.

The illustrated mask base 502 also comprises one or more strap connections 580 (see FIG. 59). The strap connections 580 can have any suitable configuration, including but not limited to any structures that connect to clips or the like described within this specification. For example, the illustrated mask base 502 comprises at least two pockets 582.

Figure 56:
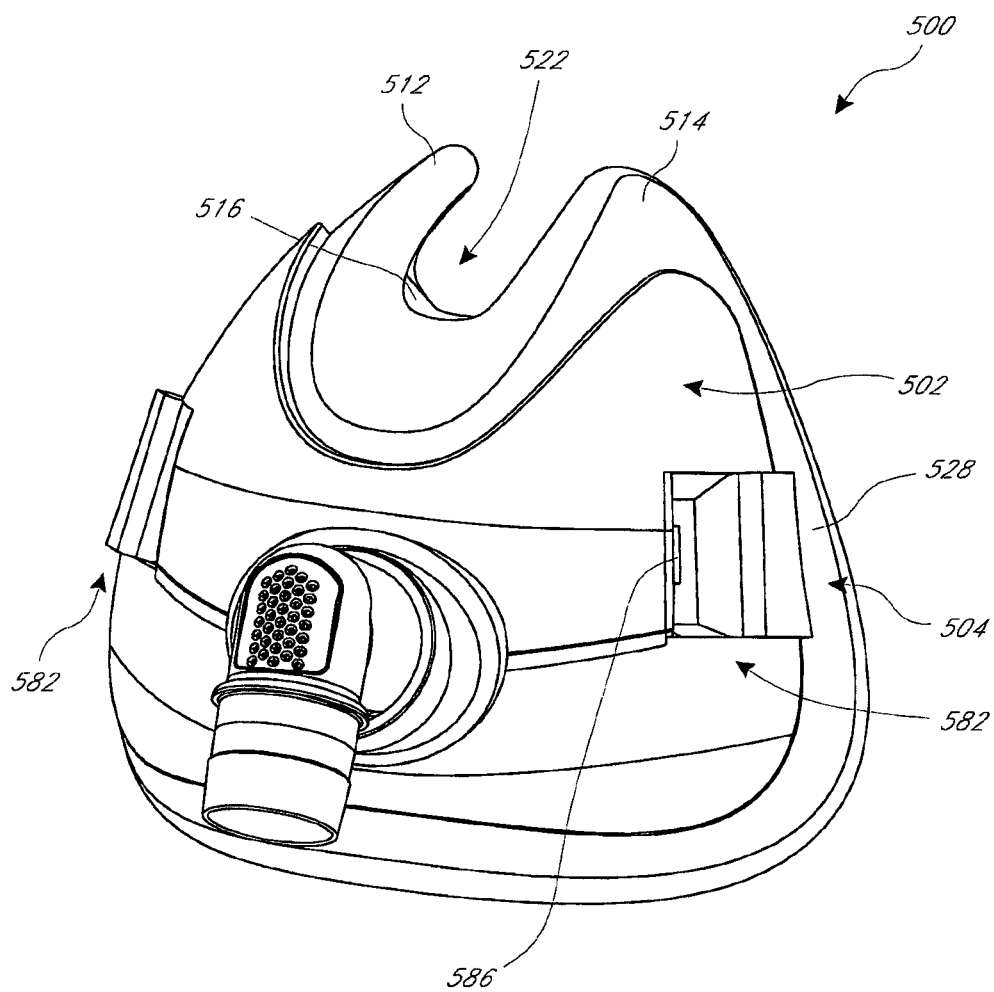
FIG. 56 is a perspective view of the mask configuration of FIG. 54.

The pockets 582 recede into the mask base 502 and protrude rearward from the mask base 502, as shown in FIG. 56. The illustrated pockets 582 are formed such that one pocket 582 is formed on each lateral side of the mask base 502. The pockets 582 can be positioned to be symmetrical relative to the central generally vertical plane, which plane substantially bisects the mask base 502. In some configurations, as shown in FIG. 56, the pockets 582 have an enlarged vertical dimension relative to a transverse or lateral dimension.

Figure 61:
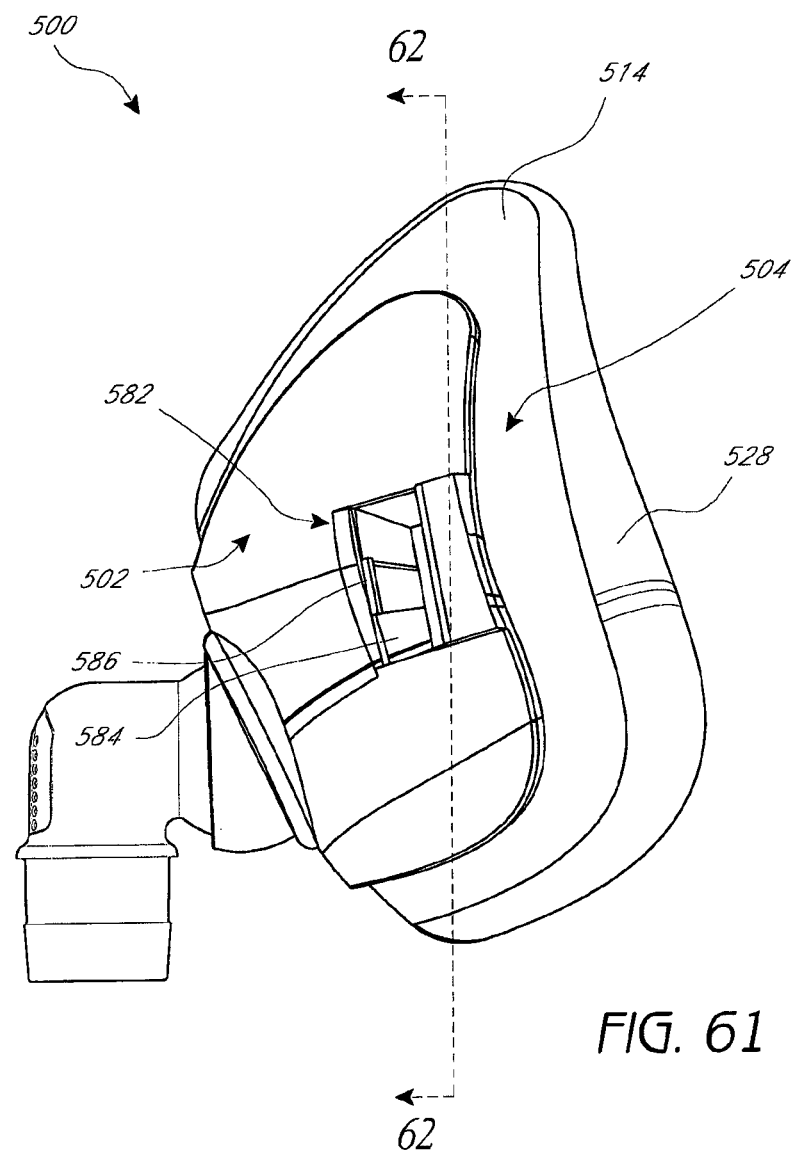
FIG. 61 is a side elevation view of the mask configuration of FIG. 54.

In the illustrated mask base 502, the laterally inward portion of each pocket 582 comprises a support wall 584, which is best shown in FIG. 61. The support wall 584 is positioned toward the center plane. Each of the pockets 582 is configured to receive a clip such as the clip 252 that is shown in FIG. 22, for example but without limitation. Once the clip 252 is installed within the pocket 582, the support wall 584 helps to limit rotation of the clip 252 relative to the pocket 582. Moreover, the large vertical dimension helps users to locate the pocket 582 with the clip 252 during installation.

With continued reference to FIG. 61, each of the pockets 582 preferably comprises a tab 586 that can engage with the interlock feature 264 of the associated clip 252. Other manners of interlocking the clip 252 with the pocket 582 also can be used. Moreover, any other suitable manner of securing the mask base 502 or the mask seal 504 to a headgear assembly 600 (see FIGS. 67-69) can be used.

Figure 66:
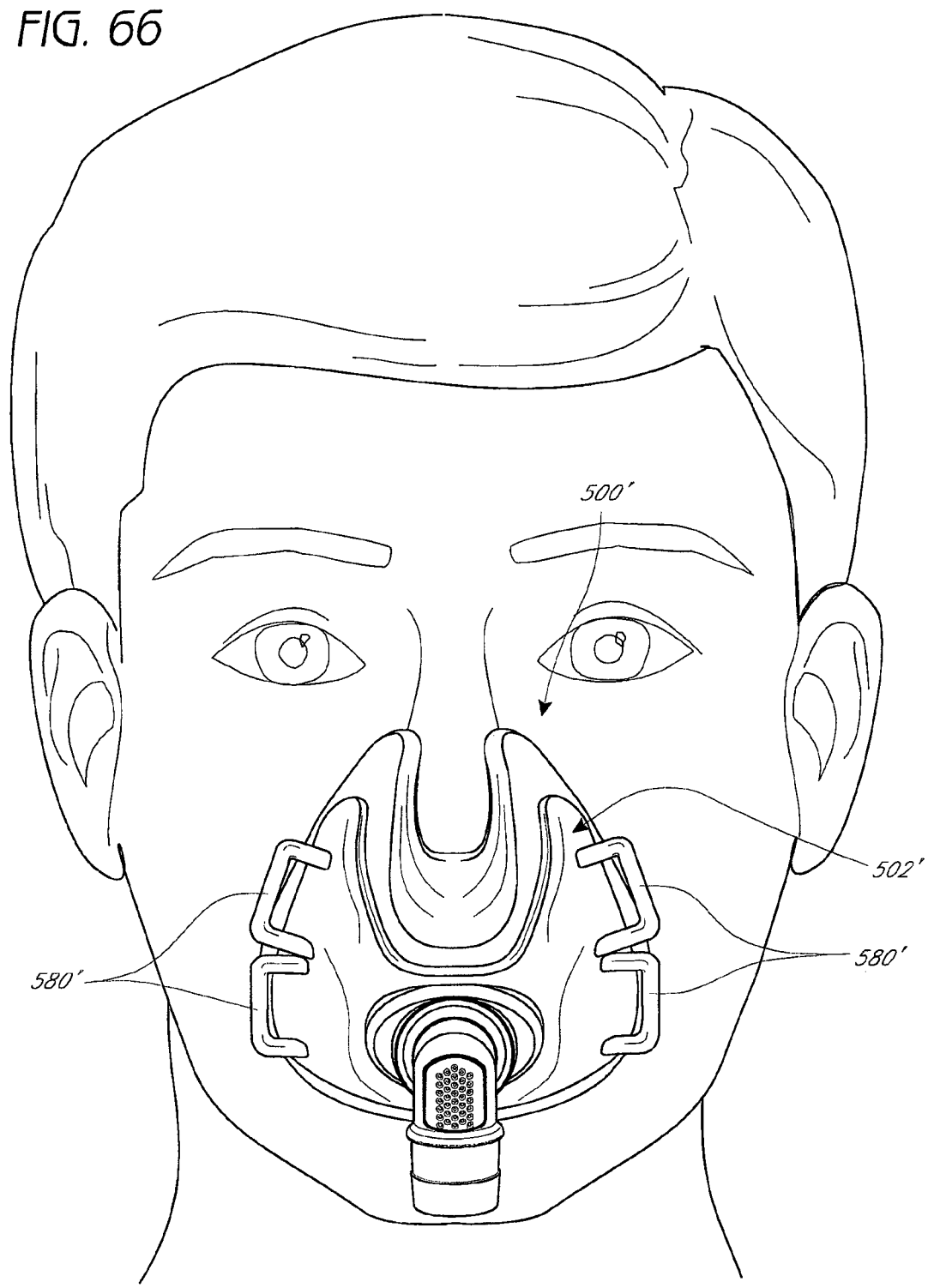
FIG. 66 is a front view of another mask configuration.

With reference now to FIG. 66, a further mask configuration 500' shows another style of strap connection but otherwise is the same as the mask configuration 500 shown and described with reference to FIGS. 54-65. The illustrated mask base 502' comprises four strap connections 580'. As shown in FIG. 66, in the illustrated configuration, the strap connections 580' have two connections 580' positioned on each lateral side of the mask configuration 500'. The illustrated strap connections 580' comprise loops through which straps 602 from any suitable headgear assembly 600 can be threaded and/or to which the straps 602 can be secured.

Figure 67:
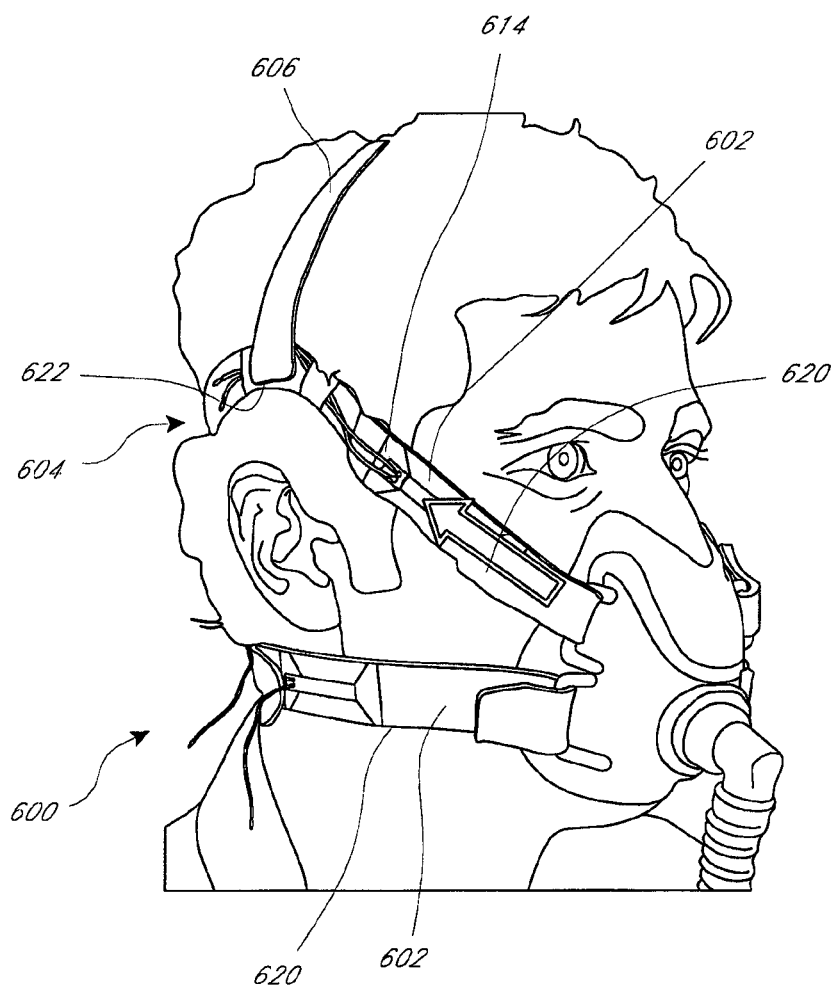
FIG. 67 is a perspective view of the mask configuration of FIG. 66 with a headgear assembly attached.
Figure 68:
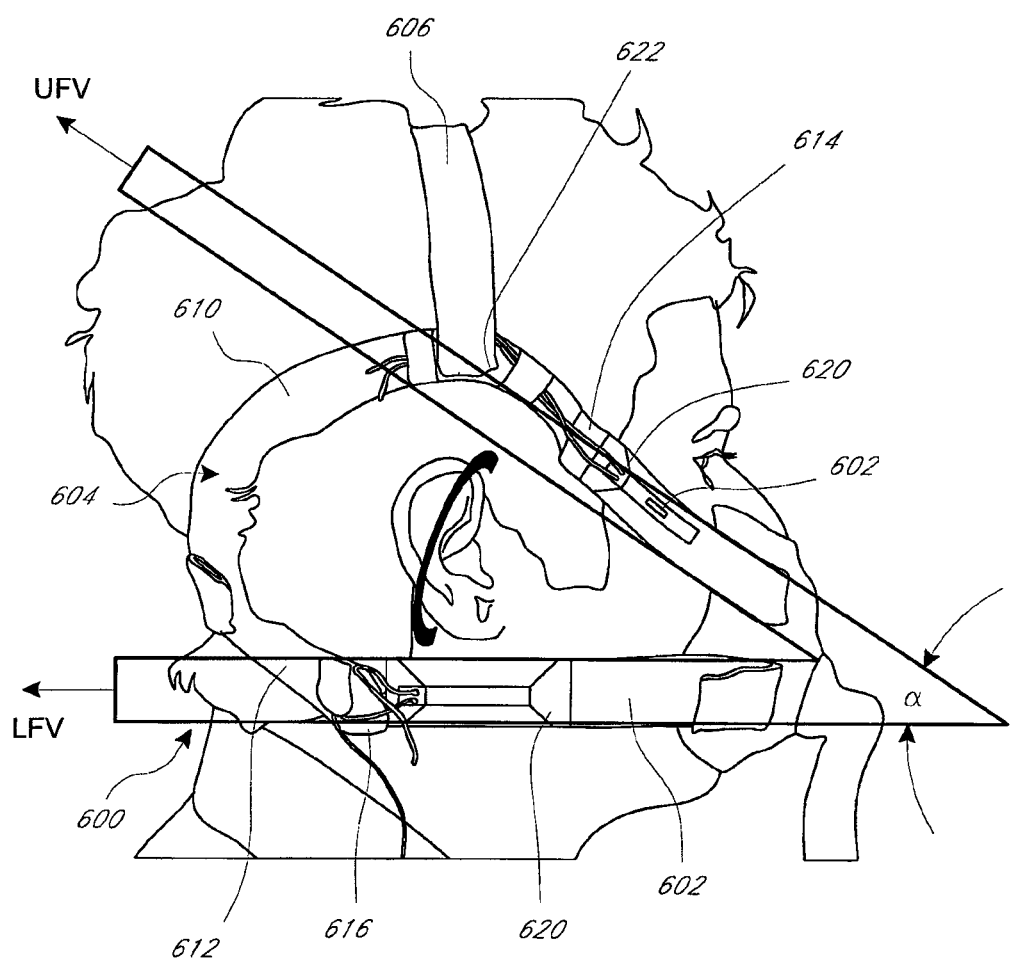
FIG. 68 is a side view of the mask configuration and headgear assembly of FIG. 67.
Figure 69:
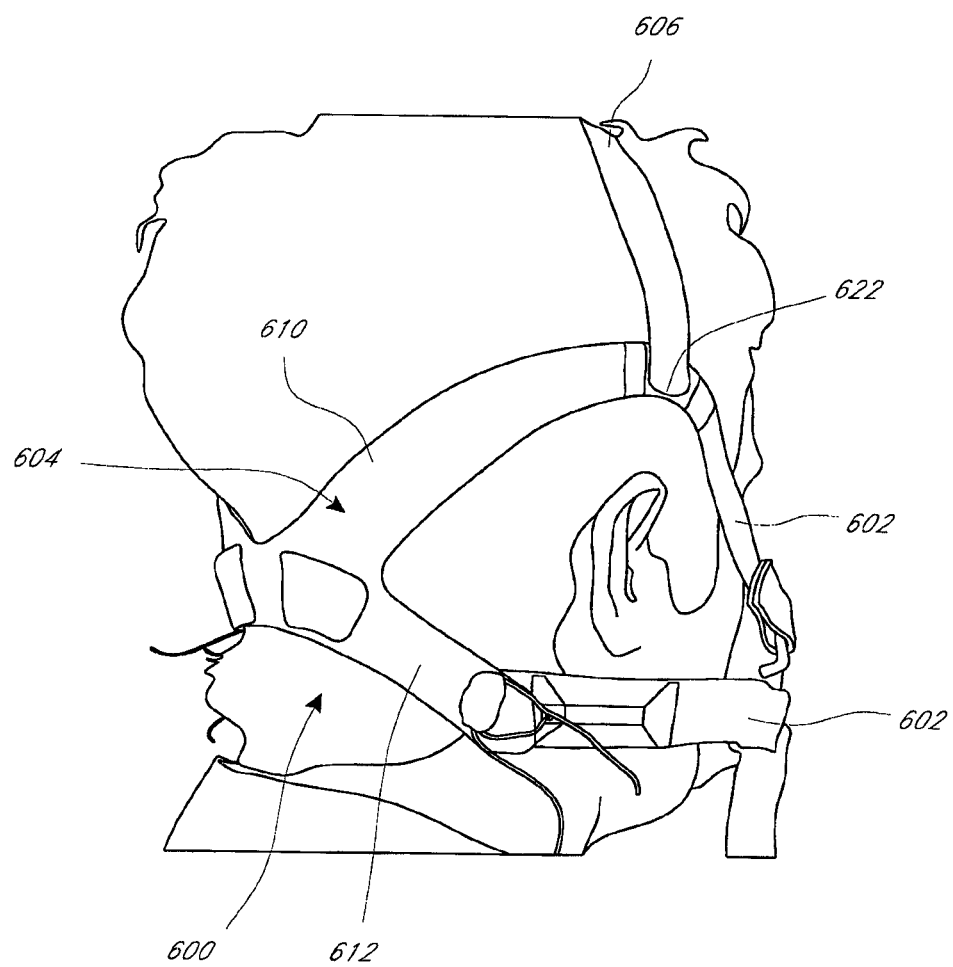
FIG. 69 is a rear perspective view of the mask configuration and headgear assembly of FIG. 69.

With reference to FIGS. 67-69, in addition to the straps 602, the headgear assembly 600 also comprises a back strap assembly 604 and a top strap 606. While the headgear assembly 600 can be used, any other suitable head gear assemblies also can be used, including but not limited to any construction disclosed herein.

The back strap 604 extends around a back of the head of the user at a location generally above a nape of the neck but generally below the occipital protuberance. Accordingly, the back strap 604 preferably arcs upward to reduce or eliminate the likelihood of the back strap 604 contacting the nape of the neck of the user. At a location rearward of the ear of the user, the back strap 604 forks into an upper arm 610 and a lower arm 612.

The upper arm 610 arcs upward to a location above the ear of the user and then arcs downward to a location generally forward of the ear of the user. The downward arc, when combined with the more rigid material of the upper arm 610, enables the attachment point between the upper arm 610 and the strap 602 to be lowered such that the strap 602 can provide a desired force vector UFV to the mask configuration 500'. If the attachment point is too high, then the headgear assembly 600 would provide too much upwards force to the mask configuration 500', which would weaken the stability of the mask configuration 500'. Moreover, as shown in FIG. 68, the lowered attachment point results in the strap 602 being positioned generally lower than the eye of the user, which improves the field of vision for the user and improves comfort for the user.

As shown in FIG. 68, the lower arm 612 extends downward and forward to a location slightly rearward of the ear. When combined with the more rigid material of the lower arm 612, the location lower than and slightly rearward of the ear results in the lower arm 612 resting relatively flat alongside the upper neck region of the user, which improves comfort for the user. When connected with the lower arm 612, the strap 602 can provide a desired lower force vector LFV to the mask configuration 500'.

The straps 602 can be connected to the back strap assembly 604 in any suitable manner. In the illustrated configuration, the straps 602 connect to the upper arm 610 and the lower arm 612 respectively. Preferably, the upper arm 610 and the lower arm 612 are more rigid than the straps 604 such that the arms 610, 612 generally maintain shape as the headgear assembly 600 is being donned. In some configurations, each of the upper arm 610 and the lower arm 612 supports its own weight. In some configurations, each of the upper arm 610 and the lower arm 612 is structured to be tangle-free during donning. For example, the arms 610, 612 have sufficient torsion stiffness to reduce the likelihood of twisting when being put on.

Preferably, the straps 602 connect to at least one of the upper arm 610 and the lower arm 612 at a location forward of the ear. Such a configuration helps the user to locate the straps 602 without much difficulty. In addition, the ends of the upper arms 610 and the lower arms 612 can comprise respective slots 614, 616 such that the straps 602 can be threaded through the slots 614, 616. In addition, the straps 602 can comprise an adjustment mechanism 620, such as a Velcro or buckle configuration. The adjustment mechanism 620 allows a force between the mask seal 504 and the face of the user to be adjusted. Any suitable adjustment mechanism 620 can be used.

With reference to FIG. 68, the top strap 606 can extend upward and over the top of the head of the user. Preferably, the top strap 606 is flexible and has an adjustable length. The top strap 606 can connect to the upper arms 610 through a slot 622 and reduces the likelihood of the upper arms 610 sliding down the head of the user and contacting the ears of the user. Preferably, the top strap 606 connects to the upper arms 610 at a location generally above the ears of the user.

With reference to FIG. 68, an angle $\alpha$ defined between the upper force vector UFV and the lower force vector LFV can be within the range of about 25 degrees and about 70 degrees. Preferably, the angle $\alpha$ can be within the range of about 30 degrees and about 60 degrees. More preferably, the angle $\alpha$ can be within the range of about 35 degrees and about 50 degrees. In some embodiments, the angle $\alpha$ can be about 40 degrees.

Advantageously, relatively small adjustments to the tension of the strap 602 that is connected to the upper arm 610 of the headgear assembly 600 (i.e., adjustment to the tension along the upper force vector UFV), when used with the mask configurations 500, 500' that include the paddles 512, 514 can greatly reduce or eliminate leakage into the eye region of the user. In other words, with the paddles 512, 514 and the upper surface 516, as the upper strap 602 is tightened, the mask configuration 500' is pulled upwards against the bottom of the nose of the user, which depresses the upper surface 516 of the mask seal 504, which in turn causes the paddles 512, 514 to pivot inwards toward the nose of the user. Thus, the upwardly directed force can help to increase the force provided by the paddles 512, 514 against the face of the user in the vicinity of the eyes. Early testing has indicated that about 75% of the force required to achieve a desired sealing level is provided by the lower straps 602 with the upper straps 602 being adjustable to minimize or eliminate leakage into the region of the eyes.

Figure 71:
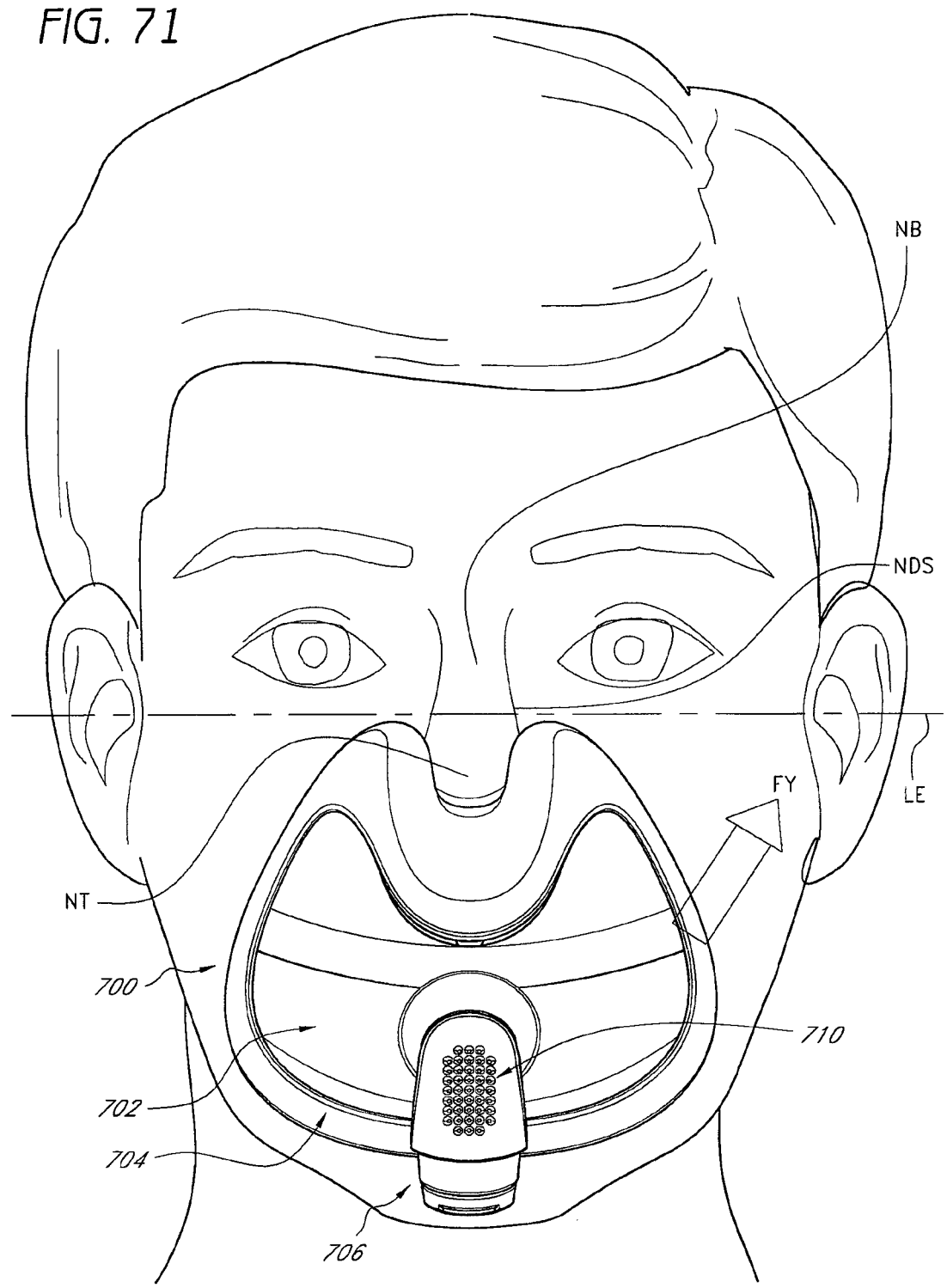
FIG. 71 is front view of mask configuration shown in position on a user.
Figure 72:
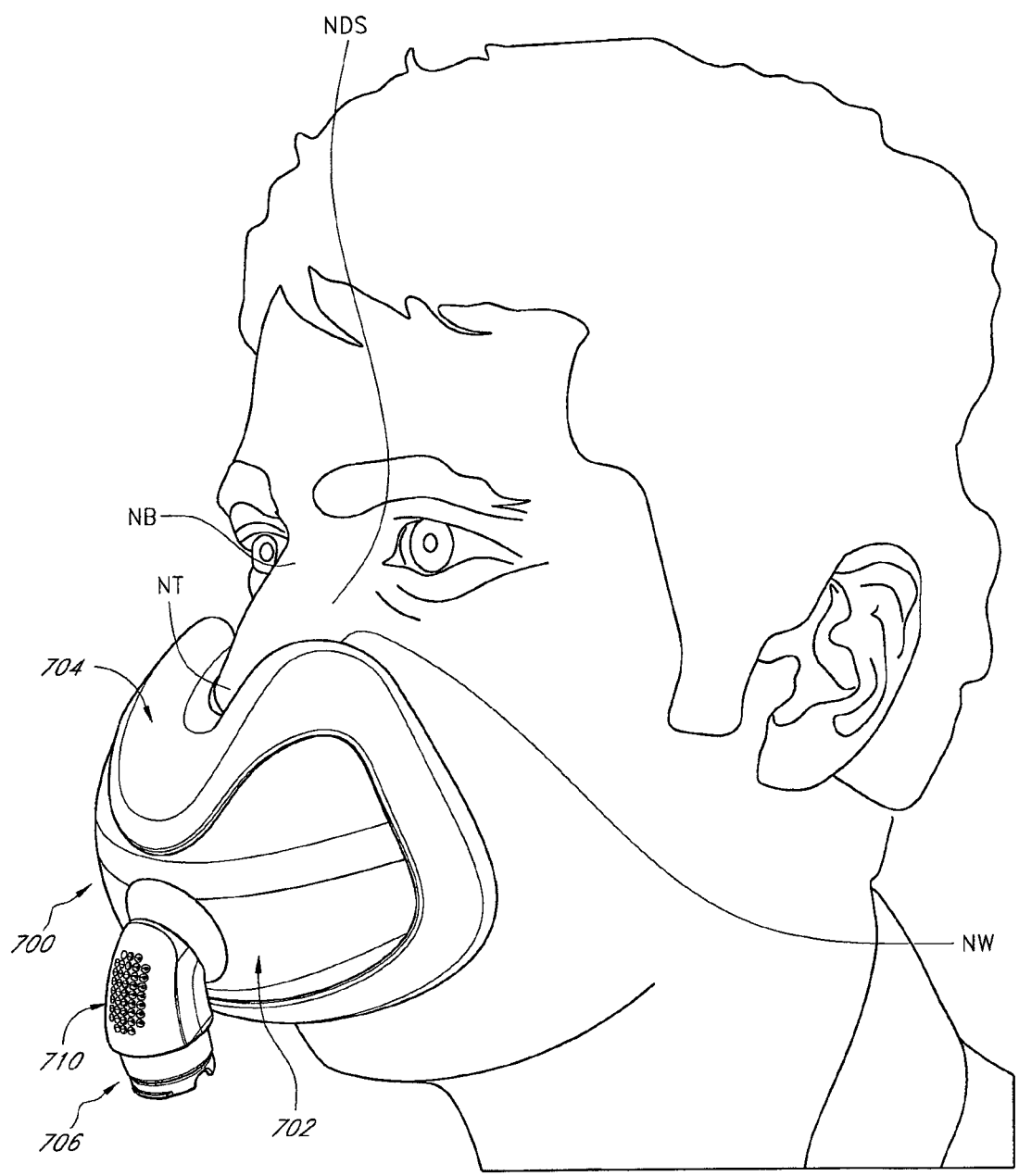
FIG. 72 is a perspective view of the mask configuration shown in position on a user.

With reference now to FIGS. 71 and 72, a further mask assembly 700 is illustrated in position on a face of a user. The illustrated mask assembly 700 is a combined oral and nasal mask. The illustrated mask assembly 700 is designed to seal under the nose of the user, along a portion of the face extending lateral to the nose, as well as around the mouth of the user.

The mask assembly 700 advantageously does not require contact with the bridge NB of the nose of the user. In the illustrated configuration, the mask assembly 700 does not extend over the bridge NB of the nose of the user. More particularly, the illustrated mask assembly 700 does not contact the bridge of the nose of the user. Even more particularly, the illustrated assembly 700 does not contact a forward facing portion of the bridge of the nose of the user. In some configurations, the assembly 700 does not contact the face in a region vertically higher than a generally horizontal plane LE extending along the lower edges of the eyes of the user.

In the illustrated configuration, the mask assembly 700 does not extend over the tip NT of the nose of the user. In some configurations, the illustrated mask assembly 700 preferably does not enshroud the tip NT of the nose of the user. In some configurations, the tip NT of the nose of the user extends over the adjoining portion of the mask assembly 700. In some configurations, the mask assembly 700 covers the tip of the nose. In some configurations, the seal of the mask assembly covers the tip of the nose.

As illustrated, the mask assembly 700 preferably is adapted to extend around and seal over the wing NW or alar of the nose, which flares out to form a rounded eminence around the nostril. The illustrated mask assembly 700 is adapted to seal around the surfaces that define the opening to the nostril, including the fleshy external end of the nasal septum, sometimes called the columella. In some configurations, the mask assembly 700 is adapted to extend upwardly to seal along at least a portion of the left and right dorsal side walls NDS of the nose of the user. In some configurations, the mask assembly 700 is adapted to extend upwardly along at least a portion of the left and right dorsal side walls NDS without extending upwardly to the region of the bridge NB of the nose of the user.

As illustrated, the mask assembly 700 comprises a mask base 702, a mask seal 704 attached to the mask base 702 and a connector 706 also attached to the mask base 702. The connector 706 can be connected to the base 702 in any suitable manner, including but not limited to any manner discussed elsewhere within this application. For example, but without limitation, the connector 706 can be connected to the base 702 such that the connector 706 can swivel, pivot and rotate relative to the base 702. In some configurations, the connector 706 can define a portion of a ball joint with the mask base 702, for example but without limitation, defining the other portion. The ball joint can have any suitable configuration and can be configured in accordance with the descriptions of ball and socket arrangements discussed elsewhere within this application. The connector 706 facilitates connection to a supply conduit or the like for the supply of pressurized breathing gases. Any suitable connector 706 can be used.

In the illustrated configuration, the connector 706 comprises an elbow, such as a polycarbonate elbow for example but without limitation, that contains bias flow holes 710. The bias flow holes 710 are a collection of orifices that are configured to circulate air and to reduce the likelihood of rebreathing expired carbon dioxide by the user. While the bias flow holes 710 are shown exclusively on the connector 706, in some configurations, the bias flow holes 710 can be provided on the mask base 702, on the mask seal 704 or on any combination of the connector 706, the base 702 and the seal 704. The bias flow holes 710 can have any suitable cross-section and can be cylindrical, hour-glass shaped, tapered in either direction, fully or partially tapered, fully or partially cylindrical, contoured to vary in cross-section or the like.

Figure 73:
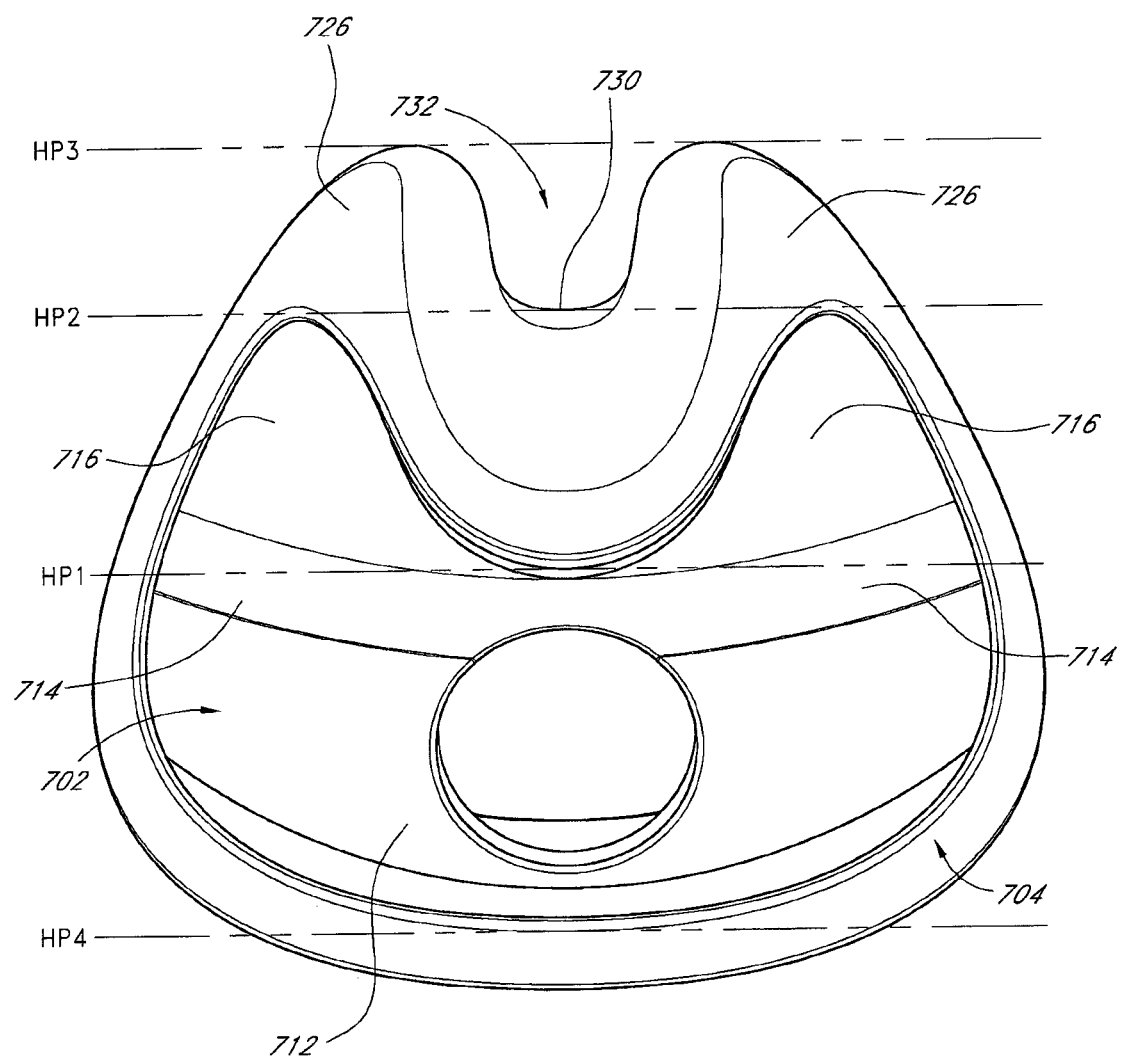
FIG. 73 is a front view of the mask configuration of FIG. 71, shown without a connector.

With reference to FIG. 73, the mask base 702 will be described in greater detail. The mask base 702 provides a support structure of sorts for the mask assembly 700 in general and for the mask seal 704 more specifically. The mask base 702 can be formed from any suitable material. In some configurations, the mask base 702 is formed from a fairly rigid material. In some configurations, the mask base 702 is formed from a plastic material, such as a polycarbonate material. In some configurations, as with the configuration of FIG. 13 above, the mask assembly 700 can comprises a mask seal that includes a mask seal clip that is separate from but attachable to a mask base. In such a configuration, the mask seal clip would connect the mask seal 704 to the mask base 702. In such configurations, the mask seal and mask seal clip can be formed separately and secured together or the mask seal and the mask seal clip can be integrated into a single component. In some configurations, the mask seal can be overmolded onto the mask seal clip and, in some configurations, the mask seal can be overmolded directly onto the mask base.

Figure 74:
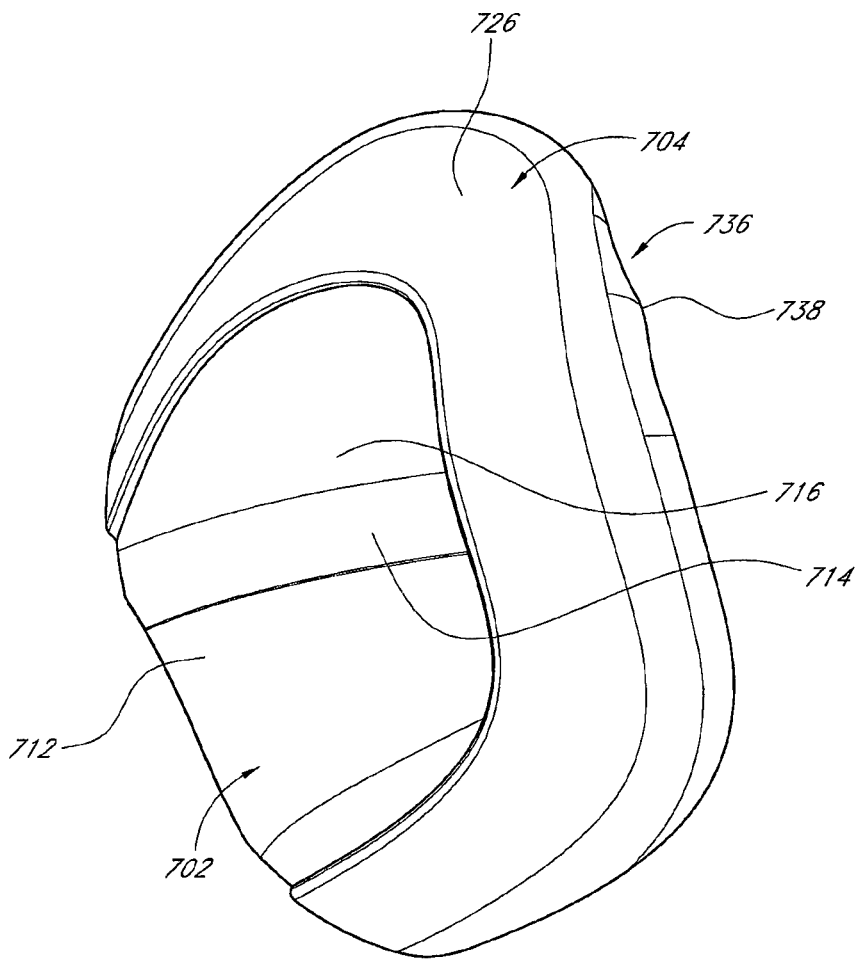
FIG. 74 is a side view of the mask configuration of FIG. 71, shown without a connector.

With reference to FIGS. 73 and 74, in the illustrated configuration, the mask base 702 sweeps rearward from a central portion 712 with a pair of wings 714. As illustrated, the wings 714 can extend rearward and upward relative to the central portion 712 of the mask base 702. Accordingly, the illustrated wings 714 include upwardly projecting portions 716. The mask base 702 generally, and the upwardly projecting portions 716 of the wings 714 as an example, can provide reinforcement to the lateral portions of the mask seal 704.

The central portion 712 can have a vertical expanse that is lower than the height of the upwardly projecting portions 716 of the wings 714. Thus, with reference to FIG. 73, when viewed from the front, the mask base 702 comprises an edge having a generally M-shaped appearance. In addition, when viewed from the front, an upper edge of a central area of the mask base 702 comprises a generally U-shaped appearance. By incorporating the recessed central portion 712 between the pair of wings 714, the mask base 702 can provide desired support to the mask seal 704 while providing adequate clearance for the nose of the user.

The mask base 702 and the mask seal 704 can be connected in any suitable manner. In the configuration illustrated in FIG. 75, the mask base 702 comprises a generally circumscribing flange 720 and the mask seal 704 can be overmolded onto the flange 720 of the mask base 702. Any other suitable technique can be used to form the junction between the mask seal 704 and the mask base 702.

In some configurations, the mask seal 704 can be formed to allow removal from the mask base 702. For example, the mask seal 704 can include a groove and the mask base 702 can include a flange, or any other cooperating structures, such that the mask seal 704 can be removably connected to the mask base 702.

Figure 75:
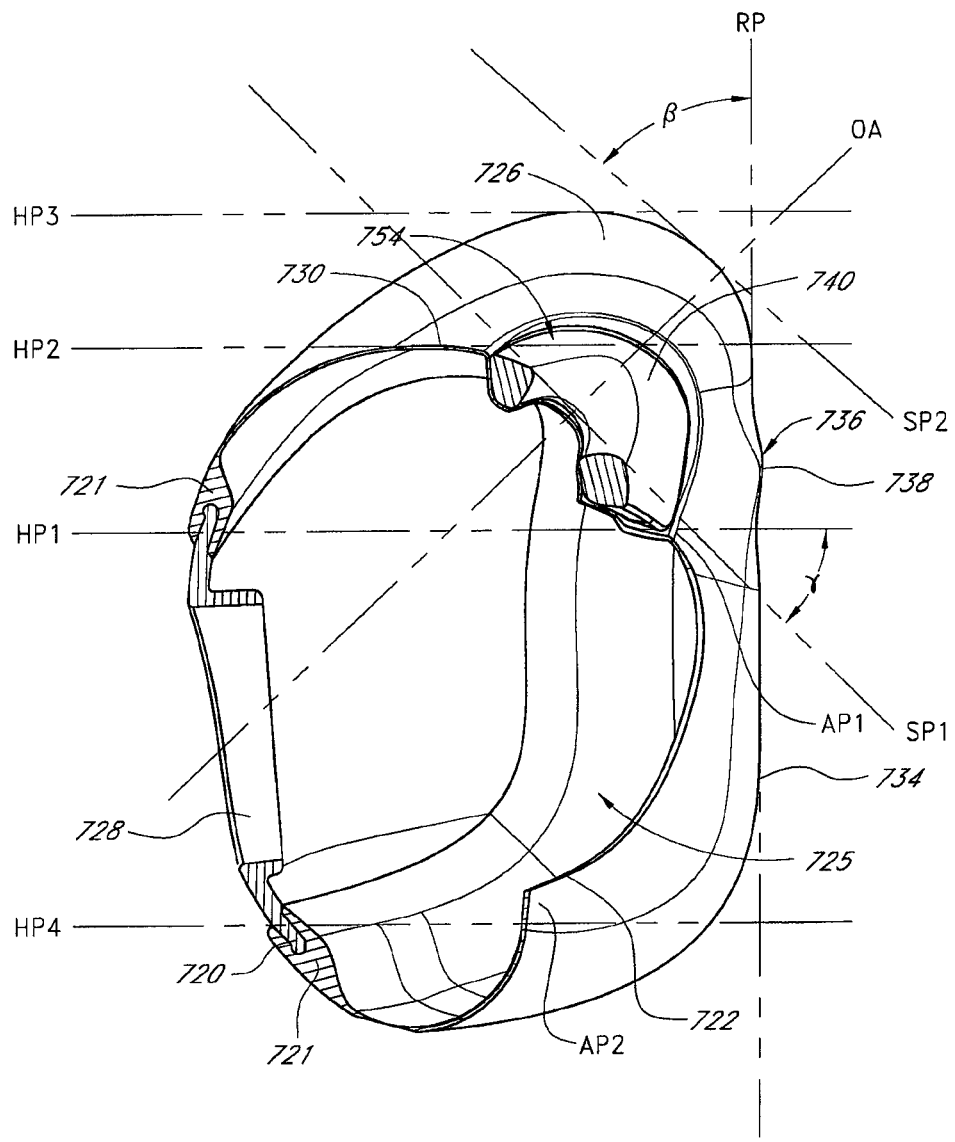
FIG. 75 is a side sectioned view of the mask configuration of FIG. 71.

As shown in FIG. 75, the illustrated mask seal 704 comprises a thickened region 721, which is thicker in cross-section, adjacent the juncture with the mask base 702. Such a configuration improves service life of the mask seal 704 as well as improves the integrity of the connection between the mask seal 704 and the mask base 702. In some configurations, the thickest region of the mask seal 704 is the thickened region 721.

The mask seal 704 is designed to seal against the face of the user. The mask seal 704 preferably is formed of a soft material, such as silicone, for example but without limitation. In some configurations, at least portions of the mask seal 704 can be textured to improve comfort to the user. For example, in some configurations, at least portions of the mold used to form the illustrated mask seal 704 can be bead blasted to provide a surface texture in at least the regions of the mask seal 704 that will contact the skin of the user. Other techniques for texturing one or more surface of the mask seal 704 can be used.

Figure 76:
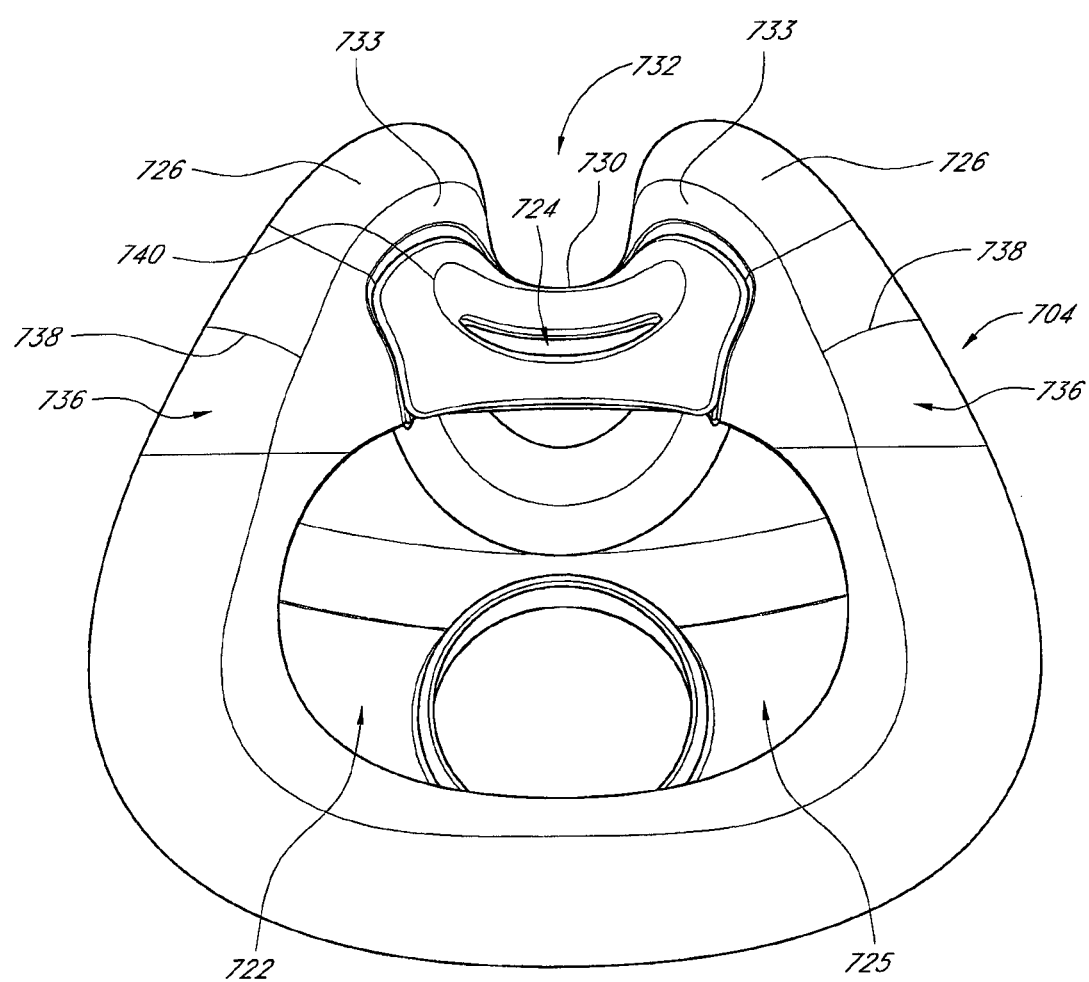
FIG. 76 is a rear view of the mask configuration of FIG. 71.

As shown in FIG. 76, the illustrated mask seal 704 comprises an oral-nasal mask seal and, therefore, comprises at least one oral opening 722 and at least one nasal opening 724. In some configurations, the mask seal 704 can comprise a combined oral-nasal opening. In some configurations, the mask seal 704 can comprise more than one nasal opening 724. In some configurations, the mask seal 704 can comprise nasal openings 724 defined within superstructures, such as pillows, prongs or the like.

The at least one oral opening 722 and the at least one nasal opening 724 preferably communicate with a single chamber 725 that is defined within the mask assembly 700. The chamber 725 of the illustrated mask assembly 700 is at least partially defined by the mask base 702 and the mask seal 704. The at least one oral opening 722 is substantially opposed to the opening 728 that receives the connector 706. The at least one nasal opening 724 can be vertically above the at least one oral opening 722. The at least one nasal opening 724 can be positioned between the opening 728 for the connector 706 and the at least one oral opening 722. The at least one oral opening can have an axis OA that is inclined relative to vertical and that generally extends through the opening 728 for the connector 706.

With reference again to FIG. 73, the mask seal 704 preferably comprises a pair of paddles 726 that extend upward above an upper surface 730. The paddles 726 are configured to extend upward alongside, and in some configurations above, the nares. In some configurations, the paddles 726 each comprise an air pocket that is in direct fluid communication with the air path through the mask assembly from the connector to the at least one nasal opening and the at least one oral opening. Preferably, as shown in FIG. 76, the upper surface 730 is hammocked between inner portions 733 of the paddles 726. In such a configuration, downward pressure applied to the upper surface 730 can cause the paddles 726 to pivot inwardly at the top. Accordingly, increasing force between the nose of the user and the upper surface 730 can result in increasing sealing force being applied between the sides of the nose of the user and the paddles 726. The degree to which the pivoting action results in increasing force can be varied by construction. In other words, longer paddles 726 display increased degrees of pivoting compared to shorter paddles 726. On the other hand, shorter paddles 726 are capable of accommodating greater variations in nasal geometries compared to longer paddles 726 and result in the mask assembly 700 being easier to put onto the face.

With reference to FIG. 75, four different planes HP1, HP2, HP3, HP4 are illustrated. The planes HP1, HP2, HP3, HP4 are shown extending generally parallel to each other and extending generally normal to a plane RP defined along a rearmost region 734 of the mask seal 704 (e.g., the rearmost region 734 could correspond to a plane such as a table top that would support the mask seal 704 if the mask seal 704 were resting on a table). In some configurations, an angle β is defined between at least one of the four planes HP1, HP2, HP3, HP4 and the rear plane RP that is between about 80 degrees and 100 degrees. In some configurations, the angle β is between about 85 degrees and about 95 degrees. In the illustrated configuration, the angle β is about 90 degrees.

As illustrated, the first plane HP1 extends through a forwardmost region or lowermost region of the upper portion of the mask base 702, the second plane HP2 extends through uppermost portion of the upper surface 730 of the mask seal 704 the third plane HP3 extends along the uppermost portion of the paddles 726, and the fourth plane HP4 extends along a lowermost portion of a face contacting surface of the mask seal 704. In the illustrated configuration, the second plane HP2 also extends through the uppermost portions of the upwardly projecting portions 716 of the wings 714. In some configurations, the upwardly projecting portions 716 may extend above the upper surface 730 and, in some configurations, the upwardly projecting portions 716 of the mask base 702 may not extend as far upward as the upper surface 730. In the illustrated configurations, the planes have the following order from top to bottom: HP3, HP2, HP1 and HP4. Preferably, HP2 is positioned between HP1 and HP3. In some configurations, the distance between the plane HP2 and the plane HP3 is between about 10 mm and about 25 mm. In some configurations, the distance between the plane HP2 and the plane HP3 is between about 15 mm and about 22 mm. In some configurations, the distance between the plane HP2 and the plane HP3 is about 17 mm.

The paddles 726 and the upper surface 730 define a valley 732. The valley 732 can be adapted to receive the tip of the nose of the user, as shown in FIGS. 71 and 72. The valley 732 in the illustrated configuration is open in an upwardly direction. In other words, the region of the illustrated mask assembly 700 that accommodates the nose is not enclosed from the top and is configured to rest under the nose. In the illustrated configuration, the valley is positioned vertically higher than the plane HP1, which extends through the highest portion of the central portion 712 of the mask base 702. In the illustrated configuration, the valley 732 can extend downward into the region of the second plane HP2, which extends along the uppermost portions of the mask base 702. In some configurations, the valley 732 extends downward to a location just vertically lower than the second plane HP2. In some configurations, the valley 732 extends downward to a location just vertically higher than the second plane HP2. In some configurations, the distance between the valley and the second plane HP2 is between about −5 mm and about 5 mm.

With reference to FIG. 75, the rearmost portion 734 of the mask seal 704 preferably comprises at least two protrusions 736. The protrusions 736 can be integrally formed with the surrounding portions of the mask seal 704 or can be separate components that are secured to the surrounding portions of the mask seal 704. In the illustrated configuration, the protrusions 736 are formed in an integrated molding with the surrounding portions of the mask seal 704, which improves the service life of the mask seal and simplifies manufacture. In some configurations, the protrusions 736 can be formed of a softer material, such as a softer grade of silicone, for comfort. In some configurations, the protrusions 736 can be formed to have a thinner cross-section. In the illustrated configuration, however, the protrusions have a cross-sectional thickness that is substantially consistent with the surrounding portions of the mask seal 704. In some configurations, the protrusions 736 can be formed of a harder material, such as a harder grade of silicone, for better sealing. In some configurations, the protrusions 736 can be formed to have a thicker cross-section than the surrounding region, which increases the perceived hardness or rigidity The protrusions 736 are configured to improve sealing with the face of the user by helping to fill pockets generally encountered adjacent to the nose on the face (e.g., recesses defined by the maxilla just below the infraorbital foramen)

and, as such, the protrusions 736 form means for sealing with facial contours in a region adjacent a nose of a user. The protrusions 736 extend rearward (i.e., toward the user) from the surrounding portions of the mask seal 704. The protrusions 736 can have a height (i.e., can extend away from the immediately surrounding portions by a distance) of between about 0 mm and about 5 mm relative to the surrounding portions of the mask seal 704. In some configurations, the protrusions 736 can have a height of between about 1.0 mm and about 3.0 mm. In some configurations, the protrusions 736 can have a height of about 2.0 mm.

At least a portion of each of the protrusions 736 can be positioned vertically between the plane HP2 and the plane HP1. In some configurations, at least a portion of the protrusions 736 is positioned vertically between the upper surface 730 (at least the uppermost extent) and the uppermost portion of the oral opening 722. In some configurations, each of the protrusions 736 has one or more peak 738 and the peak 738 is positioned vertically between the upper surface 730 (at least the uppermost extent) and the uppermost portion of the oral opening 722. In some configurations, the peak 738 is positioned vertically between a portion of the nasal opening 724 and a portion of the oral opening 722. In some configurations, the peak 738 is positioned closer to the nasal opening 724 than to the oral opening 722.

The illustrated mask seal 704 is designed to anchor on two locations of the face of the user: under the nose and below the lower lip. In some configurations, the mask seal 704 is configured to anchor below the nose and between the lower lip and the chin. In the illustrated configuration, the mask seal 704 is designed to anchor proximate the second and fourth planes HP2, HP4. In some configurations, both anchor points are positioned between the second and fourth planes HP2, HP4. In some configurations, an upper anchor point AP1 and a lower anchor point AP2 are vertically separated from each other by a gap of between about 40 mm and about 65 mm. In some configurations, the upper anchor point AP1 and the lower anchor point AP2 are separated by a gap of less than about 65 mm. In some configurations, the upper anchor point AP1 and the lower anchor point AP2 are separated by less than about 60 mm. In the illustrated configuration, the mask seal 704 also extends above the second plane HP2 with the paddles 726. In some configurations, the mask is designed to seal off airflow through the mask assembly 700 by sealing against the face of the user at locations higher than all of the anchor points. Thus, at least some sealing portions of the illustrated mask seal 704 are positioned vertically higher than the anchor points.

The mask seal 704 can have different sizes for use with faces having different sizes and/or geometries. In some configurations, different portions of the mask seal 704 can be sized and configured to accommodate users having different sizes and/or geometries. For example, portions of the mask seal 704 can extend upward to different degrees for different users. With reference to FIG. 75, a sloping plane SP2 that extends generally parallel to the plane SP1 can extend along an outer edge of the paddles 726. In some configurations, the sloping plane SP2 can be spaced apart from the plane SP1 by between about 10 mm and about 30 mm. In some configurations, the sloping plane SP2 can be spaced apart from the plane SP1 by between about 15 mm and about 25 mm. In some configurations, the sloping plane SP2 can be spaced apart from the plane SP1 by about 21 mm. The distance between the planes is related to the vertical extent of contact with the face. In some configurations, a single size mask seal 704 can be provided for all face sizes and geometries.

In some configurations, the mask seal 704 comprises multiple components formed of differing materials and/or differing shore hardnesses. For example, in some configurations, some components of the mask seal 704 can be formed of silicone, while other components are formed of foam, gels, cloth or other suitably compliant materials. For example, in the illustrated configuration, the mask seal 704 comprises a nasal pad insert 740, which is formed from a differing materials and/or differing shore hardness.

Figure 77:
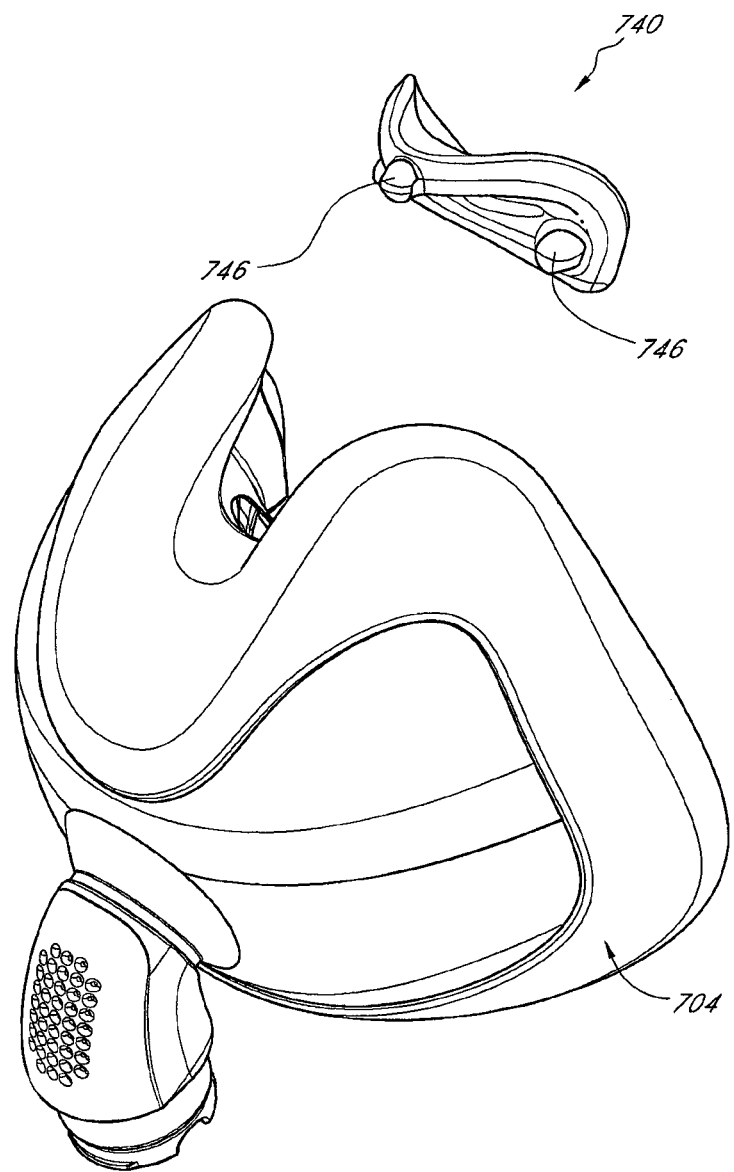
FIG. 77 is a partially exploded front perspective view of the mask configuration of FIG. 71.
Figure 78:
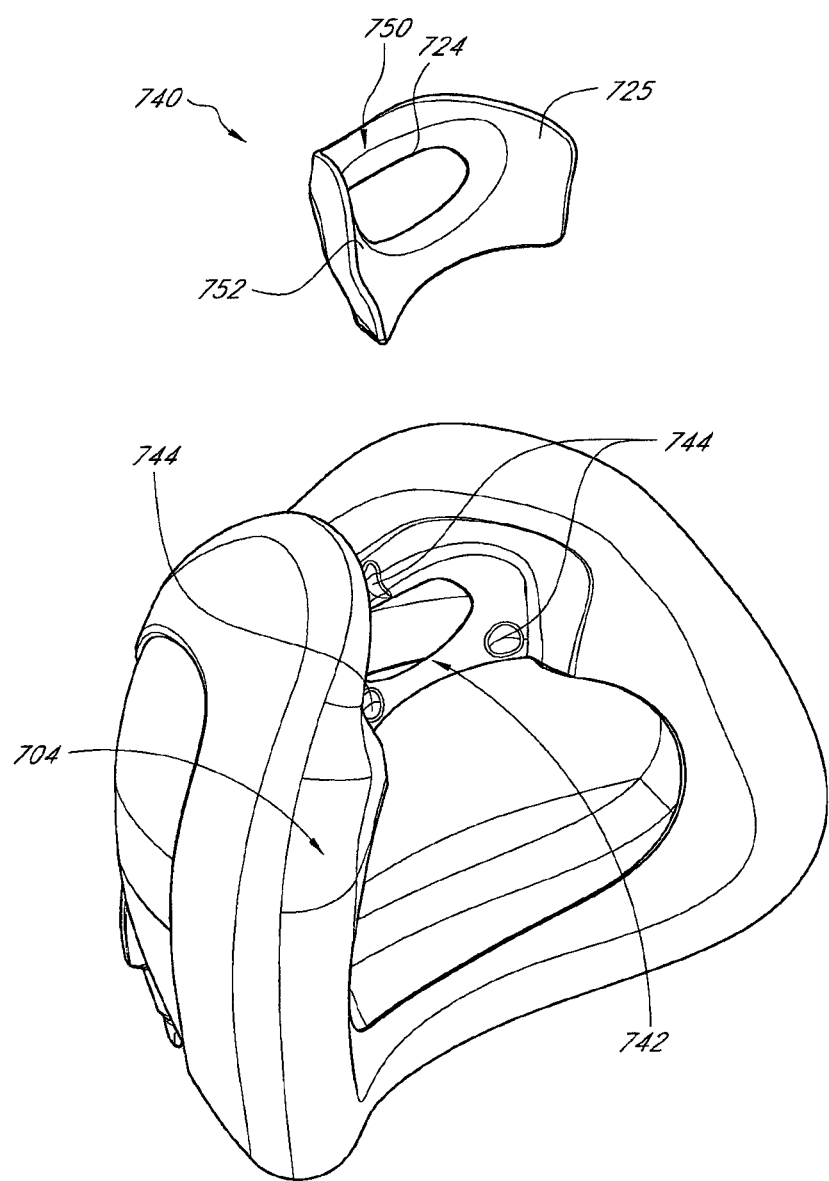
FIG. 78 is a partially exploded rear perspective view of the mask configuration of FIG. 71.
Figure 79:
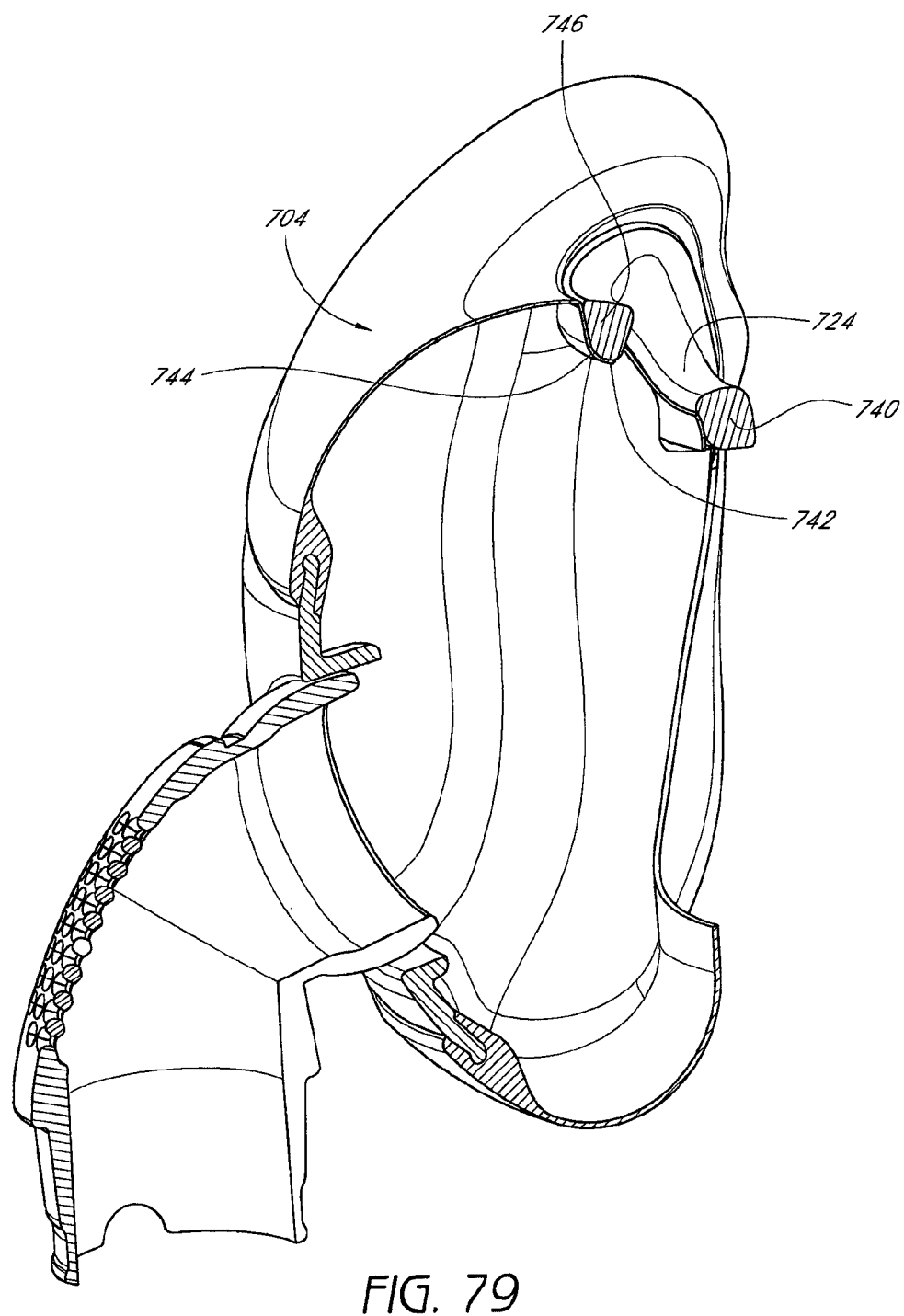
FIG. 79 is a sectioned view of the mask configuration of FIG. 71.
Figure 83:
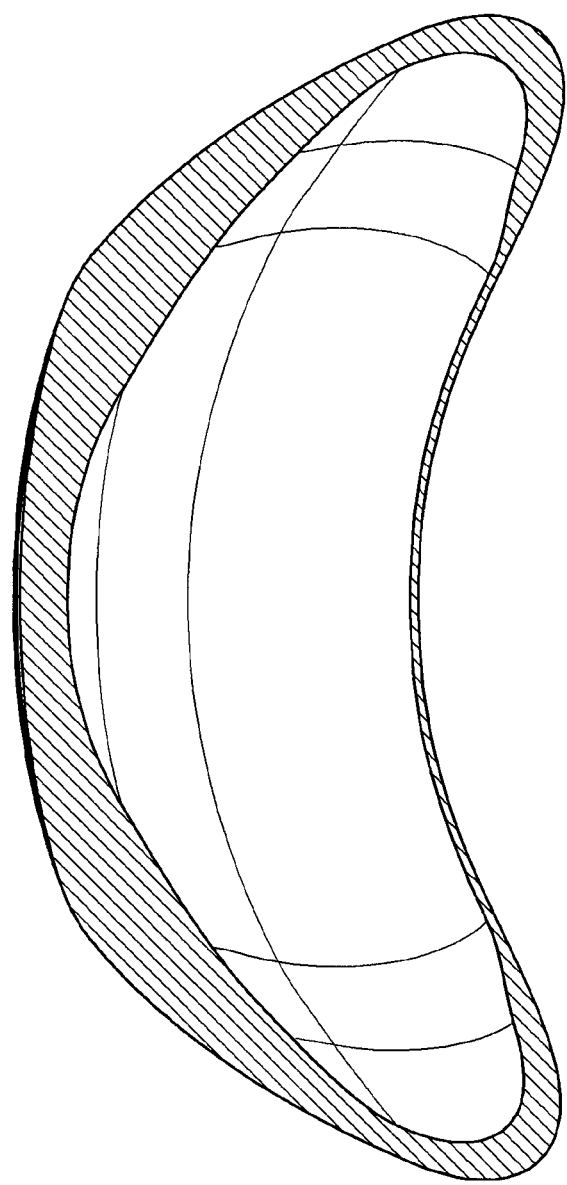
FIGS. 83-88 are cross sections taken through the mask configuration of FIG. 71 at the elevations shown on the mask seal in FIG. 81.
Figure 84:
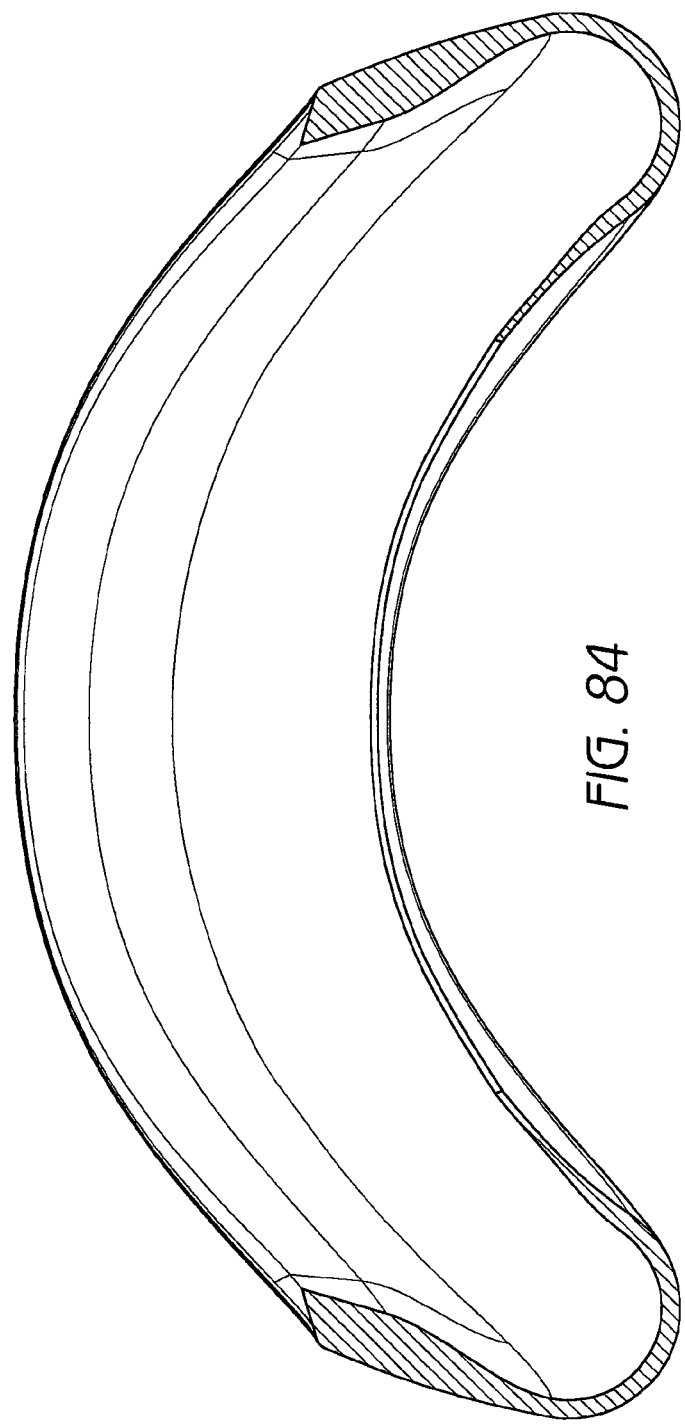
Figure 85:
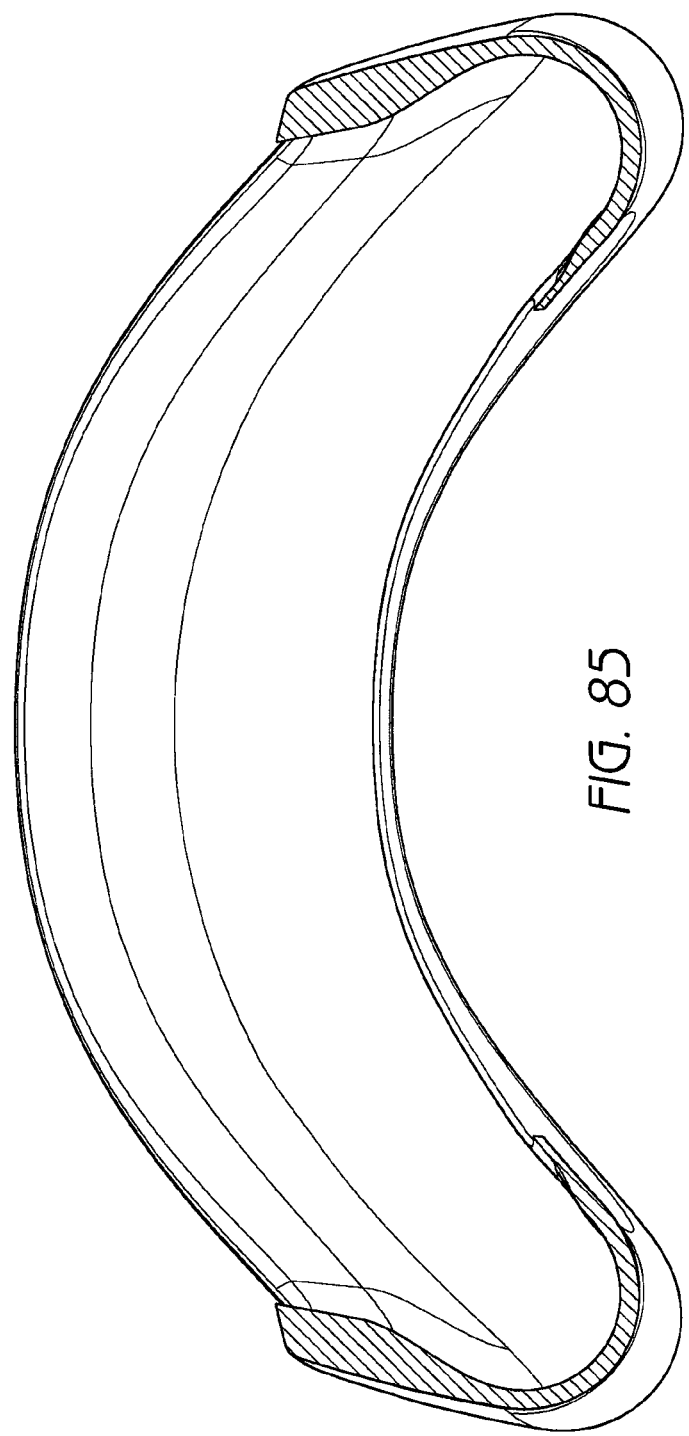
Figure 86:
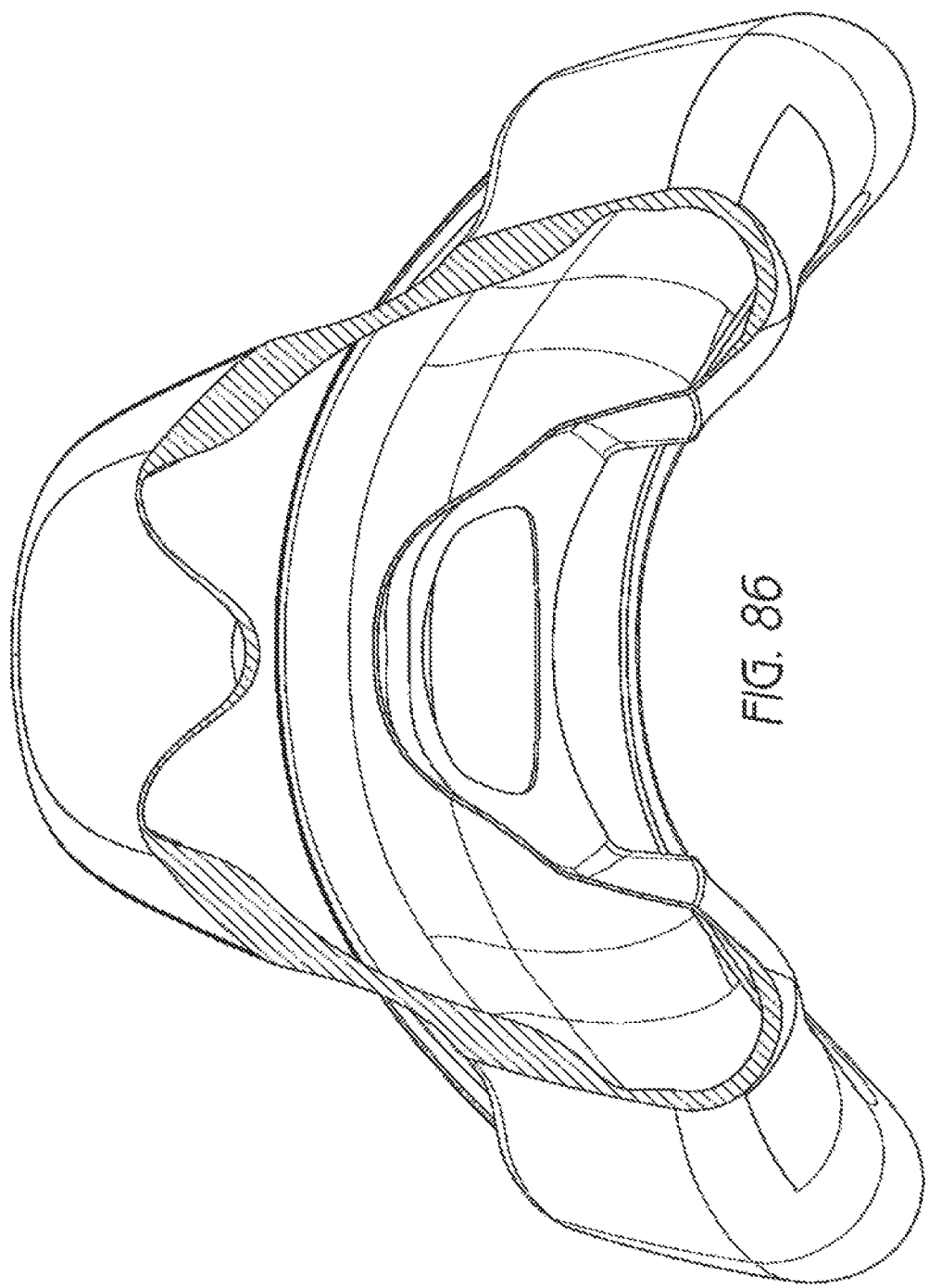

The nasal pad insert 740 is shown exploded from the mask seal 704 in FIGS. 77 and 78. The nasal pad insert 740 can be formed from a different grade of silicone relative to other portions of the mask seal 704. In some configurations, the nasal pad insert 740 can be formed from a softer grade of silicone relative to other face contacting portions of the mask seal 704.

Moreover, in some configurations, the nasal pad insert 740 have a portion that is thicker in cross-section than any other face-contacting portion of the mask seal 704. In some configurations, the nasal pad insert 740 has a maximum thickness that is thicker than any portion of the mask seal 704 that surrounds the nasal pad insert 740. In some configurations, the nasal pad inset 740 has a minimum thickness that is thicker than any portion of the mask seal 704 that surrounds the nasal pad insert. In some configurations, the nasal pad insert 740 has a maximum thickness that is thicker than any other portion of the mask seal 704. With regard to thickness, as thickness increases, a perceived hardness is believed to increase even if the nasal pad inset 740 is formed of a softer grade silicone. Thus, in some configurations, the face contacting portions of the nasal pad insert 740 have a thickness of between about 1.0 mm and about 8.0 mm, or between about 2.0 mm and about 5.0 mm, especially when formed from silicone. In some configurations, the nasal pad insert has a region with a thinner cross-section for comfort. In some configurations, at least a portion of the nasal pad insert can have a thickness that is sufficiently small to allow inflation of that portion of the nasal pad insert. In some configurations, the nasal pad insert can have at least a portion that is less than about 0.3 mm thick. In some configurations, the nasal pad insert can have at least a portion that is less than about 0.2 mm thick. In some configurations, the nasal pad insert comprises variable thickness over at least a portion of the nasal pad insert.

The mask seal 704 can comprise a pad support region 742 that connects with the nasal pad insert 740. The pad support region 742 can be recessed or not. In the illustrated configuration, the pad support region 742 is recessed to help orient, locate and/or secure the nasal pad insert 740 in position.

The nasal pad insert 740 can be secured to the mask seal 704 in any suitable manner. In the illustrated configuration, the nasal pad insert 740 can be secured to the pad support region 742 in any suitable manner. For example, the nasal pad insert 740 can be comolded, overmolded, adhered, cohered or mechanically coupled to the mask seal, or a portion of the mask seal 704 such as the pad support region 742.

With reference to FIG. 78, the mask seal 704 and the nasal pad insert 740 can include features that key the location of the nasal pad insert 740 to the mask nasal seal 704. For example, at least one keying recess 744 can be provided along a portion of the pad support region 742, for example but without limitation. In the illustrated configuration, three recesses 744 are provided that are formed in a generally triangular pattern. The illustrated generally triangular pattern is arranged such that the pattern generally overlies the at least one nasal opening 724. In some configurations, the at least one nasal opening 724 is centrally positioned within the pattern. With reference to FIG. 77, the nasal pad insert 740 can comprises protrusions 746 that mate with the recesses 744. In some configurations, the protrusions 746 can comprise posts. The protrusions 744 can be integrally formed with the nasal pad insert 740 or can be formed separately and attached to the nasal pad insert 740. Any other suitable mating or keying features can be used to locate the nasal pad insert 740 relative to the mask seal 704.

In the illustrated configuration, the recess 744 are closed on the bottom such that the nasal pad insert 740 need not fully seal any openings. In other words, if the recesses comprised an opening, then the nasal pad insert 740 would have to seal over those openings to reduce the likelihood of leaks. In some configurations, however, the recesses 744 can comprise an opening. In some such configurations, the nasal pad insert 740 can be secured in position by sandwiching at least a portion of the mask seal 704 between the nasal pad insert 740 and a member on the other side of the mask seal 704 relative to the nasal pad insert 740. For example, the member on the other side can be secured to the protrusions 744. In any event, the interface between the nasal pad insert 740 and the mask seal 704 preferably is sealed. More particularly, in the region surrounding any opening, such as the nasal opening 724, the interface between the nasal pad insert 740 and the mask seal 704 preferably is sealed.

With reference again to FIG. 78, the nasal pad insert 740 preferably is sized, shaped and configured to improve comfort of the user. For example but without limitation, the illustrated nasal pad insert 740 can comprise a sculpted axially central portion 750. The sculpted axially central portion 750 is recessed below the laterally outward edges 752. By sculpting the axially central portion 750 such that it is recessed, the nasal pad insert 740 is adapted to better cradle the more sensitive septum region of the user. In some configurations, the sculpting of the recessed region is predominately forward of the at least one nasal opening 724. In some configurations, the central portion 750 has a more pronounced recess in the portion forward of the at least one opening 724 compared to the portion rearward of the at least one opening. In some configurations, the recessed central portion 750 has a reduced thickness in the recessed regions.

In some configurations, the nasal pad insert 740 can be removable or replaceable. In some configurations, the nasal pad insert 740 can be replaceable to alter the mask assembly 700 to include a single nasal opening, a pair of nasal openings, more than a pair of nasal openings, a single or multiple nasal prongs, a single or multiple nasal pillows or any other suitable interface configuration. In some configurations, a kit can be provided that includes a mask base, a mask seal and a plurality of nasal pad inserts to allow experimentation to determine the most desired or effective configuration for any particular user. In some configurations, the nasal pad insert 740 is not removable or replaceable without damaging the mask seal 704 yet different nasal pad inserts 704 (e.g., any of the configurations described in the preceding sentence) can be provided to simply and easily vary the style of interface while using many of the same underlying components. For example, while a prongless and pillowless configuration may be desired by some for comfort, a prong can improve the ability to properly locate the mask assembly 700 on the face of the user while a pillow can further improve the ability to both locate the mask assembly 700 on the face of the user while also sealing in the nare of the user.

With reference to FIG. 75, a nose contacting portion 754 (which can include or comprise the nasal pad insert 740) that generally or substantially encircles the nasal opening 724 slopes downward in a rearward direction from the second plane HP2 to the first plane HP1. In some configurations, an angle $\gamma$ is defined between a nose contacting plane SP1 and the plane HP1. In some configurations, the angle $\gamma$ is between about 5 degrees and about 50 degrees. In some configurations, the angle $\gamma$ is between about 15 degrees and about 40 degrees. In one configuration, the angle $\gamma$ is about 30 degrees. In some configurations, it is possible for the nose contacting portion that generally or substantially encircles the nasal opening to be generally normal to the rear plane, to be generally horizontal in use, or to slope in the opposite direction from that shown in FIG. 75.

A second sloping plane SP2 extends generally parallel to the first sloping plane SP1. In some configurations, the second sloping plane SP2 and the first sloping plane SP1 are separated by a distance of between about 10 mm and about 30 mm. In some configurations, the second sloping plane SP2 and the first sloping plane SP1 are separated by a distance of between about 15 mm and about 25 mm. In some configurations, the second sloping plane SP2 and the first sloping plane SP1 are separated by about 21 mm. In such a manner, the vertical and horizontal extents of the paddles 726 can be determined and the appropriate size paddles can be derived for a particular facial geometry.

The illustrated mask seal 704 of the mask assembly 700 comprises a fairly complex range and configuration of thicknesses. The thicknesses are varied to take advantage of different characteristics in different regions of the illustrated mask seal 704. For example, with reference to FIGS. 80 and 82, the mask seal 704 illustrates a connecting region 760 that generally corresponds to the thickened portion 721. The connecting region 760 generally encircles an opening that receives the mask base 702. The connecting region 760 can be the thickest portion of the seal member 704 in some configurations. The connecting region 760 joins the mask seal 704 to the mask base 702. Accordingly, the connecting region 760 preferably has sufficient thickness to provide sufficient rigidity for connection and to provide sufficient thickness for durability. In some configurations, the thickness of the connecting region is between about 2 mm and about 5 mm. In the illustrated configuration, the thickness is between about 3 and about 3.5 mm.

To reduce the incidence of wrinkling of the face contacting regions of the mask seal 704 during use, it has been found that the outer peripheral portions 762, which are generally adjacent to the face contacting portions of the mask seal 704, should be fairly rigid. With reference to FIGS. 81 and 82, the illustrated lower outer peripheral portions 762 extend along the generally vertically extending portions on the rear of the mask seal 704 and wrap slightly inward at a bottom of the rear of the mask seal 704. In addition, the lower outer peripheral portions 762 wrap from a rear facing side of the mask seal around to at least a portion of a laterally facing side of the mask seal 704. In some configurations, the thickness of the outer peripheral portions can be between about 1.0 mm and about 1.5 mm. In the illustrated configuration, the outer peripheral portions 762 have a thickness less than that of the connecting region 760, and preferably have a thickness of about 1.25 mm. The upper outer peripheral portions 763 can be separated from the lower peripheral portions 762 and can have a different thickness. In some configurations, the upper outer peripheral portions 763 have a smaller thickness than the lower outer peripheral portions 762. In some configurations, the upper outer peripheral portions 763 can have a thickness of between about 0.5 mm and about 1.25 mm. In the illustrated configuration, the upper outer peripheral portions 763 can have a thickness of about 0.8 mm.

With reference to FIG. 81, the illustrated mask seal 704 also has protruding portions 764, which generally correspond to the protrusions 736, including the peaks 738. The protruding portions 764, as discussed above, can be the same thickness or can be thicker or thinner than the surrounding portions. In the illustrated configuration, the protruding portions 764 have a thickness that is less than the outer peripheral portions 762. In some configurations, the protruding portions have a thickness of between about 0.2 mm and about 1.5 mm. In the illustrated configuration, the protruding portion has a thickness of about 0.7 mm.

With reference to FIG. 81, the illustrated mask seal 704 also comprises an oral region 766. The oral region 766 in the illustrated mask seal 704 extends along at least a portion of the oral opening 722. In the illustrated configuration, the oral region 766 extends along at least a lower portion of the oral opening 722. In the illustrated configuration, the oral region 766 extends along at least the sides and the bottom of the oral opening 722. The oral region 766 provides a softer region that contacts the face. Accordingly, the oral region 766 can have a thinner cross-section. For example, in some configurations, the oral region 766 has a thickness less than that of the outer peripheral portions 762 and, in some configurations, has a thickness of between about 0.2 mm and about 1.0 mm. In the illustrated configuration, the thickness of the oral region is about 0.5 mm.

With reference to FIGS. 80 and 81, a nasal region 768 can wrap from the rear of the mask seal 704 toward the front. The nasal region 768 can include or underlie the nasal pad insert 740. Preferably, however, the nasal region 768 underlies the nasal pad insert 740 and includes the pad support region 742. Given a desire to gently seal against the lower portion of the nose, the nasal region 768 in the illustrated configuration has a fairly small thickness. In some configurations, the nasal region 768 has the smallest thickness of the mask seal 704. In the illustrated configuration, the nasal region 768 has a smaller thickness than the oral region 766. In some configurations, the thickness of the nasal region 768 is between about 0.1 mm and about 0.5 mm. In some configurations, the thickness of the nasal region 768 is about 0.3 mm.

With continued reference to FIGS. 80-82, a transitional portion 770 having a transitioning thickness can be defined between the nasal region 768 and the outer peripheral portions 762, between the nasal region 768 and the connecting region 760, between the nasal region 768 and the oral region 766, between the oral region 766 and the outer peripheral portions 762, between the oral region 766 and the connecting region 760, between the outer peripheral portions 762 and the connecting region 760 and the like. In the illustrated configuration, the protruding portions 764 are generally surrounded by the transitional portion 770. Other configurations also are possible.

With reference to FIG. 81 and FIGS. 83-88, various sections through the mask seal 704 shown in FIG. 81 are presented. These sections help to illustrate the various transitions occurring within the mask seal 704 that is illustrated in FIGS. 80-82.

Figure 87:
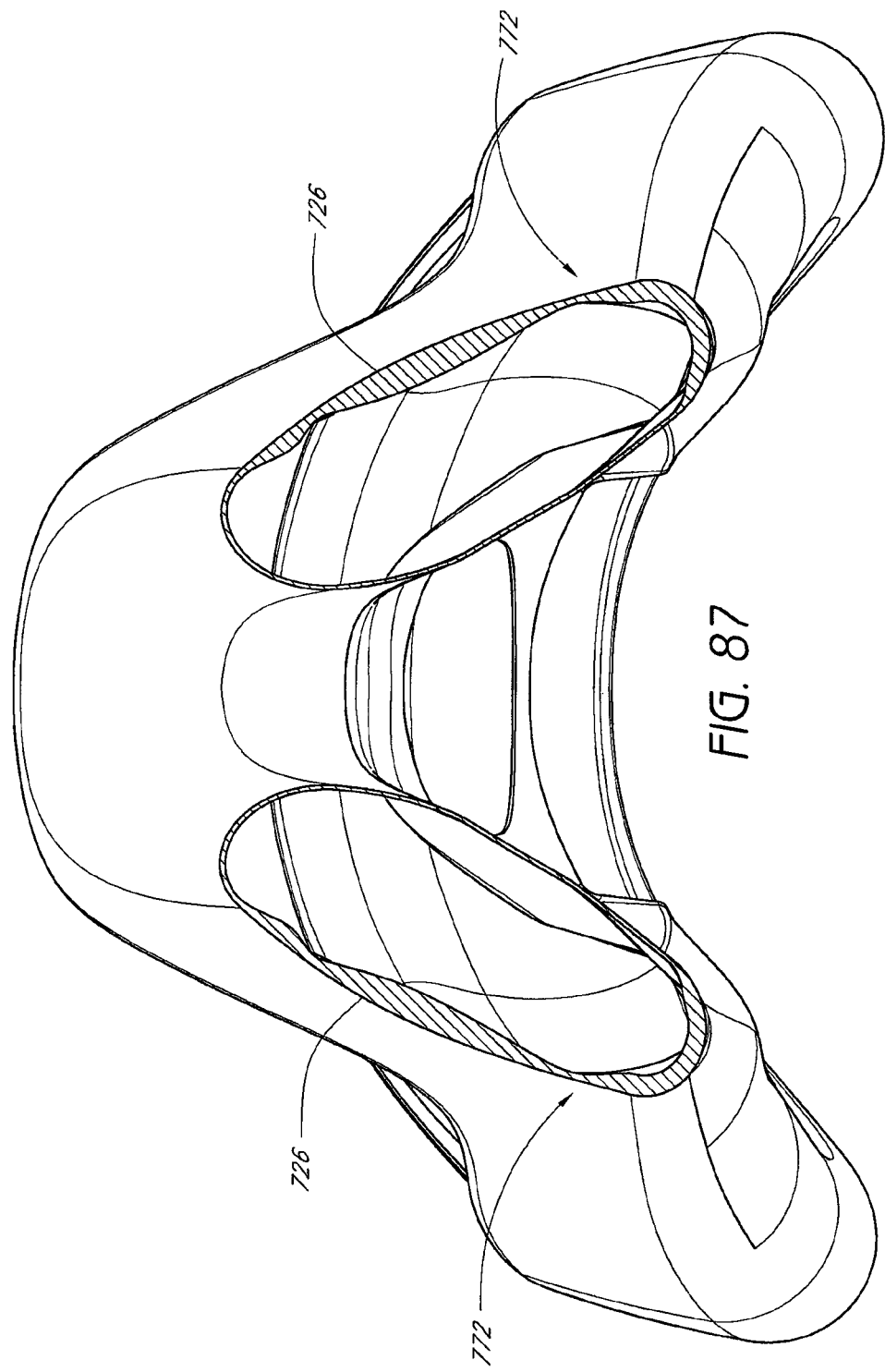
Figure 88:
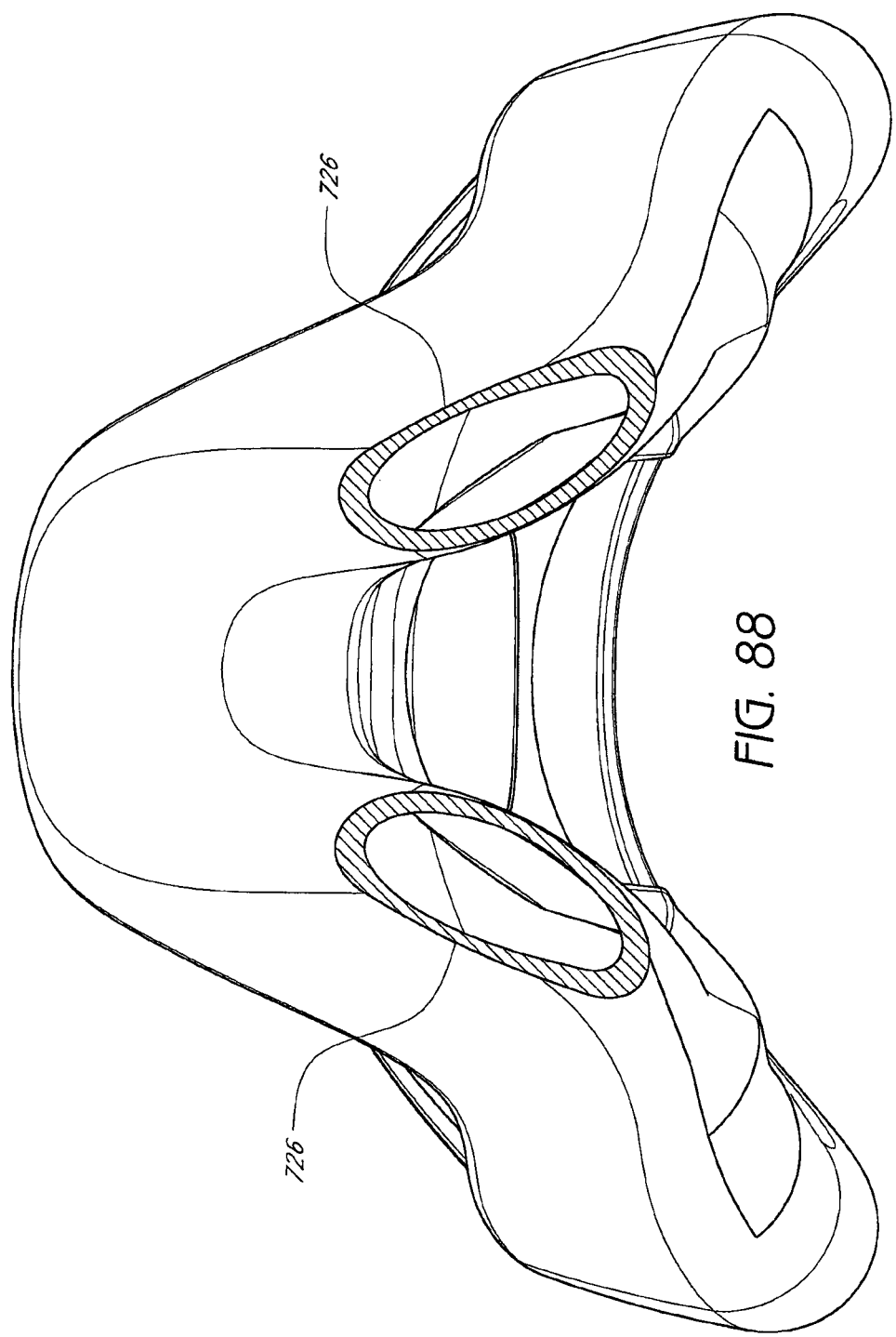

With reference to FIGS. 87 and 88, the paddles as shown in cross section. As illustrated therein, the paddles 726 can have a relatively thin cross section. In some configurations, the paddles can be formed at least in part with a cross section sufficiently thin to allow controlled inflation or controlled expansion at typical treatment pressures (e.g., about 3 to about 25 cmH2O). In some configurations, such a thickness might be lower than about 0.3 mm or lower than about 0.2 mm depending upon the material used. In some configurations, the portion of the paddles 726 that will contact the face comprises a generally constant cross-section.

In one configuration, the paddles have a thickened cross-section along the ridge that joins the laterally outer portion and the laterally inner portion. Thus, the paddles 726 can have a thicker section at a radiused portion that joins the inner portion and the outer portion. In some configurations, that thickened region can be between about 0.3 mm and about 1.25 mm. In some configurations, that thickened region is about 0.5 mm or about 1.0 mm. That thickened region helps to reduce the likelihood of wrinkling or creasing of the face contacting portions of the paddles 726 during use while allowing the laterally inner portions to be as thin as desired.

In some configurations, the paddles 726 comprise a thicker cross-section on the laterally outer portions with a thinner cross-section on the laterally inner portions. As shown in FIG. 87, the laterally outside wall 772 of the paddles 726 can comprise a thicker cross-section that the remained of the paddle 726 at the same elevation. The thicker portion of the paddle 726 provides reinforcement to support the shape of the paddle 726 and to control the shape of the paddle 726 in use. Other techniques also can be used; however, using the thicker cross section has the advantage of providing a sufficiently soft structure with sufficient reinforcement for structural performance.

With reference now to FIGS. 89-109, several styles of headgear that can be used with the mask assembly 700, or with any of the mask assemblies described herein, will be described. With reference to FIG. 71, the mask assembly 700 preferably is secured using headgear such that a force vector is generated on the mask assembly 700 that is upward, rearward, or the combination of upward and rearward. Because the mask assembly 700 is configured to anchor under the nose, and because a sealing force of the paddles 726 increases with upward pressure of the mask assembly 700 against to the bottom of the nose, the mask assembly is quite unique in the force vector most suited to the mask assembly 700. Nevertheless, in some configurations, the mask assembly can be used with headgear generating other directions of force vectors.

As will be apparent with reference to FIGS. 89-109, the illustrated headgear depicted in those figures advantageously does not feature a T-piece or any other component that extends upward over the bridge of the nose (or higher) from the associated mask assembly 700. In some configurations, neither the mask assembly nor the headgear assembly will contact the face of the user vertically higher than the eyes or horizontally between the outer edges of the eyes. Because of the construction of the mask assembly 700, the headgear used with the mask assembly need not contact the facial region of the use at all. In some configurations, the headgear does not connect the face of the user. In some configurations, the mask assembly 700 anchors onto the face in locations below the bridge of the nose. In some configurations, the mask assembly 700 anchors onto the face in locations lower than the lowermost surfaces of the nose. In some configurations, the mask assembly 700 only anchors onto the face in locations lower than the lowermost surfaces of the nose and the headgear assembly does not contact the face of the user. In some configurations, the mask assembly 700 anchors on the mandible and the nose along the maxilla and the headgear does not contact the face in a region vertically higher than the lowermost portion of the nose. In some configurations, the mask assembly 700 anchors on the mandible and the nose along the maxilla and the headgear does not contact the face in a region vertically higher than the bottom of the ear. In some configurations, the mask assembly 700 anchors on the mandible and the nose along the maxilla and the headgear does not contact the face in a region vertically higher than the eyes. In some configurations, the mask assembly 700 anchors in at least two locations vertically lower than the nose and the headgear does not contact the face in a region defined directly vertically above the mask assembly 700. In some configurations, the mask assembly 700 is secured against upward movement by a facial feature of the user and the headgear assembly applies an upwardly directed force to the mask assembly 700. In some such configurations, the facial feature is the lower portion of the nose. In some such configurations, the lower portion of the nose includes the nasal septum.

With reference initially to FIGS. 89-91, a headgear assembly 800 is shown connected to the mask assembly 700. The headgear assembly 800 generally comprises a rear strap 802 and a top strap 804. The rear strap 802 and/or the top strap 804 can be adjustable in length. In some configurations, at least one of the rear strap 802 and the top strap 804 can be fixed in length. In the illustrated configuration, the rear strap 802 is configured to pass around the back of the head at a location generally below the ear of the user while the top strap is configured to pass over the top of the head at a location generally forward of the ear. Other locations and configurations are possible. Moreover, in the illustrated configuration, the rear strap 802 and the top strap 804 can be integrally formed. In some configurations, the straps 802, 804 are separately formed and attached together using buckles or another other suitable configuration.

With continued reference to FIGS. 89-91, an extension 806 connects to one or both of the rear strap 802 and the top strap 804. Two arms 808 connect the extension 806 to the mask assembly 700 in the illustrated configuration. In some configurations, the two arms 808 are formed from a single strap. In some configurations, the two arms 808 are formed from two straps. Advantageously, the two arms 808 in the illustrated configuration can be separately adjusted in length and, as such, preferably are formed from two separate straps. Nevertheless, it is possible to have both arms 808 formed from a single component with each of the arms 808 being separately adjustable. By being separately adjustable, the arms 808 enable the illustrated headgear assembly 800 to adjust the angle of the mask. In other words, the mask assembly 700 can be tilted into a desired angular orientation using the arms 808. In addition, because the arms 808 are separately adjustable, the fit of the lower portion of the seal 704 can be adjusted separately from the fit of the upper portion of the seal 704.

With reference now to FIGS. 92-94, another headgear assembly 810 is illustrated therein. The illustrated headgear assembly 810 comprises an upper portion 812 and a lower portion 814. While the illustrated upper portion 812 is separate from the lower portion 814, in some configurations, the upper portion 812 and the lower portion 814 can be joined together. For example, in some configurations, straps can connect the upper and lower portions 812, 814 to form a single integrated headgear assembly 810. In some such configurations, the interconnecting straps can be positioned such that they would be positioned rearward of the ears or just forward of the ears. Other configurations are possible.

In the illustrated configuration, the lower portion 814 comprises a member 816 that connects to the mask assembly 700 in any suitable manner. In some configurations, the member 816 connects with hooks, snaps or other suitable types of connectors. In some configurations, the member 816 extends through loops and is secured back upon itself. In the illustrated configuration, the member 816 is a single component. In some configurations, the member 816 may comprise multiple components. Preferably, the member 816 passes around the back of the head at a location that is generally below the ear of the user.

With reference still to FIGS. 92-94, the upper portion 812 generally comprises a member 820 and a top member 822. The member 820 and/or the top member 822 can be adjustable in length. In some configurations, at least one of the member 820 and the top member 822 can be fixed in length. In the illustrated configuration, the member 820 is configured to pass around the back of the head at a location that would generally intersect at least a portion of the ear of the user while the top member 822 is configured to pass over the top of the head at a location that also would generally intersect vertically over the ear. As illustrated, the member 820 can have a portion 824 that is configured to wrap up and over the ear. Other locations and configurations are possible. Moreover, in the illustrated configuration, the member 820 and the top member 822 can be integrally formed and can meet at a location generally above the ear of the user. In some configurations, the member 820, 822 are separately formed and attached together using buckles or another other suitable configuration.

The headgear assembly 810 enables separate adjustment of the upper portion 812 and the lower portion 814. As described above, by being separately adjustable, the upper portion 812 and the lower portion 814 enable the illustrated headgear assembly 810 to adjust the angle of the mask assembly 700 as shown in FIG. 93. In other words, the mask assembly 700 can be tilted into a desired angular orientation using the separately adjustable upper and lower portions 812, 814. In addition, because the upper and lower portions 812, 814 are separately adjustable, the fit of the lower portion of the seal 704 can be adjusted separately from the fit of the upper portion of the seal 704.

With reference now to FIGS. 95-97, a further headgear assembly 830 is illustrated. The headgear assembly 830 is shown connected to the mask assembly 700. The illustrated headgear assembly 830 comprises an upper portion 832 and a lower portion 834. As shown in FIG. 97, at least one interconnecting member 836 connects the upper portion 832 to the lower portion 834. The at least one interconnecting member 836 in the illustrated configuration comprises a back panel that joins the upper portion 832 to the lower portion 834 in the region of the back of the head of the user. The illustrated interconnecting member 836 is generally hour glass in shape. Other configurations are possible.

In the illustrated configuration, the lower portion 834 comprises at least one member 838 that connects to the mask assembly 700 in any suitable manner. In some configurations, the at least one member 838 connects with hooks, snaps or other suitable types of connectors. In some configurations, the at least one member 838 extends through loops and is secured back upon itself. In the illustrated configuration, the at least one member 838 is a single component. In some configurations, the at least one member 838 may comprise multiple components. For example, two components may extend forward from the interconnecting member 836. Preferably, the at least one member 838 extends from the mask assembly 700 toward the back of the head at a location that is generally below the ear of the user.

With reference still to FIGS. 95-97, the upper portion 832 generally comprises at least one member 840 and a top member 842. The at least one member 840 and/or the top member 842 can be adjustable in length. In some configurations, at least one of the at least one member 840 and the top member 842 can be fixed in length. In the illustrated configuration, the at least one member 840 is configured to pass around the back of the head at a location that would generally pass directly from the mask assembly 700 along a location vertically above the ear of the user to the back of the head while the top member 842 is configured to pass over the top of the head at a location that would generally intersect vertically over the ear. Other locations and configurations are possible. Moreover, in the illustrated configuration, the member 840 and the top member 842 can be integrally formed and can meet at a location generally above the ear of the user. In some configurations, the member 840, 842 are separately formed and attached together using buckles or another other suitable configuration.

The headgear assembly 830 enables separate adjustment of the upper portion 832 and the lower portion 834. As described above, by being separately adjustable, the upper portion 832 and the lower portion 834 enable the illustrated headgear assembly 830 to adjust the angle of the mask assembly 700. In other words, the mask assembly 700 can be tilted into a desired angular orientation using the separately adjustable upper and lower portions 832, 834. In addition, because the upper and lower portions 832, 834 are separately adjustable, the fit of the lower portion of the seal 704 can be adjusted separately from the fit of the upper portion of the seal 704.

With reference now to FIG. 98-100, a further headgear assembly 850 is illustrated. The headgear assembly 850 is shown connected to the mask assembly 700. The illustrated headgear assembly 850 comprises an upper portion 852 and a lower portion 854. In general, the headgear assembly 850 of FIGS. 98-100 is similar to the headgear 830 of FIGS. 95-97 with the exception of having no interconnecting member. Accordingly, the details described above with respect to the headgear 830 of FIGS. 95-97 generally applies equally to the headgear 830 of FIGS. 99-100.

In the illustrated configuration of FIGS. 98-100, the upper portion 852 and the lower portion 854 of the headgear assembly 850 can be formed of a single integrated component. In some configurations, a first member 856 and a second member 858 can be formed of a single component. For example, a single loop of material can extend through loops or the like on the mask to define both the first member 856 and the second member 858. In some configurations, a separate top member 859 can be separate from the single component that defines the first member 856 and the second member 858 or can be integrally formed as part of the single component. Any suitable components can be used.

Figure 103:
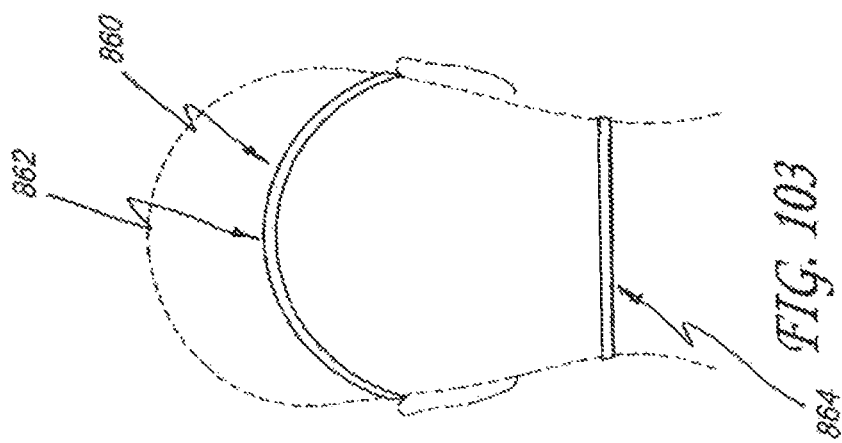
Figure 102:
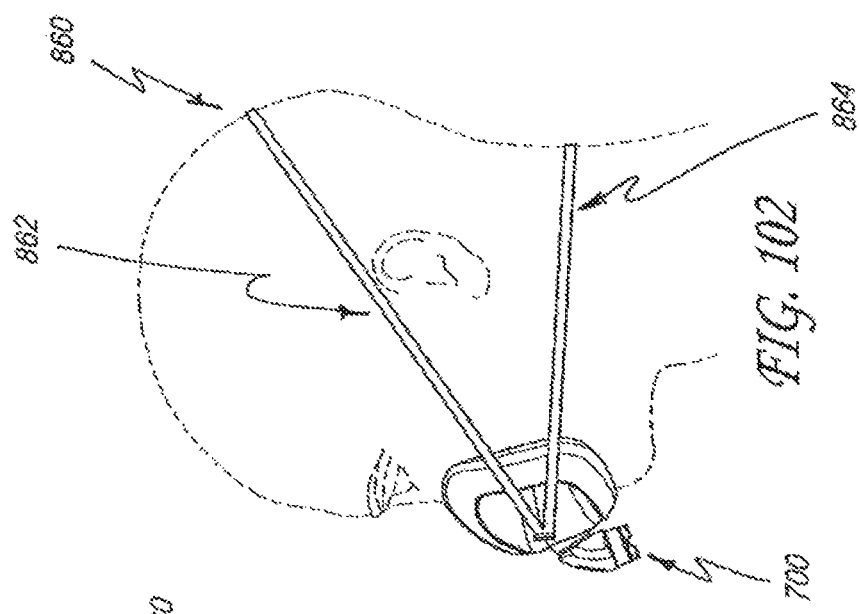
Figure 101:
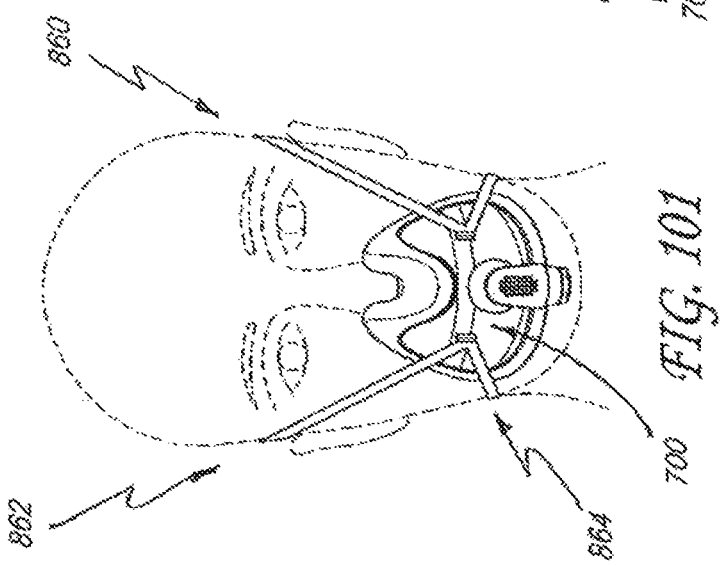

With reference now to FIGS. 101-103, a further headgear assembly 860 is illustrated. The headgear assembly 860 is shown connected to the mask assembly 700. As will be apparent from a comparison of FIGS. 98-100 and FIGS. 101-103, the headgear assembly 860 shown in FIGS. 101-103 is generally the same as the headgear assembly 850 shown in FIGS. 98-100 with the exception of the headgear assembly 860 comprising an upper portion 862 that is lacking a top member. The headgear assembly 860, as such, also comprises a lower portion 864 that is generally the same as the lower portion 854 of the headgear assembly 850 shown in FIGS. 98-100.

Figure 106:
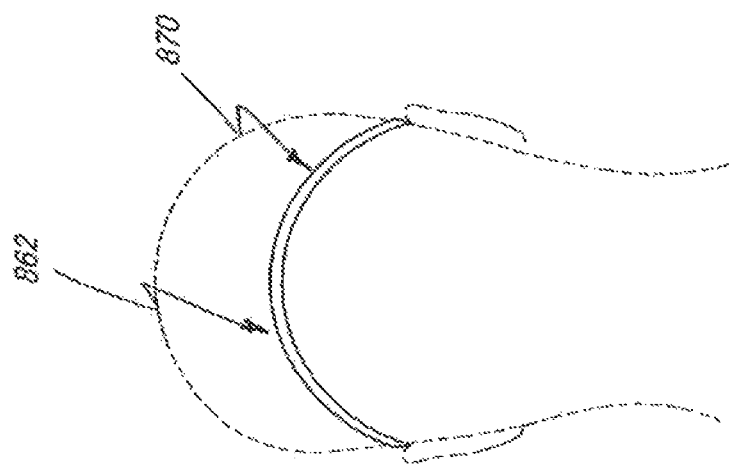
Figure 105:
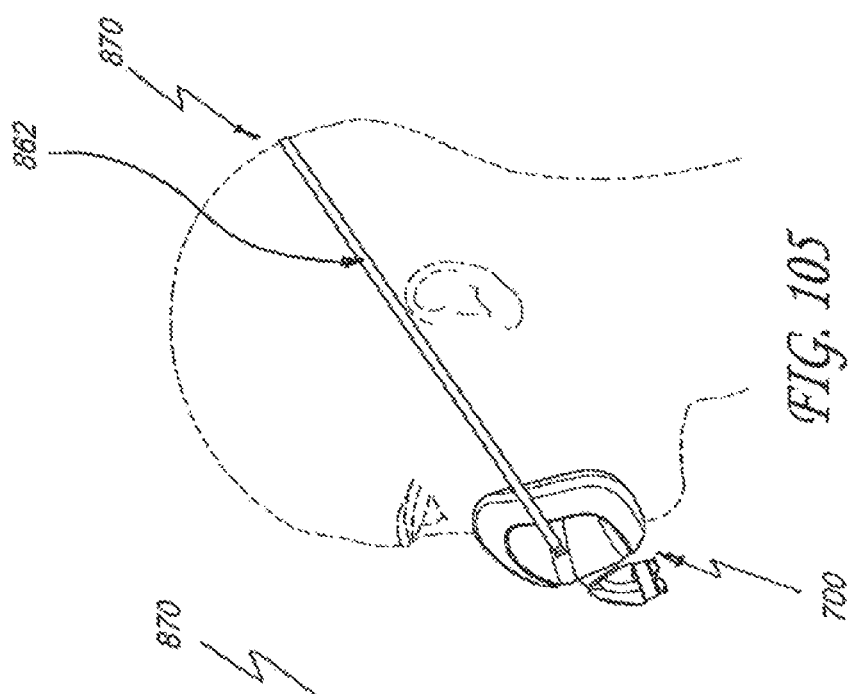
Figure 104:
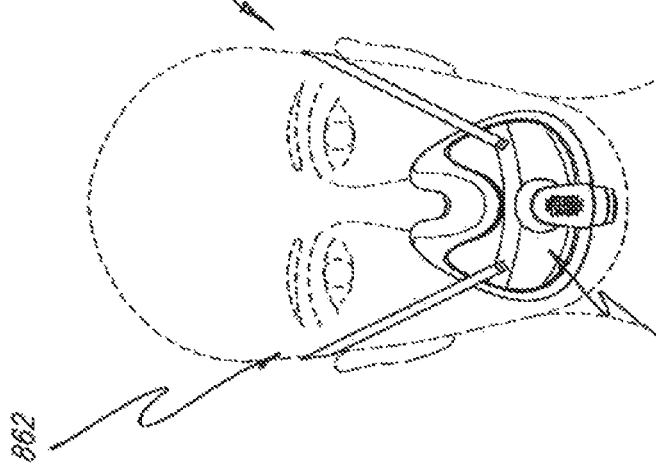

With reference now to FIGS. 104-106, a further headgear assembly 870 is illustrated. The headgear assembly 860 is shown connected to the mask assembly 700. As will be apparent from a comparison of FIGS. 101-103 and FIGS. 104-106, the headgear assembly 870 shown in FIGS. 104-106 is generally the same as the headgear assembly 860 shown in FIGS. 101-103 (including having an upper portion 862) with the exception of the headgear assembly 870 lacking a lower portion.

With reference now to FIGS. 107-109, a further headgear assembly 880 is illustrated. The headgear assembly 860 is shown connected to the mask assembly 700. Similar to the headgear 870 shown in FIGS. 104-106, the headgear 880 shown in FIGS. 107-109 comprises an upper portion 882 without including a lower portion. The upper portion 882 in the illustrated configuration comprises a member 884 that extends upwardly and rearwardly from the mask assembly 700. The member 884 can include an ear accommodation feature 886. The ear accommodation feature 886 is adapted to transfer forces from in front of the ear of the user to the rear of the ear of the user. Accordingly, the ear accommodation feature 886 enables the member 884 to sit lower on the head of the user such that, without the ear accommodation feature 886, the member 884 would intersect the ear of the user.

With reference to FIGS. 108 and 109, in the illustrated configuration, the member 884 bifurcates into an upper member 886 and a lower member 888 at a location just rearward of the ear of the user. In the illustrated configuration, the bifurcation location is adapted to be vertically higher than the ear of the user. Bifurcation of the member 884 into at least the upper member 886 and the lower member 888 can improve stability. Other configurations also can be used, including but not limited to using a wide strap instead of the at least two members 886, 888, incorporating a panel between the upper member 886 and the lower member 888, and the like. In addition, in the configuration illustrated in FIGS. 108 and 109, the connection point between the headgear and the mask assembly is lower than the configuration illustrated in FIGS. 104-106.

A variety of headgear assemblies have been described through the present disclosure. In each of the headgear assemblies, it is possible to have one or more straps, members, components or the like formed to be more flexible than others within the same headgear assembly. For example but without limitation, in some configurations, the portion of the headgear assembly that extends around the back of the head can be more elastic or flexible than the portion of the headgear assembly that extends forward of the ears. In some configurations, the portion of the headgear assembly that extends forward of the ears can be more elastic or flexible than the portion of the headgear assembly that extends rearward of the ears. In some configurations, the more elastic, more flexible or more stretchable portion of the headgear assembly has a portion that overlaps with the less elastic, less flexible or less stretchable portion.

Figure 110:
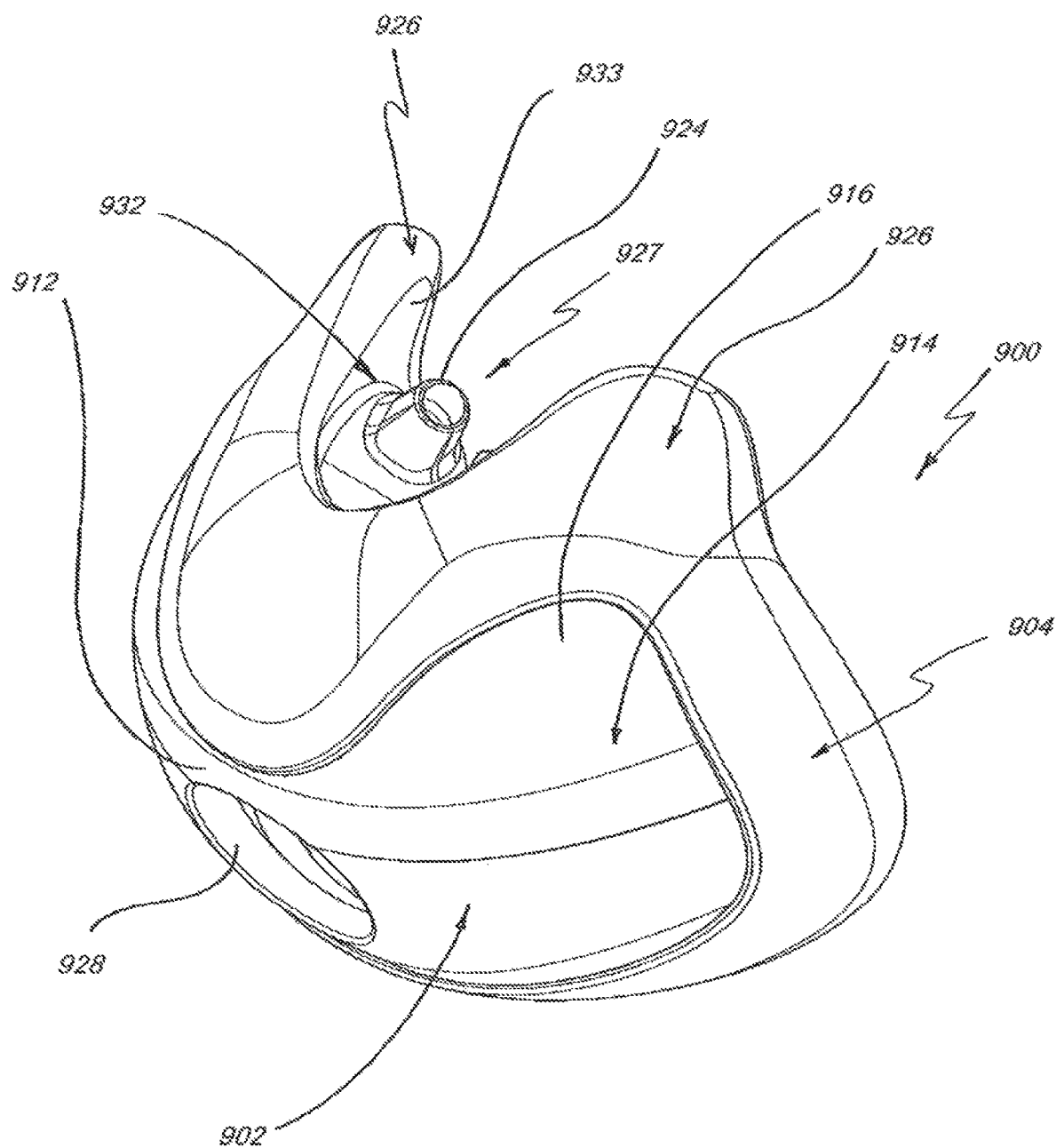
FIG. 110 is a front perspective view of another mask configuration.

With reference now to FIG. 110, an additional mask assembly 900 is illustrated. The illustrated mask assembly 900 is a combined oral nasal mask and is designed to seal below the nose (and/or within the nose) of the user, along a portion of the face extending lateral to the nose, as well as around the mouth of the user. In some configurations, the mask assembly 900 can be designed to go over the tip of the nose and, in such configurations, may seal in regions other than below the nose, within the nose, along a portion of the face extending lateral to the nose and around the mouth of the user.

As with the mask assembly 700, which is shown in FIG. 71, the mask assembly 900 advantageously does not require contact with the bridge of the nose of the user. In the illustrated configuration, the mask assembly 900 does not extend over the bridge of the nose of the user. More particularly, the illustrated mask assembly 900 does not contact the bridge of the nose of the user. Even more particularly, the illustrated assembly 900 does not contact a forward facing portion of the bridge of the nose of the user. In some configurations, the assembly 900 does not contact the face in a region vertically higher than a generally horizontal plane LE extending along the lower edges of the eyes of the user.

In some configurations, the mask assembly 900 does not extend over the tip of the nose of the user. In some configurations, the mask assembly 900 preferably does not enshroud the tip of the nose of the user. In some configurations, the tip of the nose of the user extends over the adjoining portion of the mask assembly 900. In some configurations, the mask assembly 900 can be designed to go over the tip of the nose. In some configurations, the mask assembly 900 can be designed to enshroud the tip of the nose.

The mask assembly 900 preferably is adapted to extend around and seal over the wing or alar of the nose, which flares out to form a rounded eminence around the nostril. The mask assembly 900 can be adapted to seal within and around the surfaces that define the opening to the nostril, including the fleshy external end of the nasal septum, sometimes called the columella. In some configurations, the mask assembly 900 is adapted to extend upwardly to seal along at least a portion of the left and right dorsal side walls of the nose of the user. In some configurations, the mask assembly 900 is adapted to extend upwardly along at least a portion of the left and right dorsal side walls without extending upwardly to the region of the bridge of the nose of the user. As compared to the mask assembly 700 shown in FIG. 71, the mask assembly 900 shown in FIG. 110 can extend into the nasal air passageways and seal along the nasal air passageways as desired.

As illustrated, the mask assembly 900 comprises a mask base 902, a mask seal 904 attached to the mask base 902 and, while not shown, a connector can be attached to the mask base 902. The connector can be connected to the base 902 in any suitable manner, including but not limited to any manner discussed elsewhere within this application. For example, but without limitation, the connector can be connected to the base 902 such that the connector can swivel, pivot and rotate relative to the base 902. In some configurations, the connector can define a portion of a ball joint with the mask base 902, for example but without limitation, defining the other portion. The ball joint can have any suitable configuration and can be configured in accordance with the descriptions of ball and socket arrangements discussed elsewhere within this application. The connector facilitates connection to a supply conduit or the like for the supply of pressurized breathing gases. Any suitable connector can be used.

With reference to FIG. 110, the mask base 902 will be described in greater detail. The mask base 902 provides a support structure of sorts for the mask assembly 900 in general and for the mask seal 904 more specifically. The mask base 902 can be formed from any suitable material. In some configurations, the mask base 902 is formed from a fairly rigid material. In some configurations, the mask base 902 is formed from a plastic material, such as a polycarbonate material.

With reference to FIG. 110, in the illustrated configuration, the mask base 902 sweeps rearward from a central portion 912 with a pair of wings 914. As illustrated, the wings 914 can extend rearward and upward relative to the central portion 912 of the mask base 902. Accordingly, the illustrated wings 914 include upwardly projecting portions 916. The mask base 902 generally, and the upwardly projecting portions 916 of the wings 914 as an example, can provide reinforcement to the lateral portions of the mask seal 904.

The central portion 912 can have a vertical expanse that is lower than the height of the upwardly projecting portions 916 of the wings 914. Thus, when viewed from the front, the mask base 902 comprises an edge having a generally M-shaped appearance. In addition, when viewed from the front, an upper edge of a central area of the mask base 902 comprises a generally U-shaped appearance. By incorporating the recessed central portion 912 between the pair of wings 914, the mask base 902 can provide desired support to the mask seal 904 while providing adequate clearance for the nose of the user.

Figure 112:
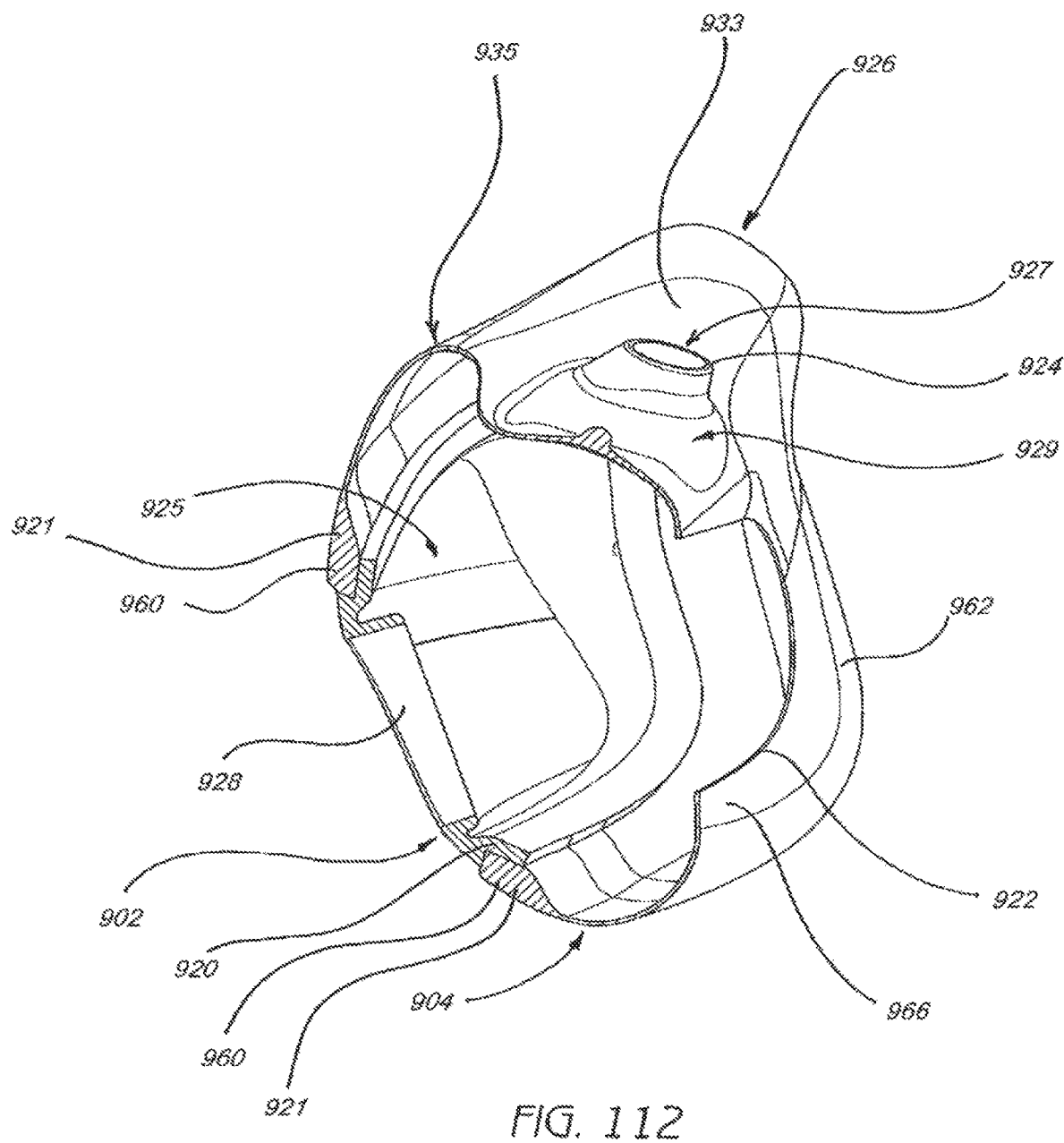
FIG. 112 is a sectioned side view of the mask configuration of FIG. 110.
Figure 113:
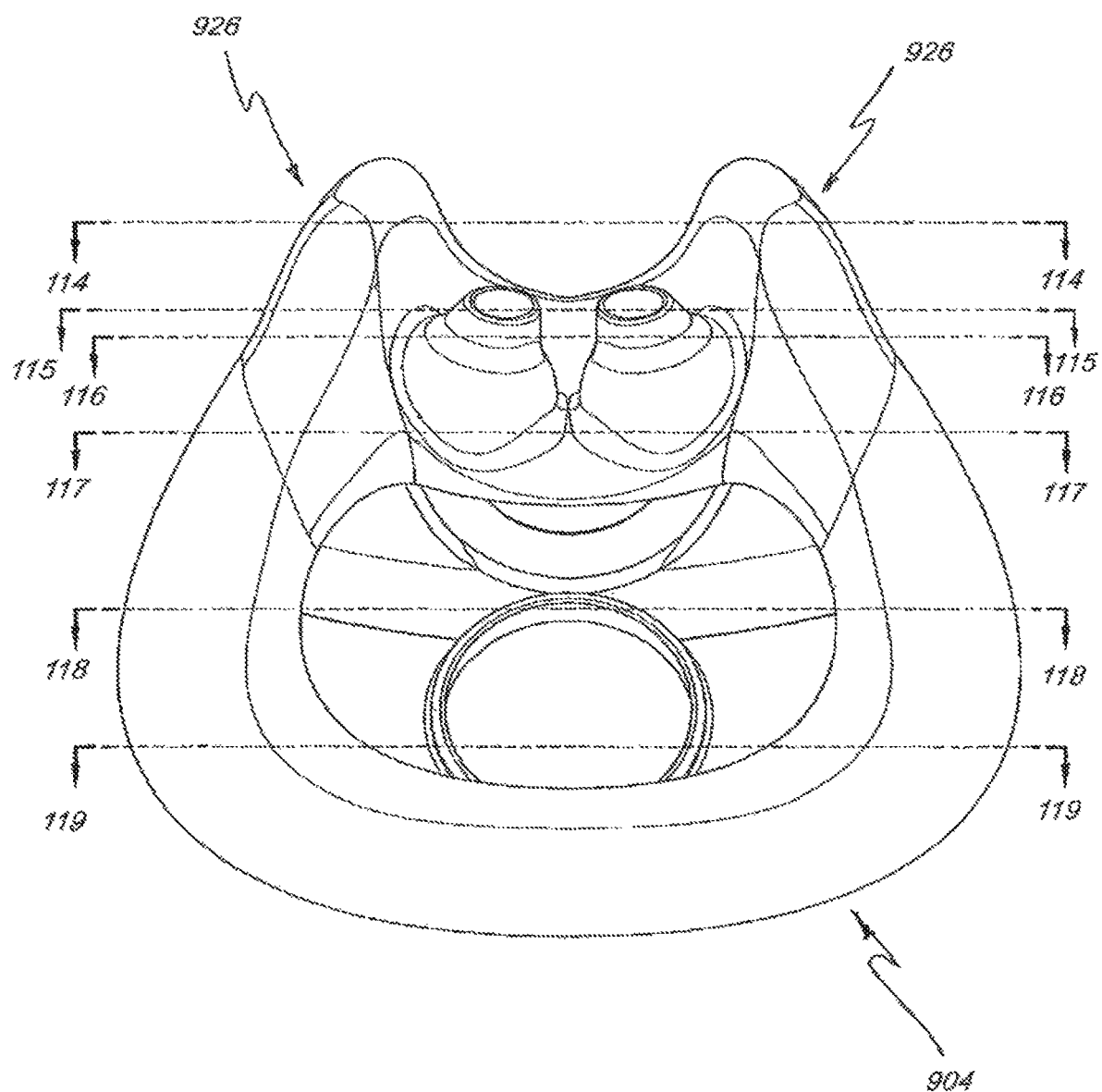
FIG. 113 is a rear perspective view of the mask configuration of FIG. 110.

The mask base 902 and the mask seal 904 can be connected in any suitable manner. With reference to FIG. 112, the mask base 902 comprises a generally circumscribing flange 920 and the mask seal 904 can be overmolded onto the flange 920 of the mask base 902. Any other suitable technique can be used to form the junction between the mask seal 904 and the mask base 902. In some configurations, the mask seal 904 can be formed to allow removal from the mask base 902. For example but without limitation, the mask seal 904 can include a groove and the mask base 902 can include a flange, or any other cooperating structures, such that the mask seal 904 can be removably connected to the mask base 902.

As shown in FIG. 112, the illustrated mask seal 904 comprises a thickened region 921, which is thicker in cross-section, adjacent the juncture with the mask base 902. Such a configuration improves service life of the mask seal 904 as well as improves the integrity of the connection between the mask seal 904 and the mask base 902. In some configurations, the thickest region of the mask seal 904 is the thickened region 921.

The mask seal 904 is designed to seal against the face of the user. The mask seal 904 preferably is formed of a soft material, such as silicone, for example but without limitation. In some configurations, at least portions of the mask seal 904 can be textured to improve comfort to the user. For example, in some configurations, at least portions of the mold used to form the illustrated mask seal 904 can be bead blasted to provide a surface texture in at least the regions of the mask seal 904 that will contact the skin of the user. Other techniques for texturing one or more surface of the mask seal 904 can be used.

As shown in FIG. 110, the illustrated mask seal 904 comprises an oral-nasal mask seal and, therefore, comprises at least one oral opening 922 and at least one nasal opening 924. In some configurations, the mask seal 904 can comprise a combined oral-nasal opening. In some configurations, such as the illustrated embodiment, the mask seal 904 can comprise more than one nasal opening 924. In the illustrated configuration, the mask seal 904 comprises nasal openings 924 defined within superstructures, such as pillows, prongs or the like. The illustrated configuration comprises prongs 927. In some configurations, a single prong (or other superstructure) can be used. In other applications, two or more prongs (or superstructures) can be used. The prong or prongs (or other superstructures) enable the mask seal 904 to be more easily positioned as desired on the face of the user. In addition, through the user of a superstructure, such as a prong, for example but without limitation, the mask is easier to seal (e.g., the superstructure can seal within the nare rather than sealing under the nare or along the face) and the mask seal 904 is less likely to have the at least one opening 924 occluded partially or fully by the facial features of the user.

Figure 114:
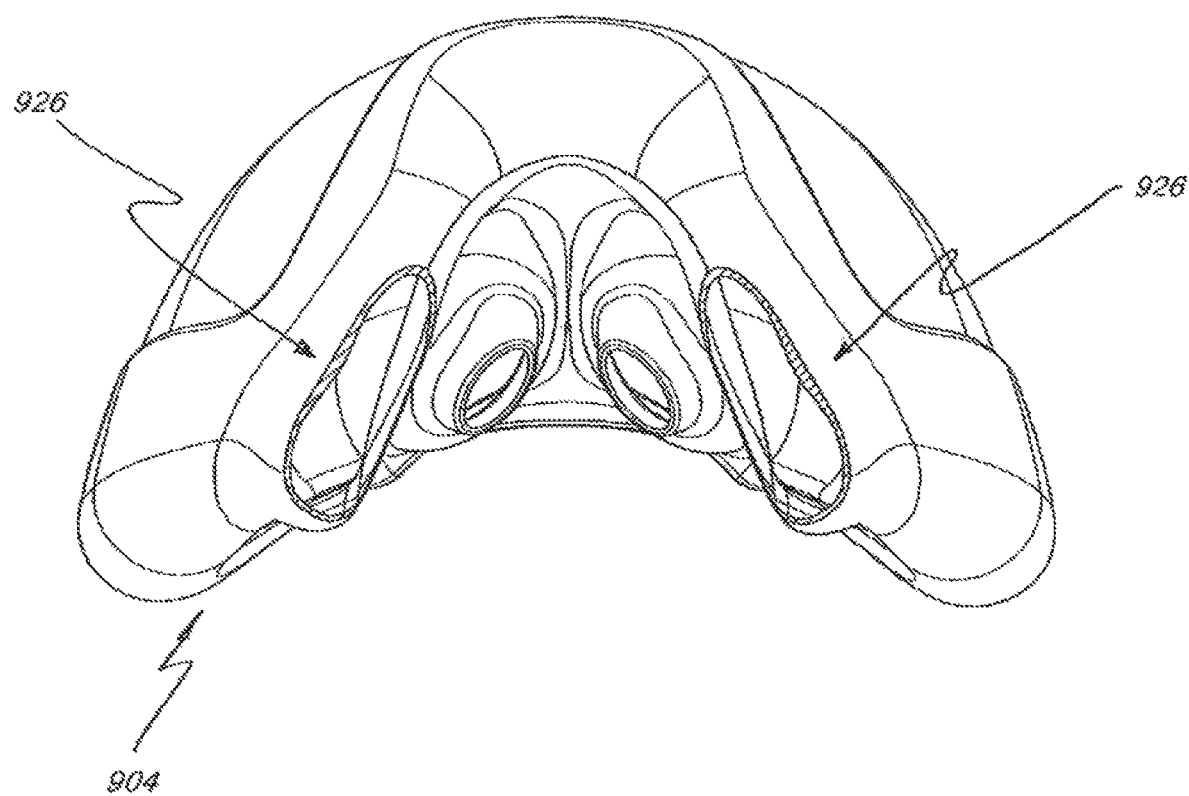
FIGS. 114-119 are sectioned views taken along the lines indicated in FIG. 113.

Any suitable prong 927 configuration can be used. In the illustrated configuration, the prong 927 generally tapers in an upwardly direction from a bulbous base 929 to the small opening 924. The opening 924 can be generally elliptical or ovular in shape. In addition, the transition from the bottom to the top of the prong 927 can be shaped to provide improved sealing for many different nasal opening geometries. As such, each prong 927 may be inclined toward a generally vertical central plane (e.g., a plane corresponding to a medial saggital plane of the user). In addition, the prong 927 may have a shape that increases in outer dimension in a non-uniform manner as best shown in FIG. 114. In other words, the base 929 may grow in size from front to back more than from side to side. In addition, the base 929 may increase in dimension greater to the rear than to the front. Other configurations are possible.

The at least one oral opening 922 and the at least one nasal opening 924 preferably communicate with a single chamber 925 that is defined within the mask assembly 900. The chamber 925 of the illustrated mask assembly 900 is at least partially defined by the mask base 902 and the mask seal 904. The at least one oral opening 922 is substantially opposed to an opening 928 that receives the connector. The at least one nasal opening 924 can be vertically above the at least one oral opening 922. The at least one nasal opening 924 can be positioned between the opening 928 for the connector and the at least one oral opening 922.

Figure 111:
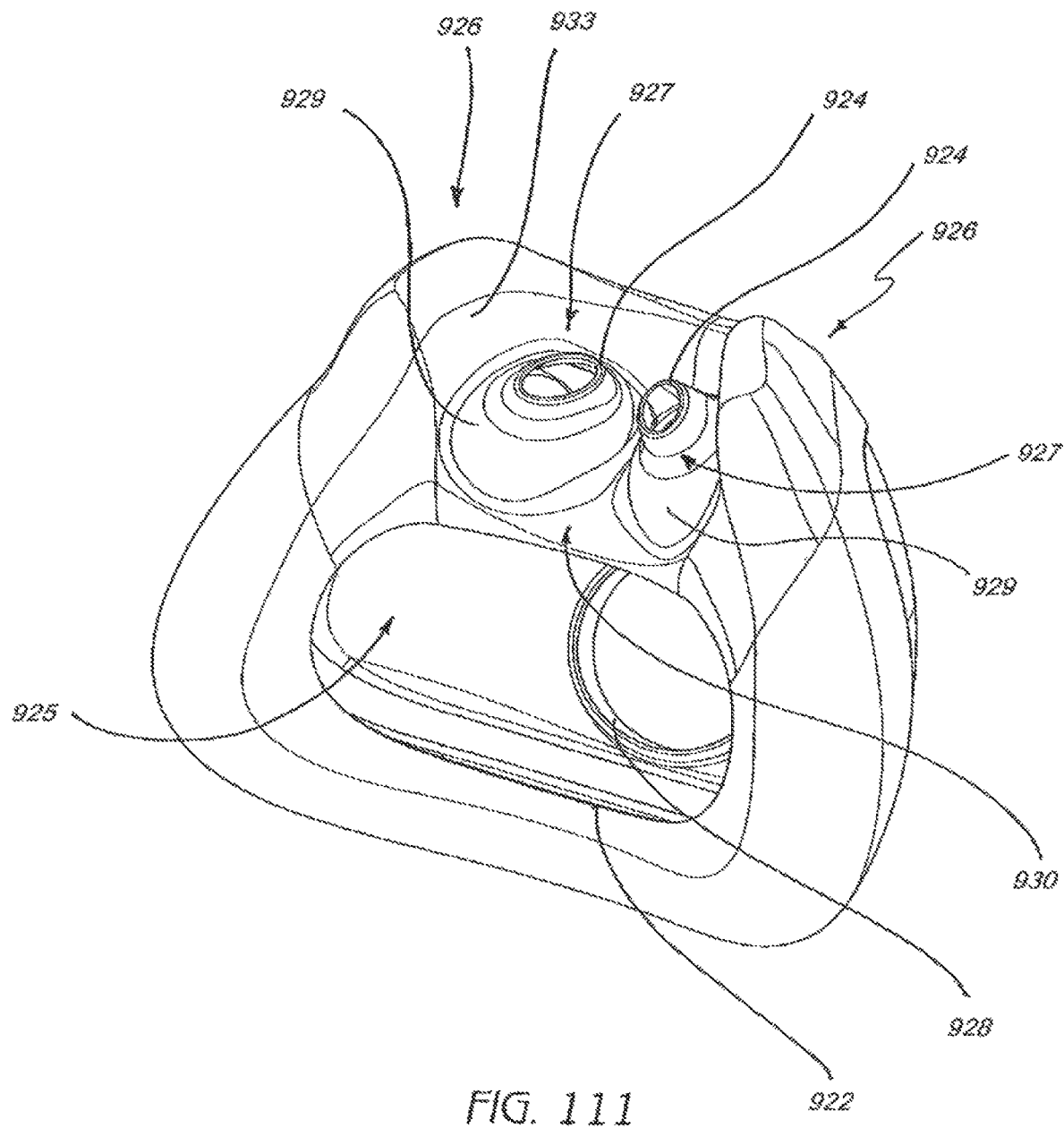
FIG. 111 is a rear perspective view of the mask configuration of FIG. 110.

With reference again to FIG. 110, the mask seal 904 preferably comprises a pair of paddles 926 that extend upward above an upper surface 930. The paddles 926 are configured to extend upward alongside, and in some configurations above, the nares. Preferably, as shown in FIG. 111, the upper surface 930 is hammocked between inner portions 933 of the paddles 926. In such a configuration, downward pressure applied to the upper surface 930 can cause the paddles 926 to pivot inwardly at the top. Accordingly, increasing force between the nose of the user and the upper surface 930 can result in increasing sealing force being applied between the sides of the nose of the user and the paddles 926. The degree to which the pivoting action results in increasing force can be varied by construction. In other words, longer paddles 926 display increased degrees of pivoting compared to shorter paddles 926. On the other hand, shorter paddles 926 are capable of accommodating greater variations in nasal geometries compared to longer paddles 926 and result in the mask assembly 900 being easier to put onto the face.

The paddles 926 and the upper surface 930 define a valley 932. The valley 932 can be adapted to receive the tip of the nose of the user. The valley 932 in the illustrated configuration is open in an upwardly direction. In other words, the region of the illustrated mask assembly 900 that accommodates the nose is not enclosed from the top and is configured to rest under the nose.

In the illustrated configuration, as shown in FIG. 112, the prongs 927 are positioned such that the at least one nasal opening 924 is positioned vertically lower than the uppermost extent of the thickened region 921. In some configurations, the prongs 927 can be positioned such that the at least one nasal opening 924 is positioned vertically higher than or at the same height as the uppermost extent of the thickened region 921.

As illustrated, forward of the prongs 927, the mask seal 904 tapers and curls downward toward the prongs 927 to define the upper surface 930 and the valley 932. The tapering and curling forms a deflection region 935. The deflection region 935 can be sufficiently thin and/or elastic that the mask seal 904 can inflate in the nasal region at least in the deflection region 935. In some configurations, both at least a portion of the inner portions 933 and the deflection region 935 are sufficiently thin to allow inflation around the nasal region of the user. In some configuration, the material is less than about 0.3 mm thick and more preferably less than about 0.2 mm thick. The deflection region 935 can also be sufficiently thicker and/or more rigid such that the mask seal 904 can retain its shape in the nasal region at least in the deflection region 935. In some configurations, both at least a portion of the inner portions 933 and the deflection region 935 are sufficiently thick for shape-retaining. In some configurations, the material is less than about 0.7 mm thick and more preferably less than about 0.5 mm thick.

As with the mask seal 700 described above and as shown in FIGS. 112-120, the illustrated mask seal 904 of the mask assembly 900 comprises a fairly complex range and configuration of thicknesses. The thicknesses are varied to take advantage of different characteristics in different regions of the illustrated mask seal 904. For example, with reference to FIG. 112, the mask seal 904 illustrates a connecting region 960 that generally corresponds to the thickened portion 921. The connecting region 960 generally encircles an opening that receives the mask base 902. The connecting region 960 can be the thickest portion of the seal member 904 in some configurations. The connecting region 960 joins the mask seal 904 to the mask base 902. Accordingly, the connecting region 960 preferably has sufficient thickness to provide sufficient rigidity for connection and to provide sufficient thickness for durability. In some configurations, the thickness of the connecting region is between about 2 mm and about 4 mm. In the illustrated configuration, the thickness is between about 3.3 mm and about 3.5 mm.

Figure 120:
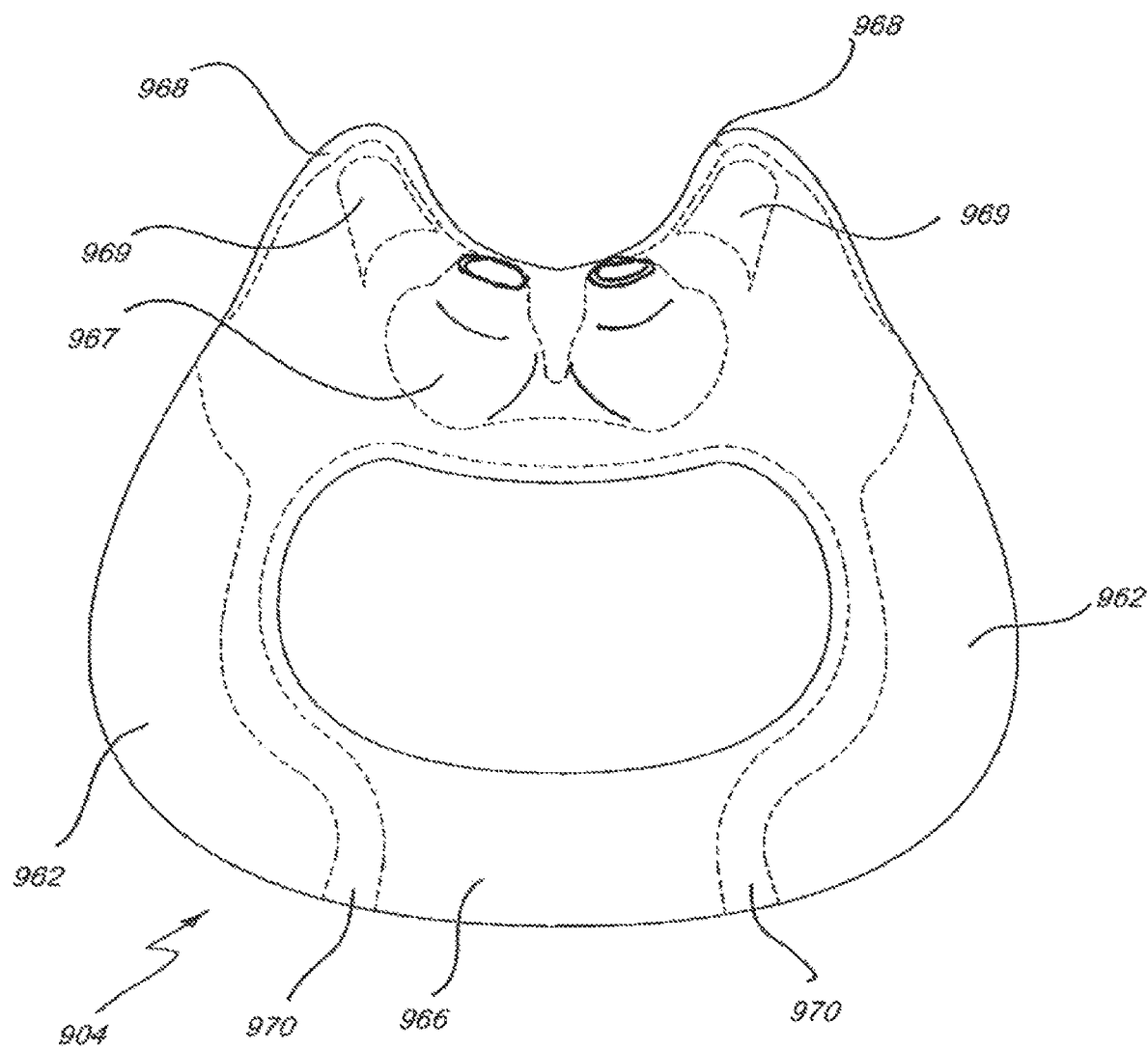
FIG. 120 is a rear view of the mask configuration of FIG. 110 with different regions of thickness indicated.

With reference primarily to FIG. 120, outer peripheral portions 962, which are generally adjacent to the face contacting portions of the mask seal 904, can be fairly rigid. The outer peripheral portions 962 can extend from a lower corner of the face contacting portion surrounding the oral opening 922 upward to a region just below the start of the paddles 926. Thus, the outer peripheral portions 962 extend along the generally vertically extending portions on the rear of the mask seal 904 and wrap slightly inward at a bottom of the rear of the mask seal 904. The outer peripheral portions 962, however, terminate short of the ultimate central portion of the lower portion of the mask, which is softer to accommodate varied contours created by differing facial geometries of the users. The outer peripheral portions 962 also can wrap from a rear facing side of the mask seal around to at least a portion of a laterally facing side of the mask seal 904. In some configurations, the thickness of the outer peripheral portions can be between about 0.8 mm and about 1.5 mm. In the illustrated configuration, the outer peripheral portions 962 have a thickness less than that of the connecting region 960, and preferably have a thickness of about 1.2 mm to about 1.3 min.

The mask seal 904 also comprises an oral region 966. The oral region 966 in the illustrated mask seal 904 extends along at least a portion of the oral opening 922. In the illustrated configuration, the oral region 966 extends along at least a lower portion of the oral opening 922. In the illustrated configuration, the oral region 966 extends along at least the sides and the bottom of the oral opening 922. The oral region 966 provides a softer region that contacts the face. Accordingly, the oral region 966 can have a thinner cross-section. For example, in some configurations, the oral region 966 has a thickness less than that of the outer peripheral portions 962 and, in some configurations, has a thickness of between about 0.3 mm and about 1.0 mm. In the illustrated configuration, the thickness of the oral region is about 0.5 mm.

The nasal prongs 927 can be formed within an interfacing region 967. The interfacing region 967 preferably has sufficient rigidity to locate within the nares of the user while remaining soft and deformable enough to be comfortable for the user over a night of use, for example. In the illustrated configuration, the interfacing region includes both of the prongs 927 as well as the immediately adjacent regions. In some configurations, the thickness of the interfacing region 967 is between about 0.5 mm and about 1.5 mm. In the illustrated configuration, the thickness is between about 0.8 mm and about 0.5 mm.

With reference to FIG. 120, a paddle region 968 can wrap over the upper portions of the paddles 926. The paddle region 968 can generally surround the valley 932. The paddle region 926 preferably is very conformable and, as such, has a thickness of between about 0.3 mm and about 1.2 mm. In the illustrated configuration, the paddle region 968 has a thickness of about 0.5 mm.

Between the paddle region 968 and the prongs 927 is a flexible zone 969. The flexible zone 969 preferably is formed along the inner portions 933 of the paddles 926. In some configurations, the flexible zone 969 is on each lateral side of the prongs 927. In some configurations, the flexible zone 969 extends on both lateral sides of the prongs 927 and wraps around to a location generally forward of the prongs 927. The flexible zone 969 overlies pockets defined within the paddles 926, which pockets are in fluid communication with the chamber 925. As such, pressure from within the chamber 925 can somewhat inflate, or cause bulging of, the flexible zones 969 to improve sealing with the nose of the user. The flexible zones 969 preferably have a thickness of less than about 0.5 mm. In some configurations, the inflation zones 969 can have a thickness of between about 0.2 mm and about 0.7 mm. In the illustrated configuration, the inflation zones 969 have a thickness of about 0.2 mm.

With continued reference to FIG. 120, a transitional portion 970 having a transitioning thickness can be defined between each of the regions described above. Other configurations also are possible.

With reference to FIGS. 113-119, various sections through the mask seal 904 shown in FIG. 110 are presented. These sections help to illustrate the various transitions occurring within the mask seal 904.

Figure 115:
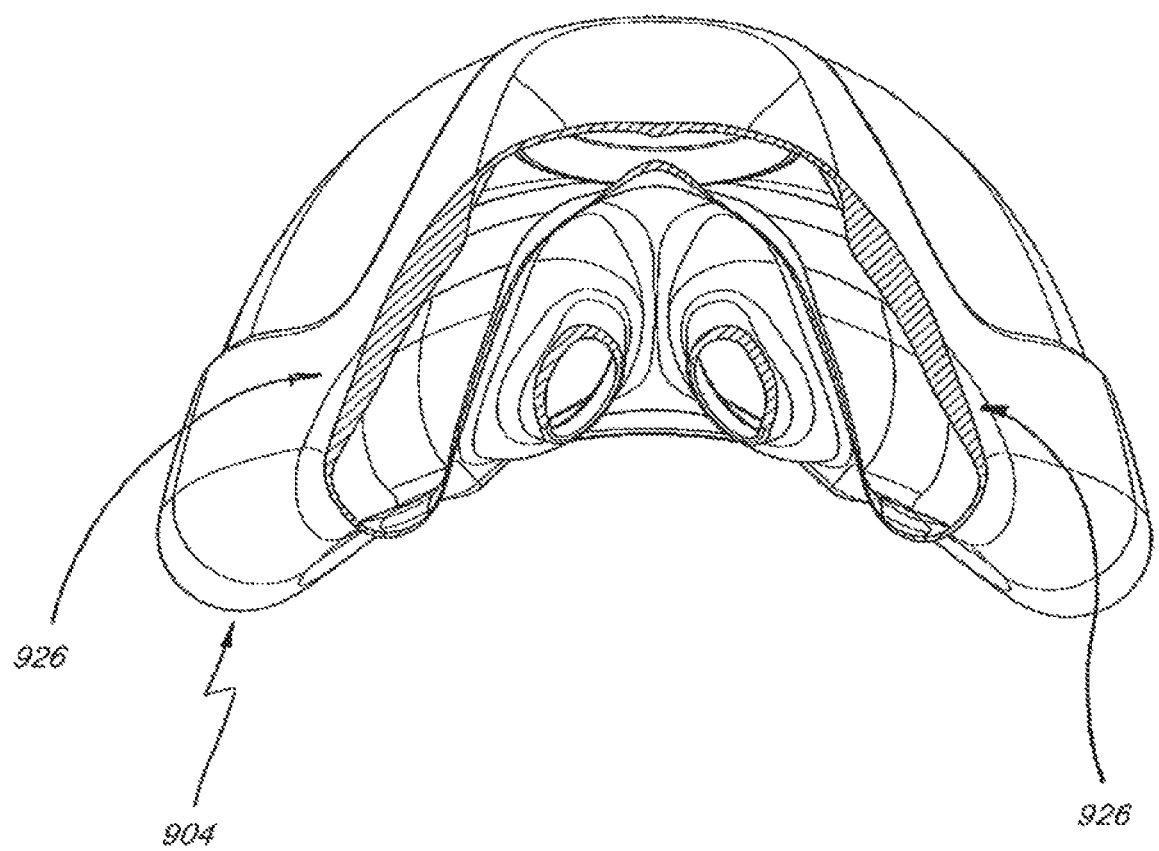
Figure 116:
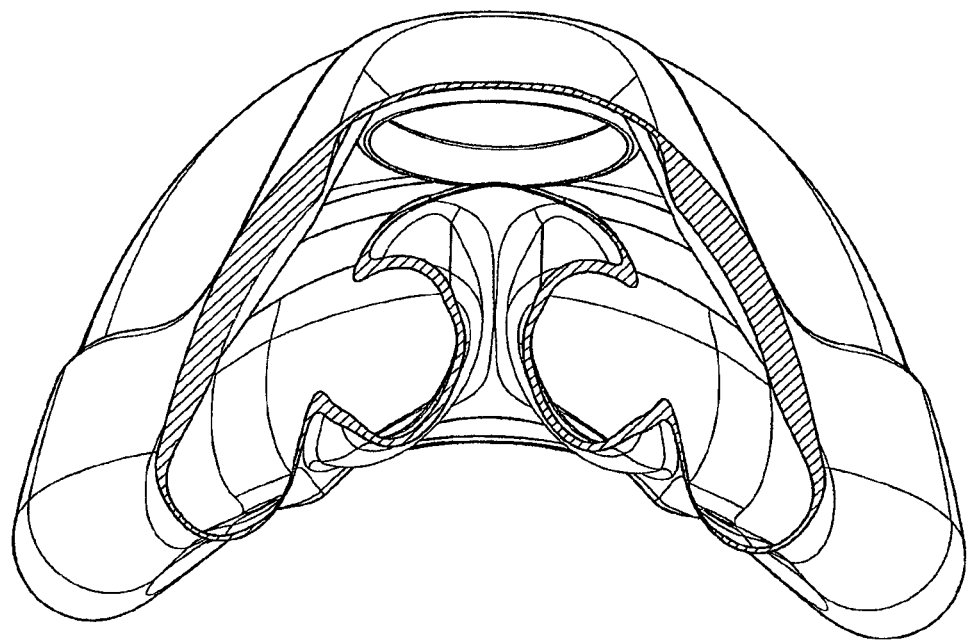
Figure 117:
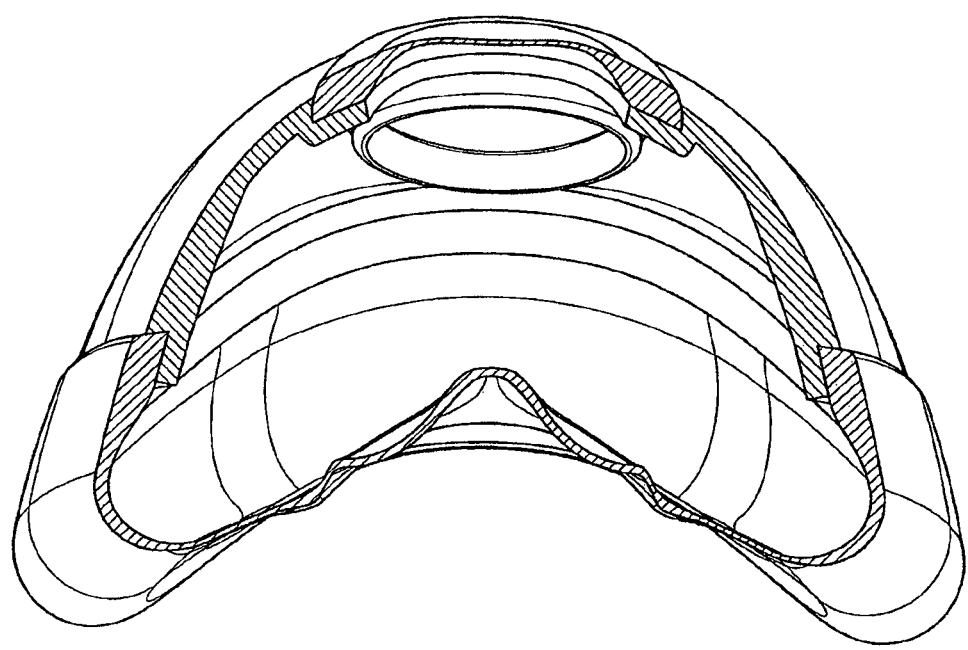
Figure 118:
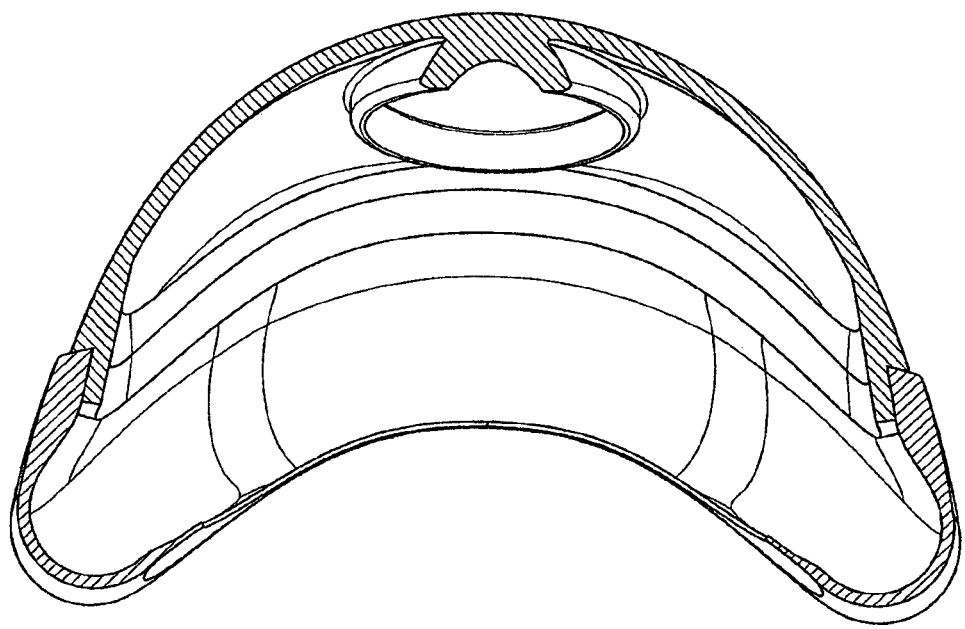
Figure 119:
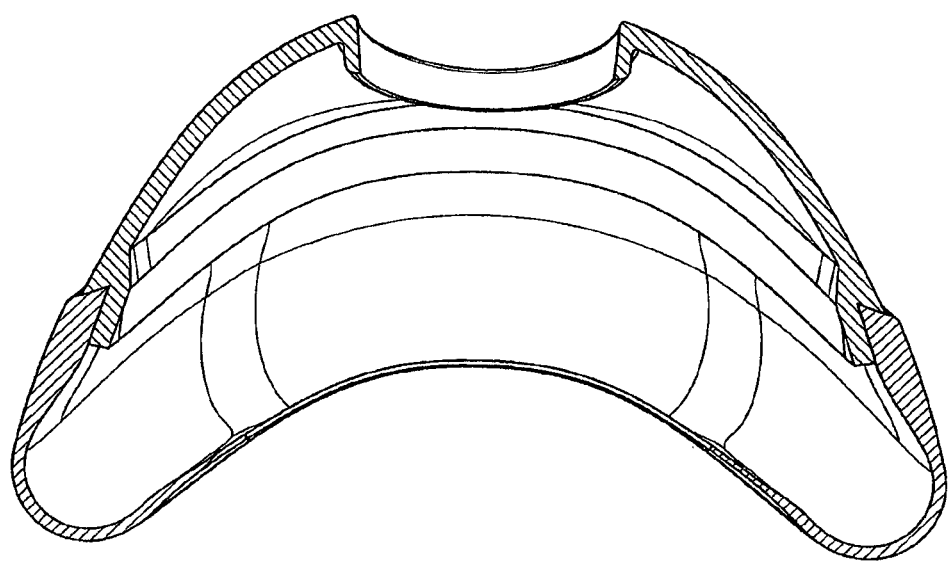

With reference to FIGS. 114 and 115, the paddles 926 as shown in cross section. As illustrated therein, the paddles 926 can have a relatively thin cross section on an inner portion while have a significantly thicker outer portion. The thicker outer portion can help provide structure and shape while the inner portion remains sufficiently thin to allow controlled inflation or controlled expansion at typical treatment pressures (e.g., about 3 cmH2O to about 25 cmH2O). In some configurations, the portion of the paddles 926 that will contact the face comprises a generally constant cross-section. In the illustrated configuration, in the upper portions of the paddles 926 (see FIG. 114), the transition between the thicker cross section and the thinner cross section occurs prior to the radius defined between the inner portion and the outer portion. Such a configuration improves the conformance of the paddles 926 to the facial geometry of the user. In the illustrated configuration, in the lower portions of the paddles 926 (see FIG. 115), the transition between thicker cross section and the thinner cross section occurs along a portion that will contact the face of the user such that greater control over deformation in the pocket between the nose and the cheek can be attained. Other configurations are possible.

The illustrated mask seal 904 is designed to anchor on two locations of the face of the user: under/within the nose and below the lower lip. In some configurations, the mask seal 904 is configured to anchor below the nose (or within the nostrils) and between the lower lip and the chin. In some configurations, the mask is designed to seal off airflow through the mask assembly 900 by sealing against the face of the user at locations higher than all of the anchor points. Thus, at least some sealing portions of the illustrated mask seal 904 are positioned vertically higher than the anchor points.

The mask seal 904 can have different sizes for use with faces having different sizes and/or geometries. In some configurations, different portions of the mask seal 904 can be sized and configured to accommodate users having different sizes and/or geometries. For example, portions of the mask seal 904 can extend upward to different degrees for different users. In some configurations, a single size mask seal 904 can be provided for all face sizes and geometries.

In some configurations, the mask seal 904 comprises multiple components formed of differing materials and/or differing shore hardnesses. For example, in some configurations, some components of the mask seal 904 can be formed of silicone, while other components are formed of foam, gels, cloth or other suitably compliant materials. In the illustrated configuration, however, the mask seal 904 is formed of a uniform material, such as silicone for example but without limitation.

Figure 122:
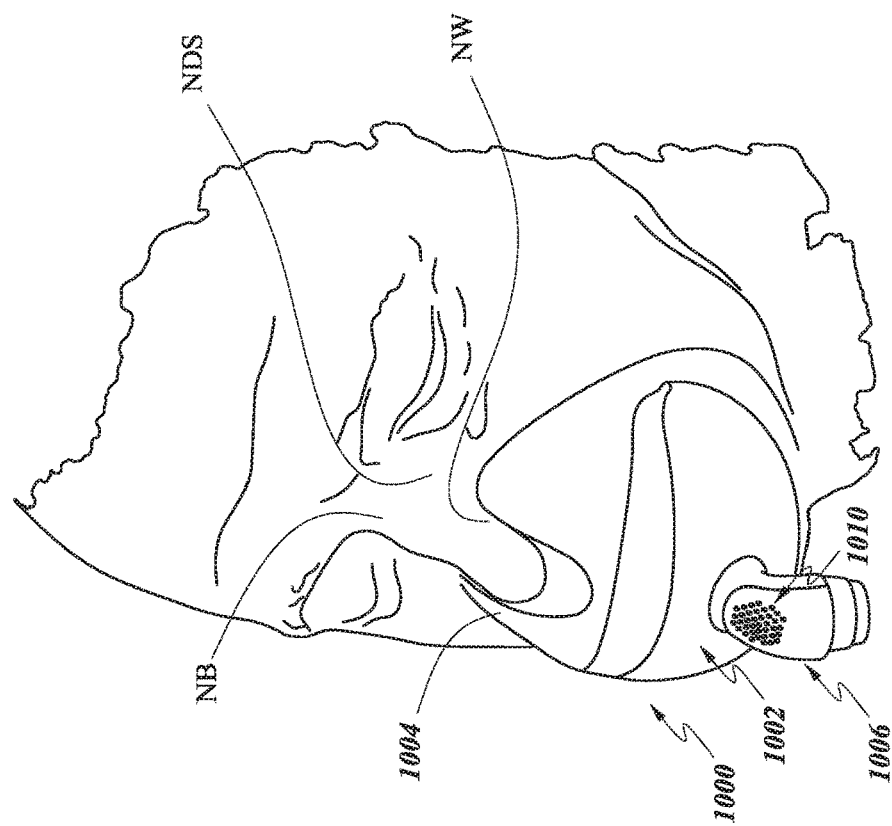
FIG. 122 is a perspective view of the mask configuration of FIG. 121 shown in position on a user.
Figure 121:
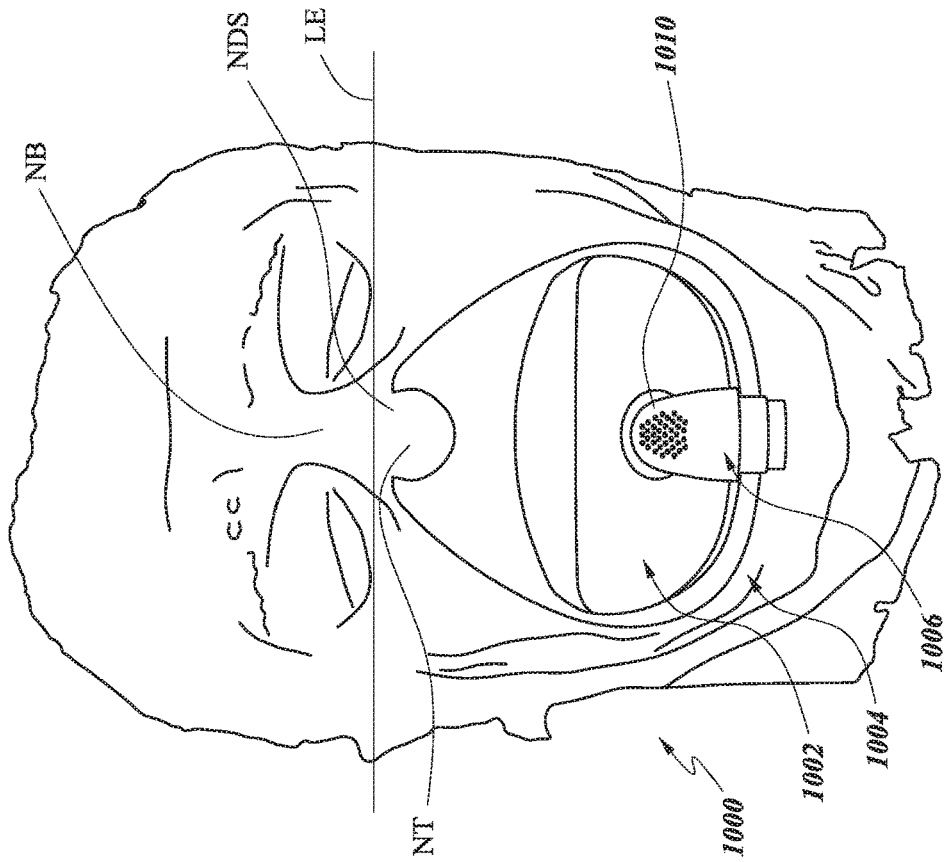
FIG. 121 is a front view of another mask configuration shown in position on a user.

With reference to FIGS. 121 and 122, a further mask assembly 1000 is illustrated in position on the face of a user. The illustrated mask assembly 1000 is a combined oral and nasal mask and is similar in many respects to the mask assembly 700 shown in and described with reference to FIGS. 71-88. That is, the illustrated mask 1000 is designed to seal under the nose of the user, along with a portion of the face extending lateral to the nose, as well as around the mouth of the user. Preferably, the mask assembly 1000 also has one portion that is deformable relative to another portion, such as utilizing a rolling hinge in a manner similar to several other of the mask assemblies disclosed herein (e.g., mask assemblies of FIGS. 1-16 and 24-27). Accordingly, features, components or portions of the mask assembly 1000 not described in detail can be assumed to be the same as or similar to the other mask assemblies described herein (including the masks of FIGS. 1-16, 24-27 and 71-88 and others) or can be of any other suitable arrangement. Moreover, the mask assembly 1000 can be used with any complementary components or other common items described herein or typically used with a mask assembly, such as any of the headgear arrangements described herein or generally suitable for use with a mask assembly, for example and without limitation.

The mask assembly 1000 advantageously does not require contact with the bridge NB of the nose of the user and, preferably, the mask assembly 1000 does not extend over the bridge NB of the nose of the user. In particular, the illustrated mask assembly 1000 does not contact the bridge of the nose of the user. More particularly, the illustrated assembly 1000 does not contact a forward facing portion of the bridge of the nose of the user. In some configurations, the assembly 1000 does not contact the face in a region vertically higher than a generally horizontal plane LE extending along the lower edges of the eyes of the user. In the illustrated configuration, the mask assembly 1000 preferably does not extend over the tip NT of the nose of the user. In some configurations, the illustrated mask assembly 1000 preferably does not enshroud the tip NT of the nose of the user. In some configurations, the tip NT of the nose of the user extends over the adjoining portion of the mask assembly 1000.

As illustrated, the mask assembly 1000 preferably is adapted to extend around and seal over the wing NW or alar of the nose. The illustrated mask assembly 1000 is adapted to seal around the surfaces that define the opening to the nostril, including the fleshy external end of the nasal septum or columella. In some configurations, the mask assembly 1000 is adapted to extend upwardly to seal along at least a portion of the left and right dorsal side walls NDS of the nose of the user. In some configurations, the mask assembly 1000 is adapted to extend upwardly along at least a portion of the left and right dorsal side walls NDS without extending upwardly to the region of the bridge NB of the nose of the user.

Figure 128:
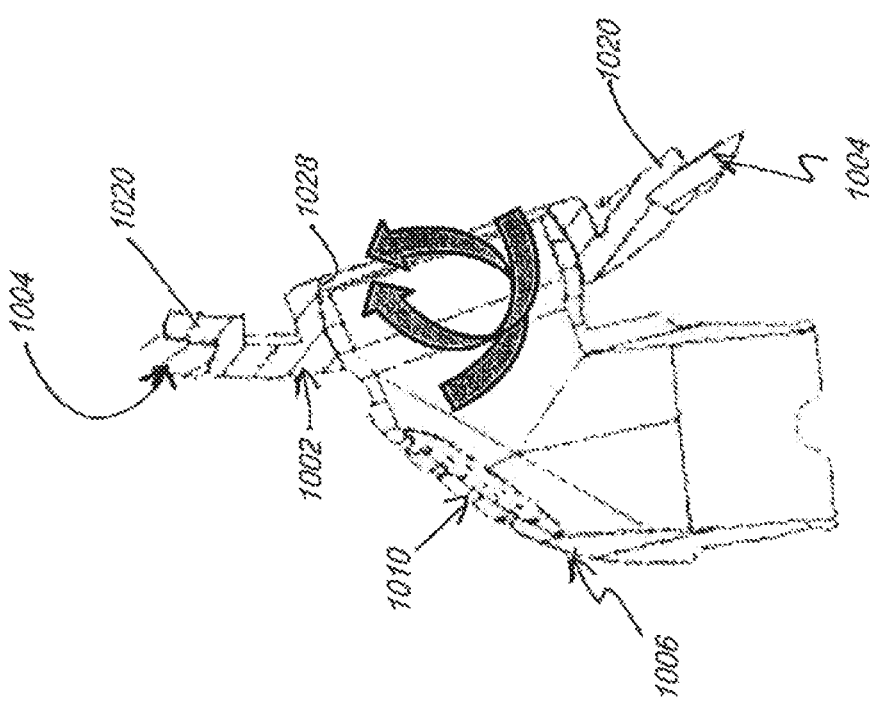
FIG. 128 is an enlarged view of a portion of the mask configuration indicated by the circle 128 of FIG. 127 and showing an intersection between the mask seal and the mask base.

As illustrated, the mask assembly 1000 comprises a mask base 1002, a mask seal 1004 attached to the mask base 1002 and a connector 1006 also attached to the mask base 1002. The connector 1006 can be connected to the base 1002 in any suitable manner, including but not limited to any manner discussed elsewhere within this application. For example, but without limitation, the connector 1006 can swivel, pivot and rotate relative to the base 1002, as shown in FIG. 128. In some configurations, the connector 1006 can define a portion of a ball joint with the mask base 1002, for example but without limitation, defining the other portion. The ball joint can have any suitable configuration and can be configured in accordance with the descriptions of ball and socket arrangements discussed elsewhere within this application. The connector 1006 facilitates connection to a supply conduit or the like for the supply of pressurized breathing gases. Any suitable connector 1006 can be used.

In the illustrated configuration, the connector 1006 comprises an elbow, such as a polycarbonate elbow, for example but without limitation, that contains bias flow holes 1010. The bias flow holes 1010 can be exclusively on the connector 1006 or, in some configurations, the bias flow holes 1010 can be provided on the mask base 1002, on the mask seal 1004 or on any combination of the connector 1006, the base 1002 and the seal 1004. The bias flow holes 1010 can have any suitable cross-section and can be cylindrical, hour-glass shaped, tapered in either direction, fully or partially tapered, fully or partially cylindrical, contoured to vary in cross-section or the like.

Figure 123:
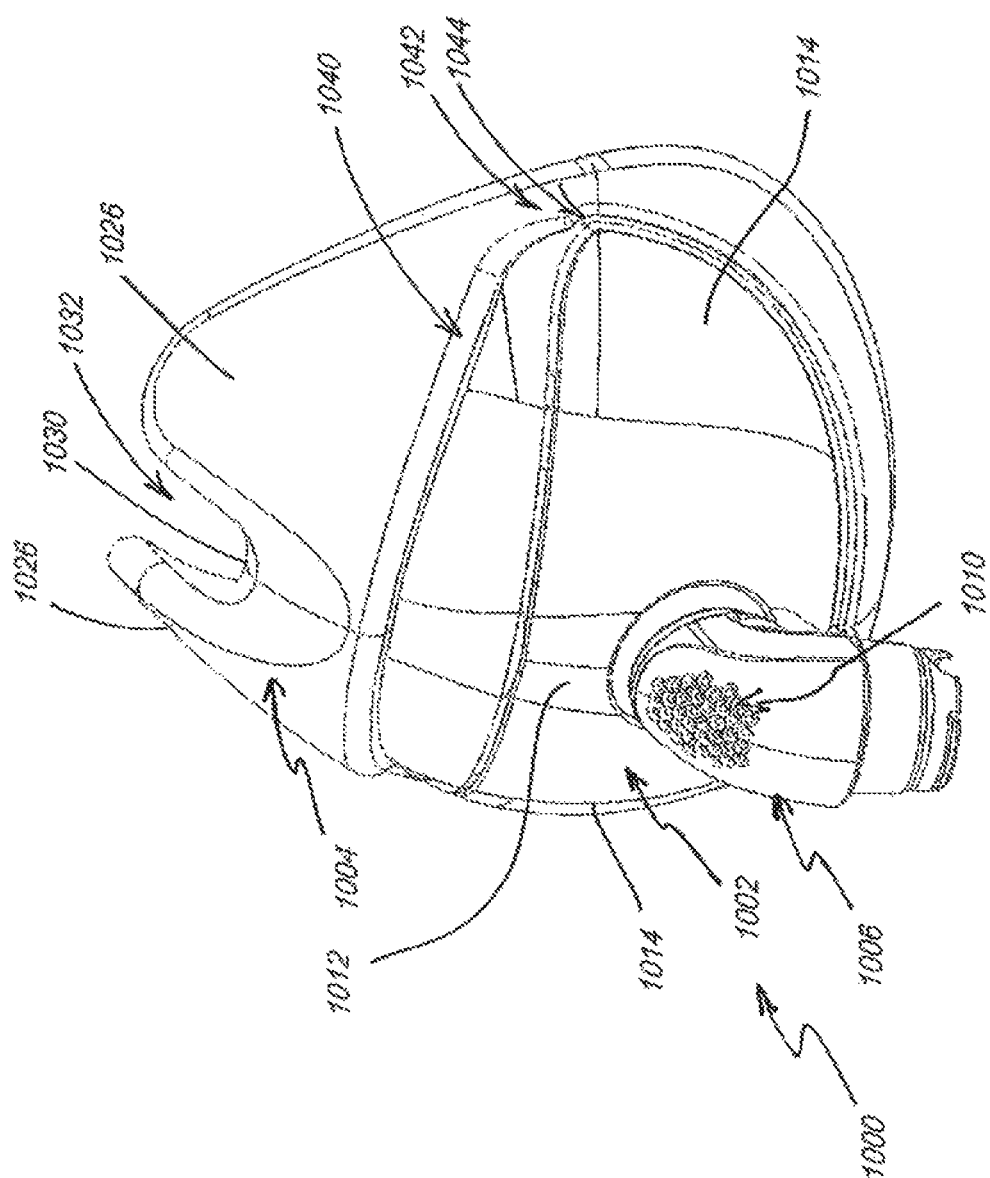
FIG. 123 is a perspective view of the mask configuration of FIG. 121.
Figure 124:
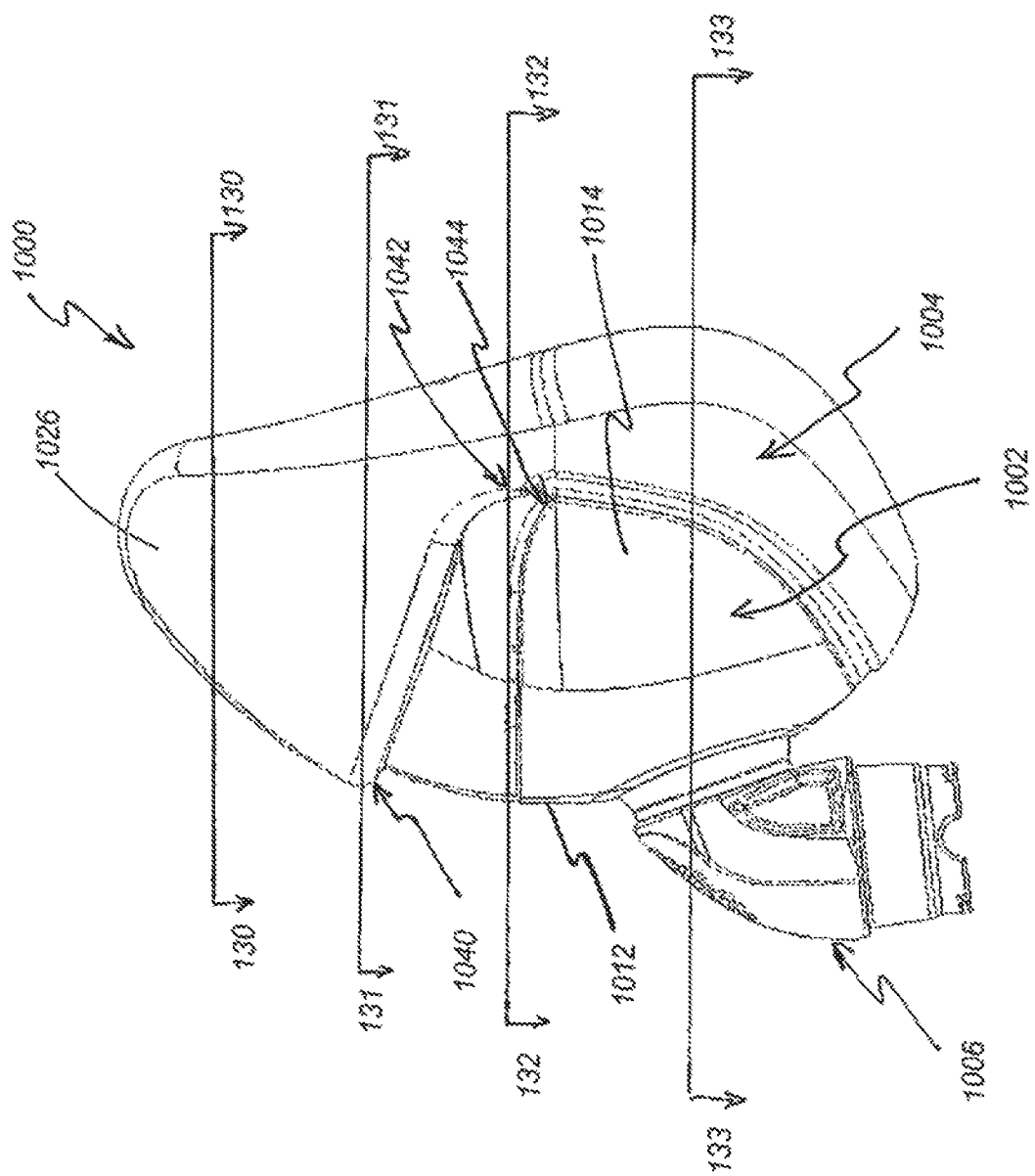
FIG. 124 is a side view of the mask configuration of FIG. 121.

With additional reference to FIGS. 123 and 124, the mask base 1002 is described in greater detail. The mask base 1002 provides a support structure of sorts for the mask assembly 1000 in general and for the mask seal 1004 more specifically. The mask base 1002 can be formed from any suitable material. In some configurations, the mask base 1002 is formed from a fairly rigid material. In some configurations, the mask base 1002 is formed from a plastic material, such as a polycarbonate material. In the illustrated configuration, the mask base 1002 sweeps rearward from a central portion 1012 with a pair of wings 1014. As illustrated, the wings 1014 can extend rearward relative to the central portion 1012 of the mask base 1002. The central portion 1012 can have a vertical dimension or height that is equal to, or greater than, the height of the wings 1014. In some embodiments, the height of the wings 1014 is greater than the height of the central portion 1012. Thus, with reference to FIG. 123, when viewed from the front, the mask base 1002 comprises a generally linear upper edge that is substantially oriented in a horizontal plane.

Figure 127:
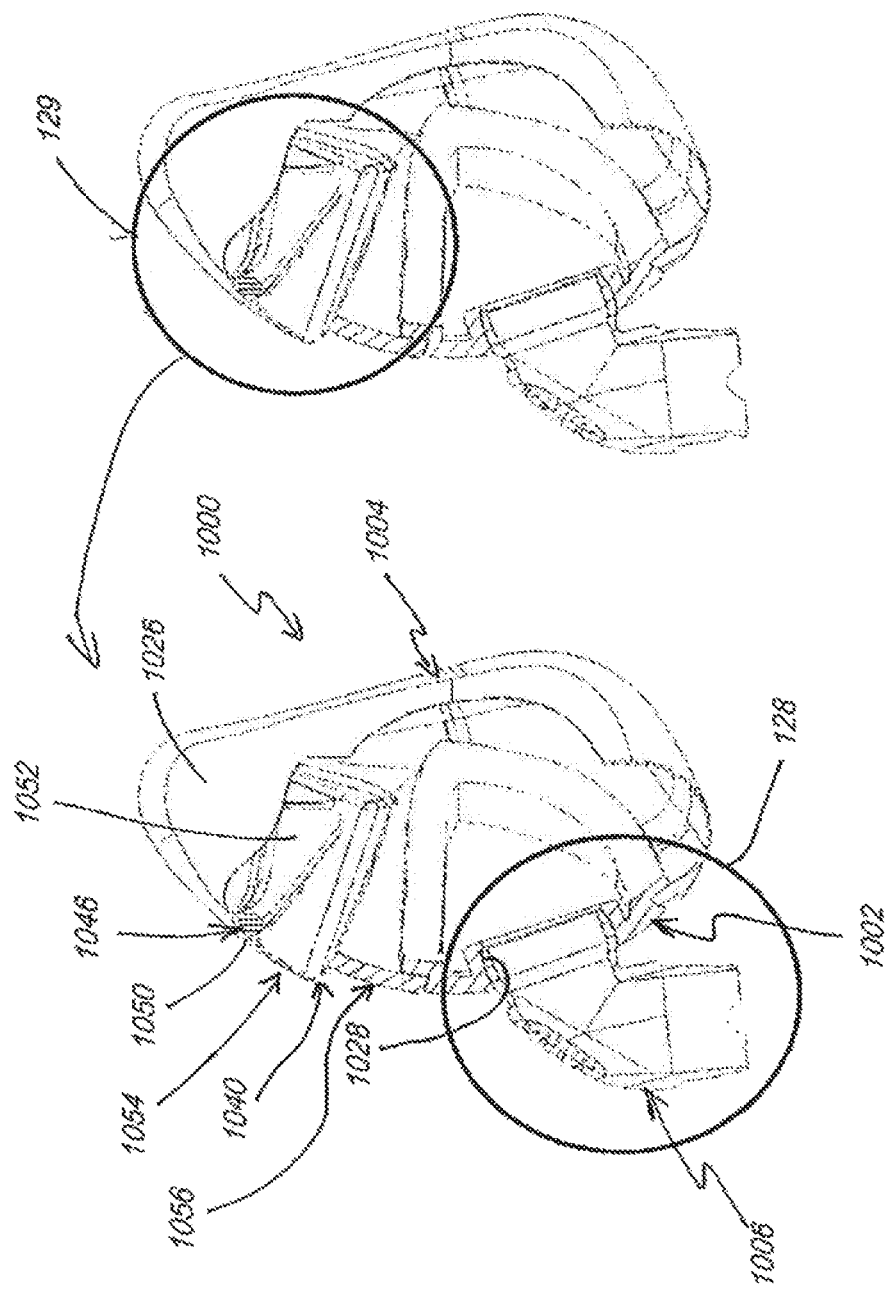
FIG. 127 is a side, partial sectional view of the mask configuration of FIG. 121.

The mask base 1002 and the mask seal 1004 can be connected in any suitable manner. As illustrated in FIGS. 127 and 128, the mask base 1002 comprises a generally circumscribing flange 1020 and the mask seal 1004 can be overmolded onto the flange 1020 of the mask base 1002. In the illustrated arrangement, the flange 1020 is positioned rearwardly of the mask seal 1004 and the outer or forward-facing surfaces of the mask base 1002 and the mask seal 1004 are substantially flush with one another at the intersection therebetween. In addition, as illustrated, the flange 1020 is positioned adjacent to the mask seal 1004; however, the flange 1020 could also include a groove that receives a portion of the mask seal 1004. Any other suitable technique can be used to form the junction between the mask seal 1004 and the mask base 1002, which can allow the mask seal 1004 to be removable or non-removable relative to the mask base 1002.

Similar to the mask seal 704 described herein, the mask seal 1004 is designed to seal against the face of the user. The mask seal 1004 preferably is formed of a soft material, such as silicone, for example but without limitation. In some configurations, at least portions of the mask seal 1004 (e.g., regions of the mask seal 1004 that will contact the skin of the user) can be textured (e.g., via a bead blasted mold surface) to improve comfort to the user. Any suitable techniques for texturing one or more surface of the mask seal 1004 can be used.

Figure 125:
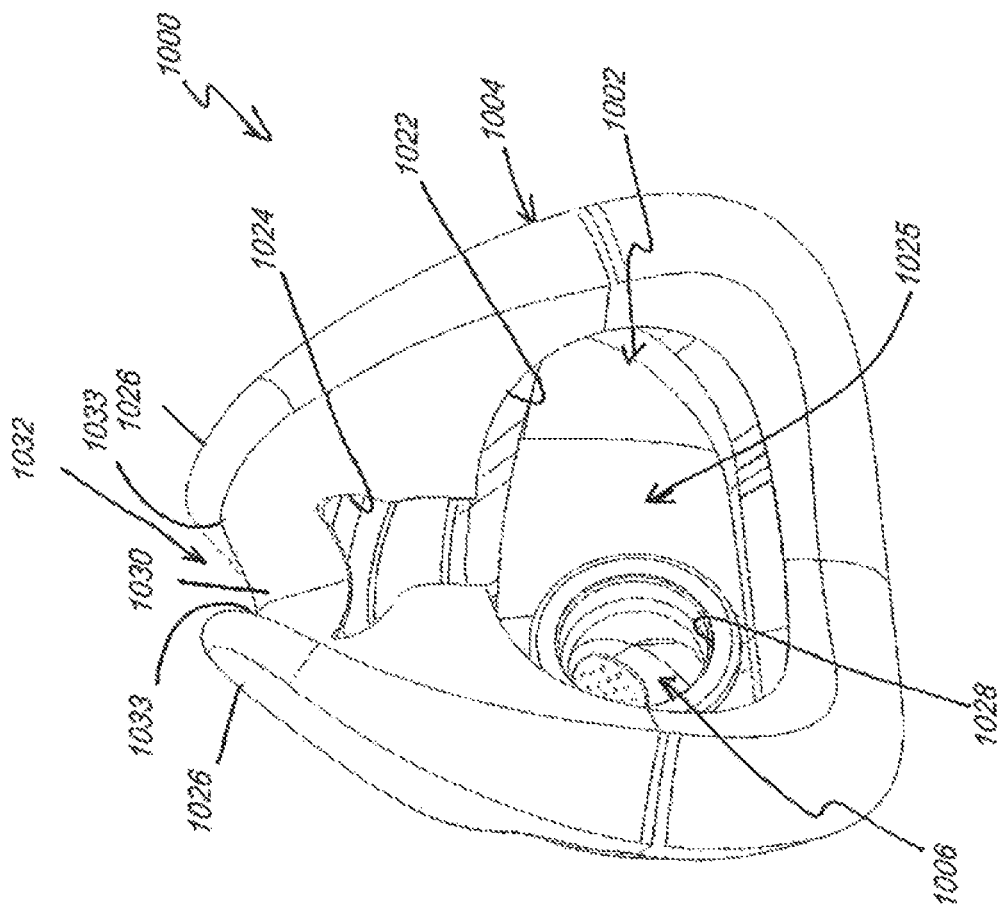
FIG. 125 is a rear perspective view of the mask configuration of FIG. 121.

With reference to FIG. 125, the mask seal 1004 comprises an oral-nasal mask seal and, therefore, comprises at least one oral opening 1022 and at least one nasal opening 1024. In the illustrated configuration, the mask seal 1004 comprises a combined oral-nasal opening in which the at least one oral opening 1022 and the at least one nasal opening 1024 cooperate to define a single opening. Thus, the at least one oral opening 1022 and the at least one nasal opening 1024 can each be portions of a single opening. In some configurations, the at least one oral opening 1022 and the at least one nasal opening 1024 can be separate from one another, such as the configuration shown in FIG. 137. In some configurations, the mask seal 1004 can comprise more than one nasal opening 1024. In some configurations, the mask seal 1004 can comprise nasal openings 1024 defined within superstructures, such as pillows, prongs or the like.

The at least one oral opening 1022 and the at least one nasal opening 1024 preferably communicate with a single chamber 1025 that is defined within the mask assembly 1000. The chamber 1025 of the illustrated mask assembly 1000 is at least partially defined by the mask base 1002 and the mask seal 1004. The at least one oral opening 1022 is substantially opposed to an opening 1028 that receives the connector 1006. The at least one nasal opening 1024 can be vertically above the at least one oral opening 1022. The at least one nasal opening 1024 can be positioned between the opening 1028 for the connector 1006 and the at least one oral opening 1022 in a fore-and-aft direction. The at least one oral opening 1022 can have an axis that is inclined relative to vertical and that generally extends through the opening 1028 for the connector 1006. In other respects, the basic spatial geometry of the mask assembly 1000 can be the same as or similar to the mask assembly 700, including without limitation, the configuration shown in and described primarily with respect to FIG. 75. For example, although not specifically identified herein, the mask assembly 1000 can have protrusions the same as or similar in construction and location to the protrusions 736 of the mask assembly 700. The mask assembly 1000 can also have anchor points the same as or similar to the anchor points AP1 and AP2 of the mask assembly 700.

With reference to FIGS. 123-125, the mask seal 1004 preferably comprises a pair of paddles 1026 that extend upward above an upper surface or upper support surface 1030 of a nose tip-accommodating space or valley 1032 defined in an upper, central portion of the mask assembly 1000. The paddles 1026 extend upward alongside, and in some configurations above, the nares. In some configurations, the paddles 1026 each comprise an air pocket that is in direct fluid communication with the air path through the mask assembly 1000 from the connector 1006 to the at least one nasal opening 1024 and the at least one oral opening 1022. Preferably, as shown in FIG. 125, the upper surface 1030 is hammocked between inner portions 1033 of the paddles 1026. Accordingly, downward pressure applied to the upper surface 1030 can tend to cause the paddles 1026 to pivot inwardly at the top. Accordingly, increasing force between the nose of the user and the upper surface 1030 can result in increasing sealing force being applied between the sides of the nose of the user and the paddles 1026. The paddles 1026 can be configured to balance sealing performance and accommodation of variations in nasal geometries in the same or a similar manner as described in relation to the mask assembly 700.

As described above, in some configurations, the mask assembly 1000 has one portion that is deformable relative to another portion and, more particularly, is configured to influence the location of the deformation, such as along at least one or preferably a pair of boundaries, as described above. In some configurations, an upper portion of the mask seal 1004 is deformable relative to a lower portion of the mask seal 1004. In particular, the upper surface 1030 can be deformable relative to a lower portion of the mask seal 1004, such as a portion that surrounds the mask base 1002. In some configurations, the deformation can be provided by a rolling hinge arrangement. The deformation of the mask assembly 1000 can increase comfort and/or allow the mask assembly 1000 to accommodate a wider range of users. That is, the deformation can allow the mask assembly 1000 to accommodate a greater variety of facial geometries and, in particular, nasal geometries, such as nose tip length and/or nose tip angle.

The mask assembly 1000 can be configured to induce deformation at a particular location or region of the mask seal 1004. In some configurations, the deformation can occur at or between the upper surface 1030 of the valley 1032 and an upper surface of the mask base 1002. In the illustrated configuration, the deformation occurs at a location spaced above the upper surface of the mask base 1002 (or an intersection between the mask base 1002 and mask seal 1004) and spaced below the upper surface 1030 of the valley 1032. In particular, the deformation can occur at a location substantially halfway between the upper surface of the mask base 1002 and spaced below the upper surface 1030 of the valley 1032. Accordingly, a section of the mask seal 1004 located above the mask base 1002 defines both a portion above the deformation location and a portion below the deformation location.

The deformation can occur at a localized point or along or within a region of any shape. In the illustrated configuration, the deformation occurs primarily along a generally linear region, which may be referred to herein for convenience simply as a line 1040. Accordingly, the use of the term "deformation line" within this disclosure can refer specifically to the illustrated generally linear deformation region or, more generally, to a deformation point, zone or region of any other shape, unless specifically indicated otherwise or dictated otherwise from the context of the disclosure. In particular, the deformation line 1040 extends in a lateral direction. The deformation line 1040 can be of any suitable length to induce the desired degree of deformation taking into account the other characteristics of the mask assembly 1000 that tend to influence the deformation, such as wall thickness or stiffness, for example and without limitation. Thus, the deformation line 1040 can have a length that is at least about one-half of the maximum width of the mask seal 1004 or the mask assembly 1000. In some configurations, the deformation line 1040 has a length that is at least about three-quarters or at least about four-fifths of the maximum width of the mask seal 1004 or the mask assembly 1000. In the illustrated configuration, the deformation line 1040 extends across a substantial entirety of the maximum width of the mask seal 1004 and the mask assembly 1000. In particular, the deformation line 1040 has a length that is approximately equal to a maximum width of the mask base 1002. More particularly, the deformation line 1040 defines end points 1042 that are located adjacent to upper corners 1044 of the mask base 1002, which can correspond to end points of the upper surface of the mask base 1002.

Figure 126:
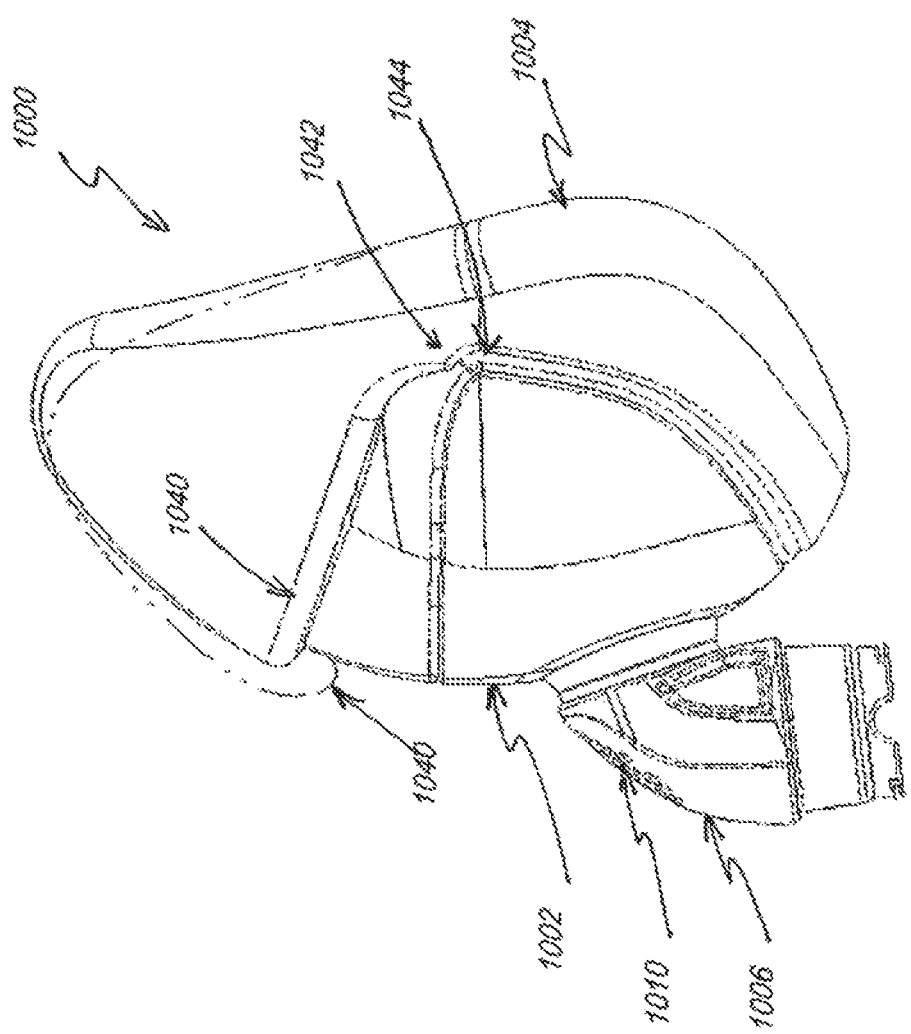
FIG. 126 is a side view of the mask configuration of FIG. 121, with a position in which a portion of a mask seal is deformed relative to a mask base shown in dashed line.

As illustrated by the dash dot line in FIG. 126, the deformation line 1040 permits an upper portion of the mask seal 1004 to deflect in a forward and/or downward direction relative to the mask base 1002 and/or a lower portion of the mask seal 1004. In particular, the deformation line 1040 permits at least a surface adjacent the at least one nasal opening 1024 to deform or deflect relative to the mask base 1002 and/or another portion (e.g., lower portion) of the mask seal 1004. More particularly, the deformation line 1040 permits at least a surface forward of the at least one nasal opening 1024 (e.g., the upper surface 1030) to deform or deflect relative to the mask base 1002 and/or another portion of the mask seal 1004. Such a configuration can assist in reducing pressure on the tip of the nose of a user or allow at least an acceptable degree of comfort for a wider variety of nasal geometries. In some configurations, the deformation line 1040 permits the upper portion of the mask seal 1004 to deform or deflect relative to a portion of the mask seal 1004 immediately below the deformation line 1040.

Figure 129:
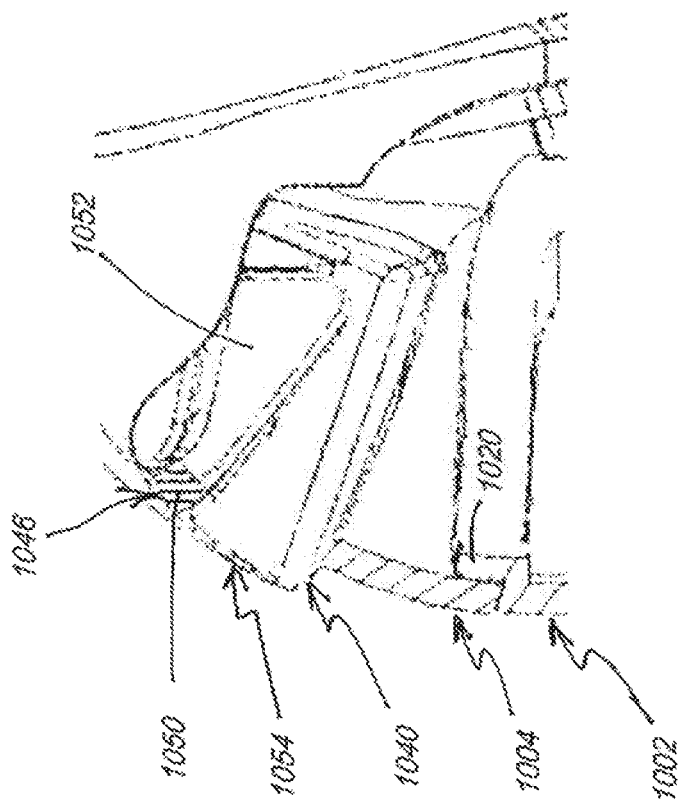
FIG. 129 is an enlarged view of a portion of the mask configuration indicated by the circle 129 of FIG. 127 and showing a deformable portion of the mask seal.

With reference to FIGS. 127 and 129, the mask assembly 1000 or, more specifically, the mask seal 1004 can include features that facilitate the deformation or rolling of the mask seal 1004 or influence the location of the deformation. Such features may be similar to those described herein with respect to FIGS. 1-16 and 24-27. For example, the mask seal 1004 can have varying thickness or a varying stiffness configured to induce deformation at a desired location. In the illustrated configuration, the mask seal 1004 comprises a thick/thin/thick arrangement along and adjacent to the deformation line 1040. More particularly, the illustrated mask seal 1004 includes a reinforcing component or components, such as a band 1046, which can be similar to the band 174 described above, for example. The band 1046 can be positioned above the deformation line 1040 and can also extend in a lateral direction. The band 1046 can be of any suitable length, such as substantially the same length as the deformation line 1040. However, in some configurations, the band 1046 can be shorter or longer than the deformation line 1040. The band 1046 can be oriented generally parallel to the deformation line 1040.

The band 1046 can have any suitable shape. In some configurations, the band 1046 has a generally rectangular cross-sectional shape. However, other shapes can also be used. The band 1046 can have a consistent or variable cross-sectional size and/or shape throughout its length. In the illustrated configuration, the band 1046 has a central portion 1050 that has a smaller height or vertical dimension relative to end portions 1052 of the band 1046. The larger end portions 1052 can provide additional support to the paddles 1026. Thus, in some configurations, an upper surface of the band 1046 can generally correspond to the shape of an upper edge of the mask seal 1004. In some configurations, at least a portion of the band 1046 (e.g., the central portion 1050) can be spaced below the upper surface 1030 of the valley 1032. In some configurations, at least a portion of the band 1046 (e.g., the outer ends 1052) can be even with or spaced above the upper surface 1030 of the valley 1032. In the illustrated configuration, the upper surface of the central portion 1050 is spaced below the upper surface 1030 of the valley 1032 and the upper surface of the ends 1052 are spaced above the upper surface 1030 of the valley 1032.

As described above, the mask seal 1004 can have variations in wall thickness and, in some configurations, can include a thick/thin/thick arrangement in the wall thickness. In the illustrated configuration, the band 1046 defines a thick section and the deformation line 1040 defines at least a portion of a thin section. In some configurations, a transition region 1054 can also define a portion of the thin section together with the deformation line 1040. The illustrated transition region 1054 increases in thickness moving in a direction from the deformation line 1040 toward the band 1046. The change in thickness can be continuous or can be done in a stepped fashion. In some configurations, the entire space between the deformation line 1040 and the band 1046 can define the transition region 1054.

Below the deformation line 1040, the mask seal 1004 can define a thickened section 1056, which can form a part of a central portion of the mask seal 1004 that defines the opening and is coupled to the flange 1020. In the illustrated configuration, the relatively more rigid band 1046 and thickened section 1056 can induce deformation or rolling of the mask seal 1004 in a region between the band 1046 and thickened section 1056, such as one or both of the deformation line 1040 and the transition region 1054. In some configurations, the deformation line 1040 defines the smallest wall thickness of the deformation line 1040, transition portion 1054, band 1046 and thickened portion 1056 such that deformation begins within the deformation line 1040 and then the mask seal 1004 continues to roll within the transition region 1054, which can have the next smallest wall thickness. The more rigid, larger wall thicknesses of the band 1046 and the thickened portion 1056 can resist deformation to a greater degree than the deformation line 1040 and the transition region 1054. In some configurations, the band 1046 and the thickened portion 1056 can have the same or a similar wall thickness. In other configurations, the band 1046 and the thickened portion 1056 can have different wall thicknesses.

Figure 130:
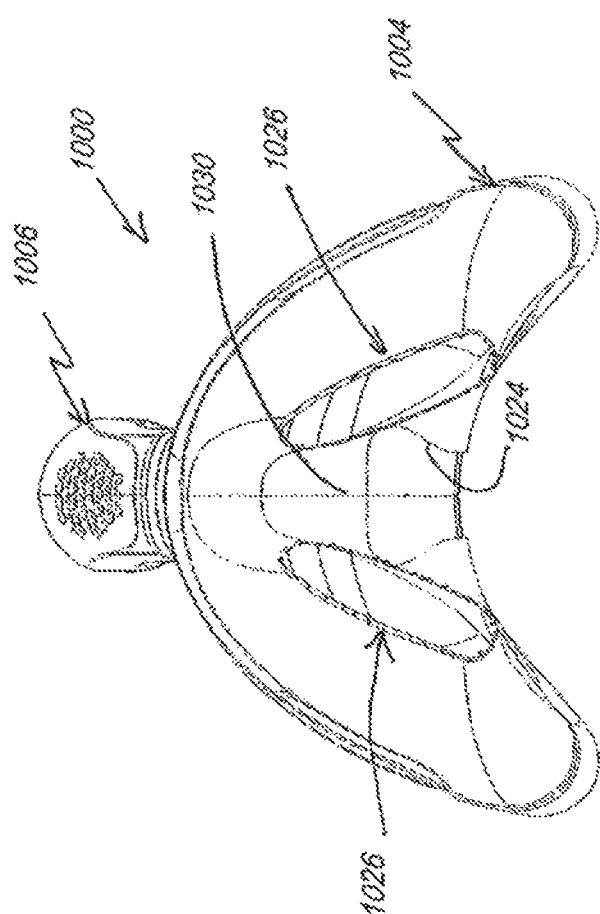
FIGS. 130-133 are sectioned views taken along the lines indicated in FIG. 124.

FIGS. 130-133 illustrate various cross-sections of the mask assembly 1000 taken along the horizontal planes indicated in FIG. 125, which move in a direction from the top toward the bottom of the mask assembly 1000. FIGS. 130-133 illustrate, among other things, previously-described features of the mask assembly 1000. For instance, FIG. 130 illustrates the wall thickness of the paddles 1026. In the illustrated configuration, the paddles 1026 have a slightly greater wall thickness on the lateral walls relative to the wall thickness on the medial walls. In other configurations, for example and without limitation, this arrangement could be reversed or the paddles 1026 could have a constant wall thickness. In some configurations, the paddles 1026 include some or all of the features of the paddles 726 described with reference to FIGS. 71-88, which can include, for example and without limitation, shapes, sizes and wall thicknesses.

Figure 131:
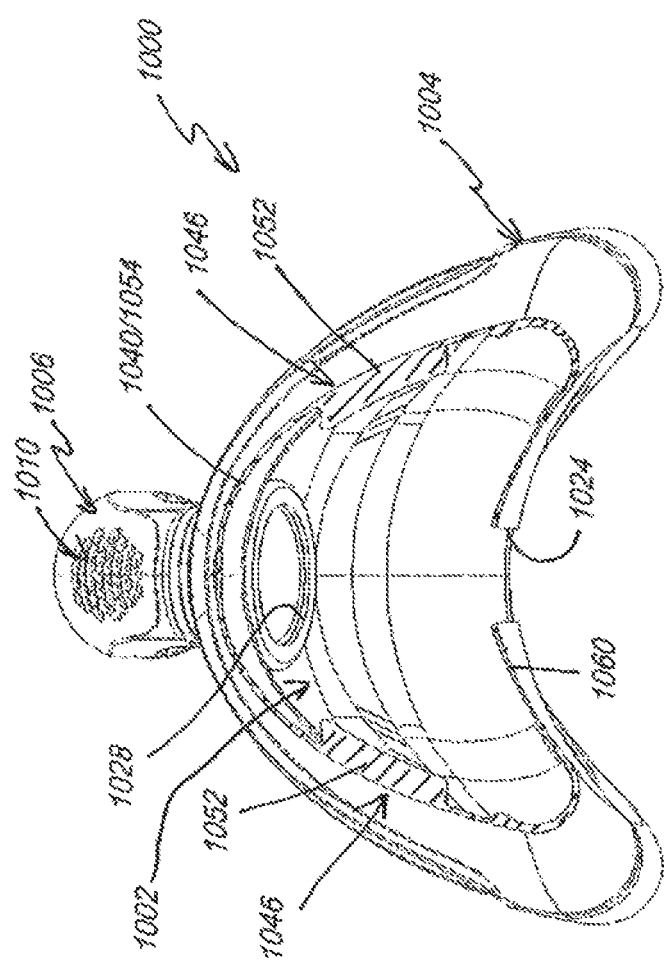
Figure 136:
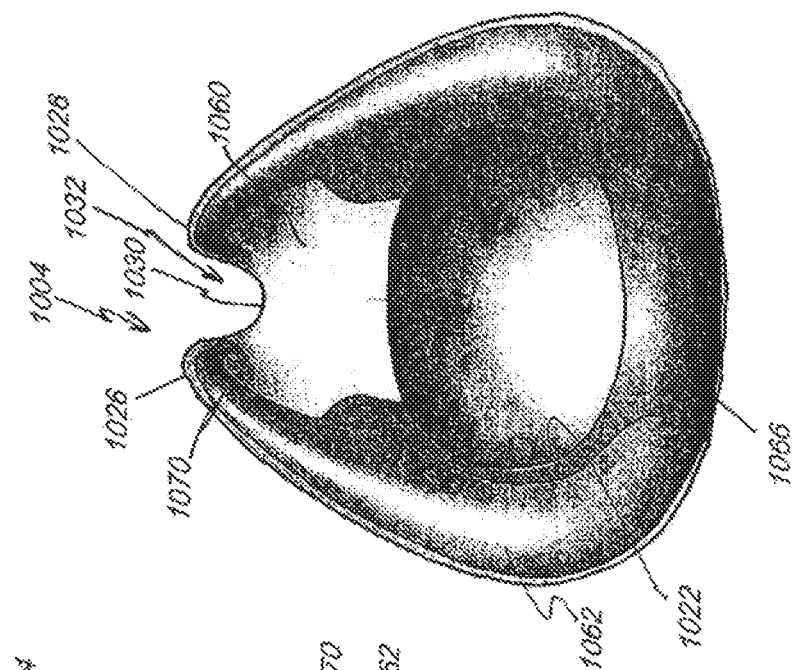
FIG. 136 is a rear view of the representation of the mask configuration of FIG. 134.

With reference to FIG. 131, a cross-section of the outer ends 1052 of the band 1046 are shown with a portion of the deformation line 1040 and/or transition region 1054 extending therebetween. In addition, FIG. 131 illustrates a thin-walled region 1060 surrounding the at least one nasal passage 1024, which is described further herein with reference to FIG. 136.

Figure 132:
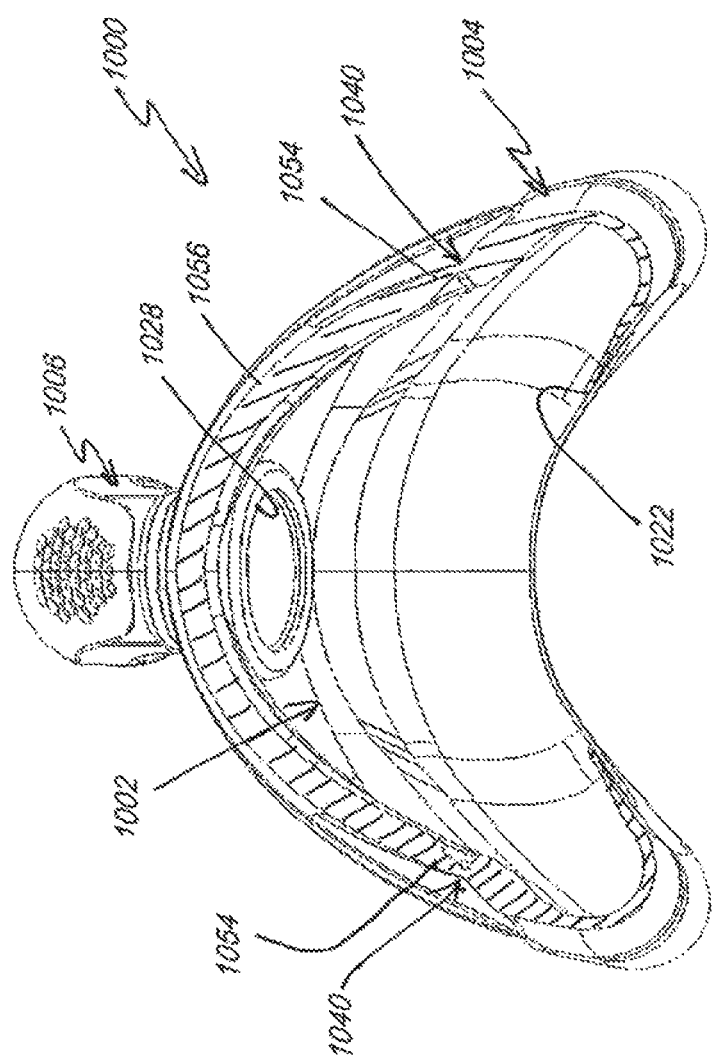

With reference to FIG. 132, a cross-section of the mask seal 1004 above and near the mask base 1002 is shown. A cross-section of the thickened portion 1056 is shown extending from the center of the mask seal 1004 laterally and rearwardly to the transition region 1054 and deformation line 1040.

Figure 133:
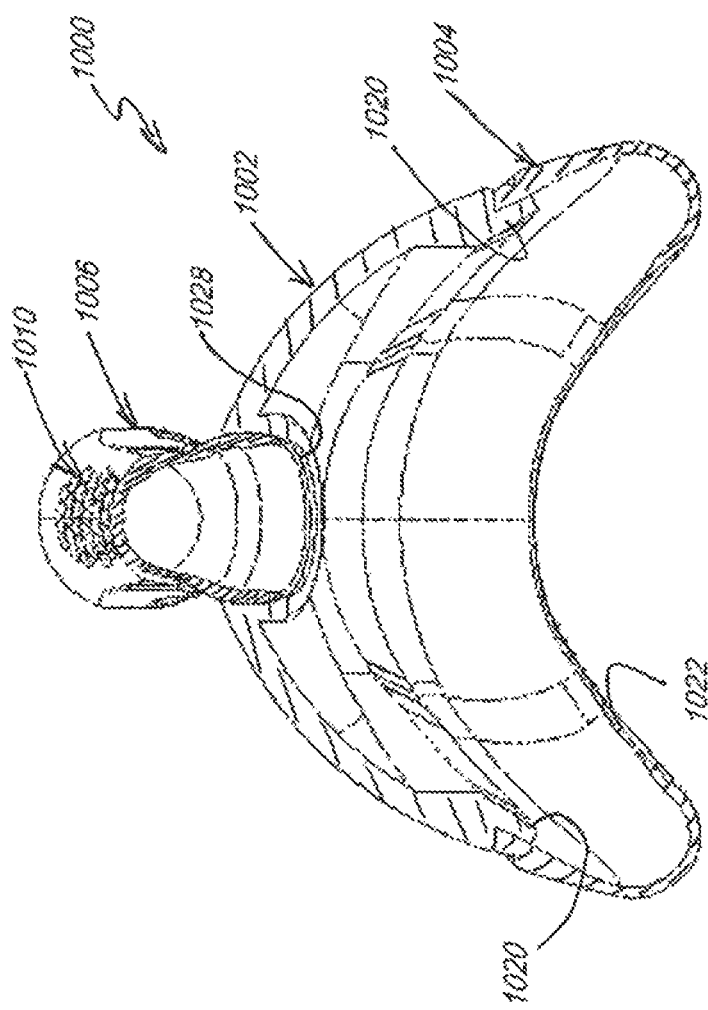

FIG. 133 shows a cross-section of the mask assembly 1000 including portions of the mask base 1002, mask seal 1004 and connector 1006. The intersection between the mask base 1002 and the mask seal 1004 is shown and, in particular, the overlapping of the mask seal 1004 with the flange 1020. In addition, the opening 1028 that receives the connector 1006 is shown.

Figure 135:
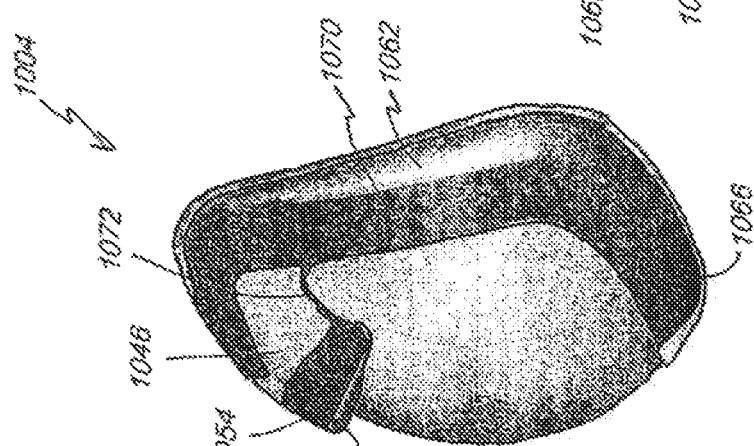
FIG. 135 is a side view of the representation of the mask configuration of FIG. 134.
Figure 134:
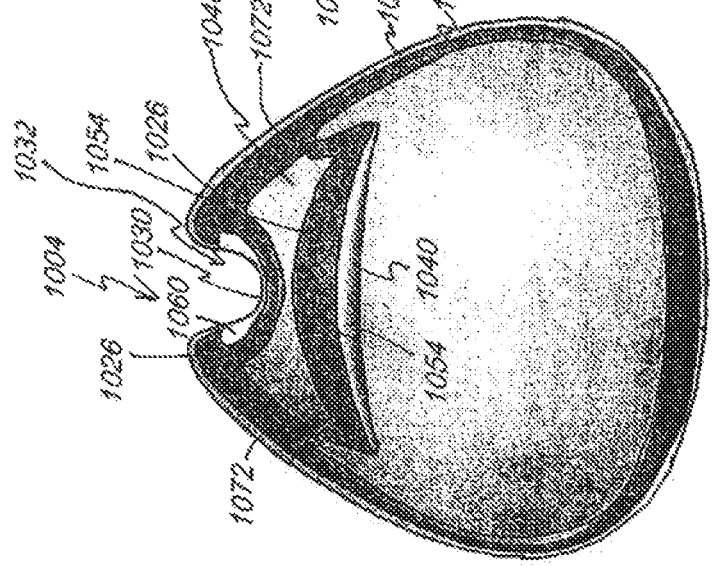
FIG. 134 is a front view of a representation of the mask configuration of FIG. 121 illustrating the variation in thickness between certain zones of the mask configuration.

Similar to the mask seal 704, the mask seal 1004 comprises a fairly complex range and configuration of thickness, some of which have been described herein. In some configurations, the mask seal 1004 includes many of the same variations and regions of varying thickness as the mask seal 704. The illustrated configuration of the mask seal 1004 includes some differences from the mask seal 704 designed to facilitate the desired rolling or deforming action of the mask seal 1004. In particular, with reference to FIGS. 134-136, configurations of the mask seal 1004 can include one or more of a connecting region, outer peripheral portions 1062, protruding portions, an oral region 1066, a nasal region 1060 and a transitional portion 1070 corresponding to the connecting region 760, outer peripheral portions 762, protruding portions 764, oral region 766, nasal region 768 and transitional portion 770, respectively, of the mask seal 704, as illustrated in FIGS. 80-82. The connecting region and protruding portions are not specifically identified in FIGS. 134-136. The connecting region can be similar on many respects to the connecting region 760, but preferably is modified to correspond to the outer shape of the mask base 1002. The connecting region is illustrated and described with respect to FIGS. 127 and 128. The protruding portions can be the same as or substantially similar to the protruding portions 764 of the mask seal 704.

The outer peripheral portions 1062, the oral region 1066, the nasal region 1060 and the transitional portion 1070 can be the same as or similar to the corresponding portions/regions of the mask seal 704. That is, these portions/regions can have generally the same or similar, for example and without limitation, shape, size, location and thickness of the corresponding portions/regions of the mask seal 704 because of the shared purpose and style of fit between the mask seal 1004 and the mask seal 704.

As described above, however, the mask seal 1004 also has differences relative to the mask seal 704, many of which have been described herein, to facilitate the deformation or rolling action of the mask seal 1004. For example, the illustrated nasal region 1060 does not extend significantly into the forward-facing surface of the mask seal 1004, at least in comparison to the nasal region 768 of the mask seal 704. In the illustrated configuration, the nasal region 1060 defines the upper surface 1030 of the valley 1032. In some configurations, the nasal region 1060 terminates just forward of the upper surface 1030. In some configurations, the nasal region 1060 extends upwardly from the upper surface 1030 and along the paddles 1026 in a manner similar to the nasal region 768. Although not shown in FIG. 136, the nasal region 1060 can define the at least one nasal opening 1024 and/or can support a separate nasal seal structure.

The mask seal 1000 also includes the previously-described deformation line 1040, transition region 1054 and band 1046. Although described for simplicity as a line, the deformation line 1040 can be a generally linear region extending laterally across the mask seal 1004 and lying in a generally horizontal plane. In some configurations, the deformation line 1040 protrudes outwardly from the thickened section 1056 such that the deformation line 1040 and, in some configurations, the transition region 1054 roll over the forward surface of the mask seal 1004. However, in other configurations, the deformation line 1040/thickened section 1056 can roll over the rearward surface (i.e., to the inside) of the mask seal 1004.

In the illustrated configuration, the deformation line 1040 has a curved cross-sectional shape when viewed along a vertical cut plane. Thus, the deformation line 1040 can have an arc length (i.e., circumferential length). The arc length can be constant or variable along the lateral length of the deformation line 1040. In the illustrated configuration, the arc length is greater in the center and decreases when moving toward the end points 1042 of the deformation line 1040. The deformation line 1040 can have any suitable wall thickness and, in some configurations, has the same or similar wall thickness as the nasal region 1060 and/or oral region 1066.

As described above, the transition region 1054 extends above the deformation line 1040. In the illustrated configuration, the transition region 1054 extends along the entire lateral length of the deformation line 1040. The transition region 1054 can have any suitable thickness and, in some configurations, has a varying thickness that increases when moving from the deformation line 1040 toward the band 1046. In some configurations, the transition region 1054 can have the same (constant or variable) thickness as the transition portion 1070. In some configurations, the transition region 1054 is connected to and forms a part of the transition portion 1070.

The mask seal 1004 also includes the band 1046, which in the illustrated configuration is defined between an upper part of the transition portion 1070 and the transition region 1054. As described previously, the band 1046 can have any suitable thickness, constant or variable. In some configurations, the band 1046 has the same or a similar thickness as the connecting region.

Figure 137:
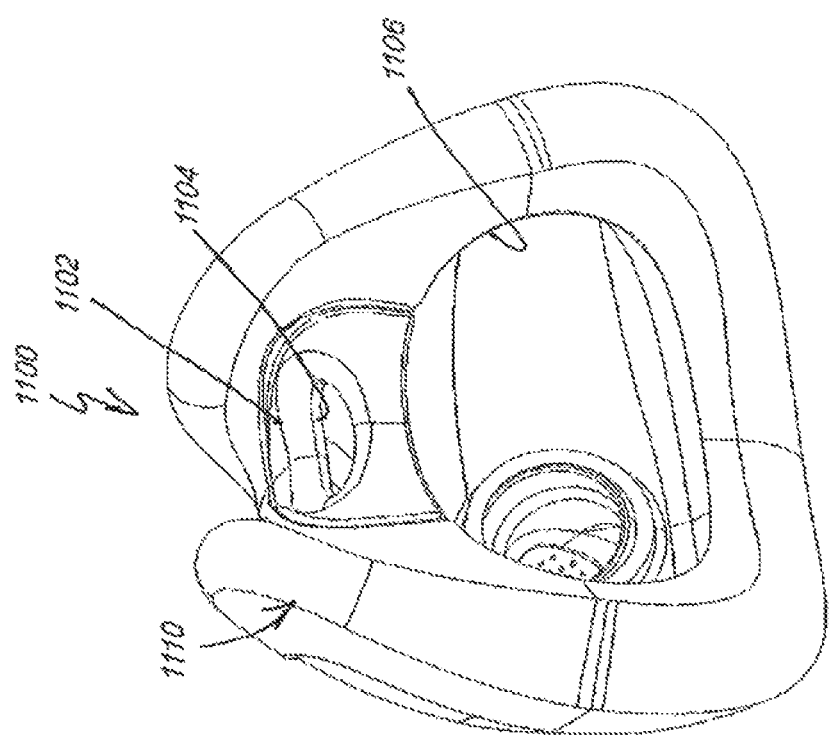
FIG. 137 is a rear perspective view of a modification of the mask configuration of FIG. 121.

FIG. 137 illustrates another configuration of a mask assembly 1100. The mask assembly 1100 is substantially similar in many respects to the mask assembly 1000, including the provision of a rolling hinge arrangement. Thus, any feature not described can be assumed to be the same as or similar to the corresponding feature of the mask assembly 1000. However, the mask assembly 1100 includes a nasal pad insert or nasal cushion 1102 that defines at least one nasal opening 1104. In the illustrated configuration, the nasal cushion 1102 defines a single nasal opening 1104 that is separate from the at least one oral opening 1106. The nasal cushion 1102 can be unitary with the mask seal 1110 or can be a separate component that is assembled to the mask seal 1110. In one configuration, the nasal cushion 1102 and mask seal 1110 are the same as or similar to the nasal pad insert 740 and mask seal 704, respectively, including any one or combination of features disclosed with respect thereto.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

The invention claimed is:

1. An interface for use in providing positive pressure respiratory therapy, the interface comprising:
   a mask assembly comprising a mask seal and a mask base, the mask assembly configured to be fully positioned lower than a bridge of a nose of a face of a user and the mask assembly configured to provide an exposed tip of the nose of the user;
   the mask base comprising a central portion and a pair of wings sweeping rearwardly of the central portion, an opening for a connector being formed on the mask base in the central portion;
   the mask seal being connected to the mask base, the mask seal comprising at least one oral opening on a lower portion and at least one nasal opening on an upper portion, the at least one oral opening being positioned opposite of the opening for the connector and the at least one nasal opening being positioned between the opening for the connector and the at least one oral opening in a front to back direction; and
   the mask seal comprising a first paddle and a second paddle, an upper support surface being positioned between the first paddle and the second paddle such that an upwardly-open valley is defined by the first paddle, the upper support surface and the second paddle, at least a portion of the at least one nasal opening being positioned on the upper support surface within the valley;

wherein the mask seal further comprises a rolling hinge positioned between an upper surface of the mask base and the upper support surface, which permits the upper portion of the mask seal to deform downwardly relative to the lower portion of the mask seal such that it rolls over and onto an outer surface of the mask seal.

2. The interface of claim 1, wherein the rolling hinge comprises a thin-walled portion positioned between a pair of thick-walled portions.

3. The interface of claim 2, wherein an upper one of the pair of thick-walled portions is defined at least in part by a thickened band.

4. The interface of claim 3, wherein the thickened band has a central portion having a first cross-sectional dimension and outer end portions having a second cross-sectional dimension that is greater than the first cross-sectional dimension.

5. The interface of claim 3, wherein the thickened band is positioned on an interior surface of the mask seal.

6. The interface of claim 3, wherein at least a portion of the thickened band is located above the upper support surface.

7. The interface of claim 2, further comprising a transition portion between the thin-walled portion and one of the pair of thick-walled portions, the transition portion defining a variable wall thickness.

8. The interface of claim 7, wherein the transition portion defines a first wall thickness that is equal to the thin-walled portion and wherein the transition portion defines a second wall thickness that is equal to the thick-walled portion.

9. The interface of claim 1, wherein the rolling hinge extends laterally across the mask seal and wherein the rolling hinge defines a length that is equal to a width of an upper surface of the mask base.

10. The interface of claim 1, wherein the rolling hinge rolls over a forward facing surface of the mask seal.

11. The interface of claim 1, wherein the mask seal is adapted to seal under the nose of the user, along a portion of the face of the user adjacent to the nose and around a mouth of the user.

12. The interface of claim 1, wherein the upper support surface is hammocked between inner portions of the first and second paddles.

13. The interface of claim 12, wherein downward pressure on the upper support surface causes the first and second paddles to deflect toward each other.

14. The interface of claim 1, wherein the mask seal comprises a rear surface that is adapted to contact the face of the user and the rear surface comprises a first protrusion and a second protrusion.

15. The interface of claim 14, wherein at least a portion of the first protrusion and at least a portion of the second protrusion are positioned vertically between the upper support surface and an uppermost portion of the at least one oral opening.

16. The interface of claim 15, wherein the portion of the first protrusion comprises a first peak and wherein the portion of the second protrusion comprises a second peak.

17. The interface of claim 16, wherein the first peak and the second peak are positioned vertically between a portion of the at least one nasal opening and the at least one oral opening.

18. The interface of any of claim 1, wherein the mask seal is adapted to anchor on two locations of the face.

19. The interface of claim 18, wherein the two locations are lower than the bottom of the nose but the mask seal is adapted to extend upward beyond the bottom of the nose.

20. The interface of claim 1, wherein the upper support surface slopes downward and rearward in a region surrounding the at least one nasal opening.

21. The interface of claim 1, wherein outer peripheral portions have an increased rigidity relative to inwardly facing portions of the first paddle and the second paddle.

22. The interface of claim 21, wherein the outer peripheral portions have an increased thickness relative to the inwardly facing portions of the first paddle and the second paddle.

23. The interface of claim 1, wherein the first paddle comprises a first ridge positioned between a first outwardly facing surface and a first inwardly facing surface and wherein the second paddle comprises a second ridge positioned between a second outwardly facing surface and a second inwardly facing surface, the first ridge and the second ridge having an increased rigidity relative to the first and second inwardly facing surfaces.

24. The interface of claim 1, wherein the first paddle comprises a first ridge positioned between a first outwardly facing surface and a first inwardly facing surface and wherein the second paddle comprises a second ridge positioned between a second outwardly facing surface and a second inwardly facing surface, the first and second ridge having an increased thickness relative to the first and second inwardly facing surfaces.

25. The interface of claim 1, further comprising a headgear assembly adapted to provide a slightly upward force application between the mask assembly and the face of the user.

26. The interface of claim 25, wherein the headgear assembly is configured to adjust an angle of the mask assembly.

27. The interface of claim 25, wherein the mask assembly and the headgear assembly are configured such that no portion of the mask assembly or the headgear assembly will contact the face of the user at any location vertically above the eyes at a location horizontally between the outsides of the eyes.

28. The interface of claim 1, wherein the rolling hinge is spaced above the upper surface of the mask base.

29. The interface of claim 1, wherein the rolling hinge is linear and lies within a plane.

30. The interface of claim 29, wherein the plane is horizontal with the interface in an upright orientation.

31. The interface of claim 1, wherein the rolling hinge defines opposing end points, wherein the end points are located adjacent to upper corners of the mask base.

32. The interface of claim 1, wherein the rolling hinge is configured such that the upper portion of the mask seal deflects at least partially in a forward direction.

33. The interface of claim 1, wherein the first and second paddles are configured to extend upwards along the lateral sides of the nose of the user.

* * * * *